US011124516B2

(12) United States Patent
Skerlj et al.

(10) Patent No.: US 11,124,516 B2
(45) Date of Patent: Sep. 21, 2021

(54) PYRROLO[1,2-A]PYRIMIDINYL CARBOXAMIDE COMPOUNDS AND THEIR USE IN THE TREATMENT OF MEDICAL DISORDERS

(71) Applicant: Bial—Biotech Investments, Inc., Coronado (PT)

(72) Inventors: Renato T. Skerlj, West Newton, MA (US); Elyse Marie Josee Bourque, L'etang-Du-Nord (CA); Peter T. Lansbury, Brookline, MA (US); William J. Greenlee, Teaneck, NJ (US); Andrew C. Good, Wallingford, CT (US)

(73) Assignee: BIAL-BIOTECH INVESTMENTS, INC., Coronado (PT)

( * ) Notice: Subject to any disclaimer, the term of this patent is extended or adjusted under 35 U.S.C. 154(b) by 0 days.

(21) Appl. No.: 16/091,337

(22) PCT Filed: Apr. 6, 2017

(86) PCT No.: PCT/US2017/026284
§ 371 (c)(1),
(2) Date: Oct. 4, 2018

(87) PCT Pub. No.: WO2017/176962
PCT Pub. Date: Oct. 12, 2017

(65) Prior Publication Data
US 2019/0315751 A1    Oct. 17, 2019

Related U.S. Application Data

(60) Provisional application No. 62/318,937, filed on Apr. 6, 2016.

(51) Int. Cl.
*C07D 487/04* (2006.01)
*C07D 493/08* (2006.01)

(52) U.S. Cl.
CPC ......... *C07D 487/04* (2013.01); *C07D 493/08* (2013.01)

(58) Field of Classification Search
CPC .................................................. C07D 487/04
See application file for complete search history.

(56) References Cited

U.S. PATENT DOCUMENTS

| 4,838,925 | A | 6/1989 | Tseng |
| 7,550,470 | B2 | 6/2009 | Fraley |
| 7,723,336 | B2 | 5/2010 | Vaccaro et al. |
| 7,795,273 | B2 | 9/2010 | Imbach et al. |
| 8,163,759 | B2 | 4/2012 | Tanimoto et al. |
| 8,372,851 | B2 | 2/2013 | Rice et al. |
| 8,680,159 | B2 | 3/2014 | Reich et al. |
| 9,085,560 | B2 | 7/2015 | Ren et al. |
| 9,127,000 | B2 | 9/2015 | Ren et al. |
| 9,353,117 | B2 | 5/2016 | Marugan et al. |
| 9,732,089 | B2 | 8/2017 | Skerlj et al. |
| 9,802,942 | B2 * | 10/2017 | Krainc ................... A61K 47/26 |
| 9,840,510 | B1 | 12/2017 | Skerlj et al. |
| 9,868,742 | B2 | 1/2018 | Skerlj et al. |
| 9,920,061 | B2 | 3/2018 | Skerlj et al. |
| 10,040,799 | B2 * | 8/2018 | Krainc ................. A61K 9/4866 |
| 10,227,352 | B2 * | 3/2019 | Krainc ................. A61K 9/0019 |
| 10,442,812 | B2 * | 10/2019 | Krainc ................. A61K 9/0019 |
| 10,570,135 | B2 | 2/2020 | Skerlj et al. |
| 10,751,341 | B2 | 8/2020 | Skerlj et al. |
| 10,786,508 | B2 | 9/2020 | Skerlj et al. |
| 10,787,454 | B2 | 9/2020 | Skerlj et al. |
| 10,934,298 | B2 | 3/2021 | Skerlj et al. |
| 2006/0287324 | A1 | 12/2006 | Sun et al. |
| 2007/0082902 | A1 | 4/2007 | Paruch et al. |
| 2008/0051409 | A1 | 2/2008 | Gmeiner et al. |
| 2008/0176870 | A1 | 7/2008 | Nolte et al. |
| 2008/0255153 | A1 | 10/2008 | Bremberg et al. |
| 2008/0287463 | A1 | 11/2008 | Herrmann et al. |
| 2012/0015962 | A1 | 1/2012 | Arora et al. |
| 2012/0071461 | A1 | 3/2012 | Reich et al. |
| 2013/0095089 | A1 | 4/2013 | Larsen et al. |

(Continued)

FOREIGN PATENT DOCUMENTS

DE    102004049363 A1    4/2006
EP        1878727 A1     1/2008
(Continued)

OTHER PUBLICATIONS

Caira M. R. "Crystalline Polymorphism of Organic Compounds." Topics in Current Chemistry. Springer, Berlin, DE, vol. 198, Jan. 1, 1998, pp. 163-208.
Almeida, MR."Glucocerebrosidase Involvement in Parkinson Disease and other Synucleinopathies," Frontiers in Neurology Apr. 27;3:65 2012.
CAS registry No. 1477723-10-6, STN entry date: Nov. 21, 2013, chemical name: Pyrazolo[1,5-a]pyrimidine-3-carboxamide, N-[2-(aminomethyl)cyclopentyl]-5,7-dimethyl.
CAS registry No. 1486188-70-8, STN entry date: Dec. 3, 2013, chemical name: Pyrazolo[1,5-a]pyrimidine-3-carboxamide, N-[1-(hydroxymethyl)cyclopentyl]-5,7-dimethyl.

(Continued)

Primary Examiner — Emily A Bernhardt
(74) Attorney, Agent, or Firm — Goodwin Procter LLP

(57) ABSTRACT

The invention provides substituted pyrrolo[1,2-a]pyrimidinyl carboxamide and related organic compounds, compositions containing such compounds, medical kits, and methods for using such compounds and compositions to treat medical disorders, e.g., Gaucher disease, Parkinson's disease, Lewy body disease, dementia, or multiple system atrophy, in a patient. Exemplary substituted pyrrolo[1,2-a]pyrimidinyl carboxamide compounds described herein include substituted 2-heterocyclyl-4-alkyl-pyrrolo[1,2-a]pyrimidine-8-carboxarnide compounds and variants thereof.

16 Claims, No Drawings

(56) References Cited

U.S. PATENT DOCUMENTS

| | | |
|---|---|---|
| 2013/0245021 A1 | 9/2013 | Bi et al. |
| 2014/0288093 A1 | 9/2014 | Krainc et al. |
| 2014/0349993 A1 | 11/2014 | Casaubon et al. |
| 2015/0175610 A1 | 6/2015 | Bi et al. |
| 2015/0183791 A1 | 7/2015 | Bi et al. |
| 2015/0191474 A1 | 7/2015 | Takahashi et al. |
| 2016/0159808 A1 | 6/2016 | Kawasaki et al. |
| 2017/0001976 A1 | 1/2017 | Krainc et al. |
| 2017/0002013 A1 | 1/2017 | Krainc et al. |
| 2017/0183354 A1 | 6/2017 | Skerlj et al. |
| 2017/0333435 A1 | 11/2017 | Skerlj et al. |
| 2017/0334916 A1 | 11/2017 | Skerlj et al. |
| 2017/0349598 A1 | 12/2017 | Skerlj et al. |
| 2017/0355702 A1 | 12/2017 | Skerlj et al. |
| 2018/0185368 A1 | 7/2018 | Skerlj et al. |
| 2018/0325899 A1 | 11/2018 | Weinstein et al. |
| 2019/0119283 A1 | 4/2019 | Skerlj et al. |
| 2019/0216813 A1 | 7/2019 | Skerlj et al. |
| 2019/0315751 A1 | 10/2019 | Skerlj et al. |
| 2019/0330213 A1 | 10/2019 | Skerlj et al. |
| 2019/0389856 A1 | 12/2019 | Skerlj et al. |
| 2019/0389865 A1 | 12/2019 | Skerlj et al. |
| 2019/0389866 A1 | 12/2019 | Skerlj et al. |
| 2020/0017507 A1 | 1/2020 | Skerlj et al. |
| 2020/0030331 A1 | 1/2020 | Skerlj et al. |
| 2020/0339587 A1 | 10/2020 | Skerlj et al. |
| 2020/0385390 A1 | 12/2020 | Skerlj et al. |

FOREIGN PATENT DOCUMENTS

| | | |
|---|---|---|
| EP | 2269990 A1 | 1/2011 |
| EP | 2746265 B1 | 11/2015 |
| EP | 3026051 A1 | 6/2016 |
| JP | 2000-318321 A | 11/2000 |
| JP | 2000-327681 A | 11/2000 |
| JP | 2004277337 A | 10/2004 |
| KR | 20140086002 A | 7/2014 |
| WO | WO-2002/064545 A1 | 8/2002 |
| WO | WO-2003/002584 A1 | 1/2003 |
| WO | WO-2003/035649 A1 | 5/2003 |
| WO | WO-2003/074525 A1 | 9/2003 |
| WO | WO-2004/026869 A1 | 4/2004 |
| WO | WO-2004026868 A1 | 4/2004 |
| WO | WO-2004/052315 A2 | 6/2004 |
| WO | WO-2004/094418 A1 | 11/2004 |
| WO | WO-2005/046611 A2 | 5/2005 |
| WO | WO-2005/058837 A1 | 6/2005 |
| WO | WO-2005/068426 A1 | 7/2005 |
| WO | WO-2005/077953 A1 | 8/2005 |
| WO | WO-2005113004 A2 | 12/2005 |
| WO | WO-2005123738 A1 | 12/2005 |
| WO | WO-2006/015737 A1 | 2/2006 |
| WO | WO-2006/078676 A2 | 7/2006 |
| WO | WO-2006084634 A1 | 8/2006 |
| WO | WO-2006115168 A1 | 11/2006 |
| WO | WO-2007/048066 A2 | 4/2007 |
| WO | WO-2007/108750 A1 | 9/2007 |
| WO | WO-2007150064 A2 | 12/2007 |
| WO | WO-2008/019363 A2 | 2/2008 |
| WO | WO-2008/063671 A2 | 5/2008 |
| WO | WO-2008063669 A1 | 5/2008 |
| WO | WO-2008/116898 A1 | 10/2008 |
| WO | WO-2008/138889 A2 | 11/2008 |
| WO | WO-2008/157575 A1 | 12/2008 |
| WO | WO-2009/060835 A1 | 5/2009 |
| WO | WO-2009060197 A1 | 5/2009 |
| WO | WO-2009/070567 A1 | 6/2009 |
| WO | WO-2009/100375 A1 | 8/2009 |
| WO | WO-2009/134973 A1 | 11/2009 |
| WO | WO-2010/043893 A1 | 4/2010 |
| WO | WO-2010/051549 A1 | 5/2010 |
| WO | WO-2010/086040 A1 | 8/2010 |
| WO | WO-2011006074 A1 | 1/2011 |
| WO | WO-2011/022439 A1 | 2/2011 |
| WO | WO-2012/007375 A1 | 1/2012 |
| WO | WO-2012/034095 A1 | 3/2012 |
| WO | WO-2012/038081 A1 | 3/2012 |
| WO | WO-2012/075393 A2 | 6/2012 |
| WO | WO-2012/078855 A1 | 6/2012 |
| WO | WO-2012/116237 A2 | 8/2012 |
| WO | WO-2012/129258 A1 | 9/2012 |
| WO | WO-2012/177997 A1 | 12/2012 |
| WO | WO-2013/030288 A1 | 3/2013 |
| WO | WO-2013/059587 A1 | 4/2013 |
| WO | WO-2013/096060 A1 | 6/2013 |
| WO | WO-2013/134079 A1 | 9/2013 |
| WO | WO-2013/148333 A1 | 10/2013 |
| WO | WO-2013/178591 A1 | 12/2013 |
| WO | WO-2014/025651 A1 | 2/2014 |
| WO | WO-2014/037340 A1 | 3/2014 |
| WO | WO-2014/075168 A1 | 5/2014 |
| WO | WO-2014/085607 A1 | 6/2014 |
| WO | WO-2014/089379 A1 | 6/2014 |
| WO | WO-2014/141129 A2 | 9/2014 |
| WO | WO-2014/144455 A1 | 9/2014 |
| WO | WO-2015/012328 A1 | 1/2015 |
| WO | WO-2015026574 A1 | 2/2015 |
| WO | WO-2015/035117 A1 | 3/2015 |
| WO | WO-2015/073267 A1 | 5/2015 |
| WO | WO-2015/147639 A1 | 10/2015 |
| WO | WO-2016/007736 A1 | 1/2016 |
| WO | WO-2016/073889 A1 | 5/2016 |
| WO | WO-2016/073891 A1 | 5/2016 |
| WO | WO-2016/073895 A1 | 5/2016 |
| WO | WO-2017/004408 A1 | 1/2017 |
| WO | WO-2017040877 A1 | 3/2017 |
| WO | WO-2017/079519 A1 | 5/2017 |
| WO | WO-2017140825 A1 | 8/2017 |
| WO | WO-2017/176960 A1 | 10/2017 |
| WO | WO-2017/176961 A1 | 10/2017 |
| WO | WO-2017/176962 A1 | 10/2017 |
| WO | WO-2017/192841 A1 | 11/2017 |
| WO | WO-2017/192929 A1 | 11/2017 |
| WO | WO-2017-192930 A1 | 11/2017 |
| WO | WO-2017/192931 A1 | 11/2017 |
| WO | WO-2019126776 A1 | 6/2019 |

OTHER PUBLICATIONS

CAS registry No. 1487377-87-6, STN entry date: Dec. 5, 2013, chemical name: Pyrazolo[1,5-a]pyrimidine-3-carboxamide, N-[1-(aminomethyl)cyclopentyl]-5,7-dimethyl.

CAS registry No. 1626061-70-8, STN entry date: Sep. 25, 2014, chemical name: Pyrazolo[1,5-a]pyrimidine-3-carboxamide, 2-methyl-N-[[2-(2-methylpropoxy)phenyl]methyl].

CAS registry No. 1626265-70-0, STN entry date: Sep. 25, 2014, chemical name: Pyrazolo[1,5-a]pyrimidine-3-carboxamide, 2-methyl-N-[[4-(2-methylpropoxy)phenyl]methyl].

CAS registry No. 1626915-96-5, STN entry date: Sep. 26, 2014, chemical name: Pyrazolo[1,5-a]pyrimidine-3-carboxamide, N-[1-[3-methoxy-4-(pentyloxy)phenyl]ethyl]-2-methyl.

CAS registry No. 1713613-74-1, STN entry date: May 27, 2015, chemical name: Pyrazolo[1,5-a]pyrimidine-3-carboxamide, N-[1-(hydroxymethyl)cyclopropyl]-5,7-dimethyl.

CAS registry No. 1775586-63-4, STN entry date: Jun. 8, 2015, chemical name: Pyrazolo[1,5-a]pyrimidine-3-carboxamide, N-[1-(hydroxymethyl)cyclobutyl]-5,7-dimethyl.

CAS registry No. 422537-28-8, STN entry date: May 29, 2002, chemical name: Pyrazolo[1,5-a]pyrimidine-3-carboxamide, 5,7-dimethyl-N-(4-phenoxyphenyl).

CAS registry No. 1050831-16-7, STN entry date: Sep. 21, 2008, chemical name: Pyrazolo[1,5-a]pyrimidine-3-carboxamide, 5,7-dimethyl-N-(1,2,3,4-tetrahydro-1-naphthalenyl).

CAS registry No. 1147832-58-3, STN entry date: May 20, 2009, chemical name: Pyrazolo[1,5-a]pyrimidine-3-carboxamide,N-[3-chloro-4-(2-methylpropoxy)phenyl].

CAS registry No. 1280061-59-7, STN entry date: Apr. 14, 2011, chemical name: Pyrazolo[1,5-a]pyrimidine-3-carboxamide, N-(2-butoxy-5-methoxyphenyl)-2,5,7-trimethyl.

CAS registry No. 1541365-83-6, STN entry date: Feb. 11, 2014, chemical name:Cyclobutanecarboxylic acid, 1-[[(5,7-dimethylpyrazolo[1,5-a]pyrimidin-3-yl)carbonyl]amino].

(56) References Cited

OTHER PUBLICATIONS

Patnaik et al., "Discovery, Structure-Activity Relationship,and Biological Evaluation of Non-inhibitory Small Molecule Chaperones of Glucocerebrosidase," Journal of Medicinal Chemistry, 55(12) 5734-5748 (2012).
Database Registry [Online]Chemical Abstracts Service, Columbus, Ohio, US; Sep. 18, 2012 (Sep. 18, 2012), XP002794417, Database accession No. 1394732-89-8 Compounds with the Registry Nos. 1394732-89-8, 1394738-37-4, 1394760-10-1, 1394789-28-6 and 1394793-42-0.
Database Registry [Online] Chemical Abstracts Service, Columbus, Ohio, US; May 14, 2013 (May 14, 2013), XP002794418, Database accession No. 1423757-47-4 Compounds with the Registry Nos. 1423757-47-4 and 1423807-67-3.
Database Registry [Online] Chemical Abstracts Service, Columbus, Ohio, US; Jun. 9, 2013 (Jun. 9, 2013), XP002794419, Database accession No. 1436029-77-4 Compounds with the Registry Nos. 1436029-77-4, 1436085-73-2, 1436108-94-9, 1436139-15-9 and 1436367-43-9.
Database Registry [Online] Chemical Abstracts Service, Columbus, Ohio, US; Sep. 29, 2015 (Sep. 29, 2015), XP002794420, Database accession No. 1808330-01-9 Compounds with the Registry Nos. 1808330-01-9, 1808808-91-4 and 1808880-93-4.
Database Registry [Online] Chemical Abstracts Service, Columbus, Ohio, US; Jul. 16, 2013 (Jul. 16, 2013), XP002794421, Database accession No. 1444105-29-6 Compound with the Registry No. 1444105-29-6.
Moraski Garrett C et al: "Scaffold-switching: An exploration of 5,6-fused bicyclic heteroaromatics systems to afford antituberculosis activity akin to the imidazo[I,2-a]pyridine-3-carboxylates", Bioorganic & Medicinal Chemistry Letters, Pergamon, Amsterdam, NL, vol. 24, No. 15, May 28, 2014 (May 28, 2014), pp. 3493-3498, XP028864111.
Database Registry [Online] Chemical Abstracts Service, Columbus, Ohio, US; Feb. 9, 2014 (Feb. 9, 2014), XP002794580, Database accession No. 1539876-08-8 compound with the Registry No. 1539876-08-8.
Database Registry [Online] Chemical Abstracts Service, Columbus, Ohio, US; Feb. 7, 2014 (Feb. 7, 2014), XP002794581, Database accession No. 1539191-30-4 compound with the Registry No. 1539191-30-4.
Database Registry [Online] Chemical Abstracts Service, Columbus, Ohio, US; Feb. 6, 2014 (Feb. 6, 2014), XP002794582, Database accession No. 1537972-48-7 compound with the Registry No. 1537972-48-7.
Database Registry [Online] Chemical Abstracts Service, Columbus, Ohio, US; Jan. 24, 2014 (Jan. 24, 2014), XP002794583, Database accession No. 1529636-26-7 compound with the Registry No. 1529636-26-7.
Database Registry [Online] Chemical Abstracts Service, Columbus, Ohio, US; Jan. 16, 2014 (Jan. 16, 2014), XP002794584, Database accession No. 1521766-89-1 compounds with the Registry Nos. 1521766-89-1 and 1522335-76-7.
Database Registry [Online] Chemical Abstracts Service, Columbus, Ohio, US; Jan. 13, 2014 (Jan. 13, 2014), XP002794585, Database accession No. 1518103-84-8 compound with the Registry No. 1518103-84-8.
Database Registry [Online] Chemical Abstracts Service, Columbus, Ohio, US; Jan. 12, 2014 (Jan. 12, 2014), XP002794586, Database accession No. 1517327-54-6 compound with the Registry No. 1517327-54-6.
Database Registry [Online] Chemical Abstracts Service, Columbus, Ohio, US; Jan. 6, 2014 (Jan. 6, 2014), XP002794587, Database accession No. 1512267-66-1 compound with the Registry No. 1512267-66-1.
Database Registry [Online] Chemical Abstracts Service, Columbus, Ohio, US; Jan. 5, 2014 (Jan. 5, 2014), XP002794588, Database accession No. 1511391-62-0 compound with the Registry Nos. 1511391-62-0 and 1510939-79-3.
Database Registry [Online] Chemical Abstracts Service, Columbus, Ohio, US; Dec. 31, 2013 (Dec. 31, 2013), XP002794589, Database accession No. 1508094-23-2 compound with the Registry No. 1508094-23-2.
Database Registry [Online] Chemical Abstracts Service, Columbus, Ohio, US; Dec. 30, 2013 (Dec. 30, 2013), XP002794590, Database accession No. 1507166-09-7 compound with the Registry No. 1507166-09-7.
Database Registry [Online] Chemical Abstracts Service, Columbus, Ohio, US; Dec. 29, 2013 (Dec. 29, 2013), XP002794591, Database accession No. 1506311-11-0 compound with the Registry No. 1506311-11-0.
Database Registry [Online] Chemical Abstracts Service, Columbus, Ohio, US; Dec. 27, 2013 (Dec. 27, 2013), XP002794592, Database accession No. 1505014-97-0 compound with the Registry No. 1505014-97-0.
Database Registry [Online] Chemical Abstracts Service, Columbus, Ohio, US; Dec. 23, 2013 (Dec. 23, 2013), XP002794593, Database accession No. 1502022-92-5 compound with the Registry No. 1502022-92-5.
Database Registry [Online] Chemical Abstracts Service, Columbus, Ohio, US; Dec. 22, 2013 (Dec. 22, 2013), XP002794594, Database accession No. 1500341-69-4 compound with the registry No. 1500341-69-4.
Brogi Simone et al: 3D-QSAR using pharmacophore-based alignment and virtual screening for discovery of novel MCF-7 cell line inhibitors11 , Composites: Part A: Applied Science and Manufacturing,, vol. 67, Jul. 1, 2013 (Jul. 1, 2013), pp. 344-351, XP028710082.
"Symptoms of Gaucher Disease" retrieved from the Internet Apr. 17, 2017 from url: http://www.gaucherdisease.org/about-gaucher-disease/symptoms/.
Ahmetaj, S. et al. "Parallel synthesis of 7-heteroaryl-pyrazolo[1,5-a]pyrimidine-3-carboxamides" *Molecular Diversity* (2013) vol. 17, No. 4, pp. 731-743.
CAS Registry No. 1022459-94-4, STN entry date: May 25, 2008, chemical name: 5-(2-furanyl)-N-[(4-methylphenyl)methyl]-7-(trifluoromethyl)-pyrazolo[1,5-a]pyrimidine-3-carboxamide.
CAS Registry No. 1027839-50-4, STN entry date: Jun. 13, 2008, chemical name: 8-Quinazolinecarboxamide, N-ethyl-2-(2-propoxyphenyl).
CAS Registry No. 1090443-11-0, STN entry date: Dec. 26, 2008, chemical name: N-(dicyclopropylmethyl)-5,7-dimethyl-pyrazolo[1,5-a]pyrimidine-3-carboxamide.
CAS Registry No. 1099976-59-6, STN entry date: Feb. 3, 2009, chemical name: N-(1-cyclopropyl-4-piperidinyl)-5,7-dimethyl-pyrazolo[1,5-a]pyrimidine-3-carboxamide.
CAS Registry No. 1121583-22-9, STN entry date: Mar. 16, 2009, chemical name: pyrrolo[1,2-a]pyrimidine-8-carboxamide, 6-chloro-N-(3-methylphenyl).
CAS Registry No. 1121584-90-4, STN entry date: Mar. 16, 2009, chemical name: pyrrolo[1,2-a]pyrimidine-8-carboxamide, 6-chloro-N-[2-(1-piperidinyl)ethyl].
CAS Registry No. 1224940-28-6, STN entry date: May 24, 2010, chemical name: N-cyclohexyl-5-methoxy-pyrazolo[1,5-a]pyrimidine-3-carboxamide.
CAS Registry No. 1224940-60-6, STN entry date: May 24, 2010, chemical name: N-cyclohexyl-5-(ethylamino)-pyrazolo[1,5-a]pyrimidine-3-carboxamide.
CAS Registry No. 1260846-47-6, STN entry date: Jan. 27, 2011, chemical name: N-(1,1-dimethylethyl)-5-[(2R)-2-(3-fluorophenyl)-4-oxo-1-pyrrolidinyl]-pyrazolo[1,5-a]pyrimidine-3-carboxamide.
CAS Registry No. 1348484-20-7, STN entry date: Dec. 4, 2011, chemical name: Imidazo[1,2-a]pyridine-8-carboxamide, N-[(1-butyl-4-piperidinyl)methyl]-6-chloro-2-ethyl-5-(methylamino).
CAS Registry No. 1348704-16-4, STN entry date: Dec. 4, 2011, chemical name: Imidazo[1,2-a]pyridine-8-carboxamide, N-[(1-butyl-4-piperidinyl)methyl]-6-chloro-2-methyl-5-(methylamino).
CAS Registry No. 1825314-78-0, STN entry date: Dec. 8, 2015, chemical name: 4-Benzoxazolecarboxamide, 2-methyl-N-6-oxa-2-thiaspiro[4.5]dec-9-yl.

(56) References Cited

OTHER PUBLICATIONS

CAS Registry No. 696640-82-1, STN entry date: Jun. 21, 2004, chemical name: 7-(difluoromethyl)-5-(4-methoxyphenyl)-N-(tricyclo[3.3.1.1³,⁷]dec-1-ylmethyl)-pyrazolo[1,5-a]pyrimidine-3-carboxamide.
CAS Registry No. 765896-16-0, STN entry date: Oct. 20, 2004, chemical name: Imidazo[1,2-a]pyridine-8-carboxamide, 5-amino-2-ethyl-N-[[1-(3-methoxypropyl)-4-piperidinyl]methyl].
CAS Registry No. 895779-11-0, STN entry date: Jul. 25, 2006, chemical name: 5-(4-bromophenyl)-N-[(4-methoxyphenyl)methyl]-7-(trifluoromethyl)-pyrazolo[1,5-a]pyrimidine-3-carboxamide.
CAS Registry No. 1116067-90-3, STN entry date: Mar. 5, 2009, chemical name: N-[3-(hexahydro-IH-azepin-l-yl)propyl]-6-phenyl-1,2,4-Triazolo[4,3-b]pyridazine-3-carboxamide.
Huppatz, J. L. "Systemic Fungicides. The Synthesis of Pyrazolo[1,5-a]pyrimidine Analogues of Carboxin," *Australian J. Chem.* (1985) vol. 38, No. 1, pp. 221-230. (Abstract Only).
Liu, K. C. C. et al. "Quinazolines with intra-molecular hydrogen bonding scaffold (iMHBS) as P13K/mTOR dual inhibitors," *Bioorg. Med. Chem. Lett.* (2011) vol. 21, Issue 4, pp. 1270-1274.
Marugan, J. J. et al. "Evaluation of Quinazoline Analogues as Glucocerebrosidase Inhibitors with Chaperone Activity," *J. Med. Chem.* (2011) vol. 54, pp. 1033-1058.
Mata, I. F. et al. "Glucocerebrosidase Gene Mutations: A Risk Factor for Lewy Body Disorders," *Arch. Neurol.* (2008) vol. 65, No. 3, pp. 379-382.
Ortega, R. A. et al. "Glucocerebrosidase enzyme activity in GBA mutation Parkinson's disease," *J. Clin. Neurosci.* (2016) vol. 28, p. 185-186. (Abstract Only—Retrieved from the internet on Apr. 17, 2017 from url: https://www.ncbi.nlm.nih.gov/pubmed/26857292).
STN Chemical Structure Search Results (dated Aug. 24, 2015). (26 pages).
STN Chemical Structure Search Results (dated Aug. 6, 2014). (61 pages).
STN Chemical Structure Search Results (dated Jul. 1, 2014). (44 pages).
STN Chemical Structure Search Results (dated Jul. 1, 2014). (8 pages).
STN Chemical Structure Search Results (dated Jul. 8, 2014). (108 pages).
STN Chemical Structure Search Results (dated Jul. 8, 2014). (38 pages).
STN Chemical Structure Search Results (dated Jun. 10, 2015). (26 pages).
STN Chemical Structure Search Results Part I (dated Aug. 18, 2016). (29 pages).
STN Chemical Structure Search Results Part I (dated Mar. 13, 2016). (39 pages).
STN Chemical Structure Search Results Part I (dated Mar. 14, 2016). (108 pages).
STN Chemical Structure Search Results Part II (dated Aug. 18, 2016). (87 pages).
STN Chemical Structure Search Results Part II (dated Mar. 13, 2016). (115 pages).
STN Chemical Structure Search Results Part II (dated Mar. 14, 2016). (28 pages).
Wang, X. et al. "Discovery of novel pyrazolo[1,5-a]pyrimidines as potent pan-Pim inhibitors by structure- and property-based drug design," *Bioorg. Med. Chem. Lett.* (2013) vol. 23, pp. 3149-3153.
International Search Report and Writen Opinion for PCT/US2017/26284 dated Jul. 3, 2017 (16 pages).
Graeme R. Robb et al. "Design of pyrazolo-pyrimidines as 11β-HSD1 inhibitors through optimisation of molecular electrostatic potential" MedChemComm, vol. 6, No. 5, 2015, pp. 926-934, XP0555534025.
International Search Report and Written Opinion for PCT/US2017/031189 dated Jul. 19, 2017 (25 pages).
International Search Report and Written Opinion for PCT/US2017/026280 dated Jul. 3, 2017 (20 pages).
CAS Abstract and Indexed Compounds, WO2013/059587 (2013).
Dalinger Igor L., Journal of Combinatorial Chemistry, 2005, 7(2), 236-245 (10 pages).

\* cited by examiner

PYRROLO[1,2-A]PYRIMIDINYL CARBOXAMIDE COMPOUNDS AND THEIR USE IN THE TREATMENT OF MEDICAL DISORDERS

CROSS-REFERENCE TO RELATED APPLICATIONS

This application is the national stage of International (PCT) Patent Application Serial No. PCT/US2017/026284, filed Apr. 6, 2017, which claims the benefit of and priority to U.S. Provisional Patent Application Ser. No. 62/318,937, filed Apr. 6, 2016, the contents of each of which are hereby incorporated by reference.

FIELD OF THE INVENTION

The invention provides substituted pyrrolo[1,2-a]pyrimidinyl carboxamide and related organic compounds, compositions containing such compounds, medical kits, and methods for using such compounds and compositions to treat medical disorders in a patient.

BACKGROUND

Gaucher disease is a genetic disorder associated with a deficiency of the lysosomal enzyme, glucocerebrosidase. Gaucher disease has been reported to have an incidence of approximately 1 in 20,000 live births in the general population, and it is a common lysosomal storage disorder. Current treatments for patients suffering from this disease include enzyme replacement therapy, which tends to be expensive, analgesics for bone pain relief, and medical procedures such as blood and platelet transfusions, splenectomy, and joint replacement for patients who experience bone erosion. However, new treatment options are needed having improved efficacy across a broader range of patients and/or reduced adverse side effects.

Mutations in the gene encoding glucocerebrosidase are also a risk factor for Parkinson's disease and diffuse Lewy Body Disease. Parkinson's disease is a degenerative disorder of the central nervous system associated with death of dopamine-containing cells in a region of the midbrain. Parkinson's disease afflicts millions of people, and the incidence of the disease increases with age. Treatment of Parkinson's disease frequently involves use of levodopa and dopamine agonists. However, these drugs can produce significant side effects such as hallucinations, insomnia, nausea, and constipation. Further, patients often develop tolerance to these drugs such that the drugs become ineffective at treating the symptoms of the disease, while sometimes also producing a movement disorder side effect called dyskinesia. Diffuse Lewy Body disease is a dementia that is sometimes confused with Alzheimer's disease.

Accordingly, the need exists for new therapeutic agents for treating Gaucher disease, Parkinson's disease, and related medical disorders. The present invention addresses this need and provides other related advantages.

SUMMARY

The invention provides substituted pyrrolo[1,2-a]pyrimidinyl carboxamide and related organic compounds, compositions containing such compounds, medical kits, and methods for using such compounds and compositions to treat medical disorders, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma, in a patient. Various aspects and embodiments of the invention are described in further detail below.

Accordingly, one aspect of the invention provides a family of substituted pyrrolo[1,2-a]pyrimidinyl carboxamide and related organic compounds embraced by Formula I that may be used in the methods, compositions, and kits described herein, wherein Formula I is represented by:

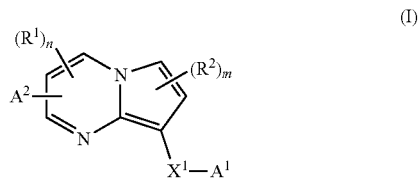

(I)

or a pharmaceutically acceptable salt thereof, wherein the variables are as defined in the detailed description. Further description of additional collections of substituted pyrrolo[1,2-a]pyrimidinyl carboxamide and related compounds embraced by Formula I are described in the detailed description.

Another aspect of the invention provides a family of substituted pyrrolo[1,2-a]pyrimidinyl carboxamide and related organic compounds embraced by Formula II that may be used in the methods, compositions, and kits described herein, wherein Formula II is represented by:

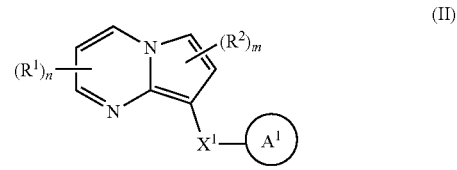

(II)

or a pharmaceutically acceptable salt thereof, wherein the variables are as defined in the detailed description. Further description of additional collections of substituted pyrrolo[1,2-a]pyrimidinyl carboxamide and related compounds embraced by Formula II are described in the detailed description Another aspect of the invention provides a family of substituted pyrrolo[1,2-a]pyrimidinyl carboxamide and related organic compounds embraced by Formula III that may be used in the methods, compositions, and kits described herein, wherein Formula III is represented by:

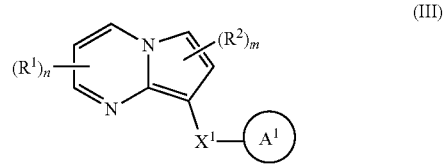

(III)

or a pharmaceutically acceptable salt thereof, wherein the variables are as defined in the detailed description. Further description of additional collections of substituted pyrrolo

[1,2-a]pyrimidinyl carboxamide and related compounds embraced by Formula III are described in the detailed description.

Another aspect of the invention provides a family of substituted pyrrolo[1,2-a]pyrimidinyl carboxamide and related organic compounds embraced by Formula IV that may be used in the methods, compositions, and kits described herein, wherein Formula IV is represented by:

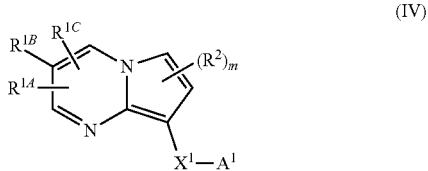

(IV)

or a pharmaceutically acceptable salt thereof, wherein the variables are as defined in the detailed description. Further description of additional collections of substituted pyrrolo[1,2-a]pyrimidinyl carboxamide and related compounds embraced by Formula IV are described in the detailed description.

Another aspect of the invention provides a family of substituted pyrrolo[1,2-a]pyrimidinyl carboxamide and related organic compounds embraced by Formula V that may be used in the methods, compositions, and kits described herein, wherein Formula V is represented by:

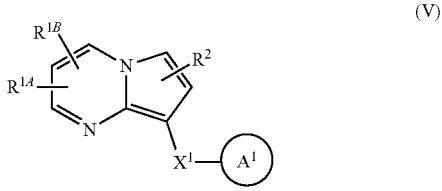

(V)

or a pharmaceutically acceptable salt thereof, wherein the variables are as defined in the detailed description. Further description of additional collections of substituted pyrrolo[1,2-a]pyrimidinyl carboxamide and related compounds embraced by Formula V are described in the detailed description.

Another aspect of the invention provides a family of substituted pyrrolo[1,2-a]pyrimidinyl carboxamide and related organic compounds embraced by Formula VI that may be used in the methods, compositions, and kits described herein, wherein Formula VI is represented by:

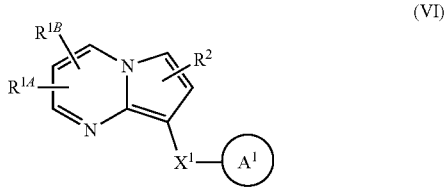

(VI)

or a pharmaceutically acceptable salt thereof, wherein the variables are as defined in the detailed description. Further description of additional collections of substituted pyrrolo[1,2-a]pyrimidinyl carboxamide and related compounds embraced by Formula VI are described in the detailed description.

Another aspect of the invention provides a pharmaceutical composition, comprising a pharmaceutically acceptable carrier and a substituted pyrrolo[1,2-a]pyrimidinyl carboxamide or related organic compound described herein, such as a compound of Formula I, II, III, IV, V, or VI.

Another aspect of the invention provides a method of treating a disorder, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma, in a patient. The method comprises administering to a patient in need thereof a therapeutically effective amount of a substituted pyrrolo[1,2-a]pyrimidinyl carboxamide or related organic compound described herein, such as a compound of Formula I, II, III, IV, V, or VI to treat the disorder, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, or multiple myeloma.

DETAILED DESCRIPTION

The invention provides substituted pyrrolo[1,2-a]pyrimidinyl carboxamide and related organic compounds, compositions containing such compounds, medical kits, and methods for using such compounds and compositions to treat medical disorders in a patient. The practice of the present invention employs, unless otherwise indicated, conventional techniques of organic chemistry, pharmacology, cell biology, and biochemistry. Such techniques are explained in the literature, such as in "Comprehensive Organic Synthesis" (B. M. Trost & I. Fleming, eds., 1991-1992); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. An exemplary alkylene group is —$CH_2CH_2$—.

The term "haloalkyl" refers to an alkyl group that is substituted with at least one halogen. For example, —CHF, —CF$_3$, —CH$_2$CF$_3$, —CF$_2$CF$_3$, and the like.

The term "hydroxyalkyl" refers to an alkyl group that is substituted with at least one hydroxyl group. For example, exemplary hydroxyalkyl groups include —CH$_2$OH, —C(H)(OH)CH$_3$, and the like. In certain embodiments, the hydroxyalkyl is an alkyl group that is substituted with just one hydroxyl group.

The term "cyanoalkyl" refers to an alkyl group that is substituted with one cyano group.

The term "heteroalkyl" as used herein refers to an "alkyl" group in which at least one carbon atom has been replaced with a heteroatom (e.g., an O, N, or S atom). The heteroalkyl may be, for example, an O—C$_1$-C$_{10}$alkyl group, an —C$_1$-C$_6$alkylene-O—C$_1$-C$_6$alkyl group, or a C$_1$-C$_6$ alkylene-OH group. In certain embodiments, the "heteroalkyl" may be 2-8 membered heteroalkyl, indicating that the heteroalkyl contains from 2 to 8 atoms selected from the group consisting of carbon, oxygen, nitrogen, and sulfur. In yet other embodiments, the heteroalkyl may be a 2-6 membered, 4-8 membered, or a 5-8 membered heteroalkyl group (which may contain for example 1 or 2 heteroatoms selected from the group oxygen and nitrogen). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C$_2$-C$_{12}$alkenyl, C$_2$-C$_{10}$alkenyl, and C$_2$-C$_6$alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C$_2$-C$_{12}$alkynyl, C$_2$-C$_{10}$alkynyl, and C$_2$-C$_6$alkynyl, respectively. Exemplary alkynyl groups include ethynyl, prop-1-yn-1-yl, and but-1-yn-1-yl.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C$_{4-8}$cycloalkyl," derived from a cycloalkane. Exemplary cycloalkyl groups include, but are not limited to, cyclohexanes, cyclopentanes, cyclobutanes and cyclopropanes. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group. An exemplary cycloalkylene group is

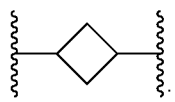

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "cycloalkenyl" as used herein refers to a monovalent unsaturated cyclic, bicyclic, or bridged cyclic (e.g., adamantyl) hydrocarbon group of 3-12, 3-8, 4-8, or 4-6 carbons containing one carbon-carbon double bond, referred to herein, e.g., as "C$_{4-8}$cycloalkenyl," derived from a cycloalkane. Exemplary cycloalkenyl groups include, but are not limited to, cyclohexenes, cyclopentenes, and cyclobutenes. Unless specified otherwise, cycloalkenyl groups are optionally substituted at one or more ring positions with, for example, alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkenyl group is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The term "aralkyl" refers to an alkyl group substituted with an aryl group.

The term "bicyclic carbocyclyl that is partially unsaturated" refers to a bicyclic carbocyclic group containing at least one double bond between ring atoms and at least one ring in the bicyclic carbocyclic group is not aromatic. Representative examples of a bicyclic carbocyclyl that is partially unsaturated include, for example:

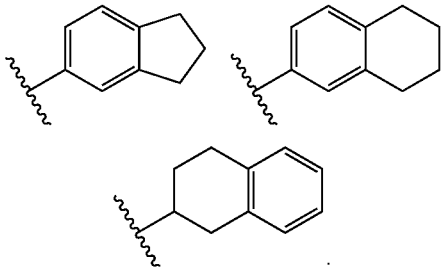

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$-$C_7$heterocyclyl is aziridinyl. Heterocycles may be, for example, mono-, bi-, or other multi-cyclic ring systems including a spirocyclic ring system where at least one ring contains a ring heteroatom. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isooxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, oxo, phosphate, phosphonato, phosphinato, sulfate, sulfide, sulfonamido, sulfonyl and thiocarbonyl. In certain embodiments, the heterocyclyl group is not substituted, i.e., it is unsubstituted.

The term "bicyclic heterocyclyl" refers to a heterocyclyl group that contains two rings that are fused together. Representative examples of a bicyclic heterocyclyl include, for example:

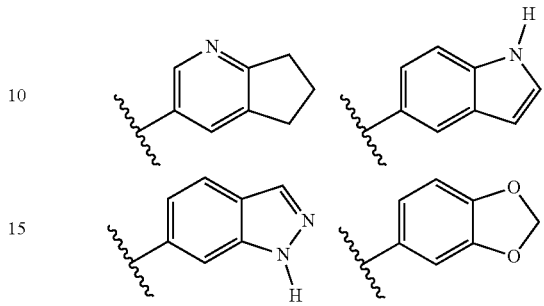

In certain embodiments, the bicyclic heterocyclyl is an carbocyclic ring fused to partially unsaturated heterocyclic ring, that together form a bicyclic ring structure having 8-10 ring atoms (e.g., where there are 1, 2, 3, or 4 heteroatoms selected from the group consisting of nitrogen, oxygen, and sulfur).

The term "heterocycloalkyl" is art-recognized and refers to a saturated heterocyclyl group as defined above. In certain embodiments, the "heterocycloalkyl" is a 3- to 10-membered ring structures, alternatively a 3- to 7-membered rings, whose ring structures include one to four heteroatoms, such as nitrogen, oxygen, and sulfur.

The term "heterocycloalkylene" refers to a diradical of a heterocycloalkyl group. An exemplary heterocycloalkylene group is

The heterocycloalkylene may contain, for example, 3-6 ring atom (i.e., a 3-6 membered heterocycloalkylene). In certain embodiments, the heterocycloalkylene is a 3-6 membered heterocycloalkylene containing 1, 2, or 3 three heteroatoms selected from the group consisting of oxygen, nitrogen, and sulfur.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted. In certain embodiments, the heteroaryl group is a 5- to 10-membered ring structure, alternatively a 5- to 6-membered ring structure, whose ring structure includes 1, 2, 3, or 4 heteroatoms, such as nitrogen, oxygen, and sulfur.

The term "heteroaralkyl" refers to an alkyl group substituted with a heteroaryl group.

The terms "amine" and "amino" are art-recognized and refer to both unsubstituted and substituted amines, e.g., a moiety represented by the general formula —N($R^{50}$)($R^{51}$), wherein $R^{50}$ and $R^{51}$ each independently represent hydrogen, alkyl, cycloalkyl, heterocyclyl, alkenyl, aryl, aralkyl, or —$(CH_2)_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—$R_{61}$, where m and $R_{61}$ are described above.

The term "carbamate" as used herein refers to a radical of the form —$R_g$OC(O)N($R_h$)—, —$R_g$OC(O)N($R_h$)$R_i$-, or —OC(O)N$R_h R_i$, wherein $R_g$, $R_h$ and $R_i$ are each independently alkoxy, aryloxy, alkyl, alkenyl, alkynyl, amide, amino, aryl, arylalkyl, carboxy, cyano, cycloalkyl, ester, ether, formyl, halogen, haloalkyl, heteroaryl, heterocyclyl, hydroxyl, ketone, nitro, sulfide, sulfonyl, or sulfonamide. Exemplary carbamates include arylcarbamates and heteroaryl carbamates, e.g., wherein at least one of $R_g$, $R_h$ and $R_i$ are independently aryl or heteroaryl, such as phenyl and pyridinyl.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —$R_a$C(O)N($R_b$)—, —$R_a$C(O)N($R_b$)$R_c$—, —C(O)N$R_b R_c$, or —C(O)NH$_2$, wherein $R_a$, $R_b$ and $R_c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring.

The term "amidino" as used herein refers to a radical of the form —C(=NR)NR'R" where R, R', and R" are each independently alkyl, alkenyl, alkynyl, amide, aryl, arylalkyl, cyano, cycloalkyl, haloalkyl, heteroaryl, heterocyclyl, hydroxyl, ketone, or nitro.

The term "alkanoyl" as used herein refers to a radical —O—CO-alkyl.

The term "oxo" is art-recognized and refers to a "=O" substituent. For example, a cyclopentane substituted with an oxo group is cyclopentanone.

The term "sulfonamide" or "sulfonamido" as used herein refers to a radical having the structure —N($R_r$)—S(O)$_2$—$R_s$— or —S(O)$_2$—N($R_r$)$R_s$, where $R_r$, and $R_s$ can be, for example, hydrogen, alkyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl), etc.

The term "sulfonyl" as used herein refers to a radical having the structure $R_u$SO$_2$—, where $R_u$ can be alkyl, aryl, cycloalkyl, and heterocyclyl, e.g., alkylsulfonyl. The term "alkylsulfonyl" as used herein refers to an alkyl group attached to a sulfonyl group.

The symbol "⌇" indicates a point of attachment.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Further, enantiomers can be separated using supercritical fluid chromatographic (SFC) techniques described in the literature. Still further, stereoisomers can be obtained from stereomerically-pure intermediates, reagents, and catalysts by well-known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in, e.g., the Examples herein by substituting an isotopically labeled reagent for a non-isotopically labeled reagent.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases.

Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Abbreviations as used herein include O-(7-azabenzotriazol-1-yl)-N,N,N',N'-tetramethyluronium hexafluorophosphate (HATU); diisopropylethylamine (DIPEA); dimethylformamide (DMF); methylene chloride (DCM); tert-butoxycarbonyl (Boc); tetrahydrofuran (THF); trifluoroacetic acid (TFA); N-methylmorpholine (NMM); triethylamine (TEA); Boc anhydride ((Boc)$_2$O); dimethylsulfoxide (DMSO); diisopropylethylamine (DIEA); N,N-Dimethylpyridin-4-amine (DMAP); flash column chromatography (FCC); and supercritical fluid chromatography (SFC).

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Substituted Pyrrolo[1,2-a]Pyrimidinyl Carboxamide and Related Organic Compounds One aspect of the invention provides substituted pyrrolo[1,2-a]pyrimidinyl carboxamide and related organic compounds. The substituted pyrrolo[1,2-a]pyrimidinyl carboxamide and related organic compounds are contemplated to be useful in the methods, compositions, and kits described herein. In certain embodiments, the substituted pyrrolo[1,2-a]pyrimidinyl carboxamide or related organic compound is a compound embraced by Formula I:

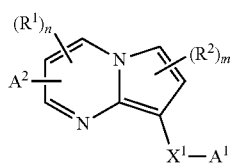

or a pharmaceutically acceptable salt thereof, wherein:

$R^1$ and $R^2$ each represent independently for each occurrence hydrogen, $C_{1-4}$ alkyl, $C_{1-4}$ haloalkyl, $C_{1-4}$ hydroxyalkyl, $C_{1-4}$ cyanoalkyl, $C_{1-4}$ alkoxyl, —($C_{1-4}$ alkylene)-(2-6 membered heteroalkyl), cyclopropyl, cyano, halogen, hydroxyl, or —N($R^4$)$_2$;

$R^3$ represents independently for each occurrence hydrogen, $C_{1-6}$ alkyl, or $C_{3-6}$ cycloalkyl;

$R^4$ represents independently for each occurrence hydrogen, $C_{1-4}$ alkyl, cyclopropyl, or —C(O)$R^3$;

$R^5$ represents independently for each occurrence $C_{1-4}$ alkyl or $C_{3-6}$ cycloalkyl;

$R^6$ represents independently for each occurrence $C_{1-4}$ alkyl, $C_{1-4}$ haloalkyl, $C_{1-4}$ alkoxyl, cyano, halogen, hydroxyl, or —N($R^4$)$_2$;

$X^1$ is a carbonyl-containing linker selected from —C(O)N(H)-ψ, —C(O)N(H)($C_{1-6}$ alkylene optionally substituted with $C_{1-4}$ alkoxyl or $C_{3-6}$ cycloalkyl)-ψ, —C(O)N(H)($C_{1-6}$ haloalkylene)-ψ, —C(O)N(H)($C_{3-6}$ cycloalkylene)-ψ, —C(O)N(H)(3-6 membered heterocycloalkylene)-ψ, —C(O)-(3-6 membered heterocycloalkylene containing at least one ring —N(H)— group)-ψ, —C(O)N(H)C(O)-ψ, and —C(O)N(H)C(O)($C_{1-6}$ alkylene)-ψ;

where ψ is a bond to $A^1$;

$A^1$ is one of the following:
a cyclic group selected from a 3-14 membered saturated carbocyclyl, a 5-14 membered partially unsaturated carbocyclyl, a 3-16 membered heterocyclyl, or phenyl; each of which is substituted by 0, 1, or 2 occurrences of $Y^1$ and 0, 1, 2, or 3 occurrences of $Y^2$; or
$C_{1-8}$ alkyl or $C_{2-6}$ alkynyl;

$A^2$ is one of the following:
a cyclic group selected from a 5-12 membered heterocyclyl, 5-10 membered cycloalkyl, or phenyl; each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, —N($R^4$)$_2$, —C(O)N($R^4$)$_2$, and heteroaryl;
—N($R^4$)(3-10 membered heterocycloalkyl or $C_{3-10}$cycloalkyl, each optionally substituted by 1, 2, or 3 $R^6$ groups) or —O-(3-10 membered heterocycloalkyl or $C_{3-10}$ cycloalkyl, each optionally substituted by 1, 2, or 3 $R^6$ groups); or —C(O)N($R^4$)(aryl or heteroaryl);

$Y^1$ represents, independently for each occurrence, one of the following:
2-8 membered heteroalkyl optionally substituted by a 6-10 membered aryl, a 3-10 membered heterocyclyl, or $C_{3-6}$ halocycloalkyl;
3-10 membered heterocyclyl, 6-10 membered aryl, $C_{3-7}$ cycloalkyl, —O—$C_{3-6}$ cycloalkyl, —O-(3-6 membered heterocyclyl), —O-(6-10 membered aryl), or —O—($C_{2-6}$ alkynyl); or
$C_{2-6}$ alkynyl, —C≡C—($C_{1-6}$ alkylene)-O$R^4$, —C≡C—($C_{1-6}$ alkylene)-N($R^3$)$_2$, —($C_{2-4}$ alkynylene)-(5-6 membered heteroaryl), or $C_{2-6}$ alkenyl;

$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, azido, —N($R^3$)$_2$, —($C_{1-6}$ alkylene)-(5-6 membered heterocyclyl), —($C_{1-6}$ alkylene)-CO$_2R^3$, —CO$_2R^3$, —C(O)$R^5$, —S(O)$_2R^5$, —C(O)N($R^5$)$_2$, —C(O)N($R^3$)$_2$, or $C_{1-6}$ haloalkyl-substituted $C_{3-6}$ cycloalkyl;

m is 1 or 2; and n is 1, 2, or 3.

Definitions of the variables in Formula I above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $X^1$ is —C(O)N(H)-ψ, $R^1$ and $R^2$ each represent independently for each occurrence hydrogen or $C_{1-4}$ alkyl, and $A^2$ is a 5-12 membered heterocyclyl.

Accordingly, in certain embodiments, $X^1$ is —C(O)N(H)-ψ. In certain embodiments, $X^1$ is —C(O)N(H)($C_{1-6}$ alkylene)-ψ. In certain embodiments, $X^1$ is —C(O)N(H)(C(CH$_3$)$_2$)-ψ or —C(O)N(H)(C(H)(CH$_3$))-ψ. In certain embodiments, $X^1$ is —C(O)N(H)($C_{1-6}$ alkylene substituted with $C_{1-4}$ alkoxyl)-ψ. In certain embodiments, $X^1$ is —C(O)N(H)($C_{1-6}$ alkylene substituted with $C_{3-6}$ cycloalkyl)-ψ. In certain embodiments, $X^1$ is —C(O)N(H)($C_{1-6}$ haloalkylene)-ψ. In certain embodiments, $X^1$ is —C(O)N(H)C(H)(CF$_3$)-ψ. In certain embodiments, $X^1$ is —C(O)N(H)($C_{3-6}$ cycloalkylene)-ψ. In certain embodiments, $X^1$ is —C(O)N(H)(3-6 membered heterocycloalkylene)-ψ.

In certain embodiments, $A^2$ is a 5-12 membered heterocyclyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N($R^4$)$_2$. In certain embodiments, $A^2$ is a 5-6 membered heteroaryl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N($R^4$)$_2$. In certain embodiments, $A^2$ is a 5-6 membered heteroaryl selected from the group consisting of pyridinyl, pyrimidinyl, pyrazinyl, furanyl, pyrrolyl, thiophenyl, imidazolyl, oxazolyl, isoxazolyl, isothiazolyl, and thiazolyl, each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$. In certain embodiments, A$^2$ is a 5-6 membered heteroaryl selected from the group consisting of pyridinyl, pyrimidinyl, pyrazinyl, furanyl, pyrrolyl, thiophenyl, oxazolyl, isoxazolyl, and thiazolyl, each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$. In certain embodiments, A$^2$ is pyridinyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$. In certain embodiments, A$^2$ is 3-pyridinyl optionally substituted by 1 or 2 substituents independently selected from the group consisting of $C_{1-4}$ alkyl, $C_{1-4}$ haloalkyl, $C_{1-4}$ alkoxyl, $C_{3-5}$ cycloalkyl, cyano, and halogen.

In certain embodiments, A$^2$ is a 5-6 membered heterocycloalkyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$. In certain embodiments, A$^2$ is a 5-6 membered heterocycloalkyl selected from the group consisting of morpholinyl, piperidinyl, pyrrolidinyl, tetrahydropyranyl, and tetrahydrofuranyl, each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$.

In certain embodiments, A$^2$ is a 5-10 membered cycloalkyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$. In certain embodiments, A$^2$ is a 5-6 membered cycloalkyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$.

In certain embodiments, A$^2$ is phenyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N(R$^4$)$_2$.

In certain embodiments, A$^2$ is —N(R$^4$)(3-10 membered heterocycloalkyl or $C_{3-10}$ cycloalkyl, each optionally substituted by 1, 2, or 3 R$^6$ groups) or —O-(3-10 membered heterocycloalkyl or $C_{3-10}$ cycloalkyl, each optionally substituted by 1, 2, or 3 R$^6$ groups). In certain embodiments, A$^2$ is —N(R$^4$)(tetrahydropyranyl, morpholinyl, or piperidinyl, each optionally substituted by 1, 2, or 3 R$^6$), —N(R$^4$)(C$_{4-6}$cycloalkyl optionally substituted by 1, 2, or 3 R$^6$), —O-(tetrahydropyranyl, morpholinyl, or piperidinyl, each optionally substituted by 1, 2, or 3 R$^6$), or —O—(C$_{4-6}$ cycloalkyl optionally substituted by 1, 2, or 3 R$^6$).

In certain embodiments, A$^2$ is located at the 2-position of the pyrrolo[1,2-a]pyrimidinyl. In certain embodiments, n is 1. In certain embodiments, A$^2$ is located at the 2-position of the pyrrolo[1,2-a]pyrimidinyl, n is 1, and the R$^1$ group is located at the 4-position of the pyrrolo[1,2-a]pyrimidinyl.

In certain embodiments, A$^2$ is located at the 4-position of the pyrrolo[1,2-a]pyrimidinyl. In certain embodiments, n is 1. In certain embodiments, A$^2$ is located at the 4-position of the pyrrolo[1,2-a]pyrimidinyl, n is 1, and R$^1$ group is located at the 2-position of the pyrrolo[1,2-a]pyrimidinyl.

In certain embodiments, R$^1$ represents independently for each occurrence $C_{1-4}$ alkyl, $C_{1-4}$ haloalkyl, —(C$_{1-4}$ alkylene)-(2-6 membered heteroalkyl), cyclopropyl, halogen, or —N(R$^4$)$_2$. In certain embodiments, R$^1$ represents independently for each occurrence $C_{1-4}$ alkyl, $C_{1-4}$ haloalkyl, $C_{1-4}$ alkoxyl, cyclopropyl, cyano, chloro, or fluoro. In certain embodiments, R$^1$ is methyl.

In certain embodiments, R$^2$ is hydrogen. In certain embodiments, and R$^2$ each represent independently for each occurrence hydrogen or $C_{1-4}$ alkyl.

In certain embodiments, R$^3$ and R$^4$ each represent independently for each occurrence hydrogen, methyl, or ethyl.

In certain embodiments, A$^1$ is a 3-14 membered saturated carbocyclyl substituted by 0, 1, or 2 occurrences of Y$^1$ and 0, 1, 2, or 3 occurrences of Y$^2$. In certain embodiments, A$^1$ is $C_{3-7}$ cycloalkyl substituted once by Y$^1$ and 0-1 occurrences of Y$^2$. In certain embodiments, A$^1$ is a 5-14 membered partially unsaturated carbocyclyl substituted by 0, 1, or 2 occurrences of Y$^1$ and 0, 1, 2, or 3 occurrences of Y$^2$. In certain embodiments, A$^1$ is a 8-12 membered bicyclic carbocyclyl that is partially unsaturated or a 8-12 membered bicyclic heterocyclyl, each of which is substituted by 0 or 1 occurrence of Y$^1$ and 0, 1, or 2 occurrences of Y$^2$. In certain embodiments, A$^1$ is phenyl substituted once by Y$^1$ and 0-1 occurrences of Y$^2$.

In certain embodiments, A$^1$ is a 5-6 membered heteroaryl substituted once by Y$^1$ and 0-1 occurrences of Y$^2$. In certain embodiments, A$^1$ is pyridinyl substituted once by Y$^1$ and 0-1 occurrences of Y$^2$.

In certain embodiments, A$^1$ is $C_{3-7}$ cycloalkyl substituted by $C_{1-6}$ alkoxyl. In certain embodiments, A$^1$ is cyclohexyl substituted by $C_{1-6}$ alkoxyl. In certain embodiments, A$^1$ is $C_{3-7}$ cycloalkyl. In certain embodiments, A$^1$ is $C_{3-7}$ cycloalkyl that is not substituted. In certain embodiments, A$^1$ is $C_{7-10}$ cycloalkyl that is spirocyclic and not substituted. In certain embodiments, A$^1$ is cyclopropyl.

In certain embodiments, A$^1$ is phenyl substituted by $C_2$ alkynyl.

In certain embodiments, A$^1$ is an 8-12 membered bicyclic carbocyclyl that is partially unsaturated or an 8-12 membered bicyclic heterocyclyl, each of which is substituted by 0 or 1 occurrence of Y$^2$ selected from the group consisting of $C_{1-6}$ alkyl, $C_{3-6}$ cycloalkyl, halogen, $C_{1-6}$haloalkyl, hydroxyl, and $C_{1-6}$ alkoxyl. In certain embodiments, A$^1$ is

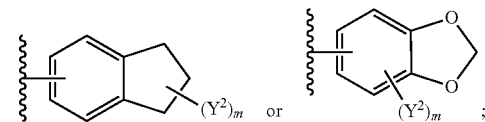

wherein m is 0, 1, or 2; and Y$^2$ represents independently for each occurrence $C_{1-6}$ alkyl, $C_{3-6}$ cycloalkyl, halogen, $C_{1-6}$haloalkyl, hydroxyl, or $C_{1-6}$ alkoxyl.

In certain embodiments, any occurrence of Y$^2$ is independently $C_{1-6}$ alkyl, $C_{3-6}$ cycloalkyl, halogen, $C_{1-6}$haloalkyl, or hydroxyl. In certain embodiments, any occurrence of Y$^2$ is independently $C_{1-3}$ alkyl. In certain embodiments, Y$^2$ is $C_{1-6}$haloalkyl-substituted $C_{3-6}$ cycloalkyl.

In certain embodiments, Y$^1$ is a 2-8 membered heteroalkyl optionally substituted by a 6-10 membered aryl or a 3-10 membered heterocyclyl. In certain embodiments, Y$^1$ is a 2-8 membered heteroalkyl substituted by a 6-10 membered aryl or a 3-10 membered heterocyclyl.

In certain embodiments, Y$^1$ is a 2-8 membered heteroalkyl substituted by a 3-10 membered heterocyclyl. In certain embodiments, $Y^1$ is a 2-8 membered heteroalkyl substituted by a 5-6 membered heteroaryl, such as pyrrolyl, furanyl, or pyridinyl. In certain embodiments, $Y^1$ is a 2-8 membered heteroalkyl.

In certain embodiments, $Y^1$ is —O—($C_{1-7}$ alkyl). In certain embodiments, $Y^1$ is —O— butyl, —O-pentyl, or —O-hexyl. In certain embodiments, $Y^1$ is —($C_{1-3}$ alkylene)-O-(5-6 membered heteroaryl). In certain embodiments, $Y^1$ is —$CH_2$—O-(5-6 membered heteroaryl). In certain embodiments, $Y^1$ is —$CH_2$—O-(5-6 membered heteroaryl), wherein the 5-6 membered heteroaryl is furanyl, pyrrolyl, thiophenyl, imidazolyl, pyrazolyl, oxazolyl, thiazolyl, pyridinyl, pyrimidinyl, pyrazinyl, isooxazolyl, isothiazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is a 3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is a 5-membered heteroaryl substituted by one or two substituents independently selected from the group consisting of $C_{1-6}$ alkyl, $C_{3-7}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$. In certain embodiments, $Y^1$ is a 5-membered heteroaryl substituted by one or two substituents independently selected from the group consisting of $C_{1-6}$ alkyl, $C_{3-6}$ cycloalkyl, halogen, $C_{1-6}$ haloalkyl, hydroxyl, and $C_{1-6}$ alkoxyl.

In certain embodiments, $Y^1$ is furanyl, pyrrolyl, thiophenyl, imidazolyl, pyrazolyl, oxazolyl, or thiazolyl. In certain embodiments, $Y^1$ is furanyl, pyrrolyl, thiophenyl, imidazolyl, pyrazolyl, oxazolyl, or thiazolyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl. In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is $C_{2-6}$ alkynyl, —C≡C—($C_{1-6}$ alkylene)-$OR^4$, —C≡C—($C_{1-6}$ alkylene)-$N(R^3)_2$, —($C_{2-4}$ alkynylene)-(5-6 membered heteroaryl), or $C_{2-6}$ alkenyl. In certain embodiments, $Y^1$ is $C_{2-6}$ alkynyl. In certain embodiments, $Y^1$ is —C≡CH. In certain embodiments, $Y^1$ is —C≡C—($C_{1-6}$ alkylene)-$OR^4$. In certain embodiments, $Y^1$ is —C≡C—($C_{1-6}$ alkylene)-O—($C_{1-2}$ alkyl). In certain embodiments, $Y^1$ is —C≡C—$CH_2$—O—$CH_3$.

In certain embodiments, $Y^1$ is —O—($C_{1-7}$ alkyl). In certain embodiments, $Y^1$ is —O— butyl, —O-pentyl, or —O-hexyl. In certain embodiments, $Y^1$ is $C_{2-6}$ alkynyl, —C≡C—($C_{1-6}$ alkylene)-$OR^4$, —C≡C—($C_{1-6}$ alkylene)-$N(R^3)_2$, —($C_{2-4}$ alkynylene)-(5-6 membered heteroaryl), or $C_{2-6}$ alkenyl. In certain embodiments, $Y^1$ is —C≡CH. In certain embodiments, $Y^1$ is —C≡C—($C_{1-6}$ alkylene)-$OR^4$. In certain embodiments, $Y^1$ is —C≡C—$CH_2$—O—$CH_3$. In certain embodiments, $Y^1$ is $C_{2-6}$ alkynyl.

In certain embodiments, $Y^1$ is a 2-8 membered heteroalkyl optionally substituted by a 6-10 membered aryl or a 3-10 membered heterocyclyl. In certain embodiments, $Y^1$ is —($C_{1-3}$ alkylene)-O-(5-6 membered heteroaryl). In certain embodiments, $Y^1$ is a 3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is furanyl, pyrrolyl, thiophenyl, imidazolyl, pyrazolyl, oxazolyl, or thiazolyl.

The description above describes multiple embodiments relating to compounds of Formula I. The patent application specifically contemplates all combinations of the embodiments. For example, the invention contemplates a compound of Formula I wherein $X^1$ is —C(O)N(H)-ψ, $R^1$ and $R^2$ each represent independently for each occurrence hydrogen or $C_{1-4}$ alkyl, and $A^2$ is a 5-12 membered heterocyclyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —$N(R^4)_2$.

In certain embodiments, the compound is a compound of Formula I-A:

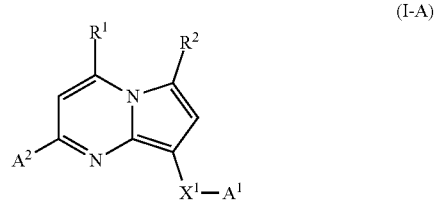

(I-A)

or a pharmaceutically acceptable salt thereof, wherein:
  $R^1$ represents independently for each occurrence $C_{1-4}$ alkyl, $C_{1-4}$ haloalkyl, $C_{1-4}$ alkoxyl, —($C_{1-4}$ alkylene)-($C_{1-4}$ alkoxyl), cyclopropyl, chloro, or fluoro;
  $R^2$ is hydrogen;
  $R^3$ and $R^4$ each represent independently for each occurrence hydrogen or $C_{1-4}$ alkyl;
  $X^1$ is a carbonyl-containing linker selected from —C(O)N(H)-ψ, —C(O)N(H)($C_{1-6}$ alkylene optionally substituted $C_{3-6}$ cycloalkyl)-ψ, or —C(O)N(H)($C_{1-6}$ haloalkylene)-ψ;
  where ψ is a bond to $A^1$;
  $A^1$ is a cyclic group selected from:
    $C_{3-10}$ cycloalkyl substituted by 0 or 1 occurrence of $Y^1$ and 0, 1, or 2 occurrences of $Y^2$; and
    phenyl substituted by 0 or 1 occurrence of $Y^1$ and 0, 1, or 2 occurrences of $Y^2$;
  $A^2$ is a 5-12 membered heterocyclyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl;

$Y^1$ represents, independently for each occurrence, one of the following:
2-8 membered heteroalkyl or —O—($C_{2-6}$ alkynyl); or $C_{2-6}$ alkynyl or —C≡C—($C_{1-6}$ alkylene)-$OR^4$; and $Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, or —$N(R^3)_2$.

Definitions of the variables in Formula I-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $X^1$ is —C(O)N(H)-ψ, $R^1$ is $C_{1-4}$ alkyl or $C_{1-4}$ haloalkyl, and $A^2$ is a 5-12 membered heterocyclyl.

Accordingly, in certain embodiments, $R^1$ represents independently for each occurrence methyl, halomethyl, —$(CH_2)_{1-2}$—O—($C_{1-3}$ alkyl), cyclopropyl, chloro, or fluoro. In certain embodiments, $R^1$ is $C_{1-4}$ alkyl or $C_{1-4}$ haloalkyl. In certain embodiments, $R^1$ is methyl.

In certain embodiments, $A^1$ is $C_{3-7}$ cycloalkyl substituted once by $Y^1$ and 0-1 occurrences of $Y^2$. In certain embodiments, $A^1$ is cyclohexyl substituted once by $Y^1$. In certain embodiments, $A^1$ is $C_{3-7}$ cycloalkyl. In certain embodiments, $A^1$ is cyclopropyl.

In certain embodiments, $A^1$ is cyclohexyl or a 8-membered bicyclic cycloalkyl, each of which is substituted once by $Y^1$ and 0-1 occurrences of $Y^2$.

In certain embodiments, $A^1$ is phenyl substituted by 0 or 1 occurrence of $Y^1$ and 0, 1, or 2 occurrences of $Y^2$. In certain embodiments, $A^1$ is phenyl substituted by 1 occurrence of $Y^1$.

In certain embodiments, $Y^2$ is independently $C_{1-3}$ alkyl, halogen, or $C_{1-3}$ haloalkyl.

In certain embodiments, $Y^1$ is a 2-8 membered heteroalkyl. In certain embodiments, $Y^1$ is —O—($C_{1-7}$ alkyl). In certain embodiments, $Y^1$ is —O-butyl, —O-pentyl, or —O-hexyl.

In certain embodiments, $A^2$ is a 5-6 membered heteroaryl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl. In certain embodiments, $A^2$ is a 5-6 membered heteroaryl selected from the group consisting of pyridinyl, pyrimidinyl, pyrazinyl, furanyl, pyrrolyl, thiophenyl, imidazolyl, oxazolyl, isoxazolyl, isothiazolyl, and thiazolyl, each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —$N(R^4)_2$. In certain embodiments, $A^2$ is a 5-6 membered heteroaryl selected from the group consisting of pyridinyl, pyrimidinyl, pyrazinyl, furanyl, pyrrolyl, thiophenyl, oxazolyl, isoxazolyl, and thiazolyl, each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl. In certain embodiments, $A^2$ is pyridinyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl. In certain embodiments, $A^2$ is 3-pyridinyl optionally substituted by 1 or 2 3 substituents independently selected from the group consisting of $C_{1-4}$ alkyl, $C_{1-4}$ haloalkyl, $C_{1-4}$ alkoxyl, $C_{3-5}$ cycloalkyl, cyano, and halogen.

In certain embodiments, $A^2$ is a 5-6 membered heterocycloalkyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl. In certain embodiments, $A^2$ is a 5-6 membered heterocycloalkyl selected from the group consisting of morpholinyl, piperidinyl, pyrrolidinyl, tetrahydropyranyl, and tetrahydrofuranyl, each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl.

In certain embodiments, $X^1$ is —C(O)N(H)($C_{1-6}$ haloalkylene)-ψ. In certain embodiments, $X^1$ is —C(O)N(H)C(H)(CF$_3$)-ψ. In certain embodiments, $X^1$ is —C(O)N(H)($C_{1-6}$ alkylene)-ψ. In certain embodiments, $X^1$ is —C(O)N(H)(C(CH$_3$)$_2$)-ψ or —C(O)N(H)(C—(H)(CH$_3$))-ψ.

The description above describes multiple embodiments relating to compounds of Formula I-A. The patent application specifically contemplates all combinations of the embodiments. For example, the invention contemplates a compound of Formula I-A wherein $X^1$ is —C(O)N(H)-ψ, $R^1$ is $C_{1-4}$ alkyl or $C_{1-4}$ haloalkyl, and $A^2$ is a 5-6 membered heteroaryl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl.

In certain embodiments, the substituted pyrrolo[1,2-a]pyrimidinyl carboxamide or related organic compound is a compound embraced by Formula II:

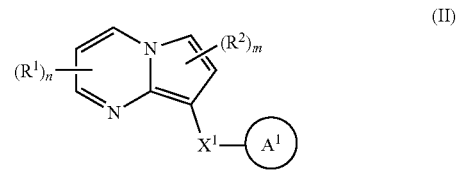

(II)

or a pharmaceutically acceptable salt thereof, wherein:

$R^1$ and $R^2$ each represent independently for each occurrence hydrogen, $C_{1-4}$ alkyl, $C_{1-4}$ haloalkyl, $C_{1-4}$ hydroxyalkyl, $C_{1-4}$ cyanoalkyl, $C_{1-4}$ alkoxyl, —($C_{1-4}$ alkylene)-(2-6 membered heteroalkyl), cyclopropyl, cyano, halogen, hydroxyl, or —$N(R^4)_2$;

$R^3$ represents independently for each occurrence hydrogen, $C_{1-6}$ alkyl, or $C_{3-6}$ cycloalkyl;

$R^4$ represents independently for each occurrence hydrogen, $C_{1-4}$ alkyl, cyclopropyl, or —C(O)$R^3$;

$R^5$ represents independently for each occurrence $C_{1-4}$ alkyl or $C_{3-6}$ cycloalkyl;

$X^1$ is a carbonyl-containing linker selected from —C(O)N(H)($C_{1-6}$ haloalkylene)-ψ, —C(O)N(H)($C_{1-6}$ alkylene substituted with $C_{1-4}$ alkoxyl or $C_{3-6}$ cycloalkyl)-ψ, —C(O)N(H)($C_{3-6}$ cycloalkylene)-ψ, —C(O)N(H)(3-6 membered heterocycloalkylene)-ψ, —C(O)N(H)C(O)-ψ, or —C(O)N(H)C(O)($C_{1-6}$ alkylene)-ψ; where ψ is a bond to $A^1$;

$A^1$ is one of the following:
a cyclic group selected from a 3-14 membered saturated carbocyclyl, a 5-14 membered partially unsaturated carbocyclyl, a 3-16 membered heterocyclyl, or phenyl; each of which is substituted by 0, 1, or 2 occurrences of $Y^1$ and 0, 1, 2, or 3 occurrences of $Y^2$; or $C_{1-8}$ alkyl or $C_{2-6}$ alkynyl;

$Y^1$ represents, independently for each occurrence, one of the following:
2-8 membered heteroalkyl optionally substituted by a 6-10 membered aryl, a 3-10 membered heterocyclyl, or $C_{3-6}$ halocycloalkyl;
3-10 membered heterocyclyl, 6-10 membered aryl, $C_{3-7}$ cycloalkyl, —O—$C_{3-6}$ cycloalkyl, —O-(3-6 membered heterocyclyl), —O-(6-10 membered aryl), or —O—($C_{2-6}$ alkynyl); or
$C_{2-6}$ alkynyl, —C≡C—($C_{1-6}$ alkylene)-OR$^4$, —C≡C—($C_{1-6}$ alkylene)-N(R$^3$)$_2$, —($C_{2-4}$ alkynylene)-(5-6 membered heteroaryl), or $C_{2-6}$ alkenyl;

$Y^2$ represents, independently for each occurrence, $C_{1-6}$ alkyl, $C_{3-6}$ cycloalkyl, halogen, $C_{1-6}$haloalkyl, $C_{1-6}$ hydroxyalkyl, hydroxyl, $C_{1-6}$ alkoxyl, —O—($C_{1-8}$haloalkyl), cyano, azido, —N(R$^3$)$_2$, —($C_{1-6}$ alkylene)-(5-6 membered heterocyclyl), —($C_{1-6}$ alkylene)-CO$_2$R$^3$, —CO$_2$R$^3$, —C(O)R$^5$, —S(O)$_2$R$^5$, —C(O)N(R$^5$)$_2$, —C(O)N(R$^3$)$_2$, or $C_{1-6}$haloalkyl-substituted $C_{3-6}$ cycloalkyl;

m is 1 or 2; and n is 1, 2, or 3;

provided that when $X^1$ is C(O)N(H)($C_{3-6}$ cycloalkylene)-ψ or —C(O)N(H)(3-6 membered heterocycloalkylene)-ψ, then $A^1$ is not a 5-membered heterocyclyl.

Definitions of the variables in Formula II above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $X^1$ is —C(O)N(H)($C_{1-6}$ haloalkylene)-ψ, R$^1$ and R$^2$ each represent independently for each occurrence hydrogen or $C_{1-4}$ alkyl, and $A^1$ is a 3-14 membered saturated carbocyclyl.

Accordingly, in certain embodiments, $X^1$ is —C(O)N(H)($C_{1-6}$ haloalkylene)-ψ. In certain embodiments, $X^1$ is —C(O)N(H)C(H)(CF$_3$)-ψ. In certain embodiments, $X^1$ is —C(O)N(H)($C_{1-6}$ alkylene substituted with $C_{1-4}$ alkoxyl)-ψ. In certain embodiments, $X^1$ is —C(O)N(H)C(H)(CH$_2$OCH$_3$)-ψ. In certain embodiments, $X^1$ is —C(O)N(H)($C_{1-6}$ alkylene substituted with $C_{3-6}$ cycloalkyl)-ψ. In certain embodiments, $X^1$ is —C(O)N(H)($C_{3-6}$ cycloalkylene)-ψ.

In certain embodiments, n is 2. In certain embodiments, R$^1$ groups are located at the 2 and 4 positions of the pyrrolo[1,2-a]pyrimidinyl.

In certain embodiments, R$^1$ represents independently for each occurrence $C_{1-4}$ alkyl, $C_{1-4}$haloalkyl, —($C_{1-4}$ alkylene)-(2-6 membered heteroalkyl), cyclopropyl, halogen, or —N(R$^4$)$_2$. In certain embodiments, R$^1$ represents independently for each occurrence $C_{1-4}$ alkyl, $C_{1-4}$ haloalkyl, $C_{1-4}$ alkoxyl, cyclopropyl, cyano, chloro, or fluoro. In certain embodiments, R$^1$ is methyl.

In certain embodiments, R$^2$ is hydrogen. In certain embodiments, and R$^2$ each represent independently for each occurrence hydrogen or $C_{1-4}$ alkyl.

In certain embodiments, R$^3$ and R$^4$ each represent independently for each occurrence hydrogen, methyl, or ethyl.

In certain embodiments, $A^1$ is a 3-14 membered saturated carbocyclyl substituted by 0, 1, or 2 occurrences of $Y^1$ and 0, 1, 2, or 3 occurrences of $Y^2$. In certain embodiments, $A^1$ is a 3-14 membered saturated carbocyclyl. In certain embodiments, $A^1$ is $C_{3-7}$ cycloalkyl substituted once by $Y^1$ and 0-1 occurrences of $Y^2$. In certain embodiments, $A^1$ is a 5-14 membered partially unsaturated carbocyclyl substituted by 0, 1, or 2 occurrences of $Y^1$ and 0, 1, 2, or 3 occurrences of $Y^2$. In certain embodiments, $A^1$ is a 8-12 membered bicyclic carbocyclyl that is partially unsaturated or a 8-12 membered bicyclic heterocyclyl, each of which is substituted by 0 or 1 occurrence of $Y^1$ and 0, 1, or 2 occurrences of $Y^2$. In certain embodiments, $A^1$ is phenyl substituted once by $Y^1$ and 0-1 occurrences of $Y^2$.

In certain embodiments, $A^1$ is a 5-6 membered heteroaryl substituted once by $Y^1$ and 0-1 occurrences of $Y^2$. In certain embodiments, $A^1$ is pyridinyl substituted once by $Y^1$ and 0-1 occurrences of $Y^2$.

In certain embodiments, $A^1$ is $C_{3-7}$ cycloalkyl substituted by $C_{1-6}$ alkoxyl. In certain embodiments, $A^1$ is cyclohexyl substituted by $C_{1-6}$ alkoxyl. In certain embodiments, $A^1$ is $C_{3-7}$ cycloalkyl. In certain embodiments, $A^1$ is $C_{3-7}$ cycloalkyl that is not substituted. In certain embodiments, $A^1$ is $C_{7-10}$ cycloalkyl that is spirocyclic and not substituted. In certain embodiments, $A^1$ is cyclopropyl.

In certain embodiments, $A^1$ is phenyl substituted by $C_2$ alkynyl.

In certain embodiments, $A^1$ is an 8-12 membered bicyclic carbocyclyl that is partially unsaturated or an 8-12 membered bicyclic heterocyclyl, each of which is substituted by 0 or 1 occurrence of $Y^2$ selected from the group consisting of $C_{1-6}$ alkyl, $C_{3-6}$ cycloalkyl, halogen, $C_{1-6}$haloalkyl, hydroxyl, and $C_{1-6}$ alkoxyl. In certain embodiments, $A^1$ is

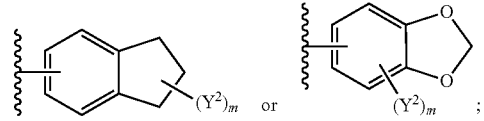

wherein m is 0, 1, or 2; and $Y^2$ represents independently for each occurrence $C_{1-6}$ alkyl, $C_{3-6}$ cycloalkyl, halogen, $C_{1-6}$haloalkyl, hydroxyl, or $C_{1-6}$ alkoxyl.

In certain embodiments, any occurrence of $Y^2$ is independently $C_{1-6}$ alkyl, $C_{3-6}$ cycloalkyl, halogen, $C_{1-6}$haloalkyl, or hydroxyl. In certain embodiments, any occurrence of $Y^2$ is independently $C_{1-3}$ alkyl. In certain embodiments, $Y^2$ is $C_{1-6}$ haloalkyl-substituted $C_{3-6}$ cycloalkyl.

In certain embodiments, $Y^1$ is —O—($C_{1-7}$ alkyl). In certain embodiments, $Y^1$ is —O— butyl, —O-pentyl, or —O-hexyl. In certain embodiments, $Y^1$ is $C_{2-6}$ alkynyl, C≡C—($C_{1-6}$ alkylene)-OR$^4$, —C≡C—($C_{1-6}$ alkylene)-N(R$^3$)$_2$, —($C_{2-4}$ alkynylene)-(5-6 membered heteroaryl), or $C_{2-6}$ alkenyl. In certain embodiments, $Y^1$ is —C≡CH. In certain embodiments, $Y^1$ is —C≡C—($C_{1-6}$ alkylene)-OR$^4$. In certain embodiments, $Y^1$ is —C≡C—CH$_2$—O—CH$_3$. In certain embodiments, $Y^1$ is $C_{2-6}$ alkynyl.

In certain embodiments, $Y^1$ is a 2-8 membered heteroalkyl optionally substituted by a 6-10 membered aryl or a 3-10 membered heterocyclyl. In certain embodiments, $Y^1$ is a 2-8 membered heteroalkyl substituted by a 6-10 membered aryl or a 3-10 membered heterocyclyl. In certain embodiments, $Y^1$ is a 2-8 membered heteroalkyl substituted by a 3-10 membered heterocyclyl. In certain embodiments, $Y^1$ is a 2-8 membered heteroalkyl substituted by a 5-6 membered heteroaryl, such as pyrrolyl, furanyl, or pyridinyl. In certain embodiments, $Y^1$ is a 2-8 membered heteroalkyl.

In certain embodiments, $Y^1$ is —O—($C_{1-7}$ alkyl). In certain embodiments, $Y^1$ is —O— butyl, —O-pentyl, or —O-hexyl. In certain embodiments, $Y^1$ is —($C_{1-3}$ alkylene)-O-(5-6 membered heteroaryl). In certain embodiments, $Y^1$ is —$CH_2$—O-(5-6 membered heteroaryl). In certain embodiments, $Y^1$ is —$CH_2$—O-(5-6 membered heteroaryl), wherein the 5-6 membered heteroaryl is furanyl, pyrrolyl, thiophenyl, imidazolyl, pyrazolyl, oxazolyl, thiazolyl, pyridinyl, pyrimidinyl, pyrazinyl, isooxazolyl, isothiazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is a 3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is a 5-membered heteroaryl substituted by one or two substituents independently selected from the group consisting of $C_{1-6}$ alkyl, $C_{3-7}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$. In certain embodiments, $Y^1$ is a 5-membered heteroaryl substituted by one or two substituents independently selected from the group consisting of $C_{1-6}$ alkyl, $C_{3-6}$ cycloalkyl, halogen, $C_{1-6}$ haloalkyl, hydroxyl, and $C_{1-6}$ alkoxyl.

In certain embodiments, $Y^1$ is furanyl, pyrrolyl, thiophenyl, imidazolyl, pyrazolyl, oxazolyl, or thiazolyl. In certain embodiments, $Y^1$ is furanyl, pyrrolyl, thiophenyl, imidazolyl, pyrazolyl, oxazolyl, or thiazolyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl. In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is $C_{2-6}$ alkynyl, alkylene)-$OR^4$, —C≡C—($C_{1-6}$ alkylene)-$N(R^3)_2$, —($C_{2-4}$ alkynylene)-(5-6 membered heteroaryl), or $C_{2-6}$ alkenyl. In certain embodiments, $Y^1$ is $C_{2-6}$ alkynyl. In certain embodiments, $Y^1$ is —C≡CH. In certain embodiments, $Y^1$ is —C≡C—($C_{1-6}$ alkylene)-$OR^4$. In certain embodiments, $Y^1$ is —C≡C—($C_{1-6}$ alkylene)-O—($C_{1-2}$ alkyl). In certain embodiments, $Y^1$ is —C≡C—$CH_2$—O—$CH_3$.

In certain embodiments, $Y^1$ is a 2-8 membered heteroalkyl optionally substituted by a 6-10 membered aryl or a 3-10 membered heterocyclyl. In certain embodiments, $Y^1$ is —($C_{1-3}$ alkylene)-O-(5-6 membered heteroaryl). In certain embodiments, $Y^1$ is a 3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is furanyl, pyrrolyl, thiophenyl, imidazolyl, pyrazolyl, oxazolyl, or thiazolyl.

The description above describes multiple embodiments relating to compounds of Formula II. The patent application specifically contemplates all combinations of the embodiments. For example, the invention contemplates a compound of Formula II wherein $X^1$ is —C(O)N(H)($C_{1-6}$ haloalkylene)-ψ, $R^1$ and $R^2$ each represent independently for each occurrence hydrogen or $C_{1-4}$ alkyl, and $A^1$ is a 3-14 membered saturated carbocyclyl.

In certain embodiments, the substituted pyrrolo[1,2-a]pyrimidinyl carboxamide or related organic compound is a compound embraced by Formula II-A:

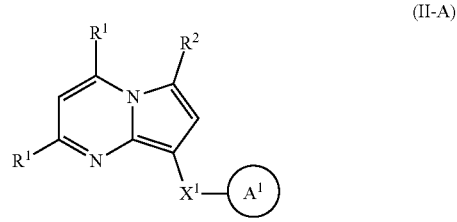

(II-A)

or a pharmaceutically acceptable salt thereof, wherein:
$R^1$ represents independently for each occurrence $C_{1-4}$ alkyl, $C_{1-4}$haloalkyl, $C_{1-4}$ alkoxyl, —($C_{1-4}$ alkylene)-($C_{1-4}$ alkoxyl), cyclopropyl, chloro, or fluoro;
$R^2$ is hydrogen;
$R^3$ and $R^4$ each represent independently for each occurrence hydrogen or $C_{1-4}$ alkyl;
$X^1$ is —C(O)N(H)($C_{1-6}$ haloalkylene)-ω or —C(O)N(H)($C_{1-6}$ alkylene substituted with $C_{1-4}$ alkoxyl or $C_{3-6}$ cycloalkyl)-ψ;
$A^1$ is a cyclic group selected from:
  $C_{3-10}$ cycloalkyl substituted by 0 or 1 occurrence of $Y^1$ and 0, 1, or 2 occurrences of $Y^2$; and
  phenyl substituted by 0 or 1 occurrence of $Y^1$ and 0, 1, or 2 occurrences of $Y^2$;
$Y^1$ represents, independently for each occurrence, one of the following:
  2-8 membered heteroalkyl or —O—($C_{2-6}$ alkynyl); or
  $C_{2-6}$ alkynyl or —C≡C—($C_{1-6}$ alkylene)-$OR^4$; and
$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, or —$N(R^3)_2$.

Definitions of the variables in Formula II-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $X^1$ is —C(O)N(H)($C_{1-6}$ haloalkylene)-ψ, $R^1$ is $C_{1-4}$ alkyl or $C_{1-4}$ haloalkyl, and $A^1$ is a $C_{3-10}$ cycloalkyl substituted by 0 or 1 occurrence of $Y^1$ and 0, 1, or 2 occurrences of $Y^2$.

Accordingly, in certain embodiments, $R^1$ represents independently for each occurrence methyl, halomethyl, —(CH$_2$)$_{1-2}$—O—(C$_{1-3}$ alkyl), cyclopropyl, chloro, or fluoro. In certain embodiments, R$^1$ is C$_{1-4}$ alkyl or C$_{1-4}$ haloalkyl. In certain embodiments, R$^1$ is methyl.

In certain embodiments, X$^1$ is —C(O)N(H)(C$_{1-6}$ haloalkylene)-ψ. In certain embodiments, X$^1$ is —C(O)N(H)C(H)(CF$_3$)-ψ.

In certain embodiments, A$^1$ is a C$_{3-10}$ cycloalkyl substituted by 0 or 1 occurrence of Y$^1$ and 0, 1, or 2 occurrences of Y$^2$. In certain embodiments, A$^1$ is C$_{3-7}$ cycloalkyl substituted once by Y$^1$ and 0-1 occurrences of Y$^2$. In certain embodiments, A$^1$ is cyclohexyl substituted once by Y$^1$. In certain embodiments, A$^1$ is C$_{3-7}$ cycloalkyl. In certain embodiments, A$^1$ is cyclopropyl.

In certain embodiments, A$^1$ is phenyl substituted by 0 or 1 occurrence of Y$^1$ and 0, 1, or 2 occurrences of Y$^2$. In certain embodiments, A$^1$ is phenyl substituted by 1 occurrence of Y$^1$.

In certain embodiments, Y$^1$ is a 2-8 membered heteroalkyl. In certain embodiments, Y$^1$ is —O—(C$_{1-7}$ alkyl). In certain embodiments, Y$^1$ is —O-butyl, —O-pentyl, or —O-hexyl.

The description above describes multiple embodiments relating to compounds of Formula II-A. The patent application specifically contemplates all combinations of the embodiments. For example, the invention contemplates a compound of Formula II-A wherein X$^1$ is —C(O)N(H)(C$_{1-6}$ haloalkylene)-ψ, R$^1$ is C$_{1-4}$ alkyl or C$_{1-4}$ haloalkyl, and A$^1$ is a C$_{3-10}$ cycloalkyl substituted by 0 or 1 occurrence of Y$^1$ and 0, 1, or 2 occurrences of Y$^2$.

In certain embodiments, the substituted pyrrolo[1,2-a]pyrimidinyl carboxamide or related organic compound is a compound embraced by Formula III:

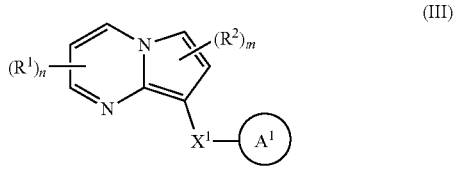

(III)

or a pharmaceutically acceptable salt thereof, wherein:
R$^1$ and R$^2$ each represent independently for each occurrence hydrogen, C$_{1-4}$ alkyl, C$_{1-4}$ haloalkyl, C$_{1-4}$ hydroxyalkyl, C$_{1-4}$ cyanoalkyl, C$_{1-4}$ alkoxyl, —(C$_{1-4}$ alkylene)-(2-6 membered heteroalkyl), cyclopropyl, cyano, halogen, hydroxyl, or —N(R$^4$)$_2$;
R$^3$ represents independently for each occurrence hydrogen, C$_{1-6}$ alkyl, or C$_{3-6}$ cycloalkyl;
R$^4$ represents independently for each occurrence hydrogen, C$_{1-4}$ alkyl, cyclopropyl, or —C(O)R$^3$;
X$^1$ is a carbonyl-containing linker selected from —C(O)N(H)-ψ, —C(O)N(H)(C$_{1-6}$ alkylene optionally substituted with C$_{1-4}$ alkoxyl or C$_{3-6}$ cycloalkyl)-ψ, —C(O)N(H)(C$_{1-6}$ haloalkylene)-ψ, —C(O)N(H)(C$_{3-6}$ cycloalkylene)-ψ, —C(O)N(H)(3-6 membered heterocycloalkylene)-ψ, —C(O)-(3-6 membered heterocycloalkylene containing at least one ring —N(H)— group)-ψ, —C(O)N(H)C(O)-ψ, and —C(O)N(H)C(O)(C$_{1-6}$ alkylene)-ψ;
where ψ is a bond to A$^1$;
A$^1$ is a C$_{3-10}$ cycloalkyl optionally substituted with 1 or 2 C$_{1-4}$ alkyl groups;
m is 1 or 2; and
n is 1, 2, or 3

Definitions of the variables in Formula III above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where X$^1$ is —C(O)N(H)-ψ, and R$^1$ and R$^2$ each represent independently for each occurrence hydrogen or C$_{1-4}$ alkyl.

Accordingly, in certain embodiments, R$^1$ represents independently for each occurrence C$_{1-4}$ alkyl, C$_{1-4}$haloalkyl, —(C$_{1-4}$ alkylene)-(2-6 membered heteroalkyl), cyclopropyl, halogen, or —N(R$^4$)$_2$. In certain embodiments, R$^1$ represents independently for each occurrence C$_{1-4}$ alkyl, C$_{1-4}$ haloalkyl, C$_{1-4}$ alkoxyl, cyclopropyl, cyano, chloro, or fluoro. In certain embodiments, R$^1$ is methyl.

In certain embodiments, n is 2. In certain embodiments, the R$^1$ groups are located at the 2 and 4 positions of the pyrrolo[1,2-a]pyrimidinyl.

In certain embodiments, R$^2$ is hydrogen. In certain embodiments, R$^1$ and R$^2$ each represent independently for each occurrence hydrogen or C$_{1-4}$ alkyl.

In certain embodiments, R$^3$ and R$^4$ each represent independently for each occurrence hydrogen, methyl, or ethyl.

In certain embodiments, X$^1$ is —C(O)N(H)(C$_{1-6}$ alkylene)-ψ. In certain embodiments, X$^1$ is —C(O)N(H)C(H)(CH$_3$)-ψ or —C(O)N(H)C(CH$_3$)$_2$-ψ. In certain embodiments, X$^1$ is —C(O)N(H)(C$_{1-6}$ haloalkylene)-ψ. In certain embodiments, X$^1$ is —C(O)N(H)C(H)(CF$_3$)-ψ. In certain embodiments, X$^1$ is —C(O)N(H)-ψ.

In certain embodiments, A$^1$ is a cyclopropyl. In certain embodiments, A$^1$ is a cyclopropyl, cyclobutyl, cyclopentyl, or cyclohexyl.

The description above describes multiple embodiments relating to compounds of Formula III. The patent application specifically contemplates all combinations of the embodiments. For example, the invention contemplates a compound of Formula III wherein X$^1$ is —C(O)N(H)-ψ, and R$^1$ and R$^2$ each represent independently for each occurrence hydrogen or C$_{1-4}$ alkyl.

Another aspect of the invention provides a compound of Formula IV:

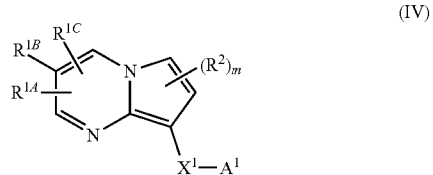

(IV)

or a pharmaceutically acceptable salt thereof, wherein:
R$^{1A}$ and R$^2$ each represent independently for each occurrence hydrogen, C$_{1-4}$ alkyl, C$_{1-4}$ haloalkyl, C$_{1-4}$ hydroxyalkyl, C$_{1-4}$ cyanoalkyl, C$_{1-4}$ alkoxyl, —(C$_{1-4}$ alkylene)-(2-6 membered heteroalkyl), cyclopropyl, cyano, halogen, hydroxyl, or —N(R$^4$)$_2$;
R$^{1C}$ is attached to a carbon atom adjacent to the carbon atom bearing substituent R$^{1B}$, and R$^{1B}$ and R$^{1C}$ are taken together with the intervening carbon atoms to form a 5-6 membered partially saturated carbocyclic ring that is optionally substituted with 1 or 2 occurrences of R$^6$;
R$^3$ represents independently for each occurrence hydrogen, C$_{1-6}$ alkyl, or C$_{3-6}$ cycloalkyl;

R$^4$ represents independently for each occurrence hydrogen, C$_{1-4}$ alkyl, cyclopropyl, or —C(O)R$^3$;

R$^5$ represents independently for each occurrence C$_{1-4}$ alkyl or C$_{3-6}$ cycloalkyl;

R$^6$ represents independently for each occurrence C$_{1-4}$ alkyl, C$_{1-4}$ haloalkyl, C$_{1-4}$ alkoxyl, cyano, halogen, hydroxyl, or —N(R$^4$)$_2$;

X$^1$ is a carbonyl-containing linker selected from —C(O)N(H)-ψ, —C(O)N(H)(C$_{1-6}$ alkylene optionally substituted with C$_{1-4}$ alkoxyl or C$_{3-6}$ cycloalkyl)-ψ, —C(O)N(H)(C$_{1-6}$ haloalkylene)-ψ, —C(O)N(H)(C$_{3-6}$ cycloalkylene)-ψ, —C(O)N(H)(3-6 membered heterocycloalkylene)-ψ, —C(O)-(3-6 membered heterocycloalkylene containing at least one ring —N(H)— group)-ψ, —C(O)N(H)C(O)-ψ, and —C(O)N(H)C(O)(C$_{1-6}$ alkylene)-ψ;

where ψ is a bond to A$^1$;

A$^1$ is one of the following:
  a cyclic group selected from a 3-14 membered saturated carbocyclyl, a 5-14 membered partially unsaturated carbocyclyl, a 3-16 membered heterocyclyl, or phenyl; each of which is substituted by 0, 1, or 2 occurrences of Y$^1$ and 0, 1, 2, or 3 occurrences of Y$^2$; or
  C$_{1-8}$ alkyl or C$_{2-6}$ alkynyl;

Y$^1$ represents, independently for each occurrence, one of the following:
  2-8 membered heteroalkyl optionally substituted by a 6-10 membered aryl, a 3-10 membered heterocyclyl, or C$_{3-6}$ halocycloalkyl;
  3-10 membered heterocyclyl, 6-10 membered aryl, C$_{3-7}$ cycloalkyl, —O—C$_{3-6}$ cycloalkyl, —O-(3-6 membered heterocyclyl), —O-(6-10 membered aryl), or —O—(C$_{2-6}$ alkynyl); or
  C$_{2-6}$ alkynyl, —C≡C—(C$_{1-6}$ alkylene)-OR$^4$, —C≡C—(C$_{1-6}$ alkylene)-N(R$^3$)$_2$, —(C$_{2-4}$ alkynylene)-(5-6 membered heteroaryl), or C$_{2-6}$ alkenyl;

Y$^2$ represents, independently for each occurrence, C$_{1-6}$ alkyl, C$_{3-6}$ cycloalkyl, halogen, C$_{1-6}$ haloalkyl, C$_{1-6}$ hydroxyalkyl, hydroxyl, C$_{1-6}$ alkoxyl, —O—(C$_{1-8}$ haloalkyl), cyano, azido, —N(R$^3$)$_2$, —(C$_{1-6}$ alkylene)-(5-6 membered heterocyclyl), —(C$_{1-6}$ alkylene)-CO$_2$R$^3$, —CO$_2$R$^3$, —C(O)R$^5$, —S(O)$_2$R$^5$, —C(O)N(R$^5$)$_2$, —C(O)N(R$^3$)$_2$, or C$_{1-6}$ haloalkyl-substituted C$_{3-6}$ cycloalkyl; and m is 1 or 2.

Definitions of the variables in Formula IV above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, X$^1$ is —C(O)N(H)-ω. In certain embodiments, X$^1$ is —C(O)N(H)(C$_{1-6}$ alkylene)-ψ. In certain embodiments, X$^1$ is —C(O)N(H)(C(CH$_3$)$_2$)-ψ or —C(O)N(H)(C(H)(CH$_3$))-ψ. In certain embodiments, X$^1$ is —C(O)N(H)(C$_{1-6}$ alkylene substituted with C$_{1-4}$ alkoxyl)-ψ. In certain embodiments, X$^1$ is —C(O)N(H)(C$_{1-6}$ alkylene substituted with C$_{3-6}$ cycloalkyl)-ψ. In certain embodiments, X$^1$ is —C(O)N(H)(C$_{1-6}$ haloalkylene)-ψ. In certain embodiments, X$^1$ is —C(O)N(H)C(H)(CF$_3$)-ψ. In certain embodiments, X$^1$ is —C(O)N(H)(C$_{3-6}$ cycloalkylene)-ψ. In certain embodiments, X$^1$ is —C(O)N(H)(3-6 membered heterocycloalkylene)-ψ.

In certain embodiments, R$^{14}$ represents independently for each occurrence C$_{1-4}$ alkyl, C$_{1-4}$ haloalkyl, —(C$_{1-4}$ alkylene)-(2-6 membered heteroalkyl), cyclopropyl, halogen, or —N(R$^4$)$_2$. In certain embodiments, R$^{14}$ represents independently for each occurrence C$_{1-4}$ alkyl, C$_{1-4}$ haloalkyl, C$_{1-4}$ alkoxyl, cyclopropyl, cyano, chloro, or fluoro. In certain embodiments, R$^{14}$ is hydrogen or methyl.

In certain embodiments, R$^2$ is hydrogen. In certain embodiments, R$^{14}$ and R$^2$ each represent independently for each occurrence hydrogen or C$_{1-4}$ alkyl.

In certain embodiments, R$^3$ and R$^4$ each represent independently for each occurrence hydrogen, methyl, or ethyl.

In certain embodiments, A$^1$ is a 3-14 membered saturated carbocyclyl substituted by 0, 1, or 2 occurrences of Y$^1$ and 0, 1, 2, or 3 occurrences of Y$^2$. In certain embodiments, A$^1$ is C$_{3-7}$ cycloalkyl substituted once by Y$^1$ and 0-1 occurrences of Y$^2$. In certain embodiments, A$^1$ is a 5-14 membered partially unsaturated carbocyclyl substituted by 0, 1, or 2 occurrences of Y$^1$ and 0, 1, 2, or 3 occurrences of Y$^2$. In certain embodiments, A$^1$ is a 8-12 membered bicyclic carbocyclyl that is partially unsaturated or a 8-12 membered bicyclic heterocyclyl, each of which is substituted by 0 or 1 occurrence of Y$^1$ and 0, 1, or 2 occurrences of Y$^2$. In certain embodiments, A$^1$ is phenyl substituted once by Y$^1$ and 0-1 occurrences of Y$^2$.

In certain embodiments, A$^1$ is a 5-6 membered heteroaryl substituted once by Y$^1$ and 0-1 occurrences of Y$^2$. In certain embodiments, A$^1$ is pyridinyl substituted once by Y$^1$ and 0-1 occurrences of Y$^2$.

In certain embodiments, A$^1$ is C$_{3-7}$ cycloalkyl substituted by C$_{1-6}$ alkoxyl. In certain embodiments, A$^1$ is cyclohexyl substituted by C$_{1-6}$ alkoxyl. In certain embodiments, A$^1$ is C$_{3-7}$ cycloalkyl. In certain embodiments, A$^1$ is C$_{3-7}$ cycloalkyl that is not substituted. In certain embodiments, A$^1$ is C$_{7-10}$ cycloalkyl that is spirocyclic and not substituted. In certain embodiments, A$^1$ is cyclopropyl.

In certain embodiments, A$^1$ is phenyl substituted by C$_2$ alkynyl.

In certain embodiments, A$^1$ is an 8-12 membered bicyclic carbocyclyl that is partially unsaturated or an 8-12 membered bicyclic heterocyclyl, each of which is substituted by 0 or 1 occurrence of Y$^2$ selected from the group consisting of C$_{1-6}$ alkyl, C$_{3-6}$ cycloalkyl, halogen, C$_{1-6}$ haloalkyl, hydroxyl, and C$_{1-6}$ alkoxyl. In certain embodiments, A$^1$ is

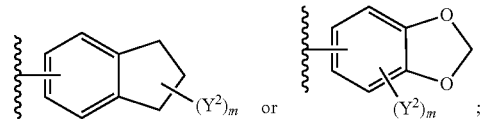

wherein m is 0, 1, or 2; and Y$^2$ represents independently for each occurrence C$_{1-6}$ alkyl, C$_{3-6}$ cycloalkyl, halogen, C$_{1-6}$ haloalkyl, hydroxyl, or C$_{1-6}$ alkoxyl.

In certain embodiments, any occurrence of Y$^2$ is independently C$_{1-6}$ alkyl, C$_{3-6}$ cycloalkyl, halogen, C$_{1-6}$ haloalkyl, or hydroxyl. In certain embodiments, any occurrence of Y$^2$ is independently C$_{1-3}$ alkyl. In certain embodiments, Y$^2$ is C$_{1-6}$ haloalkyl-substituted C$_{3-6}$ cycloalkyl.

In certain embodiments, Y$^1$ is a 2-8 membered heteroalkyl optionally substituted by a 6-10 membered aryl or a 3-10 membered heterocyclyl. In certain embodiments, Y$^1$ is a 2-8 membered heteroalkyl substituted by a 6-10 membered aryl or a 3-10 membered heterocyclyl. In certain embodiments, Y$^1$ is a 2-8 membered heteroalkyl substituted by a 3-10 membered heterocyclyl. In certain embodiments, Y$^1$ is a 2-8 membered heteroalkyl substituted by a 5-6 membered heteroaryl, such as pyrrolyl, furanyl, or pyridinyl. In certain embodiments, $Y^1$ is a 2-8 membered heteroalkyl.

In certain embodiments, $Y^1$ is —O—($C_{1-7}$ alkyl). In certain embodiments, $Y^1$ is —O— butyl, —O-pentyl, or —O-hexyl. In certain embodiments, $Y^1$ is —($C_{1-3}$ alkylene)-O-(5-6 membered heteroaryl). In certain embodiments, $Y^1$ is —$CH_2$—O-(5-6 membered heteroaryl). In certain embodiments, $Y^1$ is —$CH_2$—O-(5-6 membered heteroaryl), wherein the 5-6 membered heteroaryl is furanyl, pyrrolyl, thiophenyl, imidazolyl, pyrazolyl, oxazolyl, thiazolyl, pyridinyl, pyrimidinyl, pyrazinyl, isooxazolyl, isothiazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is a 3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is a 5-membered heteroaryl substituted by one or two substituents independently selected from the group consisting of $C_{1-6}$ alkyl, $C_{3-7}$ cycloalkyl, halogen, $C_{1-6}$haloalkyl, $C_{1-6}$ hydroxyalkyl, hydroxyl, $C_{1-6}$ alkoxyl, cyano, —$N(R^4)_2$, amide, and —$CO_2H$. In certain embodiments, $Y^1$ is a 5-membered heteroaryl substituted by one or two substituents independently selected from the group consisting of $C_{1-6}$ alkyl, $C_{3-6}$ cycloalkyl, halogen, $C_{1-6}$ haloalkyl, hydroxyl, and $C_{1-6}$ alkoxyl.

In certain embodiments, $Y^1$ is furanyl, pyrrolyl, thiophenyl, imidazolyl, pyrazolyl, oxazolyl, or thiazolyl. In certain embodiments, $Y^1$ is furanyl, pyrrolyl, thiophenyl, imidazolyl, pyrazolyl, oxazolyl, or thiazolyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl. In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is $C_{2-6}$ alkynyl, C≡C—($C_{1-6}$ alkylene)-$OR^4$, —C≡C—($C_{1-6}$ alkylene)-$N(R^3)_2$, —($C_{2-4}$ alkynylene)-(5-6 membered heteroaryl), or $C_{2-6}$ alkenyl. In certain embodiments, $Y^1$ is $C_{2-6}$ alkynyl. In certain embodiments, $Y^1$ is —C≡CH. In certain embodiments, $Y^1$ is —C≡C—($C_{1-6}$ alkylene)-$OR^4$. In certain embodiments, $Y^1$ is —C≡C—($C_{1-6}$ alkylene)-O—($C_{1-2}$ alkyl). In certain embodiments, $Y^1$ is —C≡C—$CH_2$—O—$CH_3$. In certain embodiments, $Y^1$ is $C_{2-6}$ alkynyl.

In certain embodiments, $Y^1$ is a 2-8 membered heteroalkyl optionally substituted by a 6-10 membered aryl or a 3-10 membered heterocyclyl. In certain embodiments, $Y^1$ is —($C_{1-3}$ alkylene)-O-(5-6 membered heteroaryl). In certain embodiments, $Y^1$ is a 3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is furanyl, pyrrolyl, thiophenyl, imidazolyl, pyrazolyl, oxazolyl, or thiazolyl.

The description above describes multiple embodiments relating to compounds of Formula IV. The patent application specifically contemplates all combinations of the embodiments.

Another aspect of the invention provides a compound of Formula V:

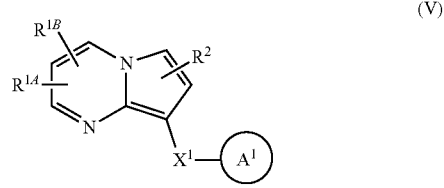

or a pharmaceutically acceptable salt thereof, wherein:
$R^{1A}$ is ($C_{1-4}$ alkylene)-(2-6 membered heteroalkyl), $C_{1-4}$ haloalkyl, or $C_{2-4}$ alkyl;
$R^{1B}$ is $C_{1-4}$ alkyl;
$R^2$ is hydrogen, $C_{1-4}$ alkyl, or $C_{1-4}$haloalkyl;
$X^1$ is a carbonyl-containing linker selected from —C(O)N(H)-ψ, —C(O)N(H)($C_{1-6}$ haloalkylene)-ψ, and —C(O)N(H)($C_{3-6}$ cycloalkylene)-ψ; where ψ is a bond to $A^1$; and
$A^1$ is a $C_{3-10}$ cycloalkyl that is (i) substituted with $C_{1-6}$ alkoxyl and (ii) optionally substituted with 1 or 2 $C_{1-4}$ alkyl groups.

Definitions of the variables in Formula V above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, $X^1$ is —C(O)N(H)-ψ. In certain embodiments, $A^1$ is a cyclohexyl that is (i) substituted with $C_{1-6}$ alkoxyl. In certain embodiments, $R^{1B}$ is methyl.

The description above describes multiple embodiments relating to compounds of Formula V. The patent application specifically contemplates all combinations of the embodiments.

Another aspect of the invention provides a compound of Formula VI:

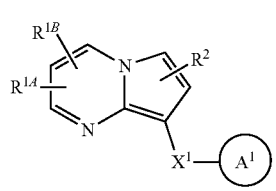

(VI)

or a pharmaceutically acceptable salt thereof, wherein:
$R^{1A}$ is —($C_{1-4}$ alkylene)-(2-6 membered heteroalkyl), $C_{1-4}$ haloalkyl, or $C_{1-4}$ alkyl;
$R^{1B}$ is $C_{1-4}$ alkyl;
$R^2$ is hydrogen, $C_{1-4}$ alkyl, or $C_{1-4}$haloalkyl;
$R^3$ and $R^5$ each represent independently for each occurrence hydrogen or $C_{1-4}$ alkyl;
$X^1$-$A^1$ is one of the following:
  $X^1$ is —C(O)N(H)C($C_{1-6}$ alkyl)(H)-$A^1$, —C(O)N(H)C($C_{1-6}$ alkyl)(H)—($C_{3-6}$ cycloalkylene)-$A^1$, or —C(O)N(H)($C_{1-3}$ alkylene)-($C_{3-6}$ cycloalkylene)-$A^1$; ψ is a bond to $A^1$; and then $A^1$ is a cyclic group selected from a 3-14 membered saturated carbocyclyl, a 5-14 membered partially unsaturated carbocyclyl, a 3-16 membered heterocyclyl, or $C_{10}$ aryl, each of which is substituted by 0, 1, or 2 occurrences of $Y^1$; or $A^1$ is $C_{6-10}$ aryl substituted by 1 or 2 occurrences of $Y^1$; or
  $X^1$ is —C(O)N(H)($C_{1-6}$ alkylene substituted with hydroxyl or $C_{3-6}$ carbocyclyl)-ψ, —C(O)N(H)C($C_6$ aryl)(H)—($C_{1-6}$ alkylene)-ψ, or —C(O)N(H)C($C_6$ aryl)($C_{1-6}$ alkyl)-iv; iv is a bond to $A^1$; and then $A^1$ is a cyclic group selected from a 3-14 membered saturated carbocyclyl, a 5-14 membered partially unsaturated carbocyclyl, a 3-16 membered heterocyclyl, or $C_{6-10}$ aryl, each which is substituted by 0, 1, or 2 occurrences of $Y^1$; and
$Y^1$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, —O—($C_{1-8}$ haloalkyl), cyano, azido, —N($R^3$)$_2$, N($R^3$)C(O)—($C_{1-6}$ alkyl), —($C_{1-6}$ alkylene)-CO$_2$R$^3$, —CO$_2$R$^3$, —C(O)R$^5$, —C(O)N(R$^3$)$_2$, 3-10 membered heterocyclyl, 6-10 membered aryl, or $C_{3-7}$ cycloalkyl.

Definitions of the variables in Formula VI above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, $X^1$ is —C(O)N(H)C($C_{1-6}$ alkyl)(H)-$A^1$, —C(O)N(H)C($C_{1-6}$ alkyl)(H)—($C_{3-6}$cycloalkylene)-$A^1$, —C(O)N(H)($C_{1-3}$ alkylene)-($C_{3-6}$ cycloalkylene)-$A^1$, ψ is a bond to $A^1$; and then $A^1$ is a cyclic group selected from a 3-14 membered saturated carbocyclyl, a 5-14 membered partially unsaturated carbocyclyl, a 3-16 membered heterocyclyl, or is $C_{10}$ aryl, each of which is substituted by 0, 1, or 2 occurrences of $Y^1$, or $A^1$ is $C_{6-10}$ aryl substituted by 1 or 2 occurrences of $Y^1$. In certain other embodiments, $X^1$ is —C(O)N(H)($C_{1-6}$ alkylene substituted with hydroxyl or $C_{3-6}$ carbocyclyl)-ψ, —C(O)N(H)C($C_6$ aryl)(H)—($C_{1-6}$ alkylene)-ψ, or —C(O)N(H)C($C_6$ aryl)($C_{1-6}$ alkyl)-ψ; ψ is a bond to $A^1$; and then $A^1$ is a cyclic group selected from a 3-14 membered saturated carbocyclyl, a 5-14 membered partially unsaturated carbocyclyl, a 3-16 membered heterocyclyl, or $C_{6-10}$ aryl, each of which is substituted by 0, 1, or 2 occurrences of $Y^1$.

In certain embodiments, $Y^1$ represents, independently for each occurrence, $C_{1-6}$ alkyl, $C_{3-6}$ cycloalkyl, halogen, $C_{1-6}$haloalkyl, $C_{1-6}$ hydroxyalkyl, hydroxyl, $C_{1-6}$ alkoxyl, —O—($C_{1-8}$ haloalkyl), 3-10 membered heterocyclyl, 6-10 membered aryl, or $C_{3-7}$ cycloalkyl.

The description above describes multiple embodiments relating to compounds of Formula VI. The patent application specifically contemplates all combinations of the embodiments.

In yet other embodiments, the compound is one of the following or a pharmaceutically acceptable salt thereof:

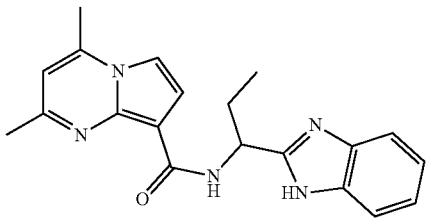

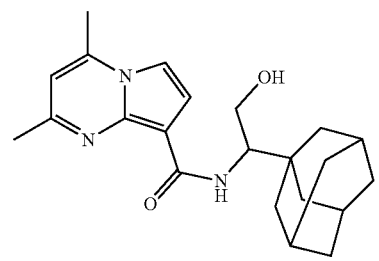

In certain embodiments, the compound is a compound described in the Examples, or a pharmaceutically acceptable salt thereof. In certain other embodiments, the compound is one of the compounds listed in Table 1 or 2 below or a pharmaceutically acceptable salt thereof. In certain other embodiments, the compound is one of the compounds listed in Table 1, 2, or 3 or a pharmaceutically acceptable salt thereof. In certain other embodiments, the compound is one of the compounds listed in Table 4 or a pharmaceutically acceptable salt thereof.

TABLE 1

| No. | R^1-A | R^1-B | R^2 | X^1 | A^1 |
|---|---|---|---|---|---|
| I-1 | 4-fluoro-phenyl | methyl | H | —C(O)N(H)—ψ | |
| I-2 | 3-pyridinyl | methyl | H | —C(O)N(H)—ψ | |
| I-3 | 3-pyridinyl | ethyl | H | —C(O)N(H)—ψ | |
| I-4 | 3-pyridinyl | methyl | H | —C(O)N(H)—ψ | |
| I-5 | 3-pyridinyl | methyl | H | —C(O)N(H)—ψ | |
| I-6 | 2-thiophenyl | methyl | H | —C(O)N(H)—ψ | |
| I-7 | 4-piperidinyl | methyl | H | —C(O)N(H)—ψ | |
| I-8 | 2-isooxazolyl | methyl | H | —C(O)N(H)—ψ | |
| I-9 | 3-furanyl | methyl | H | —C(O)N(H)—ψ | |
| I-10 | 2-pyridinyl | methyl | H | —C(O)N(H)—ψ | |

TABLE 1-continued

| No. | R$^{1-A}$ | R$^{1-B}$ | R$^2$ | X$^1$ | A$^1$ |
|---|---|---|---|---|---|
| I-11 | —C(Me)$_2$OH | methyl | H | —C(O)N(H)—ψ | spiro[3.3]heptanyl group |
| I-12 | 3-tetrahydropyranyl | methyl | H | —C(O)N(H)—ψ | isobutyl-cyclopropyl group |
| I-13 | 3-pyridinyl | methyl | H | —C(O)N(H)(CH$_2$)$_2$—ψ | tert-butyl-(oxabicyclic) group |
| I-14 | 4-fluoro-phenyl | methyl | H | —C(O)N(H)(CH$_2$)$_2$—ψ | tert-butyl-(oxabicyclic) group |
| I-15 | 3-pyridinyl | methyl | H | —C(O)N(H)(CH$_2$)$_2$—ψ | 4-isopropoxyphenyl group |
| I-16 | 4-fluoro-phenyl | methyl | H | —C(O)N(H)(CH$_2$)$_2$—ψ | 5-(furan-2-yl)pyridin-2-yl group |
| I-17 | 2-isooxazolyl | methyl | H | —C(O)N(H)(CH$_2$)$_2$—ψ | tert-butyl-cyclopropyl group |
| I-18 | 4-piperidinyl | methyl | H | —C(O)N(H)(CH$_2$)$_2$—ψ | tert-butyl-(2-methoxycyclopropyl) group |
| I-19 | morpholinyl | methyl | H | —C(O)N(H)(CH$_2$)$_2$—ψ | 4-isopropoxyphenyl group |
| I-20 | 3-pyridinyl | methyl | H | —C(O)N(H)(CH$_2$)$_2$—ψ | 4-propoxycyclohexyl group |

TABLE 1-continued

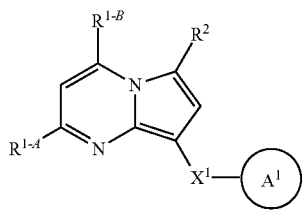

| No. | R$^{1-A}$ | R$^{1-B}$ | R$^2$ | X$^1$ | A$^1$ |
|---|---|---|---|---|---|
| I-21 | 3-pyridinyl | methyl | H | —C(O)N(H)(CH$_2$)$_2$—ψ | 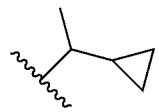 [SMILES: *C(C)C1CC1] |
| I-22 | —C(Me)$_2$OH | methyl | H | —C(O)N(H)(CF$_3$)—ψ | 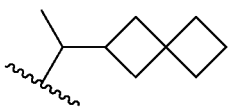 [SMILES: *C(C)C1CC2(CCC2)C1] |
| I-23 | —C(Me)$_2$CN | methyl | H | —C(O)N(H)(CF$_3$)—ψ | cyclobutyl |
| I-24 | 4-pyrrolidinyl | methyl | H | —C(O)N(H)(CF$_3$)—ψ | cyclopropyl |
| I-25 | 3-pyridinyl | methyl | H | —C(O)N(H)(CF$_3$)—ψ | 2-thiophenyl |
| I-26 | 3-pyridinyl | methyl | H | —C(O)N(H)(CF$_3$)—ψ | 2-thiazolyl |
| I-27 | 2-pyridinyl | methyl | H | —C(O)N(H)(CF$_3$)—ψ | 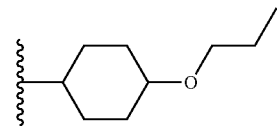 |
| I-28 | methyl | —CN | H | —C(O)N(H)(CF$_3$)—ψ | 2-thiophenyl |
| I-29 | methyl | —CN | H | —C(O)N(H)(CF$_3$)—ψ | cyclopropyl |
| I-30 | —CN | methyl | H | —C(O)N(H)(CF$_3$)—ψ | 2-thiophenyl |
| I-31 | —CN | methyl | H | —C(O)N(H)(CF$_3$)—ψ | cyclopropyl |
| I-32 | methyl | cyclo-propyl | H | —C(O)N(H)(CF$_3$)—ψ | 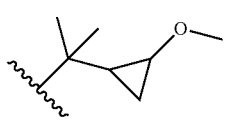 [SMILES: *C(C)(C)C1CC1OC] |
| I-33 | methyl | cyclo-propyl | H | —C(O)N(H)(CF$_3$)—ψ | 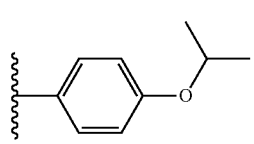 [SMILES: *c1ccc(OC(C)C)cc1] |
| I-34 | 3-pyridinyl | methyl | H | —C(O)N(H)C(O)—ψ | 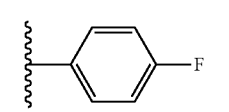 [SMILES: *c1ccc(F)cc1] |
| I-35 | 3-pyridinyl | methyl | H | —C(O)N(H)C(O)—ψ | 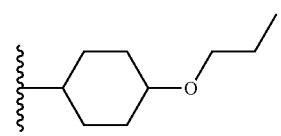 |
| I-36 | 4-tetrahydropyranyl | methyl | H | —C(O)N(H)C(O)—ψ |  |

TABLE 1-continued

| No. | R$^{1-A}$ | R$^{1-B}$ | R$^2$ | X$^1$ | A$^1$ |
|---|---|---|---|---|---|
| I-37 | 2-thiophenyl | methyl | H | —C(O)N(H)C(O)—ψ | cyclohexyl-O-isopropyl |
| I-38 | 2-furanyl | methyl | H | —C(O)N(H)C(O)—ψ | dimethyl-cyclopropyl |
| I-39 | 2-pyridinyl | methyl | H | —C(O)N(H)C(O)—ψ | spiro[3.3]heptyl |

Where in Table 1, ψ is a bond to A$^1$.

TABLE 2

| No. | Compound Structure |
|---|---|
| II-1 | (structure) |
| II-2 | (structure) |
| II-3 | (structure) |
| II-4 | (structure) |
| II-5 | (structure) |
| II-6 | (structure) |
| II-7 | (structure) |

TABLE 2-continued

| No. | Compound Structure |
|---|---|
| II-8 | 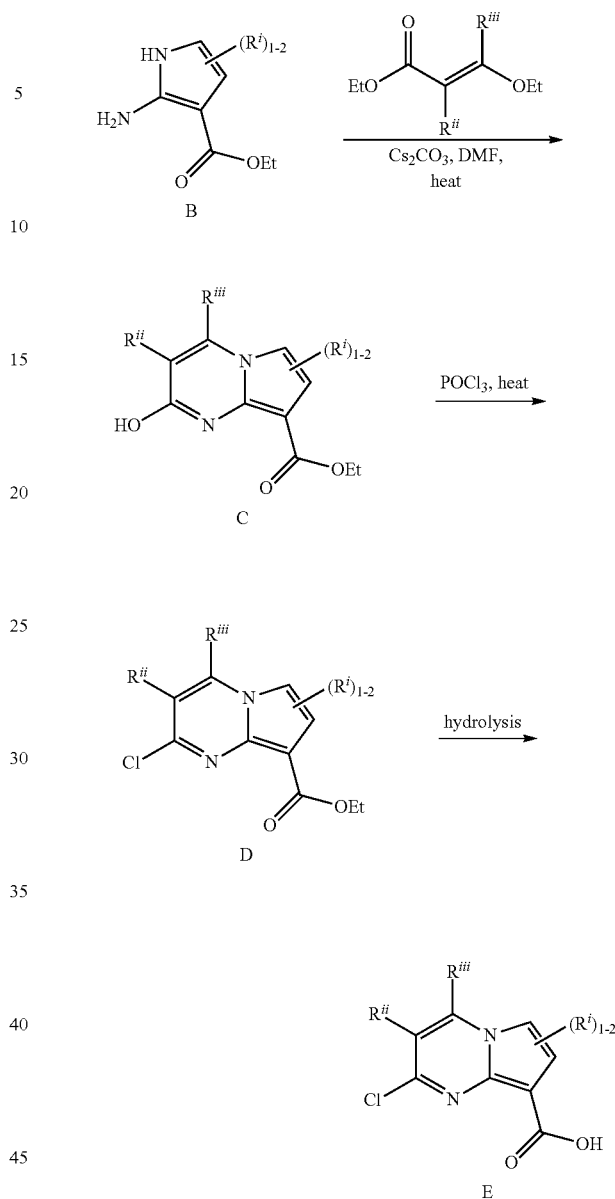 |
| II-9 | 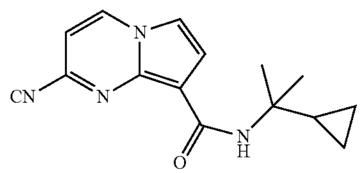 |
| II-10 | 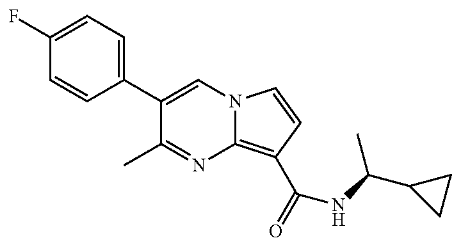 [SMILES: Cc1nc2c(C(=O)N[C@@H](C)C3CC3)ccn2cc1-c1ccc(F)cc1] |

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme 1 depicts an exemplary procedure for preparing substituted pyrrolo[1,2-a]pyrimidine compounds. In the first step, 2-amino-1H-pyrrole-3-carboxamide ($R^i$=H) A is treated with methylsulfonic acid in ethanol to afford ethyl-2-amino-1H-pyrrole-3-carboxylate ($R^i$=H) B which is condensed with ethyl (E)-3-ethoxybut-2-enoate ($R^{ii}$=H, $R^{iii}$=Me) in DMF and Cs$_2$CO$_3$ to afford ethyl 2-hydroxy-4-methylpyrrolo[1,2-a]pyrimidine-8-carboxylate C. Heating of carboxylate C with phosphoryl trichloride affords ethyl 2-chloro-4-methylpyrrolo[1,2-a]pyrimidine-8-carboxylate D. Hydrolysis of D provides 2-chloro-4-methylpyrrolo[1,2-a]pyrimidine-8-carboxylic acid E.

SCHEME 1

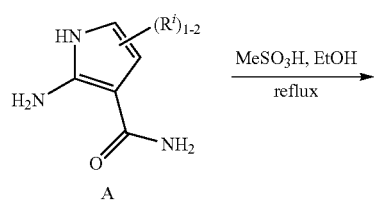

The synthetic route illustrated in Scheme 2 depicts an exemplary procedure for preparing substituted pyrrolo[1,2-a]pyrimidinyl carboxamide compounds. In the first step, Pd-catalyzed coupling of chloro-carboxylic ester D with a variety of aryl or heteroaryl boronic acids, halides or trialkylstannyl reagents may be accomplished using standard Pd-catalyzed coupling procedures (such as Pd(dppf)$_2$Cl$_2$.CH$_2$Cl$_2$ in DME in the presence of K$_3$PO$_4$) to afford the substituted carboxylic ester F. Alternatively, substitution of chloro-carboxylic ester D with a primary or secondary amine affords the substituted carboxylic ester F. Hydrolysis of the carboxylic acid under basic or neutral conditions then affords carboxylic acid G. In the final step, coupling of carboxylic acid G with a variety of substituted aromatic or aliphatic amines may be accomplished using standard peptide coupling procedures (such as HATU and/or HOBT in DMF in the presence of DIPEA) to afford carboxamide H.

SCHEME 2

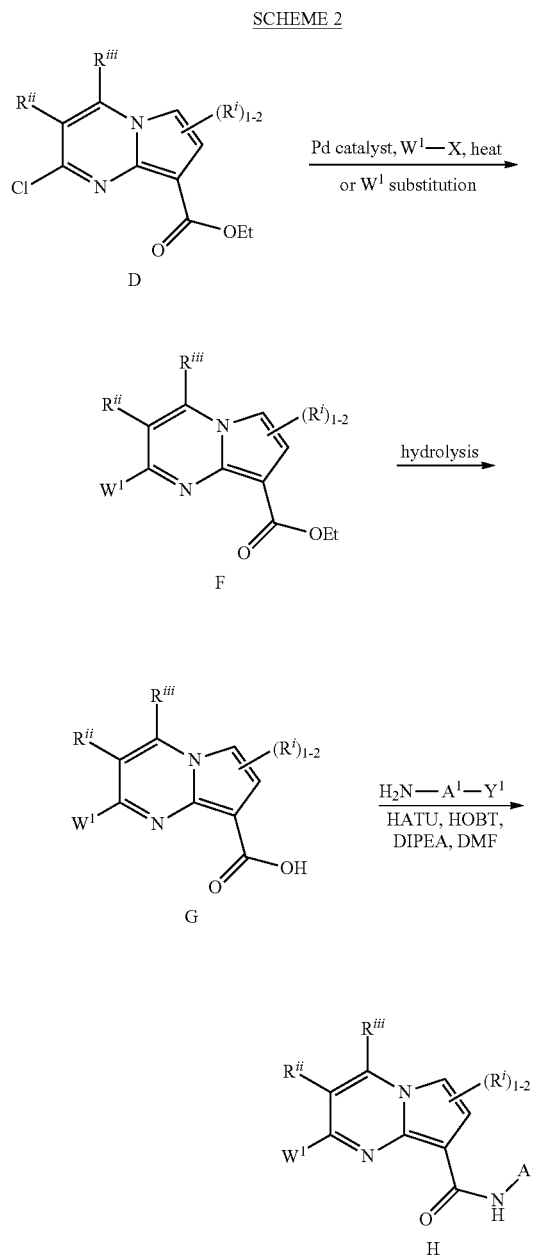

SCHEME 3

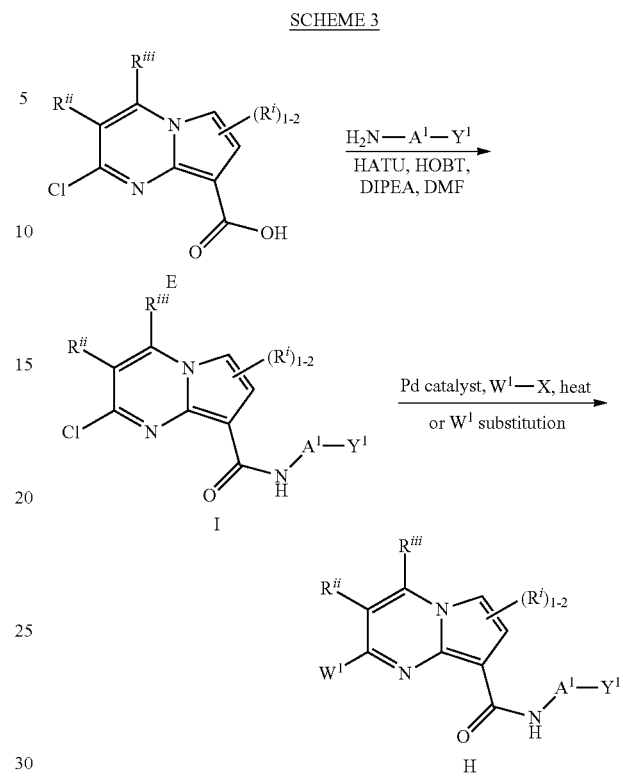

The synthetic route illustrated in Scheme 3 depicts an alternative exemplary procedure for preparing substituted pyrrolo[1,2-a]pyrimidinyl carboxamide compounds. In the first step, coupling of carboxylic acid E with a variety of substituted aromatic or aliphatic amines may be accomplished using standard peptide coupling procedures, such as HATU and/or HOBT in DMF in the presence of DIPEA to afford chloro amide I. In the final step, Pd-catalyzed coupling of chloro amide I with a variety of aryl or heteroaryl boronic acids, halides or trialkylstannyl reagents may be accomplished using standard Pd catalyzed coupling procedures (such as $Pd(dppf)_2Cl_2 \cdot CH_2Cl_2$ in DME in the presence of $K_3PO_4$) to afford the substituted carboxamide H. Alternatively, substitution of chloro-carboxylic ester I with a primary or secondary amine affords the substituted carboxamide H.

The reaction procedures in Schemes 1-3 are contemplated to be amenable to preparing a wide variety of substituted pyrrolo[1,2-a]pyrimidinyl carboxamide compounds having different substituents at the $A^1$ and $Y^1$ positions. Furthermore, if a functional group that is part of the $A^1$ and/or $Y^1$ would not be amenable to a reaction condition described in Scheme 2, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, $2^{nd}$ ed.; Wiley: New York, 1991, for further description of protecting chemistry and strategies. In certain other embodiments, a functional group in substituent $A^1$ and $Y^1$ can converted to another functional group using standard functional group manipulation procedures known in the art. See, for example, "Comprehensive Organic Synthesis" (B. M. Trost & I. Fleming, eds., 1991-1992).

III. Therapeutic Applications

The invention provides methods of treating medical disorders, such as Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma, using the substituted pyrrolo[1,2-a]pyrimidinyl carboxamide and related compounds, and pharmaceutical compositions described herein. Treatment methods include the use of substituted pyrrolo[1,2-a]pyrimidinyl carboxamide or related organic compounds described herein as stand-alone therapeutic agents and/or as part of a combination therapy with another therapeutic agent. Although not wishing to be bound by a particular theory, it is understood that substituted pyrrolo[1,2-a]pyrimidinyl carboxamide and related organic compounds described herein may activate glucocerebrosidase (Gcase).

Methods of Treating Medical Disorders

One aspect of the invention provides a method of treating disorder selected from the group consisting of Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma. The method comprises administering to a patient in need thereof a therapeutically effective amount of a substituted pyrrolo[1,2-a]pyrimidinyl carboxamide or related organic compound described herein to treat the disorder. The compound may be a compound of Formula I, II, III, IV, V, or VI as described above in Section II.

In certain embodiments, the disorder is Gaucher disease, Parkinson's disease, Lewy body disease, dementia, or multiple system atrophy. In certain other embodiments, the disorder is Gaucher disease. In certain embodiments, the disorder is Parkinson's disease. In certain embodiments, the disorder is Lewy body disease. In certain embodiments, the disorder is dementia. In certain embodiments, the disorder is a dementia selected from the group consisting of Alzheimer's disease, frontotemporal dementia, and a Lewy body variant of Alzheimer's disease. In certain embodiments, the disorder is multiple system atrophy.

In certain embodiments, the disorder is an anxiety disorder, such as panic disorder, social anxiety disorder, or generalized anxiety disorder.

Efficacy of the compounds in treating Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma may be evaluated by testing the compounds in assays known in the art for evaluating efficacy against these diseases and/or, e.g., for activation of glucocerebrosidase (Gcase), as discussed in the Examples below.

In certain embodiments, the patient is a human.

In certain embodiments, the compound is one of the generic or specific compounds described in Section II, such as a compound of Formula I, a compound embraced by one of the further embodiments describing definitions for certain variables of Formula I, a compound of Formula I-A, or a compound embraced by one of the further embodiments describing definitions for certain variables of Formula I-A. In certain other embodiments, the compound is a compound of Formula II or II-A or a compound embraced by one of the further embodiments describing definitions for certain variables of Formula II or II-A.

The description above describes multiple embodiments relating to methods of treating various disorders using certain substituted pyrrolo[1,2-a]pyrimidinyl carboxamide or related organic compounds. The patent application specifically contemplates all combinations of the embodiments. For example, the invention contemplates methods for treating Gaucher disease, Parkinson's disease, Lewy body disease, dementia, or multiple system atrophy by administering a therapeutically effective amount of a compound of Formula I-A.

Medical Use and Preparation of Medicament

Another aspect of the invention relates to compounds and compositions described herein for use in treating a disorder described herein. Another aspect of the invention pertains to use of a compound or composition described herein in the preparation of a medicament for treating a disorder described herein.

Combination Therapy

The invention embraces combination therapy, which includes the administration of a substituted pyrrolo[1,2-a]pyrimidinyl carboxamide or related compound described herein (such as compound of Formula I, I-A, II, II-A, III, IV, V, or VI) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents.

Exemplary second agents for use in treating Gaucher disease include, for example, taliglucerase alfa, velaglucerase alfa, eliglustat, and miglustat. Exemplary second agents for use in treating Parkinson's disease include, for example, a glucosylceramide synthase inhibitor (e.g., ibiglustat), an acid ceramidase inhibitor (e.g., carmofur), an acid sphingomyelinase activator, levodopa, pramipexole, ropinirole, rotigotine, apomorphine, or salt thereof. Additional glucosylceramide synthase inhibitors for use in combination therapies include, for example, those described in International Patent Application Publications WO 2015/089067, WO 2014/151291, WO 2014/043068, WO 2008/150486, WO 2010/014554, WO 2012/129084, WO 2011/133915, and WO 2010/091164; U.S. Pat. Nos. 9,126,993, 8,961,959, 8,940,776, 8,729,075, and 8,309,593; and U.S. Patent Application Publications US 2014/0255381 and US 2014/0336174; each of which are hereby incorporated by reference. Additional acid ceramidase inhibitors for use in combination therapies include, for example, those described in International Patent Application Publications WO 2015/173168 and WO 2015/173169, each of which are hereby incorporated by reference.

IV. Pharmaceutical Compositions

The invention provides pharmaceutical compositions comprising a substituted pyrrolo[1,2-a]pyrimidinyl carboxamide or related organic compound described herein, such as a compound of Formula I, I-A, II, II-A, III, IV, V, or VI. In certain embodiments, the pharmaceutical compositions preferably comprise a therapeutically-effective amount of one or more of the substituted pyrrolo[1,2-a]pyrimidinyl carboxamide or related organic compounds described above, formulated together with one or more pharmaceutically acceptable carriers. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration.

The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

V. Kits for Use in Medical Applications

Another aspect of the invention provides a kit for treating a disorder. The kit comprises: i) instructions for treating a medical disorder, such as Gaucher disease, Parkinson's disease, Lewy body disease, dementia, or multiple system atrophy; and ii) a substituted pyrrolo[1,2-a]pyrimidinyl carboxamide or related organic compound described herein, such as a compound of Formula I, I-A, II, II-A, III, IV, V, or VI. The kit may comprise one or more unit dosage forms containing an amount of a substituted pyrrolo[1,2-a]pyrimidinyl carboxamide or related organic compound described herein, such as a compound of Formula I, that is effective for treating said medical disorder, e.g., Gaucher disease, Parkinson's disease, Lewy body disease, dementia, or multiple system atrophy.

The description above describes multiple aspects and embodiments of the invention, including substituted pyrrolo[1,2-a]pyrimidinyl carboxamide and related organic compounds, compositions comprising a substituted pyrrolo[1,2-a]pyrimidinyl carboxamide or related organic compounds, methods of using the substituted pyrrolo[1,2-a]pyrimidinyl carboxamide or related organic compounds, and kits. The patent application specifically contemplates all combinations and permutations of the aspects and embodiments. For example, the invention contemplates treating Gaucher disease, Parkinson's disease, Lewy body disease, dementia, or multiple system atrophy in a human patient by administering a therapeutically effective amount of a compound of Formula I-A. Further, for example, the invention contemplates a kit for treating Gaucher disease, Parkinson's disease, Lewy body disease, dementia, or multiple system atrophy, the kit comprising instructions for treating Gaucher disease, Parkinson's disease, Lewy body disease, dementia, or multiple system atrophy and ii) a substituted pyrrolo[1,2-a]pyrimidinyl carboxamide or related organic compound described herein, such as a compound of Formula I-A.

EXAMPLES

The invention now being generally described, will be more readily understood by reference to the following examples, which are included merely for purposes of illustration of certain aspects and embodiments of the present invention, and are not intended to limit the invention. Standard abbreviations have been used in the Examples in certain instances, such as the abbreviation "RT" for room temperature, and the abbreviation "h" for hours.

Example 1 Preparation of
Pyrrolo[1,2-a]Pyrimidine-8-Carboxamide
Compounds

Pyrrolo[1,2-a]pyrimidine-8-carboxamide compounds were prepared based on general procedures described in Part I below. Exemplary procedures for preparing specific amine compounds useful as synthetic intermediates in the preparation of certain substituted pyrrolo[1,2-a]pyrimidine-8-carboxamide compounds are provided in Part II below. Exemplary procedures for preparing specific carboxylic acid compounds useful as synthetic intermediates in the preparation of certain substituted pyrrolo[1,2-a]pyrimidine-8-carboxamide compounds are provided in Part III below. Specific pyrrolo[1,2-a]pyrimidine-8-carboxamide compounds prepared according to the general procedures are provided in Part IV below.

Part I—General Procedures

General Procedure A: Preparation of Amide by Coupling of a Carboxylic Acid Compound with an Amine Compound To a stirred solution of carboxylic acid compound (1.0 equivalent), HATU (1.5 equivalents), and DIPEA (3.75 equivalents) in DCM or DMF (~4 mL/0.2 mmol) was added amine compound (1.25-2.0 equivalents). The reaction mixture was stirred at room temperature for 4-16 hours, and then washed with saturated aqueous $NaHCO_3$ solution (5 mL/0.2 mmol), aqueous citric acid solution (5 mL/0.2 mmol) and brine (5 mL/0.2 mmol). The combined extracts were dried over anhydrous $Na_2SO_4$, filtered and concentrated in vacuo. The resulting crude material was purified by silica gel column chromatography or preparatory HPLC to give the amide compound.

General Procedure B: Conversion of Carboxylic Ester Compound to Carboxylic Acid Compound To a solution of carboxylic ester (1.0 equivalent) in EtOH (5.0 mL/1.0 mmol) and water (0-3.0 mL/1.0 mmol) was added NaOH (2.0-5.0 equivalents) and the mixture was heated at 80° C. for 2 hours and then concentrated. To the concentrate, 6N HCl solution was added to adjust the pH to 5~6 and then the mixture was stirred for 10 minutes and subsequently filtered. The resulting solid was collected and dried to give the carboxylic acid compound.

General Procedure B*: Conversion of Carboxylic Ester Compound to Carboxylic Acid Compound To a solution of carboxylic ester (1.0 equivalent) in EtOH (5.0 mL/1.0 mmol) and water (0-3.0 mL/1.0 mmol) was added NaOH (2.0-5.0 equivalents) and the mixture was heated at 80° C. for 2 hours and then concentrated. To the concentrate, 6N HCl solution was added to adjust the pH to 5~6 and then the mixture was stirred for 10 minutes and subsequently filtered. The resulting solid was collected and dried to give the carboxylic acid compound.

Alternatively, to a solution of carboxylic ester (1.0 equivalent) in THF (5.0 mL/1.0 mmol) was added LiOH (1M solution, 3 equivalents) and the mixture was stirred at 60° C. for 1-2 h and then the pH was adjusted to 7 with 1 N HCl. The resulting solution was lyophilized to afford the crude carboxylic acid.

General Procedure C: Preparation of a Heteroaryl Amine Using Substitution Between an Organohalide and Aliphatic Amine A solution of organochloride (1.0 equivalent), amine hydrochloride (1.3 equivalent) and DIEA (3.0 equivalents) in DMF (5 mL/1 mmol) was stirred at 60° C. for 5 h, then, cooled to RT and diluted with EA (30 mL/mmol). The resulting mixture was washed with $H_2O$ (10 mL/mmol×3) and the orgc phases were dried over anhydrous $Na_2SO_4$ and filtered. The filtrate was concentrated in vacuo, and the resulting residue was purified by silica gel column chromatography to afford the amine compound.

General Procedure D: Preparation of Coupled Aryl and Heteroaryl Groups Using Suzuki-Catalyzed Coupling Conditions Between an Organoboronic Acid or Ester and an Aryl Halide or Heteroaryl Halide A suspension of heteroaryl chloride (1 equivalent), organoboronic acid or organoboronic ester (1.2 equivalents), $K_3PO_4$ (3.0 equivalents) and Pd(dppf)$Cl_2$.DCM (5 mol %) or $Pd_2(dba)_3$ (10 mol %) in DME or 1,4-dioxane (40 mL/mmol) was stirred at 70-100° C. for 2-6 hours under $N_2$. Then, the reaction mixture was quenched with water (30 mL/mmol) and resulting mixture extracted with EtOAc (30 mL/mmol×3). The organic phases were washed with water (30 mL/mmol) and brine (30 mL/mmol), dried over anhydrous $Na_2SO_4$ and filtered. The filtrate was concentrated in vacuo, and the resulting residue was purified by silica gel column chromatography to afford the coupled ring system.

General Procedure E: Preparation of Coupled Aryl and Heteroaryl Groups Using Buchwald-Catalyzed Coupling Conditions Between an Organohalide and Organotin Reagent A solution of organochloride (1.0 equivalent) and organotin reagent (1.0 equivalent) in 1,4-dioxane (20 mL/mmol) was stirred and purged with $N_2$ three times at RT. Then Pd(dppf)$Cl_2$.DCM (10 mol %) was quickly added under a $N_2$ atmosphere to the reaction mixture, followed by additional purging with $N_2$ (×3) and the resulting mixture was stirred at 120° C. for overnight. Next, the reaction mixture was cooled to RT and then quenched with water (20 mL/mmol). The resulting mixture was extracted with EA (20 mL/mmol×3), and the organic phases were dried over anhydrous $Na_2SO_4$ and filtered and concentrated in vacuo. The resulting residue was purified by silica gel column chromatography or preparative-TLC to afford the coupled ring system.

Part II Preparation of Specific Amine Compounds

Exemplary procedures for preparing specific amine compounds useful in the preparation of certain pyrrolo[1,2-a] pyrimidine-8-carboxamide compounds are provided below.

2-Cyclopropylpropan-2-amine

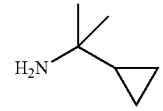

To a solution of 1-cyclopropylethan-1-one (1.0 g, 11.2 mmol) in anhydrous $Et_2O$ (5 mL) was added a solution of MgMeBr (4.4 mL, 13.2 mmol) at a rate suitable to maintain gentle reflux of the solvent, to afford the expected alcoholate as a white precipitate. The reaction mixture was maintained refluxing for an additional 30 minutes, then stirred at RT overnight, and quenched with sat. $NH_4Cl$ solution (5 mL). The resulting mixture was extracted with $Et_2O$ (5 mL), and the combined organic layers were washed with brine (5 mL), dried over $Na_2SO_4$, and filtered. The filtrate was concentrated in vacuo to afford 2-cyclopropylpropan-2-ol as a pale yellow oil (1.1 g, 92%). $^1H$ NMR (500 MHz, CDCl$_3$) δ 1.18 (s, 6H), 0.97-0.94 (m, 1H), 0.39-0.30 (m, 4H).

To a stirred solution of 2-cyclopropylpropan-2-ol (1.1 g, 11.2 mmol) in CHCl$_3$ (10 mL) was added NaN$_3$ (1.08 g, 15.8 mmol) and Cl$_3$CO$_2$H (2.8 g, 17.2 mmol) successively at RT. The mixture was stirred at RT for 2 h, washed with two portions of 10% aqueous $NaHCO_3$ solution (5 mL), brine (10 mL), dried over $Na_2SO_4$ and filtered. The filtrate was concentrated in vacuo to afford (2-azidopropan-2-yl)cyclopropane as a clear oil (1.2 g, 85%).

To a suspension of LiAlH$_4$ (670 mg, 17.7 mmol) in anhydrous diethyl ether (6 mL) was added a solution of (2-azidopropan-2-yl)cyclopropane (1.2 g, 11.2 mmol) in 4 mL of anhydrous diethyl ether at a rate such that reflux was maintained. After refluxing for 2 h, the reaction mixture was cooled to 0° C., quenched by careful addition of 0.67 mL of $H_2O$, 0.67 mL of 15% NaOH solution, and 2.0 mL of $H_2O$, successively. The solid was filtered off and the filtrate was concentrated in vacuo to afford 2-cyclopropylpropan-2-amine as a clear oil (1.0 g, 90%).

[1,1'-Bi(cyclopropan)]-1-amine

To a solution of cyclopropanecarbonitrile (1.0 g, 15 mmol) in diethyl ether (15 mL) was added Ti(OiPr)$_4$ (4.66 g, 16.4 mmol) and the solution was cooled to −78° C. and EtMgBr solution (3 M in ether, 30 mmol) was slowly added. After 10 minutes at −78° C., the slurry was allowed to warm up to RT and stirred for 1 h. BF$_3$.OEt$_2$ (4.26 g, 30 mmol) was added and the mixture was stirred at RT for 18 h. To this mixture, 2N NaOH (30 mL) was slowly added at 0° C. The organic phase was separated and extracted with 2N HCl (30 mL). The aqueous phase was concentrated in vacuo and the residue was triturated in diethyl ether to afford [1,1'-bi(cyclopropan)]-1-amine (0.5 g, 34%) as the hydrochloride salt.

1-Cyclopropyl-3-methylbutan-1-amine

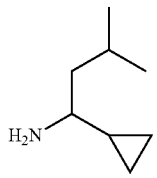

A mixture of cyclopropanecarbonitrile (5.0 g, 74.6 mmol) and iBuMgBr (326 mg, 2.4 mmol) in diethyl ether (10 mL) was stirred at reflux for 5 h, quenched with sat. NH$_4$Cl solution (10 mL) and extracted with EtOAc (10 mL×3). The combined organic layers were dried over anhydrous Na$_2$SO$_4$ and filtered. The filtrate was concentrated in vacuo to give crude imine (7.5 g, 80%), which was used directly in the next step. A mixture of imine (7.5 g, 60 mmol) and NaBH$_4$ (2.28 g, 60 mmol) in MeOH (50 mL) was stirred at RT for 3 h, quenched with water (50 mL) and extracted with EtOAc (50 mL×3). The organic layers were dried over anhydrous Na$_2$SO$_4$, and filtered. The filtrate was concentrated in vacuo, and the residue was dissolved in HCl/dioxane (50 mL, 4M). The resulting mixture was stirred at RT for 30 min and concentrated in vacuo. Diethyl ether (50 mL) was added resulting in a precipitate, which was filtered and dried to give 1-cyclopropyl-3-methylbutan-1-amine (1.5 g, 16%) as a pale yellow solid.

2-(Spiro[3.3]heptan-2-yl)propan-2-amine

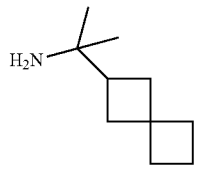

Concentrated H$_2$SO$_4$ (0.5 mL) was added dropwise to a solution of spiro[3.3]heptane-2-carboxylic acid (1 g, 7.14 mmol) in EtOH (30 mL) at 0° C. and the reaction mixture was refluxed for 20 h. After completion of the reaction, the solvent was removed and the reaction mixture was dissolved in EtOAc (150 mL). The organic layer was washed with saturated NaHCO$_3$ solution (100 mL), dried over anhydrous MgSO$_4$, and filtered. The filtrate was concentrated in vacuo to give ethyl spiro[3.3]heptane-2-carboxylate (1.2 g, 100%) as a colorless oil which was used directly in the next step. $^1$H NMR (500 MHz, CDCl$_3$) δ 4.04 (q, J=7.0 Hz, 2H), 2.94-2.78 (m, 1H), 2.14 (p, J=11.0 Hz, 4H), 1.95 (t, J=7.5 Hz, 2H), 1.85 (t, J=7.4 Hz, 2H), 1.73 (dd, J=15.0 Hz, 7.5 Hz, 2H), 1.17 (t, J=7.5 Hz, 3H).

To a solution of ethyl spiro[3.3]heptane-2-carboxylate (1.2 g, 7.14 mmol) in anhydrous THF (20 mL) at −78° C. was added dropwise a solution of MeMgBr (3.0 M in Et$_2$O; 9.52 mL, 28.56 mmol). The reaction mixture was then stirred at RT for 18 h, poured cautiously into sat. NH$_4$Cl solution (20 mL) and extracted with EtOAc (30 mL×3). The combine organic layers were washed with brine (40 mL), dried over Na$_2$SO$_4$ and filtered. The filtrate was concentrated in vacuo to give 2-(spiro[3.3]heptan-2-yl)propan-2-ol (1.0 g, 96%) as a colorless oil, which was used in the next step without further purification. $^1$H NMR (500 MHz, DMSO-d$_6$) δ 3.94 (s, 1H), 2.02-2.04 (m, 1H), 1.96 (t, J=7.0 Hz, 2H), 1.87-1.80 (m, 2H), 1.78-1.73 (m, 6H), 0.93 (s, 6H).

A stirred mixture of 2-(spiro[3.3]heptan-2-yl)propan-2-ol (1.0 g, 6.49 mmol), TMSN$_3$ (2.95 g, 25.96 mmol) and molecular sieve (100 mg) in dry CH$_2$Cl$_2$ (40 mL) at RT under Ar was treated with BF$_3$Et$_2$O (1.8 g, 12.98 mmol). After stirring for 24 h, the resulting solution was quenched with water (100 mL). The organic layer was separated, washed with saturated NaHCO$_3$ solution (30 mL), water (30 mL) and brine (30 mL), dried over anhydrous MgSO$_4$ and filtered. The filtrate was concentrated in vacuo. The resulting residue was purified by silica gel column (PE/EtOAc; 3:1) to give 2-(2-azidopropan-2-yl)spiro[3.3]heptane (1.1 g) as a colorless oil.

A mixture of 2-(2-azidopropan-2-yl)spiro[3.3]heptane (1.1 g, 6.14 mmol) and Pd/C (100 mg, 10% w/w) in MeOH (5 mL) was stirred under a H$_2$ atmosphere at room temperature for 20 hours. The catalyst was removed by filtration through a pad of celite and the filtrates were concentrated to give 2-(spiro[3.3]heptan-2-yl)propan-2-amine (580 mg, 52%) as a colorless oil. LC-MS m/z: 157.2 [M+H]$^+$.

1-Cyclopropyl-2,2,2-trifluoroethan-1-amine

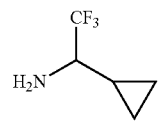

A suspension of cyclopropanecarbaldehyde (7.0 g, 100 mmol), benzylamine (11.2 g, 105 mmol) and MgSO$_4$ (62 g, 500 mmol) in DCM (200 mL) was stirred for 48 h at RT. After reaction completion the solution was filtered through celite and the filtrate was concentrated in vacuo to give N-benzyl-1-cyclopropyl methanimine as a light yellow oil (16 g, 100%). LC-MS weak MS: m/z: 159.1 [M+H]$^+$.

To a solution of N-benzyl-1-cyclopropyl methanimine (6.0 g, 37.7 mmol) in MeCN (70 mL) was added KHF$_2$ (2.35 g, 30.2 mmol), CF$_3$COOH (5.54 g, 48.6 mmol) and DMF (5 mL) and the mixture was stirred at RT. The reaction mixture was cooled to 0° C. for 5 minutes, and then TMSCF$_3$ (8.4 mL, 56.6 mmol) was added. After addition, the reaction mixture was stirred for 12 h at RT until the starting material was completely consumed (LCMS). Saturated Na$_2$CO$_3$ solution (20 mL) was added, stirred for 5 minutes and then 150 mL of water was added and the mixture was extracted with EtOAc (150 mL×3). The organic phases were combined, dried over Na$_2$SO$_4$, filtered and concentrated in vacuo. The residue was purified by flash chromatography on silica gel (DCM:MeOH; 30:1 to 5:1) to give N-benzyl-1-cyclopropyl-2,2,2-trifluoroethan-1-amine as a colorless oil (3.5 g, yield: 41%). LC-MS m/z: 230.1 [M+H]$^+$. LC-MS Purity (214 nm): 97%; $t_R$=1.82 minutes.

To a solution of N-benzyl-1-cyclopropyl-2,2,2-trifluoroethan-1-amine (3.5 g, 15.3 mmol) in MeOH (50 mL) was added 6 N HCl (4 mL) at RT. The mixture was purged with N$_2$ three times and then Pd/C (350 mg, 10%, w/w) was added quickly under N$_2$ flow. The mixture was purged with H$_2$ three more times, and stirred for 16 hours at room temperature. Pd/C was removed by filtration, and the filtrate was concentrated in vacuo to give 1-cyclopropyl-2,2,2-trifluoroethan-1-amine as a white solid (3.5 g, 100%). $^1$H NMR (500 MHz, DMSO-d$_6$) δ 9.35 (s, 3H), 3.63-3.58 (m, 1H), 1.11-1.06 (m, 1H), 0.72-0.66 (m, 4H). LC-MS m/z: 140.2 [M+H]+.

1-(4,4-Difluorocyclohexyl)ethan-1-amine

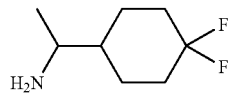

To a solution of 4,4-difluorocyclohexane-1-carboxylic acid (1.64 g, 10 mmol) and DIPEA (2.58 g, 20 mmol) in DMF (10 mL) at 0° C. was added HATU (5.7 g, 15 mmol) and the reaction mixture was stirred at 0° C. for 30 min, followed by the addition of N, O-dimethylhydroxylamine hydrochloride (970 mg, 10 mmol). The reaction mixture was allowed to warm to RT and stirred overnight, then quenched with saturated NaHCO$_3$ solution, and separated. The aqueous phase was extracted with EtOAc (100 mL×3), and the combined organic phases were dried over Na$_2$SO$_4$, filtered and concentrated in vacuo. The resulting residue was purified by silica gel chromatography (PE/EtOAc; 4:1) to afford 4,4-difluoro-N-methoxy-N-methylcyclohexane-1-carboxamide (880 mg, 42%) as a colorless oil. LC-MS m/z: 208.0 [M+H]$^+$. LCMS: $t_R$=1.58 min.

To a solution of 4,4-difluoro-N-methoxy-N-methylcyclohexane-1-carboxamide (880 mg, 4.25 mmol) in THF (12 mL) was added a solution of MeLi in 1,2-diethoxyethane (3 mol/L, 2 mL) dropwise at 0° C. After the addition was complete, the reaction mixture was allowed to warm to RT and stirred overnight, then quenched with saturated NH$_4$Cl solution and separated. The aqueous phase was extracted with EtOAc (120 mL×3), and the combined organic phases were dried over Na$_2$SO$_4$, filtered and concentrated in vacuo. The resulting residue was purified by silica gel chromatography (PE/EA=4:1) to afford 1-(4,4-difluorocyclohexyl) ethan-1-one (400 mg, 43%) as a light yellow oil. $^1$H NMR (500 MHz, CDCl$_3$) δ 2.44 (m, 1H), 2.19 (s, 3H), 2.13-2.16 (m, 2H), 1.96-1.98 (m, 2H), 1.74-1.83 (m, 4H).

A mixture of 1-(4,4-difluorocyclohexyl)ethan-1-one ((200 mg, 1.23 mmol), NH$_4$OAc (1.9 g, 24.6 mmol) and NaBH$_3$CN (388 mg, 6.15 mmol) in i-PrOH (15 mL) was stirred at RT for 4 h and then at 90° C. for 2 h. Then, the reaction mixture was poured into water (15 mL), extracted with CH$_2$Cl$_2$ (30 ml, ×3) and dried over Na$_2$SO$_4$, filtered and concentrated in vacuo. The resulting residue was purified by silica gel chromatography (EtOAc/MeOH; 10:1) to afford 1-(4,4-difluorocyclohexyl)ethan-1-amine as a colorless oil. LC-MS m/z: 164.1 [M+H]$^+$. LCMS: $t_R$=1.13 min.

2-(4-Chlorophenyl)propan-2-amine

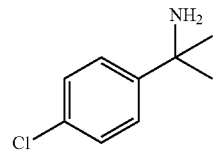

MgBrMe (3M in THF, 5 mL, 15 mmol) was added dropwise at RT to a solution of 1-(4-chlorophenyl)ethan-1-one (1.54 g, 10 mol) in Et$_2$O (60 mL). After the addition was complete the reaction mixture was stirred at RT for 12 hours and then quenched by the careful addition of saturated NH$_4$Cl solution (30 mL). The resulting mixture was stirred for 1 hour and then extracted with EtOAc (100 mL×3). The combined organic layers were dried over Na$_2$SO$_4$, filtered, concentrated in vacuo, and purified by silica gel chromatography (PE/EtOAc; 5:1) to give 2-(4-chlorophenyl)propan-2-ol (1.365 g, 80%) as a colorless oil. $^1$H NMR (400 MHz, CDCl$_3$) δ 7.42 (dd, J=6.8 Hz, 2.0 Hz, 2H). 7.29 (dd, J=6.8 Hz, 2.0 Hz, 2H), 1.78 (s, 1H), 1.56 (s, 6H).

A mixture of 2-(4-chlorophenyl)propan-2-ol (1.36 g, 8 mmol), TMSN$_3$ (2.4 g, 16 mmol) and BF$_3$.Et$_2$O (16 mL) in CH$_2$Cl$_2$ (20 mL) was stirred at RT for 2 h and quenched with saturated NaHCO$_3$ solution. The resulting mixture was separated, and the aqueous phase was extracted with CH$_2$Cl$_2$ (30 mL×3). The combined organic phases were dried over Na$_2$SO$_4$ and filtered. The filtrate was concentrated in vacuo to afford the target compound 1-(2-azidopropan-2-yl)-4-chlorobenzene as colorless oil, which was used in the next step without further purification. LC-MS m/z: 153.0 [M−N$_3$]$^+$. LCMS: Purity (254 nm): 44%; $t_R$=1.44 min.

The crude azide from the previous step was dissolved in THF (15 mL) at RT and trimethylphosphine (16 mL, 1.0 M in THF) was added. After 15 minutes, 3 mL of water was added, and the resulting mixture was stirred at RT for 2 h until the reaction was complete (monitored by LC/MS.) The solvent was removed in vacuo and the residue was diluted with water (75 mL), extracted with CH$_2$Cl$_2$, dried over sodium sulfate and filtered. The filtrate was concentrated in vacuo, and the resulting residue was purified by reversed-phase chromatography (0.05% TFA/MeCN) to give the desired product 2-(4-chlorophenyl)propan-2-amine (200 mg, 57% over two steps) as a pale oil. LC-MS m/z: 153.0 [M−NH$_2$]$^+$. LCMS: Purity (214 nm): 98%; $t_R$=1.71 min.

Part III—Preparation of Specific Carboxylic Acid Compounds

Exemplary procedures for preparing specific carboxylic acid compounds useful in the preparation of certain substituted pyrrolo[1,2-a]pyrimidine-8-carboxamide compounds are provided below.

4-Chloro-2-methylpyrrolo[1,2-a]pyrimidine-8-carboxylic acid

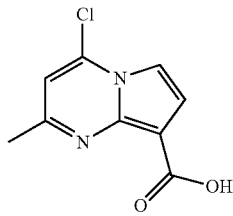

To a solution of ethyl 2-amino-1H-pyrrole-3-carboxylate (3.0 g, 19.48 mmol) in AcOH (20 mL) was added 4-methyleneoxetan-2-one (4.58 g, 54.55 mmol) in one portion at RT. The reaction mixture was stirred at 110° C. (preheated) for 2 h, cooled and concentrated in vacuo. The resulting residue was purified by flash chromatography on silica gel column (EA/PE: 0-90%) to afford ethyl 2-methyl-4-oxo-1,4-dihydropyrrolo[1,2-a]pyrimidine-8-carboxylate (750 mg, 18%) and ethyl 4-methyl-2-oxo-1,2-dihydropyrrolo[1,2-a]pyrimidine-8-carboxylate (1.5 g, 36%) as orange solids. LC-MS m/z: 221.2 [M+H]$^+$. $^1$H NMR (400 MHz, CDCl$_3$) of ethyl 2-methyl-4-oxo-1,4-dihydropyrrolo[1,2-a]pyrimidine-8-carboxylate: δ 9.67 (s, 1H), 7.26 (d, J=3.2 Hz, 1H), 6.76 (d, J=3.2 Hz, 1H), 5.63 (s, 1H), 4.34 (q, J=3.2 Hz, 2H), 2.39 (s, 3H), 1.39 (t, J=3.2 Hz, 3H).

A solution of ethyl 2-methyl-4-oxo-1,2-dihydropyrrolo[1,2-a]pyrimidine-8-carboxylate (1.0 g, 4.5 mmol) in 5 mL of POCl$_3$ was stirred for 3 h at 55° C., cooled and poured into 100 mL of ice-water. The resulting mixture was extracted with DCM (20 mL×3), and the organic phases were dried over anhydrous Na$_2$SO$_4$ and filtered. The filtrate was concentrated in vacuo, and the residue was purified by silica gel column (DCM/MeOH: 20/1) to afford ethyl 4-chloro-2-methylpyrrolo[1,2-a]pyrimidine-8-carboxylate (330 mg, 31%) as a yellow solid. LC-MS m/z: 239.7 [M+H]$^+$.

A mixture of ethyl 4-chloro-2-methylpyrrolo[1,2-a]pyrimidine-8-carboxylate (190 mg, 0.8 mmol) and (Bu$_3$Sn)$_2$O (1.3 g, 1.6 mmol) was refluxed in 10 mL of toluene for 1 week, cooled and concentrated in vacuo. The resulting residue was diluted with EA (10 mL) and washed with saturated NaHCO$_3$ solution (5 mL×3). The aqueous phases were neutralized to pH 4~5 with 3N HCl, and extracted with DCM (10 mL×3). The organic phases were dried over anhydrous Na$_2$SO$_4$ and filtered. The filtrate was concentrated in vacuo to afford the title compound (120 mg, 71%) as a white solid. LC-MS m/z: 193.1 [M−OH]$^+$.

2-Chloro-4-methylpyrrolo[1,2-a]pyrimidine-8-carboxylic acid

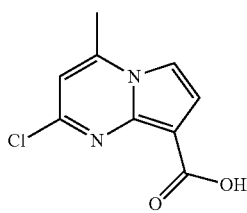

The solution of ethyl 4-methyl-2-oxo-1,2-dihydropyrrolo[1,2-a]pyrimidine-8-carboxylate (1.0 g, 4.5 mmol) in 2 mL of POCl$_3$ was stirred for 3 hours at 55° C., cooled and poured into 50 mL of ice-water. The resulting mixture was extracted with DCM (20 mL×3), and the organic phases were dried over anhydrous Na$_2$SO$_4$ and filtered. The filtrate was concentrated in vacuo, and the resulting residue was purified by flash chromatography on silica gel column (EA/PE; 0-50%) to afford ethyl 2-chloro-4-methylpyrrolo[1,2-a]pyrimidine-8-carboxylate (650 mg, 60%) as a yellow solid. LC-MS m/z: 239.7 [M+H]$^+$.

A mixture of ethyl 2-chloro-4-methylpyrrolo[1,2-a]pyrimidine-8-carboxylate (190 mg, 0.8 mmol), (Bu$_3$Sn)$_2$O (1.3 g, 1.6 mmol) was refluxed in 10 mL of toluene for 1 week, cooled and concentrated in vacuo. The resulting residue was diluted by EA (10 mL) and washed with saturated NaHCO$_3$ solution (5 mL×3). The aqueous phases were neutralized to pH 4~5 with 3N HCl, and extracted with DCM (10 mL×3). The organic phases were dried over Na$_2$SO$_4$ and filtered. The filtrate was concentrated in vacuo to afford the title compound (120 mg, 71%) as a white solid. LC-MS m/z: 193.1 [M−OH]$^+$.

2-(Difluoromethyl)-4-(methoxymethyl)pyrrolo[1,2-a]pyrimidine-8-carboxylic acid

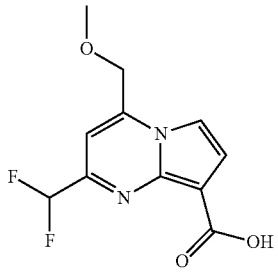 [SMILES: COCc1cc(C(F)F)nc2c(C(=O)O)ccn12]

To a solution of 1-methoxypropan-2-one (880 mg, 10 mmol) in anhydrous THF (30 mL) was added LiHMDS (12 mL, 12 mmol) at −78° C. under N$_2$. The mixture was stirred for 30 min and then methyl 2,2-difluoroacetate (1.1 g, 10 mmol) was slowly added resulting in a brown and viscous solution. The reaction mixture was stirred at RT for 20 h, diluted with EA (250 mL) and water (50 mL), and acidified with 2N H$_2$SO$_4$ solution to pH ~6. The organic layer was separated, washed with brine (50 mL), dried over anhydrous Na$_2$SO$_4$, and filtered. The filtrate was concentrated in vacuo, and the resulting residue was purified by flash chromatography on silica gel (PE/EA; 4/1) to afford 1,1-difluoro-5-methoxypentane-2,4-dione (1.3 g, 78%) as a yellow oil. $^1$H NMR (500 MHz, CDCl$_3$) (δ 6.21 (s, 1H), 5.96 (t, J=54.0 Hz, 1H), 4.10 (s, 2H), 3.45 (s, 3H).

To a solution of 1,1-difluoro-5-methoxypentane-2,4-dione (1.1 g, 6.63 mmol) in AcOH (15 mL) was added ethyl 2-amino-1H-pyrrole-3-carboxylate (1.02 g, 6.63 mmol). The solution was heated at 110° C. for 20 min, cooled to RT, basified with saturated NaHCO$_3$ to adjust pH to about 8, and extracted with EA (200 mL×2). The combined extracts were washed with water (100 mL×2), dried over anhydrous Na$_2$SO$_4$, and filtered. The filtrate was concentrated in vacuo, and resulting residue was purified by silica gel column chromatography (PE/EA: 3/2) to afford ethyl 2-(difluoromethyl)-4-(methoxymethyl)pyrrolo[1,2-a]pyrimidine-8-carboxylate (620 mg, 33%) as a yellow solid and ethyl 4-(difluoromethyl)-2-(methoxymethyl)pyrrolo[1,2-a]pyrimidine-8-carboxylate (180 mg, 10%) as a brown solid. Ethyl 2-(difluoromethyl)-4-(methoxymethyl)pyrrolo[1,2-a]pyrimidine-8-carboxylate: $^1$H NMR (500 MHz, CDCl$_3$) δ 7.56 (d, J=4.0 Hz, 1H), 7.31 (d, J=3.0 Hz, 1H), 7.16 (s, 1H), 6.71 (t, J=54.5 Hz, 1H), 4.74 (s, 2H), 4.42 (q, J=7.0 Hz, 2H), 3.52 (s, 3H), 1.42 (t, J=7.0 Hz, 3H). LC-MS m/z: 285.1 [M+H]$^+$; Purity (214 nm): >99%; $t_R$=1.94 min. Ethyl 4-(difluoromethyl)-2-(methoxymethyl)pyrrolo[1,2-a]pyrimidine-8-carboxylate: $^1$H NMR (500 MHz, CDCl$_3$) δ 7.49 (d, J=3.5 Hz, 1H), 7.36 (t, J=1.5 Hz, 1H), 7.22 (s, 1H), 6.81 (t, J=54.5 Hz, 1H), 4.69 (s, 2H), 4.41 (q, J=7.0 Hz, 2H), 3.50 (s, 3H), 1.42 (t, J=7.0 Hz, 3H). LC-MS m/z: 285.1 [M+H]$^+$; Purity (214 nm): >99%; $t_R$=1.90 min.

Following general procedure B, ethyl 2-(difluoromethyl)-4-(methoxymethyl)pyrrolo[1,2-a]pyrimidine-8-carboxylate (590 mg, 2.08 mmol) afforded the title compound (370 mg, 70%) as a brown solid. LC-MS m/z: 257.1 [M+H]$^+$; Purity (214 nm): 90%; $t_R$=1.26 min.

Part IV Compounds Prepared Following General Procedures

The following compounds were prepared based on the general procedures described in Part I above.

N-((1R,4R)-4-Butoxycyclohexyl)-4-methyl-2-(tetrahydro-2H-pyran-4-yl)pyrrolo[1,2-a]pyrimidine-8-carboxamide

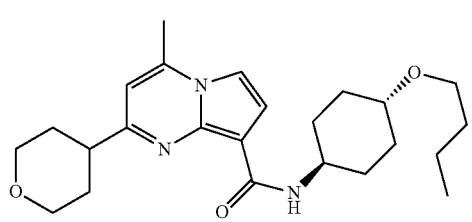

Following general procedure A, 2-chloro-4-methylpyrrolo[1,2-a]pyrimidine-8-carboxylic acid (90 mg, 0.43 mmol) and (1R,4R)-4-butoxycyclohexanamine afforded N-((1R, 4R)-4-butoxycyclohexyl)-2-chloro-4-methylpyrrolo[1,2-a]pyrimidine-8-carboxamide (110 mg, 71%) as a yellow solid. $^1$H NMR (500 MHz, CDCl$_3$): δ 7.97 (d, J=7.5 Hz, 1H), 7.57 (d, J=3.0 Hz, 1H), 7.09 (d, J=3.0 Hz, 1H), 6.60 (d, J=1.0 Hz, 1H), 4.05-4.01 (m, 1H), 3.47 (t, J=7.0 Hz, 2H), 3.33-3.30 (m, 1H), 2.60 (d, J=0.5 Hz, 3H), 2.18-2.15 (m, 2H), 2.08-2.05 (m, 2H), 1.58-1.44 (m, 2H), 1.42-1.26 (m, 6H), 0.92 (t, J=7.0 Hz, 3H). LC-MS m/z: 364.3 [M+H]$^+$. HPLC Purity (214 nm): >99%; $t_R$=11.35 min.

A mixture of 2-(3,6-dihydro-2H-pyran-4-yl)-4,4,5,5-tetramethyl-1,3,2-dioxaborolane (1.52 g, 7.24 mmol), and KHF$_2$ solution (3 M, 12 mL, 36 mmol) in MeOH was stirred at RT for 2 h. The solvent was concentrated in vacuo. The residue was extracted with hot acetone (50 mL×2), and this solution was dried over anhydrous Na$_2$SO$_4$ and filtered. The filtrate was concentrated in vacuo to afford (3,6-dihydro-2H-pyran-4-yl)trifluoro-[$^4$-borane, potassium salt (575 mg, 42%) as a white solid.

A mixture of N-((1R,4R)-4-butoxycyclohexyl)-2-chloro-4-methylpyrrolo[1,2-a]pyrimidine-8-carboxamide (80 mg, 0.22 mmol), (3,6-dihydro-2H-pyran-4-yl)trifluoro-[$^4$-borane, potassium salt (125 mg, 0.66 mmol), Pd(dppf)Cl$_2$.CH$_2$Cl$_2$ (36 mg, 0.044 mmol) and K$_3$PO$_4$ (233 mg, 1.1 mmol) in DME (5 mL) was purged with nitrogen and stirred at 120° C. for 4 h under microwave condition, cooled and filtered. The filtrate was concentrated in vacuo, and the residue was purified by silica gel column chromatography (EA) to afford N-((1R,4R)-4-butoxycyclohexyl)-2-(3,6-dihydro-2H-pyran-4-yl)-4-methylpyrrolo[1,2-a]pyrimidine-8-carboxamide (54 mg, 60%) as a yellow solid. LC-MS m/z: 412.2 [M+H]$^+$, Purity (254 nm): >80%; $t_R$=2.04 min.

A mixture of N-((1R,4R)-4-butoxycyclohexyl)-2-(3,6-dihydro-2H-pyran-4-yl)-4-methylpyrrolo[1,2-a]pyrimidine-8-carboxamide (30 mg, 0.073 mmol) and 10% Pd/C (6 mg) in ethyl acetate (5 mL) was stirred at RT for 3 h under hydrogen atmosphere. The Pd/C was removed by filtration through Celite, the filtrate was concentrated in vacuo, and the residue was purified by prep-HPLC (MeCN/10 mM NH$_4$HCO$_3$) to afford the title compound (7 mg, 23%) as a white solid. $^1$H NMR (500 MHz, DMSO-d$_6$) δ 8.50 (d, J=7.5 Hz, 1H), 7.39 (d, J=3.5 Hz, 1H), 7.26 (d, J=3.5 Hz, 1H), 6.90 (s, 1H), 3.99 (d, J=14.0 Hz, 2H), 3.79 (brs, 1H), 3.49 (t, J=11.5 Hz, 2H), 3.41 (t, J=6.5 Hz, 2H), 3.03-2.98 (m, 1H), 2.62 (s, 3H), 2.00 (t, J=12.0 Hz, 4H), 1.92 (d, J=12.5 Hz, 2H), 1.74 (qd, J=12.0 Hz, 4.5 Hz, 2H), 1.46 (m, 2H), 1.30 (m, 6H), 0.88 (t, J=7.0 Hz, 3H); LC-MS m/z: 414.3 [M+H]$^+$, HPLC Purity (214 nm): >99%; $t_R$=8.59 min.

N-(2-Cyclopropylpropan-2-yl)-4-methyl-2-(tetrahydro-2H-pyran-4-yl)pyrrolo[1,2-a]pyrimidine-8-carboxamide

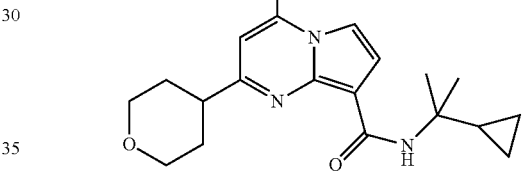

Following general procedure A, 2-chloro-4-methylpyrrolo[1,2-a]pyrimidine-8-carboxylic acid (70 mg, 0.33 mmol) and 2-cyclopropylpropan-2-amine afforded 2-chloro-N-(2-cyclopropylpropan-2-yl)-4-methylpyrrolo[1,2-a]pyrimidine-8-carboxamide as a yellow solid (69 mg, 72%). $^1$H NMR (500 MHz, DMSO-d$_6$): δ 7.88 (s, 1H), 7.51 (d, J=3.0 Hz, 1H), 7.30 (d, J=3.0 Hz, 1H), 7.04 (s, 1H), 2.66 (s, 3H), 1.34 (s, 6H), 1.34-1.31 (m, 1H), 0.45-0.42 (m, 4H). LC-MS m/z: 292.7 [M+H]$^+$. HPLC Purity (214 nm): >99%; $t_R$=9.09 mM.

Following general procedure D, 2-chloro-N-(2-cyclopropylpropan-2-yl)-4-methylpyrrolo[1,2-a]pyrimidine-8-carboxamide (100 mg, 0.34 mmol) and 2-(3,6-dihydro-2H-pyran-4-yl)-4,4,5,5-tetramethyl-1,3,2-dioxaborolane afforded N-(2-cyclopropylpropan-2-yl)-2-(3,6-dihydro-2H-pyran-4-yl)-4-methylpyrrolo[1,2-a]pyrimidine-8-carboxamide (60 mg, 52%) as a white solid. LC-MS m/z: 340.2 [M+H. Purity (254 nm): >90%; $t_R$=1.79 min.

A mixture of N-(2-cyclopropylpropan-2-yl)-2-(3,6-dihydro-2H-pyran-4-yl)-4-methylpyrrolo[1,2-a]pyrimidine-8-carboxamide (60 mg, 0.177 mmol) and 10% Pd/C (6 mg) in ethyl acetate (5 mL) was stirred at RT for 3 h under hydrogen atmosphere. The reaction was mixture was filtered to remove Pd/C, the filtrate was concentrated in vacuo, and the residue was purified by prep-HPLC (MeCN/10 mM NH$_4$HCO$_3$) to afford the title compound (18 mg, 30%) as a white solid. $^1$H NMR (500 MHz, DMSO-d$_6$): δ 8.53 (s, 1H), 7.38 (d, J=3.0 Hz, 1H), 7.24 (d, J=3.5 Hz, 1H), 6.88 (s, 1H), 3.97 (dd, J=10.0 Hz, 2.5 Hz, 2H), 3.47 (t, J=10.0 Hz, 2H), 3.01-2.96 (m, 1H), 2.62 (s, 3H), 1.90 (d, J=11.0 Hz, 2H), 1.79 (qd, J=13.0 Hz, J=4.5 Hz, 2H), 1.34 (s, 6H), 1.34-1.33 (m, 1H), 0.43-0.42 (m, 4H). LC-MS m/z: 342.3 [M+H]⁺, HPLC Purity (214 nm): >99%; $t_R$=8.02 min.

(S)—N-(1-Cyclopropylethyl)-2-(4-fluorophenyl)-4-methylpyrrolo[1,2-a]pyrimidine-8-carboxamide

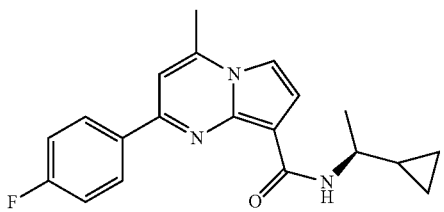 [SMILES: Cc1cc(-c2ccc(F)cc2)nc2c(C(=O)N[C@@H](C)C3CC3)ccn12]

Following general procedure D, 2-chloro-4-methylpyrrolo[1,2-a]pyrimidine-8-carboxylic acid (100 mg, 0.48 mmol) and 4-fluorophenylboronic acid afforded 2-(4-fluorophenyl)-4-methylpyrrolo[1,2-a]pyrimidine-8-carboxylic acid (130 mg, 83.3%) as a brown solid. LC-MS m/z: 271.1 [M+H]⁺. LC-MS: $t_R$=1.48 min.

Following general procedure A, 2-(4-fluorophenyl)-4-methylpyrrolo[1,2-a]pyrimidine-8-carboxylic acid (60 mg, 0.20 mmol) and (S)-1-cyclopropylethanamine afforded the title compound (2.6 mg, 3.8%) as a yellow solid. ¹H NMR (400 MHz, MeOD-d₄) δ 9.08 (d, J=6.8 Hz, 1H), 8.24-8.20 (m, 2H), 7.46 (d, J=2.8 Hz, 1H), 7.42-7.40 (m, 2H), 7.30 (t, J=8.4 Hz, 2H), 3.74-3.68 (m, 1H), 2.77 (s, 3H), 1.39 (d, J=6.8 Hz, 3H), 1.13-1.08 (m, 1H), 0.63-0.55 (m, 2H), 0.48-0.40 (m, 1H), 0.39-0.36 (m, 1H). LC-MS m/z: 338.2 [M+H]⁺. HPLC: Purity (254 nm): 97%; $t_R$=10.64 min.

2-(4-Fluorophenyl)-N-((1R,4R)-4-methoxycyclohexyl)-4-methylpyrrolo[1,2-a]pyrimidine-8-carboxamide

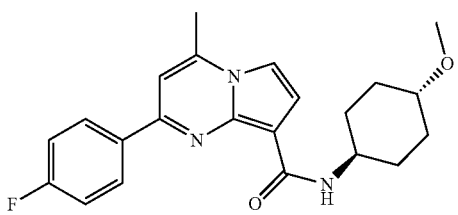 [SMILES: CO[C@H]1CC[C@H](NC(=O)c2ccn3c(C)cc(-c4ccc(F)cc4)nc23)CC1]

Following general procedure A, 2-(4-fluorophenyl)-4-methylpyrrolo[1,2-a]pyrimidine-8-carboxylic acid (120 mg, 0.44 mmol) and (1R,4R)-4-methoxycyclohexanamine afforded the title compound (30 mg, 18%) as a yellow solid. ¹H NMR (500 MHz, MeOD-d₄) δ 8.91 (d, J=7.5 Hz, 1H), 8.15-8.10 (m, 2H) 7.45 (d, J=3.5 Hz, 1H), 7.37 (d, J=3.5 Hz, 1H), 7.33 (d, J=0.5 Hz, 1H), 7.30 (d, J=8.5 Hz, 2H), 4.62-4.58 (m, 1H), 3.94-3.91 (m, 1H), 3.45 (s, 3H), 2.72 (s, 3H), 2.20-2.13 (m, 4H), 1.51-1.41 (m, 4H). LC-MS m/z: 382.2 [M+H]⁺. HPLC: Purity (254 nm): >97%; $t_R$=8.36 min.

(S)—N-(1-Cyclopropylethyl)-4-(4-fluorophenyl)-2-methylpyrrolo[1,2-a]pyrimidine-8-carboxamide

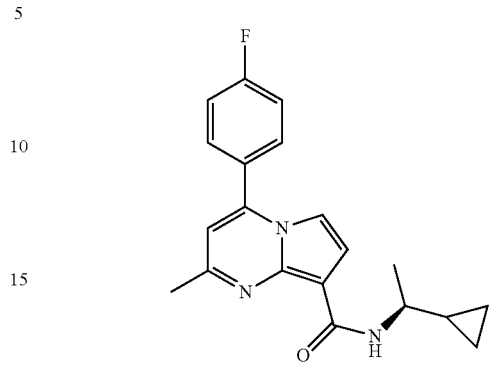

A mixture of ethyl 2-amino-1H-pyrrole-3-carboxylate (1.0 g, 6.45 mmol) and 1-(4-fluorophenyl)butane-1,3-dione (1.28 g, 7.1 mmol) in acetic acid (10 mL) was heated at 110° C. overnight until the reaction was complete, monitored by LC-MS. The acetic acid was removed in vacuo, and the residue was purified by silica gel column (PE/EA; 2/1) to afford ethyl 4-(4-fluorophenyl)-2-methylpyrrolo[1,2-a]pyrimidine-8-carboxylate (500 mg, 26%) as a yellow solid. ¹H NMR (400 MHz, CDCl₃): δ 7.65-7.62 (m, 2H), 7.32 (d, J=3.2 Hz, 1H), 7.30-7.25 (m, 2H), 7.10 (d, J=3.6 Hz, 1H), 6.57 (s, 1H), 4.41 (q, J=7.2 Hz, 2H), 2.67 (s, 3H), 1.42 (t, J=7.2 Hz, 3H).

Following general procedure B, ethyl 4-(4-fluorophenyl)-2-methylpyrrolo[1,2-a]pyrimidine-8-carboxylate (400 mg, 0.13 mmol) afforded 4-(4-fluorophenyl)-2-methylpyrrolo[1,2-a]pyrimidine-8-carboxylic acid (420 mg, salt contained) as a yellow solid, which was used directly. LC-MS m/z: 271.2 [M+H]⁺.

Following general procedure A, 4-(4-fluorophenyl)-2-methylpyrrolo[1,2-a]pyrimidine-8-carboxylic acid (50 mg, 0.2 mmol) and (S)-1-cyclopropylethanamine afforded the title compound (26.6 mg, 79%) as a yellow solid. ¹H NMR (500 MHz, CDCl₃): δ 8.61 (d, J=8.0 Hz, 1H), 7.64 (dd, J=8.5 Hz, 5.5 Hz, 2H), 7.47 (d, J=3.0 Hz, 1H), 7.27 (d, J=8.5 Hz, 2H), 7.14 (d, J=3.5 Hz, 1H), 6.53 (s, 1H), 3.83 (m, J=7.0 Hz, 1H), 2.62 (s, 3H), 1.36 (d, J=6.5 Hz, 3H), 1.06-0.99 (m, 1H), 0.55-0.46 (m, 3H), 0.35-0.30 (m, 1H). LC-MS m/z: 338.2 [M+H]⁺. HPLC Purity (214 nm): 98%; $t_R$=9.16 min.

N-((1R,4R)-4-tert-Butoxycyclohexyl)-4-methyl-2-(pyridin-3-yl)pyrrolo[1,2-a]pyrimidine-8-carboxamide

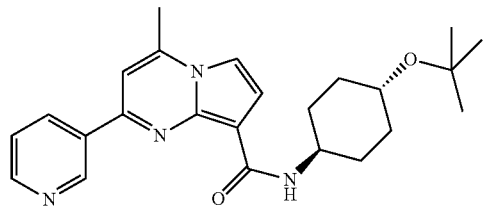 [SMILES: Cc1cc(-c2cccnc2)nc2c(C(=O)N[C@H]3CC[C@H](OC(C)(C)C)CC3)ccn12]

Following general procedure D, ethyl 2-chloro-4-methylpyrrolo[1,2-a]pyrimidine-8-carboxylate (400 mg, 1.3 mmol) and pyridin-3-ylboronic acid afforded ethyl 4-methyl-2-(pyridin-3-yl)pyrrolo[1,2-a]pyrimidine-8-carboxylate as a yellow solid (300 mg, 64%). LC-MS m/z: 282.1 [M+H]⁺.

Following general procedure B, ethyl 4-methyl-2-(pyridin-3-yl)pyrrolo[1,2-a]pyrimidine-8-carboxylate (250 mg, 0.89 mmol) afforded 4-methyl-2-(pyridin-3-yl)pyrrolo[1,2-a]pyrimidine-8-carboxylic acid (200 mg, 89%) as a yellow solid. LC-MS m/z: 254.1 [M+H]⁺.

Following general procedure A, 4-methyl-2-(pyridin-3-yl)pyrrolo[1,2-a]pyrimidine-8-carboxylic acid (60 mg, 0.24 mmol) and (1R,4R)-4-tert-butoxycyclohexanamine afforded the title compound (27 mg, 28%) as a yellow solid. $^1$H NMR (500 MHz, CDCl$_3$): δ 9.35 (d, J=1.5 Hz, 1H), 8.72 (dd, J=4.5 Hz, 1.5 Hz, 1H), 8.48 (dt, J=8.5 Hz, 2.0 Hz, 1H), 8.39 (d, J=7.5 Hz, 1H), 7.66-7.64 (m, 2H), 7.55 (d, J=3.0 Hz, 1H), 7.40 (d, J=3.5 Hz, 1H), 3.77-3.75 (m, 1H), 3.55-3.33 (m, 1H), 2.74 (s, 3H), 2.06-2.02 (m, 2H), 1.82-1.78 (m, 2H), 1.48-1.32 (m, 4H), 1.15-1.13 (s, 9H). LC-MS m/z: 407.1 [M+H]⁺. HPLC Purity (214 nm): >95%; t$_R$=7.73 min.

N-((1R,4R)-4-Butoxycyclohexyl)-4-methyl-2-(pyridin-3-yl)pyrrolo[1,2-a]pyrimidine-8-carboxamide

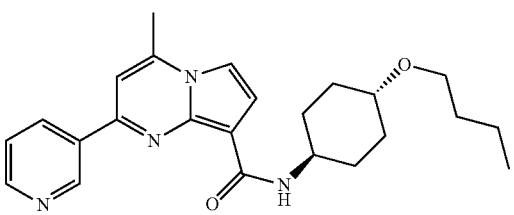 [SMILES: CCCCO[C@H]1CC[C@H](NC(=O)c2ccn3c(C)cc(-c4cccnc4)nc23)CC1]

Following general procedure A, 4-methyl-2-(pyridin-3-yl)pyrrolo[1,2-a]pyrimidine-8-carboxylic acid (41 mg, 0.16 mmol) and (1R,4R)-4-butoxycyclohexanamine afforded the title compound (15 mg, 23%) as a light yellow solid. $^1$H NMR (500 MHz, DMSO-d$_6$) δ 9.35 (d, J=2.0 Hz, 1H), 8.73 (d, J=4.5 Hz, 1H), 8.48 (d, J=7.5 Hz, 1H), 8.45 (d, J=7.5 Hz, 1H), 7.66 (s, 1H), 7.65-7.63 (m, 1H), 7.56 (d, J=3.0 Hz, 1H), 7.40 (d, J=3.5 Hz, 1H), 3.87-3.81 (m, 1H), 3.43 (t, J=6.5 Hz, 2H), 3.33-3.30 (m, 1H), 2.75 (s, 3H), 2.09-2.06 (m, 2H), 2.01-1.99 (m, 2H), 1.49-1.44 (m, 2H), 1.41-1.28 (m, 6H), 0.89 (t, J=7.5 Hz, 3H). LC-MS m/z: 407.3 [M+H]⁺. HPLC Purity (214 nm): >99%; t$_R$=8.16 min.

4-Methyl-N-((1R,4R)-4-(neopentyloxy)cyclohexyl)-2-(pyridin-3-yl)pyrrolo[1,2-a]pyrimidine-8-carboxamide

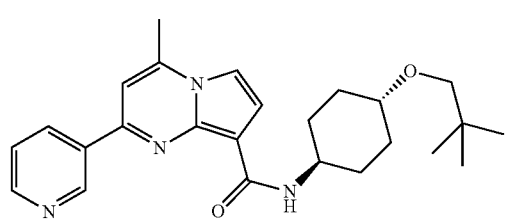 [SMILES: Cc1cc(-c2cccnc2)nc2c(C(=O)N[C@H]3CC[C@H](OCC(C)(C)C)CC3)ccn12]

Following general procedure A, 4-methyl-2-(pyridin-3-yl)pyrrolo[1,2-a]pyrimidine-8-carboxylic acid (42 mg, 0.17 mmol) and (1R,4R)-4-(neopentyloxy)cyclohexanamine afforded the title compound (24 mg, 34%) as a yellow solid. $^1$H NMR (500 MHz, CDCl$_3$) δ 9.31 (d, J=2.0 Hz, 1H), 8.75 (dd, J=5.0 Hz, 1.5 Hz, 1H), 8.53 (d, J=7.5 Hz, 1H), 8.30 (dt, J=8.0 Hz, 1.5 Hz, 1H), 7.68 (d, J=3.0 Hz, 1H), 7.50 (dd, J=8.0 Hz, 5.0 Hz, 1H), 7.20 (d, J=3.5 Hz, 1H), 7.09 (s, 1H), 4.14-4.07 (m, 1H), 3.32-3.27 (m, 1H), 3.13 (s, 2H), 2.73 (s, 3H), 2.25 (m, 2H), 2.08 (m, 2H), 1.56-1.51 (m, 2H), 1.46-1.39 (m, 2H), 0.93 (s, 9H). LC-MS m/z: 421.3 [M+H]⁺. HPLC: Purity (214 nm): >99%; t$_R$=9.00 min.

N-((1R,4R)-4-Isobutoxycyclohexyl)-4-methyl-2-(pyridin-3-yl)pyrrolo[1,2-a]pyrimidine-8-carboxamide

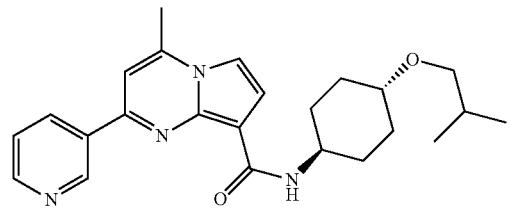 [SMILES: Cc1cc(-c2cccnc2)nc2c(C(=O)N[C@H]3CC[C@H](OCC(C)C)CC3)ccn12]

Following general procedure A, 4-methyl-2-(pyridin-3-yl)pyrrolo[1,2-a]pyrimidine-8-carboxylic acid (40 mg, 0.16 mmol) and (1R,4R)-4-isobutoxycyclohexanamine afforded the title compound (26 mg, 41%) as a light yellow solid. $^1$H NMR (500 MHz, CDCl$_3$) δ 9.32 (d, J=2.5 Hz, 1H), 8.75 (dd, J=5.0 Hz, 2.0 Hz, 1H), 8.52 (d, J=7.0 Hz, 1H), 8.30 (dt, J=8.0 Hz, 2.0 Hz, 1H), 7.69 (d, J=3.0 Hz, 1H), 7.50 (dd, J=8.0 Hz, 5.0 Hz, 1H), 7.20 (d, J=3.0 Hz, 1H), 7.09 (s, 1H), 4.13-4.05 (m, 1H), 3.35-3.29 (m, 1H), 3.25 (d, J=6.5 Hz, 2H), 2.74 (s, 3H), 2.29-2.25 (m, 2H), 2.12-2.09 (m, 2H), 1.90-1.82 (m, 1H), 1.56-1.48 (m, 2H), 1.46-1.38 (m, 2H), 0.94 (d, J=7.0 Hz, 6H). LC-MS m/z: 407.2 [M+H]⁺. HPLC: Purity (214 nm): >96%; t$_R$=8.25 min.

4-Methyl-N-((1R,4R)-4-propoxycyclohexyl)-2-(pyridin-3-yl)pyrrolo[1,2-a]pyrimidine-8-carboxamide

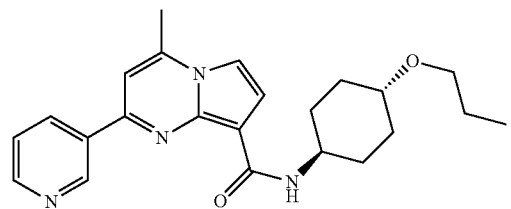 [SMILES: CCCO[C@H]1CC[C@H](NC(=O)c2ccn3c(C)cc(-c4cccnc4)nc23)CC1]

Following general procedure A, 4-methyl-2-(pyridin-3-yl)pyrrolo[1,2-a]pyrimidine-8-carboxylic acid (60 mg, 0.24 mmol) and (1R,4R)-4-propoxycyclohexanamine afforded the title compound (28 mg, 30%) as a yellow solid. $^1$H NMR (500 MHz, DMSO-d$_6$): δ 9.33 (s, 1H), 8.71 (d, J=2.0 Hz, 1H), 8.44 (dd, J=13.0 Hz, 8.5 Hz, 2H), 7.62 (s, 2H), 7.53 (s, 1H), 7.39 (s, 1H), 3.85-3.79 (m, 1H), 3.40-3.32 (m, 3H), 2.72 (s, 3H), 2.04-1.98 (m, 4H), 1.51-1.33 (m, 6H), 0.87 (t, J=4.8 Hz, 3H). LC-MS m/z: 392.9 [M+H]⁺. HPLC Purity (214 nm): >98%; t$_R$=7.61 min.

N-((1R,4R)-4-Isobutoxycyclohexyl)-4-methyl-2-(pyridin-3-0)pyrrolo[1,2-a]pyrimidine-8-carboxamide

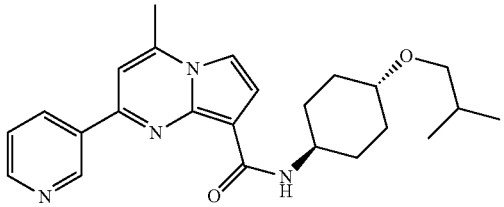 [SMILES: Cc1cc(-c2cccnc2)nc2c(C(=O)N[C@H]3CC[C@H](OCC(C)C)CC3)ccn12]

Following general procedure A, 4-methyl-2-(pyridin-3-yl)pyrrolo[1,2-a]pyrimidine-8-carboxylic acid (60 mg, 0.24 mmol) and (1R,4R)-4-isobutoxycyclohexanamine afforded the title compound (62 mg, 64%) as a yellow solid. $^1$H NMR (500 MHz, CDCl$_3$): δ 9.34 (d, J=1.5 Hz, 1H), 8.72 (dd, J=5.0 Hz, 2.0 Hz, 1H), 8.48 (dt, J=8.5 Hz, 2.0 Hz, 1H), 8.45 (d, J=8.0 Hz, 1H), 7.65 (d, J=1.0 Hz, 1H), 7.63 (dd, J=5.0 Hz, 4.5 Hz, 1H), 7.55 (d, J=3.0 Hz, 1H), 7.40 (d, J=3.0 Hz, 1H), 3.85-3.82 (m, 1H), 3.35-3.33 (m, 1H), 3.19 (d, J=6.5 Hz, 2H), 2.74 (s, 3H), 2.07-1.98 (m, 4H), 1.78-1.73 (m, 1H), 1.44-1.32 (m, 4H), 0.87 (d, J=7.0 Hz, 6H). LC-MS m/z: 407.7 [M+H]$^+$. HPLC Purity (214 nm): >98%; $t_R$=8.27 min.

N-(1-Cyclopropyl-2,2,2-trifluoroethyl)-4-methyl-2-(pyridin-3-yl)pyrrolo[1,2-a]pyrimidine-8-carboxamide

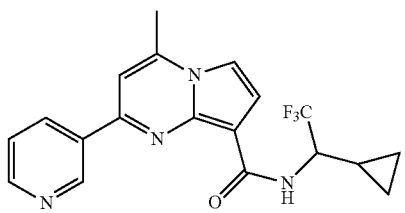 [SMILES: Cc1cc(-c2cccnc2)nc2c(C(=O)NC(C3CC3)C(F)(F)F)ccn12]

Following general procedure A, 4-methyl-2-(pyridin-3-yl)pyrrolo[1,2-a]pyrimidine-8-carboxylic acid (30 mg, 0.12 mmol) and 1-cyclopropyl-2,2,2-trifluoroethanamine afforded the title compound (11 mg, 26%). $^1$H NMR (400 MHz, DMSO-d$_6$): δ 9.35 (s, 1H), 8.94 (d, J=9.2 Hz, 1H), 8.72 (d, J=4.4 Hz, 1H), 8.47 (d, J=7.6 Hz, 1H), 7.72 (s, 1H), 7.64-7.61 (m, 2H), 7.45 (m, 1H), 4.54-4.44 (m, 1H), 2.76 (s, 3H), 1.26-1.22 (m, 1H), 0.65-0.64 (m, 1H), 0.55-0.52 (m, 2H), 0.37-0.36 (m, 2H). LC-MS m/z: 374.9 [M+H]$^+$. HPLC Purity (214 nm): >98%; $t_R$=7.60 min.

(S)-2-Chloro-N-(1-cyclopropylethyl)-4-methylpyrrolo[1,2-a]pyrimidine-8-carboxamide

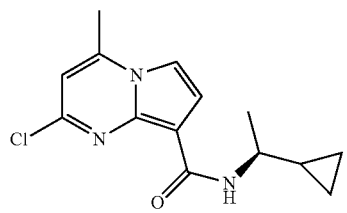 [SMILES: Cc1cc(Cl)nc2c(C(=O)N[C@@H](C)C3CC3)ccn12]

Following general procedure A, 2-chloro-4-methylpyrrolo[1,2-a]pyrimidine-8-carboxylic acid (58 mg, 0.28 mmol) and (S)-1-cyclopropylethan-1-amine afforded the title compound (40 mg, 53%) as a yellow solid. $^1$H NMR (500 MHz, CDCl$_3$): δ 8.04 (d, J=7.0 Hz, 1H), 7.58 (d, J=3.0 Hz, 1H), 7.09 (d, J=3.0 Hz, 1H), 6.60 (s, 1H), 3.75 (m, J=7.0 Hz, 1H), 2.60 (s, 3H), 1.35 (d, J=7.0 Hz, 3H), 1.02-0.88 (m, 1H), 0.57-0.44 (m, 3H), 0.31-0.28 (m, 1H). LC-MS m/z: 278.1 [M+H]$^+$. HPLC Purity (214 nm): >99%; $t_R$=10.1 min.

N-(2-Cyclopropylpropan-2-yl)-2-(difluoromethyl)-4-(methoxymethyl)pyrrolo[1,2-a]pyrimidine-8-carboxamide

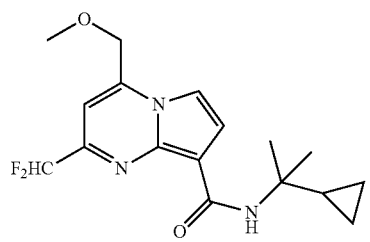 [SMILES: COCc1cc(C(F)F)nc2c(C(=O)NC(C)(C)C3CC3)ccn12]

Following general procedure A, 2-(difluoromethyl)-4-(methoxymethyl)pyrrolo[1,2-c]pyrimidine-8-carboxylic acid (20 mg, 0.09 mmol) and 2-cyclopropylpropan-2-amine (25 mg, 0.1 mmol) afforded the title compound (5.6 mg, 16%) as a yellow solid. $^1$H NMR (500 MHz, CDCl$_3$) δ 8.23 (s, 1H), 7.69 (d, J=3.0 Hz, 1H), 7.29 (d, J=3.0 Hz, 1H), 7.09 (s, 1H), 6.56 (t, J=55.0 Hz, 1H), 4.73 (s, 2H), 3.53 (s, 3H), 1.45 (s, 6H), 1.38-1.33 (m, 1H), 0.50-0.48 (m, 4H). LC-MS m/z: 337.1 [M+H]$^+$. HPLC: Purity (214 nm): >98%; $t_R$=10.46 min.

N-(2-Cyclopropylpropan-2-yl)-4-(difluoromethyl)-2-(methoxymethyl)pyrrolo[1,2-a]pyrimidine-8-carboxamide

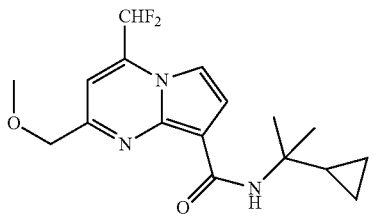 [SMILES: COCc1cc(C(F)F)n2ccc(C(=O)NC(C)(C)C3CC3)c2n1]

Following general procedure A, 4-(difluoromethyl)-2-(methoxymethyl)pyrrolo[1,2-c]pyrimidine-8-carboxylic acid 20 mg, 0.09 mmol) and 2-cyclopropylpropan-2-amine afforded the title compound (12.2 mg, 26%) as a yellow solid. $^1$H NMR (500 MHz, CDCl$_3$) δ 8.32 (s, 1H), 7.62 (d, J=3.5 Hz, 1H), 7.36 (t, J=1.5 Hz, 1H), 7.11 (s, 1H), 6.80 (t, J=53.0 Hz, 1H), 4.59 (s, 2H), 3.51 (s, 3H), 1.45 (s, 6H), 1.37-1.34 (m, 1H), 0.50-0.48 (m, 4H). LC-MS m/z: 337.1 [M+H]$^+$. HPLC: Purity (214 nm): >99%; $t_R$=10.38 min.

N-(2-Cyclobutylpropan-2-yl)-2-(difluoromethyl)-4-(methoxymethyl)pyrrolo[1,2-a]pyrimidine-8-carboxamide

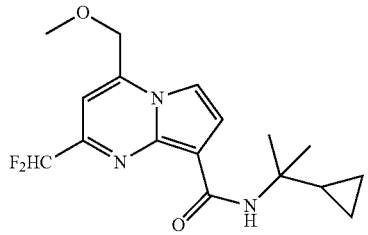

Following general procedure A, 2-(difluoromethyl)-4-(methoxymethyl)pyrrolo[1,2-c]pyrimidine-8-carboxylic acid (40 mg, 0.156 mmol) and 2-cyclobutylpropan-2-amine afforded the title compound (6.1 mg, 11%) as a light yellow oil. $^1$H NMR (500 MHz, CDCl$_3$): δ 8.22 (s, 1H), 7.72 (d, J=3.0 Hz, 1H), 7.32 (d, J=3.5 Hz, 1H), 7.11 (s, 1H), 6.58 (t, J=55.0 Hz, 1H), 4.75 (s, 2H), 3.55 (s, 3H), 2.78-2.75 (m, 1H), 2.09-1.78 (m, 6H), 1.47 (s, 6H). LC-MS m/z: 352.2 [M+H]$^+$. HPLC Purity (214 nm): >97%; $t_R$=10.89 min.

(S)—N-(1-Cyclopropylethyl)-2,4-bis(difluoromethyl)pyrrolo[1,2-a]pyrimidine-8-carboxamide

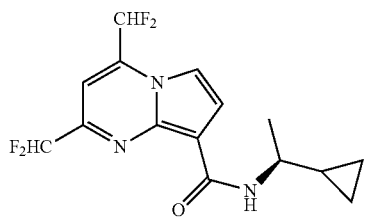 [SMILES: C[C@H](NC(=O)c1ccn2c(C(F)F)cc(C(F)F)nc12)C1CC1]

Following general procedure A, 2,4-bis(difluoromethyl)pyrrolo[1,2-a]pyrimidine-8-carboxylic acid (20 mg, 0.08 mmol) and (S)-1-cyclopropylethan-1-amine afforded the title compound (7.7 mg, 29%) as a yellow solid. $^1$H NMR (500 MHz, CDCl$_3$): δ 8.02 (d, J=7.0 Hz, 1H), 7.80 (d, J=3.0 Hz, 1H), 7.55 (s, 1H), 7.24 (s, 1H), 6.88 (t, J=52.5 Hz, 1H), 6.63 (t, J=55.0 Hz, 1H), 3.79-3.74 (m, 1H), 1.35 (d, J=6.5 Hz, 3H), 1.02-0.96 (m, 1H), 0.57-0.42 (m, 3H), 0.34-0.29 (m, 1H). LC-MS m/z: 330.1 [M+H]$^+$. HPLC Purity (214 nm): >99%; $t_R$=10.03 minutes.

(S)—N-(1-Cyclopropylethyl)-2-(difluoromethyl)-4-methylpyrrolo[1,2-a]pyrimidine-8-carboxamide

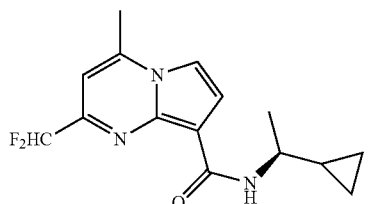

Following general procedure A, 2-(difluoromethyl)-4-methylpyrrolo[1,2-a]pyrimidine-8-carboxylic acid (30 mg, 0.133 mmol) and (S)-1-cyclopropylethan-1-amine afforded the title compound (34 mg, 86%) as a yellow solid. $^1$H NMR (500 MHz, CDCl$_3$): δ 8.18 (d, J=8.0 Hz, 1H), 7.71 (d, J=3.0 Hz, 1H), 7.24 (d, J=3.0 Hz, 1H), 6.90 (s, 1H), 6.57 (t, J=55.0 Hz, 1H), 3.81-3.76 (m, 1H), 2.69 (s, 3H), 1.35 (d, J=6.5 Hz, 3H), 1.02-0.97 (m, 1H), 0.55-044 (m, 3H), 0.33-0.28 (m, 1H). LC-MS m/z: 294.2 [M+H]$^+$. HPLC Purity (214 nm): >99%; $t_R$=9.77 minutes.

(S)—N-(1-Cyclopropylethyl)-4-(difluoromethyl)-2-methylpyrrolo[1,2-a]pyrimidine-8-carboxamide

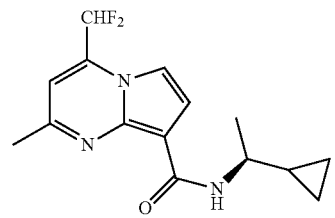 [SMILES: Cc1cc(C(F)F)n2ccc(C(=O)N[C@@H](C)C3CC3)c2n1]

Following general procedure A, 4-(difluoromethyl)-2-methylpyrrolo[1,2-a]pyrimidine-8-carboxylic acid (20 mg, 0.09 mmol) and (S)-1-cyclopropylethan-1-amine afforded the title compound (21 mg, 81%) as a yellow solid. $^1$H NMR (500 MHz, CDCl$_3$): δ 8.41 (d, J=8.0 Hz, 1H), 7.58 (d, J=3.5 Hz, 1H), 7.28 (d, J=3.0 Hz, 1H), 6.81 (s, 1H), 6.77 (t, J=53.5 Hz, 1H), 3.82-3.77 (m, 1H), 2.65 (s, 3H), 1.34 (d, J=6.5 Hz, 3H), 1.02-0.98 (m, 1H), 0.54-045 (m, 3H), 0.33-0.27 (m, 1H). LC-MS m/z: 294.2 [M+H]$^+$. HPLC Purity (214 nm): 99.8%; $t_R$=9.91 min.

4-(Difluoromethyl)-N-(1-(3,5-difluorophenyl)cyclopropyl)-2-(methoxymethyl)pyrrolo[1,2-a]pyrimidine-8-carboxamide

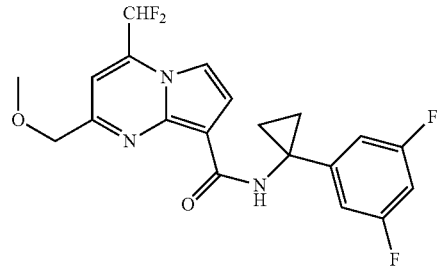 [SMILES: COCc1cc(C(F)F)n2ccc(C(=O)NC3(c4cc(F)cc(F)c4)CC3)c2n1]

Following general procedure A, 4-(difluoromethyl)-2-(methoxymethyl)pyrrolo[1,2-a]pyrimidine-8-carboxylic acid (50 mg, 0.20 mmol) and 1-(3,5-difluorophenyl)cyclopropan-1-amine afforded the title compound (2.6 mg, 4%) as a yellow solid. $^1$H NMR (400 MHz, MeOD-d$_4$) δ 7.62-7.61 (m, 1H), 7.53 (d, J=3.2 Hz, 1H), 7.32 (s, 1H), 7.28 (t, J=52.0 Hz, 1H), 6.86 (dd, J=9.2 Hz, 2.0 Hz, 2H), 6.74 (tt, J=9.2 Hz, 2.0 Hz, 1H), 4.70 (s, 2H), 3.54 (s, 3H), 1.49-1.46 (m, 2H), 1.46-1.44 (m, 2H). LC-MS m/z: 408.0 [M+H]$^+$. HPLC: Purity (214 nm): >94%; $t_R$=8.75 min.

2-Chloro-N-(2-cyclopropylpropan-2-yl)-4-methylpyrrolo[1,2-a]pyrimidine-8-carboxamide

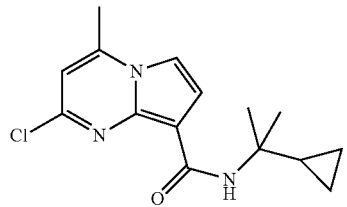 [SMILES: Cc1cc(Cl)nc2c(C(=O)NC(C)(C)C3CC3)ccn12]

Following general procedure A, 2-chloro-4-methylpyrrolo[1,2-a]pyrimidine-8-carboxylic acid (70 mg, 0.33 mmol) and 2-cyclopropylpropan-2-amine afforded the title compound (69 mg, 72%) as a pale yellow solid. $^1$H NMR (500 MHz, DMSO-$d_6$): δ 7.88 (s, 1H), 7.51 (d, J=3.0 Hz, 1H), 7.30 (d, J=3.0 Hz, 1H), 7.04 (s, 1H), 2.66 (s, 3H), 1.34 (s, 6H), 1.34-1.31 (m, 1H), 0.45-0.42 (m, 4H). LC-MS m/z: 292.7 [M+H]$^+$. HPLC Purity (214 nm): >99%; $t_R$=9.09 min.

4-Chloro-N-(2-cyclopropylpropan-2-yl)-2-methylpyrrolo[1,2-a]pyrimidine-8-carboxamide

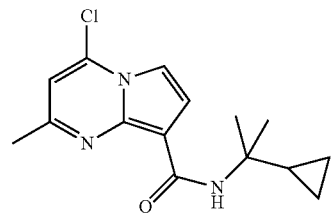 [SMILES: Cc1cc(Cl)n2ccc(C(=O)NC(C)(C)C3CC3)c2n1]

Following general procedure A, 4-chloro-2-methylpyrrolo[1,2-a]pyrimidine-8-carboxylic acid (25 mg, 0.01 mmol) and 2-cyclopropylpropan-2-amine afforded the title compound (6 mg, 16%) as a yellow solid. $^1$H NMR (500 MHz, MeOD-$d_4$): δ 8.66 (s, 1H), 7.38 (d, J=3.5 Hz, 1H), 7.29 (d, J=3.5 Hz, 1H), 6.93 (s, 1H), 2.49 (s, 3H), 1.34 (s, 6H), 1.25-1.21 (m, 1H), 0.43-0.41 (m, 4H). LC-MS m/z: 292.1 [M+H]$^+$. HPLC Purity (214 nm): 95%; $t_R$=9.01 min.

2-Bromo-N-(2-cyclopropylpropan-2-yl)-4-methylpyrrolo[1,2-a]pyrimidine-8-carboxamide

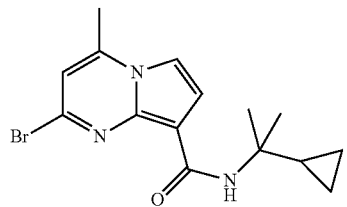

Following general procedure A, 2-bromo-4-methylpyrrolo[1,2-a]pyrimidine-8-carboxylic acid (20 mg, 0.08 mmol) and 2-cyclopropylpropan-2-amine afforded the title compound (1.6 mg, 6%) as a yellow solid. $^1$H NMR (500 MHz, CDCl$_3$): δ 8.12 (s, 1H), 7.53 (d, J=3.0 Hz, 1H), 7.08 (d, J=3.0 Hz, 1H), 6.71 (s, 1H), 2.58 (s, 3H), 1.44 (s, 6H), 1.37-1.35 (m, 1H), 0.52-0.50 (m, 4H). LC-MS m/z: 338.0 [M+H]$^+$. HPLC Purity (214 nm): >99%; $t_R$=10.88 min.

N-(2-Cyclopropylpropan-2-yl)-2-(methoxymethyl)-4-methylpyrrolo[1,2-a]pyrimidine-8-carboxamide

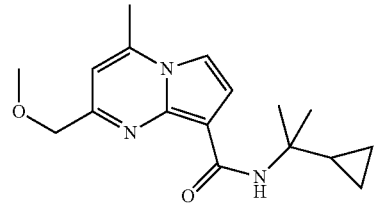 [SMILES: COCc1cc(C)n2ccc(C(=O)NC(C)(C)C3CC3)c2n1]

Following general procedure A, 2-(methoxymethyl)-4-methylpyrrolo[1,2-a]pyrimidine-8-carboxylic acid (50 mg, 0.22 mmol) and 2-cyclopropylpropan-2-amine afforded the title compound (7.7 mg, 11%) as a yellow solid. $^1$H NMR (500 MHz, CDCl$_3$): δ 8.51 (s, 1H), 7.58 (d, J=3.0 Hz, 1H), 7.10 (d, J=3.0 Hz, 1H), 6.79 (s, 1H), 4.57 (s, 2H), 3.51 (s, 3H), 2.63 (s, 3H), 1.48 (s, 6H), 1.40-1.36 (m, 1H), 0.52-0.50 (m, 4H). LC-MS m/z: 302.3 [M+H]$^+$. HPLC Purity (214 nm): >99%; $t_R$=8.22 minutes.

N-(2-Cyclopropylpropan-2-yl)-4-(methoxymethyl)-2-methylpyrrolo[1,2-a]pyrimidine-8-carboxamide

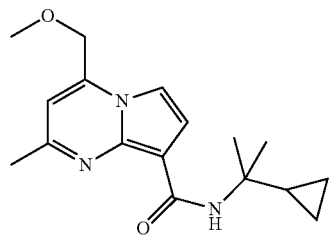 [SMILES: COCc1cc(C)nc2c(C(=O)NC(C)(C)C3CC3)ccn12]

Following general procedure A, 4-(methoxymethyl)-2-methylpyrrolo[1,2-a]pyrimidine-8-carboxylic acid (50 mg, 0.22 mmol) and 2-cyclopropylpropan-2-amine afforded the title compound (7.7 mg, 11%) as a yellow solid. $^1$H NMR (500 MHz, CDCl$_3$): δ 8.83 (s, 1H), 7.51 (d, J=3.0 Hz, 1H), 7.09 (d, J=3.0 Hz, 1H), 6.67 (s, 1H), 4.66 (s, 2H), 3.51 (s, 3H), 2.61 (s, 3H), 1.48 (s, 6H), 1.41-1.38 (m, 1H), 0.53-0.50 (m, 4H). LC-MS m/z: 302.3 [M+H]$^+$. HPLC Purity (214 nm): 99%; $t_R$=10.38 minutes.

2,4-Dimethyl-N-(1-phenylcyclopropyl)pyrrolo[1,2-a]pyrimidine-8-carboxamide

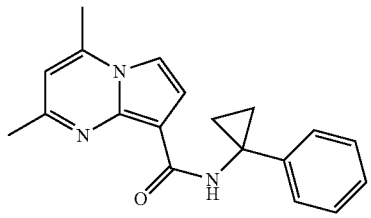 [SMILES: Cc1cc(C)n2ccc(C(=O)NC3(c4ccccc4)CC3)c2n1]

Following general procedure A, 2,4-dimethylpyrrolo[1,2-a]pyrimidine-8-carboxylic acid (40 mg, 0.21 mmol) and 1-phenylcyclopropanamine hydrochloride afforded the title compound (39 mg, 62%) as a yellow solid. $^1$H NMR (500 MHz, CDCl$_3$): δ 9.23 (s, 1H), 7.54 (d, J=3.5 Hz, 1H), 7.32 (dd, J=7.5 Hz, 1.0 Hz, 2H), 7.29 (d, J=6.0 Hz, 2H), 7.15 (t, J=7.0 Hz, 1H), 7.04 (d, J=3.0 Hz, 1H), 6.48 (s, 1H), 2.58 (s, 3H), 2.56 (s, 3H), 1.49-1.46 (m, 2H), 1.40-1.38 (m, 2H). LC-MS m/z: 306.3 [M+H]$^+$. HPLC Purity (214 nm): >97%; $t_R$=8.41 min.

N-(1-Cyclopropyl-2-methylpropan-2-yl)-2,4-dimethylpyrrolo[1,2-a]pyrimidine-8-carboxamide

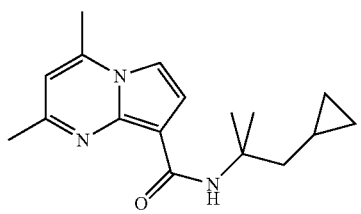 [SMILES: Cc1cc(C)n2ccc(C(=O)NC(C)(C)CC3CC3)c2n1]

Following general procedure A, 2,4-dimethylpyrrolo[1,2-a]pyrimidine-8-carboxylic acid (30 mg, 0.16 mmol) and 1-cyclopropyl-2-methylpropan-2-amine afforded the title compound (7.7 mg, 17%) as a yellow solid. $^1$H NMR (500 MHz, CDCl$_3$): δ 8.83 (s, 1H), 7.19 (d, J=3.5 Hz, 1H), 7.11 (d, J=3.0 Hz, 1H), 6.55 (s, 1H), 2.48 (s, 3H), 2.42 (s, 3H), 1.64 (d, J=6.5 Hz, 1H), 1.63 (d, J=6.5 Hz, 1H), 1.41 (s, 6H), 0.71-0.68 (m, 1H), 0.33-0.30 (m, 2H), 0.02-0.01 (m, 2H). HPLC m/z: 286.3[M+H]$^+$. HPLC Purity (214 nm): >99%; $t_R$=10.77 min.

N-(2-Methoxy-1-phenylethyl)-2,4-dimethylpyrrolo[1,2-a]pyrimidine-8-carboxamide

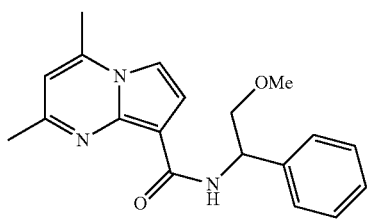 [SMILES: COCC(NC(=O)c1ccn2c(C)cc(C)nc12)c1ccccc1]

Following general procedure A, 2,4-dimethylpyrrolo[1,2-a]pyrimidine-8-carboxylic acid (8 mg, 0.04 mmol) and 2-methoxy-1-phenylethanamine afforded the title compound (3 mg, 22%) as a yellow solid. $^1$H NMR (500 MHz, CDCl$_3$) δ 9.40 (d, J=7.5 Hz, 1H), 7.50 (d, J=3.5 Hz, 1H), 7.48 (d, J=7.0 Hz, 2H), 7.33 (t, J=7.5 Hz, 2H), 7.24 (t, J=7.5 Hz, 1H), 7.02 (d, J=3.5 Hz, 1H), 6.48 (s, 1H), 5.46 (q, J=2.5 Hz, 1H), 3.84 (dd, J=10.0 Hz, 5.5 Hz, 1H), 3.78 (dd, J=10.0 Hz, 5.0 Hz, 1H), 3.43 (s, 3H), 2.57 (s, 3H), 2.56 (s, 3H). LC-MS m/z: 323.1 [M+H]$^+$. HPLC Purity (214 nm): >99%; $t_R$=7.88 min.

N-([1,1'-Bi(cyclopropan)]-yl)-2,4-dimethylpyrrolo[1,2-a]pyrimidine-8-carboxamide

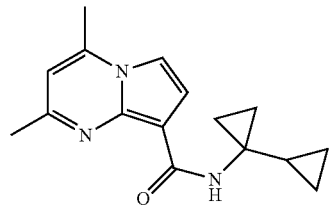 [SMILES: Cc1cc(C)n2ccc(C(=O)NC3(C4CC4)CC3)c2n1]

Following general procedure A, 2,4-dimethylpyrrolo[1,2-a]pyrimidine-8-carboxylic acid (37 mg, 0.19 mmol) and [1,1'-bi(cyclopropan)]-1-amine afforded the title compound (34 mg, 65%) as a yellow solid. $^1$H NMR (500 MHz, DMSO-d$_6$) δ 8.49 (s, 1H), 7.16 (d, J=3.5 Hz, 1H), 7.03 (d, J=3.5 Hz, 1H), 6.57 (s, 1H), 2.39 (s, 3H), 2.31 (s, 3H), 1.24-1.18 (m, 1H), 0.52-0.49 (m, 2H), 0.42-0.40 (m, 2H), 0.17-0.13 (m, 2H), 0.01-0.00 (m, 2H). LC-MS m/z: 269.1 [M+H]$^+$. HPLC: Purity (214 nm): >99%; $t_R$=7.96 min.

N-(2-Cyclopropylpropan-2-yl)-2,4-dimethylpyrrolo[1,2-a]pyrimidine-8-carboxamide

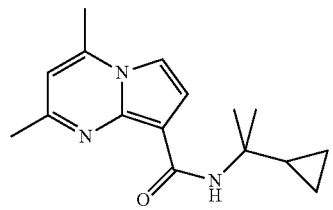 [SMILES: Cc1cc(C)n2ccc(C(=O)NC(C)(C)C3CC3)c2n1]

Following general procedure A, 2,4-dimethylpyrrolo[1,2-a]pyrimidine-8-carboxylic acid (40 mg, 0.21 mmol) and 2-cyclopropylpropan-2-amine afforded the title compound (33 mg, 57%) as a yellow solid. $^1$H NMR (500 MHz, CDCl$_3$) δ 8.63 (s, 1H), 7.49 (d, J=3.5 Hz, 1H), 7.00 (d, J=3.0 Hz, 1H), 6.44 (s, 1H), 2.55 (s, 3H), 2.54 (s, 3H), 1.46 (s, 6H), 1.39-1.36 (m, 1H), 0.51-0.46 (m, 4H). LC-MS m/z: 271.1 [M+H]$^+$. HPLC: Purity (214 nm): >99%; $t_R$=10.32 min.

N-((1R,4R)-4-Butoxycyclohexyl)-4-methyl-2-morpholinopyrrolo[1,2-a]pyrimidine-8-carboxamide

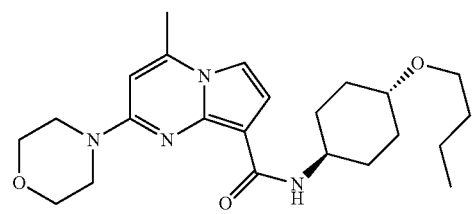 [SMILES: CCCCO[C@H]1CC[C@H](NC(=O)c2ccn3c(C)cc(N4CCOCC4)nc23)CC1]

Following general procedure C, N-((1R,4R)-4-butoxycyclohexyl)-2-chloro-4-methylpyrrolo[1,2-a]pyrimidine-8-carboxamide (30 mg, 0.08 mmol) and morpholine afforded the title compound (21 mg, 64%) as a yellow solid. $^1$H NMR (500 MHz, CDCl$_3$): δ 8.17 (d, J=7.5 Hz, 1H), 7.29 (d, J=3.5

Hz, 1H), 6.80 (d, J=3.5 Hz, 1H), 6.16 (s, 1H), 4.00-3.94 (m, 1H), 3.85 (t, J=5.0 Hz, 4H), 3.59 (t, J=5.0 Hz, 4H), 3.46 (t, J=6.5 Hz, 2H), 3.27-3.22 (m, 1H), 2.51 (s, 3H), 2.22-2.20 (m, 2H), 2.08-2.04 (m, 2H), 1.58-1.52 (m, 2H), 1.50-1.44 (m, 2H), 1.42-1.34 (m, 2H), 1.27-1.19 (m, 2H), 0.92 (t, J=7.0 Hz, 3H). LC-MS m/z: 415.3 [M+H]$^+$. HPLC Purity (214 nm): >98%; $t_R$=10.14 min.

N-((1R,4R)-4-Butoxycyclohexyl)-4-methyl-2-(tetrahydro-2H-pyran-4-yl)pyrrolo[1,2-a]pyrimidine-8-carboxamide

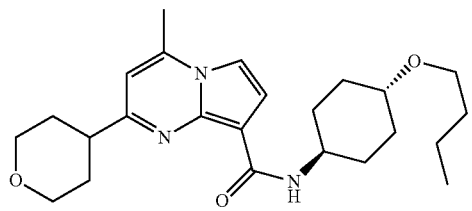 [SMILES: CCCCO[C@H]1CC[C@H](NC(=O)c2ccn3c(C)cc(C4CCOCC4)nc23)CC1]

Following general procedure A, 2-chloro-4-methylpyrrolo[1,2-a]pyrimidine-8-carboxylic acid (90 mg, 0.43 mmol) and (1R,4R)-4-butoxycyclohexanamine afforded N-((1R,4R)-4-butoxycyclohexyl)-2-chloro-4-methylpyrrolo[1,2-a]pyrimidine-8-carboxamide (110 mg, 71%) as a yellow solid. $^1$H NMR (500 MHz, CDCl$_3$): δ 7.97 (d, J=7.5 Hz, 1H), 7.57 (d, J=3.0 Hz, 1H), 7.09 (d, J=3.0 Hz, 1H), 6.60 (d, J=1.0 Hz, 1H), 4.05-4.01 (m, 1H), 3.47 (t, J=7.0 Hz, 2H), 3.33-3.30 (m, 1H), 2.60 (d, J=0.5 Hz, 3H), 2.18-2.15 (m, 2H), 2.08-2.05 (m, 2H), 1.58-1.44 (m, 2H), 1.42-1.26 (m, 6H), 0.92 (t, J=7.0 Hz, 3H). LC-MS m/z: 364.3 [M+H]$^+$. HPLC Purity (214 nm): >99%; $t_R$=11.35 min.

A mixture of 2-(3,6-dihydro-2H-pyran-4-yl)-4,4,5,5-tetramethyl-1,3,2-dioxaborolane (1.52 g, 7.24 mmol), and KHF$_2$ solution (3 M, 12 mL, 36 mmol) in MeOH was stirred at RT for 2 h. The solvent was concentrated in vacuo. The residue was extracted with hot acetone (50 mL×2), and this solution was dried over anhydrous Na$_2$SO$_4$ and filtered. The filtrate was concentrated in vacuo to afford (3,6-dihydro-2H-pyran-4-yl)trifluoro-[$^4$-borane, potassium salt (575 mg, 42%) as a white solid.

Following general procedure D, N-((1R,4R)-4-butoxycyclohexyl)-2-chloro-4-methylpyrrolo[1,2-a]pyrimidine-8-carboxamide (80 mg, 0.22 mmol) and (3,6-dihydro-2H-pyran-4-yl)trifluoro-[$^4$-borane, potassium salt afforded N-((1R,4R)-4-butoxycyclohexyl)-2-(3,6-dihydro-2H-pyran-4-yl)-4-methylpyrrolo[1,2-a]pyrimidine-8-carboxamide (54 mg, 60%) as a yellow solid. LC-MS m/z: 412.2 [M+H]$^+$, Purity (254 nm): >80%; $t_R$=2.04 mM.

A mixture of N-((1R,4R)-4-butoxycyclohexyl)-2-(3,6-dihydro-2H-pyran-4-yl)-4-methylpyrrolo[1,2-a]pyrimidine-8-carboxamide (30 mg, 0.073 mmol) and 10% Pd/C (6 mg) in ethyl acetate (5 mL) was stirred at RT for 3 h under hydrogen atmosphere. The Pd/C was removed by filtration through Celite, the filtrate was concentrated in vacuo, and the residue was purified by prep-HPLC (MeCN/10 mM NH$_4$HCO$_3$) to afford the title compound (7 mg, 23%) as a white solid. $^1$H NMR (500 MHz, DMSO-d$_6$) δ 8.50 (d, J=7.5 Hz, 1H), 7.39 (d, J=3.5 Hz, 1H), 7.26 (d, J=3.5 Hz, 1H), 6.90 (s, 1H), 3.99 (d, J=14.0 Hz, 2H), 3.79 (brs, 1H), 3.49 (t, J=11.5 Hz, 2H), 3.41 (t, J=6.5 Hz, 2H), 3.03-2.98 (m, 1H), 2.62 (s, 3H), 2.00 (t, J=12.0 Hz, 4H), 1.92 (d, J=12.5 Hz, 2H), 1.74 (qd, J=12.0 Hz, 4.5 Hz, 2H), 1.46 (m, 2H), 1.30 (m, 6H), 0.88 (t, J=7.0 Hz, 3H); LC-MS m/z: 414.3 [M+H]$^+$, HPLC Purity (214 nm): >99%; $t_R$=8.59 min.

N-(1-Cyclopropyl-3-methylbutyl)-2,4-dimethylpyrrolo[1,2-a]pyrimidine-8-carboxamide

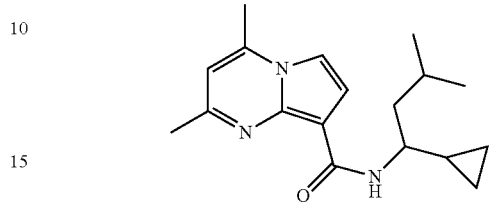

Following general procedure A, 2,4-dimethylpyrrolo[1,2-a]pyrimidine-8-carboxylic acid (38 mg, 0.20 mmol) and 1-cyclopropyl-3-methylbutan-1-amine afforded the title compound (22.6 mg, 36%) as a pale yellow solid. $^1$H NMR (500 MHz, CDCl$_3$) δ 8.47 (d, J=8.5 Hz, 1H), 7.52 (d, J=3.0 Hz, 1H), 7.03 (d, J=3.5 Hz, 1H), 6.46 (s, 1H), 3.89-3.87 (m, 1H), 2.56 (s, 6H), 1.87-1.79 (m, 1H), 1.65-1.60 (m, 1H), 1.55-1.52 (m, 1H), 0.97-0.93 (m, 1H), 0.96 (d, J=6.5 Hz, 3H), 0.95 (d, J=7.0 Hz, 3H), 0.47-0.52 (m, 2H), 0.40-0.42 (m, 1H), 0.28-0.32 (m, 1H). LC-MS m/z: 300.2 [M+H]$^+$. HPLC: Purity (254 nm): >98%; $t_R$=10.97 min.

N-(1-Cyclopropyl-2,2,2-trifluoroethyl)-2,4-dimethylpyrrolo[1,2-a]pyrimidine-8-carboxamide

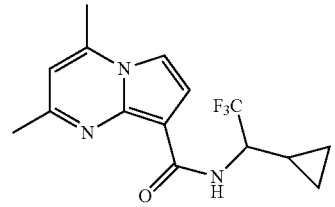 [SMILES: Cc1cc(C)n2ccc(C(=O)NC(C3CC3)C(F)(F)F)c2n1]

Following general procedure A, 2,4-dimethylpyrrolo[1,2-a]pyrimidine-8-carboxylic acid (40 mg, 0.21 mmol) and 1-cyclopropyl-2,2,2-trifluoroethanamine afforded the title compound (48 mg, 74%) as a yellow solid. $^1$H NMR (500 MHz, DMSO-d$_6$): δ 8.90 (d, J=9.5 Hz, 1H), 7.44 (d, J=3.5 Hz, 1H), 7.28 (d, J=3.0 Hz, 1H), 6.87 (s, 1H), 4.55-4.50 (m, 1H), 2.64 (s, 3H), 2.54 (s, 3H), 1.25-1.20 (m, 1H), 0.60-0.54 (m, 4H). LC-MS m/z: 312.1 [M+H]$^+$. HPLC Purity (214 nm): >99%; $t_R$=8.46 min.

(S)—N-(1-Cyclopropylethyl)-6-fluoro-2,4-dimethylpyrrolo[1,2-a]pyrimidine-8-carboxamide

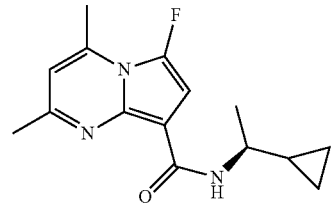

The mixture of ethyl 2,4-dimethylpyrrolo[1,2-a]pyrimidine-8-carboxylate (140 mg, 0.64 mmol) and NFSI (404 mg, 1.28 mmol) in acetonitrile (10 mL) was stirred at 50° C. for 1 day. The product was purified by reverse-phase chromatography (MeCN/10 mM NH₄HCO₃) to afford ethyl 6-fluoro-2,4-dimethylpyrrolo[1,2-a]pyrimidine-8-carboxylate (70 mg, 58%) as a yellow solid. $^1$H NMR (500 MHz, CDCl₃): δ 6.69 (d, J=2.0 Hz, 1H), 6.38 (s, 1H), 4.37 (q, J=7.5 Hz, 2H), 2.71 (d, J=6.0 Hz, 3H), 2.56 (s, 3H), 1.39 (t, J=7.5 Hz, 3H). LC-MS m/z: 237.1 [M+H]⁺.

Following general procedure B, ethyl 6-fluoro-2,4-dimethylpyrrolo[1,2-a]pyrimidine-8-carboxylate (70 mg, 0.30 mmol) afforded 6-fluoro-2,4-dimethylpyrrolo[1,2-a]pyrimidine-8-carboxylic acid (30 mg, 48%) as a brown solid. LC-MS m/z: 219.1 [M+H]⁺.

Following general procedure A, 6-fluoro-2,4-dimethylpyrrolo[1,2-a]pyrimidine-8-carboxylic acid (5 mg, 0.024 mmol) and (S)-1-cyclopropylethanamine afforded the title compound (2 mg, 30%) as a yellow solid. $^1$H NMR (500 MHz, MeOD-d₄): δ 8.86 (d, J=8.5 Hz, 1H), 6.73 (d, J=1.5 Hz, 1H), 6.64 (s, 1H), 3.72-3.67 (m, 1H), 2.77 (d, J=5.5 Hz, 3H), 2.54 (s, 3H), 1.34 (d, J=6.5 Hz, 3H), 0.60-0.49 (m, 2H), 0.45-0.41 (m, 1H), 0.33-0.29 (m, 1H). LC-MS m/z: 276.0 [M+H]⁺. HPLC Purity (214 nm): 97%; $t_R$=10.11 min.

(S)—N-(1-Cyclopropylethyl)-2,4,7-trimethylpyrrolo[1,2-a]pyrimidine-8-carboxamide

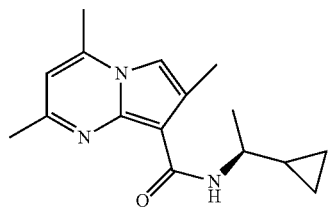 [SMILES: Cc1cc(C)n2cc(C)c(C(=O)N[C@@H](C)C3CC3)c2n1]

To a stirred solution of propionaldehyde (290 mg, 5.0 mmol) in 15 mL of dichloromethane was added a solution of bromine (800 mg, 5.0 mmol) at 0° C. Then the reaction mixture was stirred at 0° C. for 0.5 h, washed with a saturated NaHCO₃ solution (50 mL), and brine (50 mL), dried over Na₂SO₄, and filtered. The filtrate was used for the next step directly as the solution of 2-bromopropanal in DCM.

To a mixture of ethyl 3-amino-3-iminopropanoate hydrochloride (1.83 g, 11 mmol) and Et₃N (3.3 g, 33 mmol) in 25 mL of ethyl acetate was added a solution of 2-bromopropanal (680 mg, 5.0 mmol) in DCM. Then the reaction mixture was stirred at RT for 4 h, and filtered. The filtrate was concentrated in vacuo, and the residue was further purified by Combi flash (EA/PE; 63/37) to afford ethyl 2-amino-4-methyl-1H-pyrrole-3-carboxylate (330 mg, 39%) as a blue solid. LC-MS m/z: 169.1 [M+H]⁺.

A mixture of pentane-2,4-dione (300 mg, 3.0 mmol) and ethyl 2-amino-4-methyl-1H-pyrrole-3-carboxylate (420 mg, 2.5 mmol) in 5 mL of AcOH was stirred at 110° C. for 1 h, and concentrated in vacuo. The resulting residue was further purified by Combi flash (EA/PE; 70/30) to afford ethyl 2,4,7-trimethylpyrrolo[1,2-a]pyrimidine-8-carboxylate (340 mg, 59%) as a red solid. LC-MS m/z: 233.0 [M+H]⁺.

Following general procedure B, ethyl 2,4,7-trimethylpyrrolo[1,2-a]pyrimidine-8-carboxylate (340 mg, 1.48 mmol) afforded 2,4,7-trimethylpyrrolo[1,2-a]pyrimidine-8-carboxylic acid (182 mg, 60%) as a brown solid. LC-MS m/z: 205.2 [M+H]⁺.

Following general procedure A, 2,4,7-trimethylpyrrolo[1,2-a]pyrimidine-8-carboxylic acid (20 mg, 0.10 mmol) and (S)-1-cyclopropylethanamine afforded the title compound (5.8 mg, 21.4%) as a yellow solid. $^1$H NMR (500 MHz, MeOD-d₄): δ 9.19 (d, J=8.0 Hz, 1H), 7.08 (s, 1H), 6.66 (s, 1H), 3.78-3.72 (m, 1H), 2.58 (s, 3H), 2.56 (s, 3H), 2.55 (s, 3H), 1.35 (d, J=7.0 Hz, 1H), 1.08-1.01 (m, 1H), 0.59-0.54 (m, 2H), 0.53-0.42 (m, 1H), 0.34-0.29 (m, 1H). LC-MS m/z: 272.2 [M+H]⁺. HPLC Purity (214 nm): >99.5%; $t_R$=8.53 min.

(S)—N-(1-Cyclopropylethyl)-2,4,6-trimethylpyrrolo[1,2-a]pyrimidine-8-carboxamide

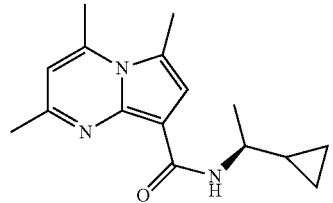 [SMILES: Cc1cc(C)n2c(C)cc(C(=O)N[C@@H](C)C3CC3)c2n1]

A mixture of ethyl 2-amino-5-methyl-1H-pyrrole-3-carboxylate (250 mg, 1.48 mmol) and pentane-2,4-dione (178 mg, 1.78 mmol) in acetic acid (5 mL) was stirred at 110° C. for 1 h, and concentrated in vacuo. The residue was purified by silica gel chromatography (eluted with 1/3 hexane/EA) to afford ethyl 2,4,6-trimethylpyrrolo[1,2-a]pyrimidine-8-carboxylate (200 mg, 57.9%) as a yellow solid. LC-MS m/z: 233.0 [M+H]⁺. LCMS: $t_R$=1.60 min.

Following general procedure B, ethyl 2,4,6-trimethylpyrrolo[1,2-a]pyrimidine-8-carboxylate afforded 2,4,6-trimethylpyrrolo[1,2-a]pyrimidine-8-carboxylic acid (120 mg, 68%) as a yellow solid. LC-MS m/z: 205.0 [M+H]⁺. LCMS: $t_R$=1.22 min.

Following general procedure A, 2,4,6-trimethylpyrrolo[1,2-a]pyrimidine-8-carboxylic acid (45 mg, 0.22 mmol) and (S)-1-cyclopropylethanamine afforded the title compound (30 mg, 51%) as a yellow solid. $^1$H NMR (400 MHz, CDCl₃) δ 8.83 (s, 1H), 7.17 (s, 1H), 6.29 (s, 1H), 3.79-3.78 (m, 1H), 2.84 (s, 3H), 2.77 (s, 3H), 2.50 (s, 3H), 1.35 (d, J=6.8 Hz, 3H), 1.02-1.00 (m, 1H), 0.53-0.44 (m, 3H), 0.32-0.29 (m, 1H). LC-MS m/z: 272.0 [M+H]⁺. HPLC: Purity (254 nm): >99%; $t_R$=7.36 min.

N-(2-Cyclopropylpropan-2-yl)-4-methyl-2-(methylamino)pyrrolo[1,2-a]pyrimidine-8-carboxamide

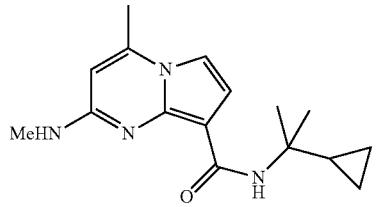 [SMILES: CNc1cc(C)n2ccc(C(=O)NC(C)(C)C3CC3)c2n1]

A solution of 2-chloro-N-(2-cyclopropylpropan-2-yl)-4-methylpyrrolo[1,2-a]pyrimidine-8-carboxamide (30 mg, 0.1 mmol) in methylamine/MeOH (2 mL) was stirred for 2 h at 70° C. The resulting product was purified by pre-HPLC (MeCN/10 mM NH$_4$HCO$_3$) to afford the title compound (14.6 mg, 51%) as a yellow solid. $^1$H NMR (500 MHz, DMSO-d$_6$): δ 8.44 (s, 1H), 7.41 (d, J=4.0 Hz, 1H), 6.92 (d, J=3.5 Hz, 1H), 6.80 (d, J=3.5 Hz, 1H), 6.07 (s, 1H), 2.84 (d, J=4.5 Hz, 3H), 2.44 (s, 3H), 1.36-1.30 (m, 1H), 1.27 (s, 6H), 0.38-0.32 (m, 4H). LC-MS m/z: 287.2 [M+H]$^+$. LC-MS Purity (214 nm): >98%.

N-(2-Cyclopropylpropan-2-yl)-4-methyl-2-morpholinopyrrolo[1,2-a]pyrimidine-8-carboxamide

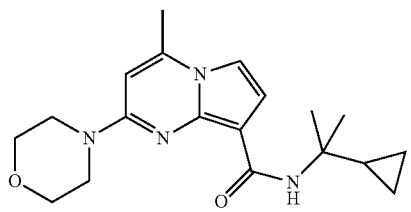 [SMILES: Cc1cc(N2CCOCC2)nc2c(C(=O)NC(C)(C)C3CC3)ccn12]

Following general procedure C, 2-chloro-N-(2-cyclopropylpropan-2-yl)-4-methylpyrrolo[1,2-a]pyrimidine-8-carboxamide (30 mg, 0.1 mmol) and morpholine afforded the title compound (5.5 mg, 15%) as a pale yellow solid. $^1$H NMR (500 MHz, CDCl$_3$): δ 8.36 (s, 1H), 7.41 (s, 1H), 6.80 (d, J=3.5 Hz, 1H), 6.16 (s, 1H), 3.83 (t, J=5.0 Hz, 4H), 3.63 (t, J=5.0 Hz, 4H), 2.51 (s, 3H), 1.41 (s, 6H), 1.39-1.34 (m, 1H), 0.46-0.38 (m, 4H). LC-MS m/z: 343.3 [M+H]$^+$. LC-MS Purity (214 nm): >99%.

N-(2-Cyclopropylpropan-2-yl)-2-methoxy-4-methylpyrrolo[1,2-a]pyrimidine-8-carboxamide

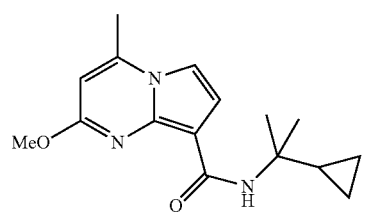 [SMILES: COc1cc(C)n2ccc(C(=O)NC(C)(C)C3CC3)c2n1]

To a solution of 2-chloro-N-(2-cyclopropylpropan-2-yl)-4-methylpyrrolo[1,2-a]pyrimidine-8-carboxamide (10 mg, 0.03 mmol) in MeOH (10 mL) was added NaOMe (18 mg, 0.3 mmol). The reaction mixture was stirred at RT overnight and the crude was purified by prep-HPLC (MeCN/10 mM NH$_4$HCO$_3$) to afford the title compound (3.5 mg, 41%) as a yellow solid. $^1$H NMR (500 MHz, DMSO-d$_6$): δ 8.09 (s, 1H), 7.23 (d, J=3.0 Hz, 1H), 7.05 (d, J=3.0 Hz, 1H), 6.46 (s, 1H), 3.95 (s, 3H), 2.57 (s, 3H), 1.37-1.35 (m, 1H), 1.32 (s, 6H), 0.41-0.36 (m, 4H). LC-MS m/z: 288.2 [M+H]$^+$. HPLC Purity (214 nm): >99%; t$_R$=8.34 min.

N-(2-Cyclopropylpropan-2-yl)-2-(((1S,4S)-4-methoxycyclohexyl)amino)-4-methylpyrrolo[1,2-a]pyrimidine-8-carboxamide

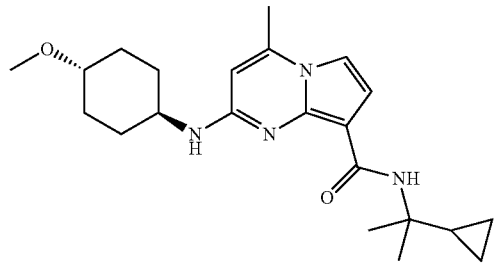 [SMILES: CO[C@H]1CC[C@H](Nc2cc(C)n3ccc(C(=O)NC(C)(C)C4CC4)c3n2)CC1]

Following general procedure C, 2-chloro-N-(2-cyclopropylpropan-2-yl)-4-methylpyrrolo[1,2-a]pyrimidine-8-carboxamide (15 mg, 0.05 mmol) and (1S,4S)-4-methoxycyclohexan-1-amine afforded the title compound (6.1 mg, 32%) as a pale yellow solid. $^1$H NMR (500 MHz, CD$_3$OD-d$_4$): δ 6.86 (d, J=3.5 Hz, 1H), 6.77 (d, J=3.5 Hz, 1H), 5.91 (s, 1H), 3.86-3.82 (m, 1H), 3.26 (s, 3H), 3.16-3.12 (m, 1H), 2.36 (s, 3H), 2.04-2.00 (m, 4H), 1.32 (s, 6H), 1.32-1.18 (m, 5H), 0.36-0.35 (m, 4H). LC-MS m/z: 385.2 [M+H]$^+$. HPLC Purity (214 nm): >80%; t$_R$=9.72 min.

N-(2-Cyclopropylpropan-2-yl)-4-methyl-2-((tetrahydro-2H-pyran-4-yl)amino)pyrrolo[1,2-a]pyrimidine-8-carboxamide

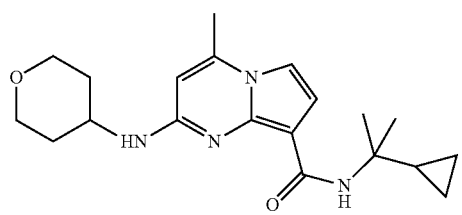 [SMILES: Cc1cc(NC2CCOCC2)nc2c(C(=O)NC(C)(C)C3CC3)ccn12]

Following general procedure C, 2-chloro-N-(2-cyclopropylpropan-2-yl)-4-methylpyrrolo[1,2-a]pyrimidine-8-carboxamide (15 mg, 0.05 mmol) and tetrahydro-2H-pyran-4-amine afforded the title compound (5.5 mg, 31%) as a pale yellow solid. $^1$H NMR (500 MHz, DMSO-d$_6$): δ 8.12 (s, 1H), 7.37 (d, J=7.5 Hz, 1H), 6.93 (d, J=3.5 Hz, 1H), 6.80 (d, J=3.5 Hz, 1H), 6.06 (s, 1H), 4.03-4.02 (m, 1H), 3.90 (dt, J=8.5 Hz, 3.5 Hz, 2H), 3.32-3.28 (m, 2H), 2.44 (s, 3H), 1.92-1.90 (m, 2H), 1.53-1.46 (m, 2H), 1.44-1.30 (m, 1H), 1.23 (s, 6H), 0.36-0.35 (m, 4H). LC-MS m/z: 357.2 [M+H]$^+$. HPLC Purity (214 nm): >99%; t$_R$=7.31 min.

N-(2-Cyclopropylpropan-2-yl)-4-methyl-2-(pyridin-2-yl)pyrrolo[1,2-a]pyrimidine-8-carboxamide

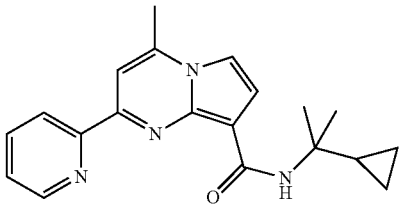

Following general procedure E, 2-chloro-N-(2-cyclopropylpropan-2-yl)-4-methylpyrrolo[1,2-a]pyrimidine-8-carboxamide (30 mg, 0.10 mmol) and 2-(tributylstannyl)pyridine afforded the title compound (5 mg 15%) as a yellow solid. $^1$H NMR (500 MHz, DMSO-$d_6$): δ 8.75 (d, J=4.5 Hz, 1H), 8.54 (s, 1H), 8.42 (d, J=8.5 Hz, 1H), 8.04 (t, J=9.0 Hz, 1H), 7.85 (s, 1H), 7.56 (d, J=3.5 Hz, 1H), 7.54 (t, J=6.0 Hz, 1H), 7.39 (d, J=3.0 Hz, 1H), 2.76 (s, 3H), 1.46 (m, 1H), 1.39 (s, 6H), 0.50-0.48 (m, 4H). LC-MS m/z: 335.1 [M+H]$^+$. HPLC Purity (214 nm): >99%; $t_R$=8.88 min.

7-Cyclopropyl-N-(2-cyclopropylpropan-2-yl)-2,4-dimethylpyrrolo[1,2-a]pyrimidine-8-carboxamide

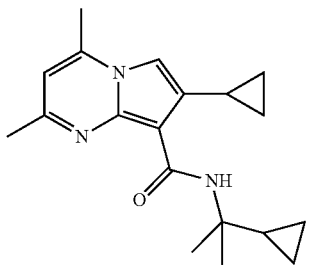 [SMILES: Cc1cc(C)n2cc(C3CC3)c(C(=O)NC(C)(C)C3CC3)c2n1]

A mixture of 2-bromo-1-cyclopropylethanone (7.4 g, 45.5 mmol) and potassium 1,3-dioxoisoindolin-2-ide (10.1 g, 55 mmol) in dimethylformamide (50 mL) was stirred at 80° C. overnight, then cooled and diluted with water (200 mL). The precipitate was collected by filtration and dried in vacuo to afford 2-(2-cyclopropyl-2-oxoethyl)isoindoline-1,3-dione (6.5 g, 63%) as a white solid. LC-MS m/z: 229.9 [M+H]$^+$; Purity (254 nm): >84%; $t_R$=1.61 min.

A mixture of 2-(2-cyclopropyl-2-oxoethyl)isoindoline-1,3-dione (1.0 g, 4.36 mmol), malononitrile (400 mg, 6.06 mmol) and 25% NaOH aqueous solution (w/w, 1.75 g) in MeOH (5 mL) was refluxed for 2 h, cooled and partitioned between ethyl acetate (100 mL) and water (50 mL). The organic layer was separated, dried over anhydrous Na$_2$SO$_4$, and filtered. The filtrate was concentrated in vacuo to afford crude 2-amino-4-cyclopropyl-1H-pyrrole-3-carbonitrile (600 mg, 93%) as black oil. LC-MS m/z: 148.2 [M+H]$^+$; Purity (254 nm): >60%; $t_R$=1.40 min.

A mixture of 2-amino-4-cyclopropyl-1H-pyrrole-3-carbonitrile (2.62 g, 17.8 mmol) and conc. H$_2$SO$_4$ (18 mL) in ethanol (100 mL) was stirred at 120° C. for 1.5 days, then cooled and concentrated in vacuo. The resulting residue was partitioned between ethyl acetate (200 mL) and water (100 mL). The organic layer was separated, dried over anhydrous Na$_2$SO$_4$ and filtered. The filtrate was concentrated in vacuo, and the residue was purified by silica gel column chromatography (PE/EA; 1/1) to afford ethyl 2-amino-4-cyclopropyl-1H-pyrrole-3-carboxylate (287 mg, 8.8% over 2 steps) as dark green oil. LC-MS m/z: 195.1 [M+H]$^+$; Purity (214 nm): >68%; $t_R$=1.68 min.

A mixture of ethyl 2-amino-4-cyclopropyl-1H-pyrrole-3-carboxylate (277 mg, 1.42 mmol) and 2, 4-pentanedione (157 mg, 1.57 mmol) in HOAc (4 mL) was stirred at 100° C. for 30 min, cooled and concentrated in vacuo. The resulting residue was partitioned between ethyl acetate (50 mL) and sat. NaHCO$_3$ solution (15 mL). The organic layer was separated, dried over anhydrous Na$_2$SO$_4$ and filtered. The filtrate was concentrated in vacuo to afford crude ethyl 7-cyclopropyl-2,4-dimethylpyrrolo[1,2-a]pyrimidine-8-carboxylate (270 mg, 73%) as dark oil. LC-MS m/z: 259.0 [M+H]$^+$; Purity (214 nm): >71%; $t_R$=1.67 min.

Following general procedure B, ethyl 7-cyclopropyl-2,4-dimethylpyrrolo[1,2-a]pyrimidine-8-carboxylate (270 mg, 1.0 mmol) afforded 7-cyclopropyl-2,4-dimethylpyrrolo[1,2-a]pyrimidine-8-carboxylic acid (21 mg, 81%) as a brown solid. (148 mg, 45% yield over 2 steps). LC-MS m/z: 231.1 [M+H]$^+$; Purity (254 nm): >87%; $t_R$=1.55 min.

Following general procedure A, 7-cyclopropyl-2,4-dimethylpyrrolo[1,2-a]pyrimidine-8-carboxylic acid (30 mg, 0.11 mmol) and 2-cyclopropylpropan-2-amine afforded the title compound (10 mg, 29%) as a white solid. $^1$H NMR (500 MHz, DMSO-$d_6$) δ 8.88 (s, 1H), 6.97 (s, 1H), 6.69 (s, 1H), 3.02-2.98 (m, 1H), 2.52 (s, 3H), 2.48 (s, 3H), 1.36 (s, 6H), 1.43-1.39 (m, 1H), 1.33-1.29 (m, 1H), 0.94 (d, J=10 Hz, 2H), 0.67 (d, J=4.0 Hz, 1H)), 0.46-0.43 (m, 4H). LC-MS m/z: 312.2 [M+H]$^+$. HPLC Purity (214 nm): >98%; $t_R$=9.61 min.

N-(2-Cyclopropylpropan-2-yl)-4-methyl-2-(pyridin-4-yl)pyrrolo[1,2-a]pyrimidine-8-carboxamide

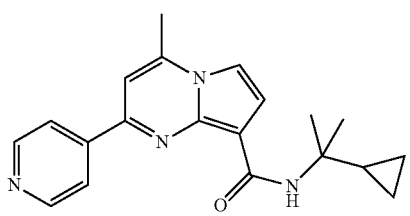 [SMILES: Cc1cc(-c2ccncc2)nc2c(C(=O)NC(C)(C)C3CC3)ccn12]

Following general procedure D, 2-chloro-N-(2-cyclopropylpropan-2-yl)-4-methylpyrrolo[1,2-a]pyrimidine-8-carboxamide (30 mg, 0.10 mmol) and pyridin-4-ylboronic acid afforded the title compound (5 mg 11%) as a yellow solid. $^1$H NMR (500 MHz, DMSO-$d_6$): δ 8.78 (d, J=5.5 Hz, 2H), 8.51 (s, 1H), 8.11 (d, J=5.5 Hz, 2H), 7.66 (s, 1H), 7.59 (d, J=3.5 Hz, 1H), 7.42 (d, J=3.5 Hz, 1H), 2.76 (s, 3H), 1.47-1.41 (m, 1H), 1.39 (s, 6H), 0.49-0.47 (m, 4H). LC-MS m/z: 335.1 [M+H]$^+$. HPLC Purity (214 nm): >99%; $t_R$=7.53 min.

N-(2-Cyclopropylpropan-2-yl)-4-methyl-2-(pyridin-3-yl)pyrrolo[1,2-a]pyrimidine-8-carboxamide

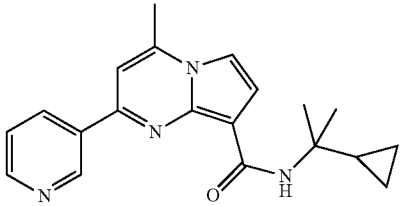 [SMILES: Cc1cc(-c2cccnc2)nc2c(C(=O)NC(C)(C)C3CC3)ccn12]

Following general procedure D, 2-chloro-N-(2-cyclopropylpropan-2-yl)-4-methylpyrrolo[1,2-a]pyrimidine-8-carboxamide (40 mg, 0.14 mmol) and pyridin-3-ylboronic acid afforded the title compound (12 mg 26%) as a yellow solid. $^1$H NMR (400 MHz, DMSO-d$_6$): δ 8.41 (d, J=2.0 Hz, 1H), 8.70 (dd, J=4.8 Hz, 1.6 Hz, 1H), 8.57 (s, 1H), 8.52 (dt, J=6.4 Hz, 2.0 Hz, 1H), 7.64 (s, 1H), 7.61 (dd, J=8.5 Hz, 5.0 Hz, 1H), 7.54 (d, J=4.0 Hz, 1H), 7.37 (d, J=4.0 Hz, 1H), 2.74 (s, 3H), 1.41-1.37 (m, 1H), 1.37 (s, 6H), 0.49-0.47 (m, 4H). LC-MS m/z: 335.1 [M+H]$^+$, HPLC Purity (214 nm): >98%; t$_R$=7.59 min.

N-(2-Cyclopropylpropan-2-yl)-4-methyl-2-(pyrimidin-5-yl)pyrrolo[1,2-a]pyrimidine-8-carboxamide

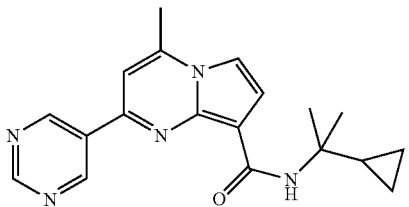 [SMILES: Cc1cc(-c2cncnc2)nc2c(C(=O)NC(C)(C)C3CC3)ccn12]

Following general procedure D, 2-chloro-N-(2-cyclopropylpropan-2-yl)-4-methylpyrrolo[1,2-a]pyrimidine-8-carboxamide (40 mg, 0.14 mmol) and pyrimidin-5-ylboronic acid afforded the title compound (15 mg 28%) as a yellow solid. $^1$H NMR (400 MHz, DMSO-d$_6$): δ 9.54 (s, 2H), 9.31 (s, 1H), 8.50 (s, 1H), 7.71 (s, 1H), 7.60 (d, J=3.2 Hz, 1H), 7.41 (d, J=3.2 Hz, 1H), 2.76 (s, 3H), 1.41 (m, 1H), 1.37 (s, 6H), 0.48 (d, J=6.4 Hz, 4H); LC-MS m/z: 336.2 [M+H]$^+$, HPLC Purity (214 nm): >98%; t$_R$=7.23 min.

N-(2-Cyclopropylpropan-2-yl)-4-methyl-2-(pyrimidin-2-yl)pyrrolo[1,2-a]pyrimidine-8-carboxamide

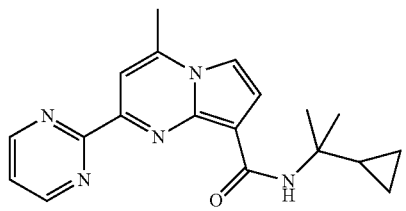 [SMILES: Cc1cc(-c2ncccn2)nc2c(C(=O)NC(C)(C)C3CC3)ccn12]

Following general procedure E, 2-chloro-N-(2-cyclopropylpropan-2-yl)-4-methylpyrrolo[1,2-a]pyrimidine-8-carboxamide (30 mg, 0.10 mmol) and 2-(tributylstannyl)pyrimidine afforded the title compound (5 mg 15%) as a yellow solid. $^1$H NMR (500 MHz, DMSO-d$_6$): δ 9.01 (d, J=5.0 Hz, 1H), 8.94 (s, 1H), 7.85 (s, 1H), 7.62 (d, J=3.5 Hz, 1H), 7.60 (t, J=4.5 Hz, 1H), 7.43 (d, J=3.0 Hz, 1H), 2.78 (s, 3H), 1.40 (s, 6H), 1.40-1.39 (m, 1H), 0.48-0.46 (m, 2H). LC-MS m/z: 336.2 [M+H]$^+$. HPLC Purity (214 nm): >99%; t$_R$=7.94 min.

N-(2-Cyclopropylpropan-2-yl)-2-(4,4-difluoropiperidin-1-yl)-4-methylpyrrolo[1,2-a]pyrimidine-8-carboxamide

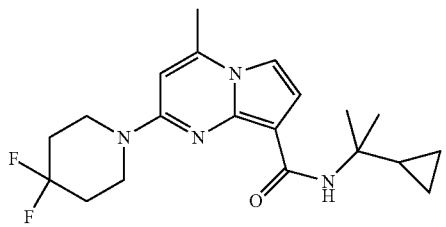 [SMILES: Cc1cc(N2CCC(F)(F)CC2)nc2c(C(=O)NC(C)(C)C3CC3)ccn12]

Following general procedure C, 2-chloro-N-(2-cyclopropylpropan-2-yl)-4-methylpyrrolo[1,2-a]pyrimidine-8-carboxamide (20 mg, 0.07 mmol) and 4,4-difluoropiperidine afforded the title compound (1.1 mg, 4%) as a yellow solid. $^1$H NMR (500 MHz, CDCl$_3$): δ 8.22 (s, 1H), 7.35 (d, J=3.0 Hz, 1H), 6.81 (d, J=3.0 Hz, 1H), 6.21 (s, 1H), 3.81 (t, J=6.0 Hz, 4H), 2.52 (s, 3H), 2.11-2.02 (m, 4H), 1.39 (s, 6H), 0.89-0.88 (m, 1H), 0.45-0.39 (m, 4H). LC-MS m/z: 377.2 [M+H]$^+$. HPLC Purity (214 nm): >98%; t$_R$=10.44 min.

2-(8-Oxabicyclo[3.2.1]octan-3-ylamino)-N-(2-cyclopropylpropan-2-yl)-4-methylpyrrolo[1,2-a]pyrimidine-8-carboxamide

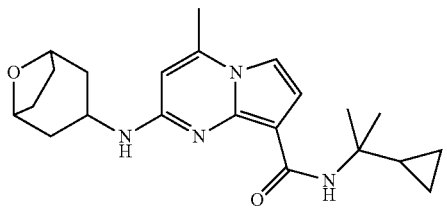 [SMILES: Cc1cc(NC2CC3CCC(C2)O3)nc2c(C(=O)NC(C)(C)C3CC3)ccn12]

Following general procedure C, 2-chloro-N-(2-cyclopropylpropan-2-yl)-4-methylpyrrolo[1,2-a]pyrimidine-8-carboxamide (20 mg, 0.07 mmol) and 8-oxabicyclo[3.2.1]octan-3-amine afforded the stereoisomeric mixture of the title compound (4.5 mg, 17%) as a yellow solid. $^1$H NMR (500 MHz, CD$_3$OD-d$_4$): δ 7.00 (d, J=3.5 Hz, 0.67H), 6.98 (d, J=3.5 Hz, 0.29H), 6.92 (d, J=3.0 Hz, 0.64H), 6.91 (d, J=3.5 Hz, 0.28H), 6.17 (s, 0.69H), 6.03 (s, 0.25H), 4.47-4.41 (m, 2H), 4.26-4.23 (m, 1H), 2.50 (s, 2H), 2.48 (s, 1H), 2.29-2.24 (m, 3H), 2.21-2.17 (m, 1H), 2.02-1.97 (m, 2H), 1.91-1.85 (m, 2H), 1.49 (s, 2H), 1.43 (s, 5H), 0.48-0.46 (m, 4H). LC-MS m/z: 383.3 [M+H]$^+$. HPLC Purity (214 nm): >99%; t$_R$=7.61 min.

N-(2-Cyclopropylpropan-2-yl)-2-(4-fluorophenyl)pyrrolo[1,2-a]pyrimidine-8-carboxamide

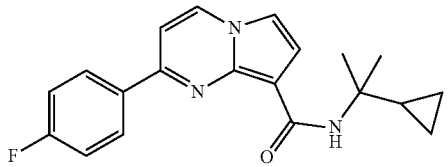 [SMILES: CC(C)(NC(=O)c1ccn2ccc(-c3ccc(F)cc3)nc12)C1CC1]

Following general procedure A, 2-(4-fluorophenyl)pyrrolo[1,2-a]pyrimidine-8-carboxylic acid (80 mg, 0.31 mmol) and 2-cyclopropylpropan-2-amine afforded the title compound (20 mg, 19%) as a yellow solid. $^1$H NMR (500 MHz, DMSO-d6): δ 8.94 (d, J=7.5 Hz, 1H), 8.44 (s, 1H), 8.24 (dd, J=6.0 Hz, 3.5H z, 2H), 7.55 (d, J=7.5 Hz, 1H), 7.53 (d, J=3.5 Hz, 1H), 7.42 (t, J=6.5 Hz, 2H), 7.27 (d, J=3.0 Hz, 1H), 1.41-1.40 (m, 1H), 1.39 (s, 6H), 0.47-0.46 (m, 2H), 0.46-0.45 (m, 2H). LC-MS m/z: 338.1 [M+fl]$^+$. HPLC Purity (214 nm): >99%; $t_R$=9.23 min.

(S)—N-(1-Cyclopropylethyl)-2-(4-fluorophenyl)pyrrolo[1,2-a]pyrimidine-8-carboxamide

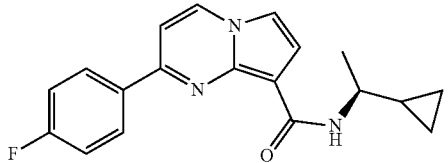 [SMILES: C[C@H](NC(=O)c1ccn2ccc(-c3ccc(F)cc3)nc12)C1CC1]

A mixture of ethyl 2-amino-1H-pyrrole-3-carboxylate (3 g, 19.5 mmol) and NaH (60%, 1.0 g, 23.4 mmol) in DMF (6 mL) was stirred at 0° C. for 30 minutes and then ethyl 3-ethoxyacrylate (3.0 g, 23.4 mmol) was added. The reaction mixture was stirred at RT for 3 h, diluted with ethyl acetate (100 mL), and neutralized with 1N HCl to pH=7. The organic layer was separated, dried over anhydrous Na$_2$SO$_4$ and filtered. The filtrate was concentrated in vacuo, and the residue was purified by silica gel column chromatography (EA) to afford ethyl 2-hydroxypyrrolo[1,2-a]pyrimidine-8-carboxylate (2.5 g, 63%) as a purple solid. LC-MS m/z: 207.1 [M+H]$^+$. Purity (254 nm): >95%; $t_R$=1.40 min.

A mixture of ethyl 2-hydroxypyrrolo[1,2-a]pyrimidine-8-carboxylate (2.5 g, 12.1 mmol) in phosphorus oxychloride (6 mL) was stirred at 50° C. for 3 h, diluted with ethyl acetate (100 mL), and neutralized with sat. Na$_2$CO$_3$ to pH=7 at 0° C. The organic layer was separated, dried over anhydrous Na$_2$SO$_4$ and filtered. The filtrate was concentrated in vacuo, and the residue was purified by silica gel column chromatography (EA) to afford ethyl 2-chloropyrrolo[1,2-a]pyrimidine-8-carboxylate (200 mg, 7%) as a yellow solid. LC-MS m/z: 225.0 [M+H]$^+$, Purity (254 nm): >95%; $t_R$=1.69 min.

Following general procedure D, ethyl 2-chloropyrrolo[1,2-a]pyrimidine-8-carboxylate (150 mg, 0.67 mmol) and (4-fluorophenyl)boronic acid afforded ethyl 2-(4-fluorophenyl)pyrrolo[1,2-a]pyrimidine-8-carboxylate (180 mg, 95%) as a yellow solid. LC-MS m/z: 285.1 [M+H]$^+$. Purity (254 nm): >80%; $t_R$=1.79 min.

Following general procedure B, ethyl 2-(4-fluorophenyl)pyrrolo[1,2-a]pyrimidine-8-carboxylate (160 mg, 0.56 mmol) afforded 2-(4-fluorophenyl)pyrrolo carboxylic acid (115 mg, 80%) as a white solid. LC-MS m/z: 257.0 [M+H]$^+$. Purity (254 nm): >80%; $t_R$=1.29 min.

Following general procedure A, 2-(4-fluorophenyl)pyrrolo[1,2-a]pyrimidine-8-carboxylic acid (100 mg, 0.39 mmol) and (S)-1-cyclopropylethanamine afforded the title compound (20 mg, 19%) as a yellow solid. $^1$H NMR (500 MHz, DMSO-d$_6$), δ 8.95 (d, J=7.5 Hz, 1H), 8.45 (s, 1H), 8.25 (dd, J=6.5 Hz, 3.5 Hz, 2H), 7.58 (d, J=7.5 Hz, 1H), 7.54 (d, J=3.0 Hz, 1H), 7.44 (t, J=8.5 Hz, 2H), 7.29 (d, J=3.0 Hz, 1H), 3.61 (q, J=6.5 Hz, 1H), 1.28 (d, J=6.5 Hz, 3H), 1.09 (m, 1H), 0.49 (m, 2H), 0.33 (m, 2H). LC-MS m/z: 324.1 [M+H]$^+$. Purity (214 nm): >99%; $t_R$=1.97 min.

N-((1R,4R)-4-(tert-Butoxy)cyclohexyl)-5-methyl-7,8-dihydro-6H-cyclopenta[e]pyrrolo[1,2-a]pyrimidine-3-carboxamide

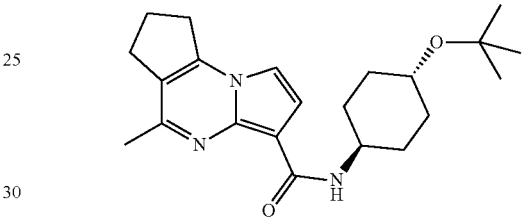

A solution of 2-acetylcyclopentanone (1.5 g, 9.7 mmol) and ethyl 2-amino-1H-pyrrole-3-carboxylate (1.2 g, 9.5 mmol) in acetic acid (10 mL) was stirred at 110° C. for 1 hour. The solution was concentrated in vacuo, and the resulting residue was purified by silica gel column to afford ethyl 5-methyl-7,8-dihydro-6H-cyclopenta[e]pyrrolo[1,2-a]pyrimidine-3-carboxylate (500 mg, 17%) and ethyl 9-methyl-2,3-dihydro-1H-cyclopenta[d]pyrrolo[1,2-a]pyrimidine-5-carboxylate (370 mg, 13%) as yellow solids. Ethyl 5-methyl-7,8-dihydro-6H-cyclopenta[e]pyrrolo[1,2-a]pyrimidine-3-carboxylate: $^1$H NMR (400 MHz, DMSO-d$_6$): δ 7.22 (d, J=4.0 Hz, 1H), 7.18 (d, J=4.0 Hz, 1H), 4.23 (q, J=9.0 Hz, 2H), 3.14 (t, J=10.0 Hz, 2H), 2.90 (t, J=9.5 Hz, 2H), 2.44 (s, 3H), 2.18 (m, 2H), 1.30 (t, J=9.0 Hz, 3H). LC-MS m/z: 245.0 [M+H]$^+$. LC-MS Purity (254 nm): 98%; $t_R$=1.63 min Ethyl 9-methyl-2,3-dihydro-1H-cyclopenta[d]pyrrolo[1,2-a]pyrimidine-5-carboxylate: $^1$H NMR (400 MHz, DMSO-d$_6$): δ 7.30 (d, J=4.5 Hz, 1H), 7.20 (d, J=4.5 Hz, 1H), 4.23 (q, J=9.0 Hz, 2H), 2.95-2.89 (m, 4H), 2.53 (s, 3H), 2.12-2.08 (m, 2H), 1.28 (t, J=9.0 Hz, 3H). LC-MS m/z: 245.0 [M+H]$^+$. LC-MS Purity (254 nm): 97%; $t_R$=1.61 min.

Following general procedure B, ethyl 5-methyl-7,8-dihydro-6H-cyclopenta[e]pyrrolo[1,2-a]pyrimidine-3-carboxylate (350 mg, 1.43 mmol) afforded 5-methyl-7,8-dihydro-6H-cyclopenta[e]pyrrolo[1,2-a]pyrimidine-3-carboxylic acid (280 mg, 90%) as a brown solid.

Following general procedure A, 5-methyl-7,8-dihydro-6H-cyclopenta[e]pyrrolo[1,2-a]pyrimidine-3-carboxylic acid (40 mg, 0.19 mmol) and (1R,4R)-4-(tert-butoxy)cyclohexanamine afforded the title compound (18.8 mg, 27%) as an off-white solid. $^1$H NMR (500 MHz, CDCl$_3$): δ 8.57 (d, J=8.0 Hz, 1H), 7.50 (d, J=3.0 Hz, 1H), 6.90 (d, J=3.0 Hz, 1H), 4.02-3.98 (m, 1H), 3.50-3.46 (m, 1H), 3.15 (t, J=7.5 Hz, 2H), 3.01 (t, J=7.5 Hz, 2H), 2.54 (s, 3H), 2.38-2.32 (m, 2H), 2.22-2.18 (m, 2H), 1.90-1.86 (m, 2H), 1.56-1.50 (m,

N-((1R,4R)-4-(tert-Butoxy)cyclohexyl)-9-methyl-2,3-dihydro-1H-cyclopenta[d]pyrrolo[1,2-a]pyrimidine-5-carboxamide

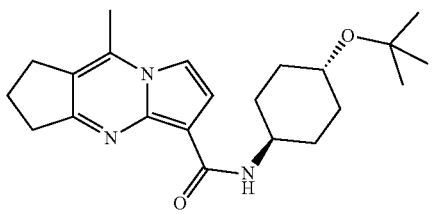 [SMILES: Cc1c2c(nc3c(C(=O)N[C@H]4CC[C@H](OC(C)(C)C)CC4)ccn13)CCC2]

Following general procedure B, ethyl 9-methyl-2,3-dihydro-1H-cyclopenta[d]pyrrolo[1,2-a]pyrimidine-5-carboxylate (260 mg, 1.06 mmol) afforded 9-methyl-2,3-dihydro-1H-cyclopenta[d]pyrrolo[1,2-a]pyrimidine-5-carboxylic acid (210 mg, 90%) as a brown solid.

Following general procedure A, 9-methyl-2,3-dihydro-1H-cyclopenta[d]pyrrolo[1,2-a]pyrimidine-5-carboxylic acid (40 mg, 0.19 mmol) and (1R,4R)-4-(tert-butoxy)cyclohexanamine afforded the title compound (18.6 mg, 27%) as an off-white solid. $^1$H NMR (500 MHz, DMSO-$d_6$): δ 8.30 (d, J=8.0 Hz, 1H), 7.33 (d, J=3.5 Hz, 1H), 7.19 (d, J=3.0 Hz, 1H), 3.78-3.75 (m, 1H), 3.58-5.52 (m, 1H), 2.97 (d, J=7.5 Hz, 2H), 2.94 (d, J=7.5 Hz, 2H), 2.56 (s, 3H), 2.15-2.10 (m, 2H), 1.96-1.94 (m, 2H), 1.78-1.74 (m, 2H), 1.40-1.34 (m, 4H), 1.15 (s, 9H). LC-MS m/z: 370.2 [M+H]$^+$. HPLC Purity (254 nm): 98%; $t_R$=9.25 min.

N-(2-Cyclopropylpropan-2-yl)-5-methyl-7,8-dihydro-6H-cyclopenta[e]pyrrolo[1,2-a]pyrimidine-3-carboxamide

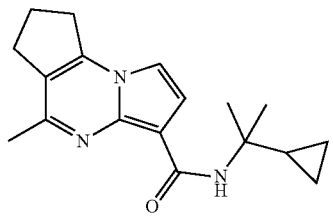 [SMILES: Cc1nc2c(C(=O)NC(C)(C)C3CC3)ccn2c2c1CCC2]

Following general procedure A, 5-methyl-7,8-dihydro-6H-cyclopenta[e]pyrrolo[1,2-a]pyrimidine-3-carboxylic acid (40 mg, 0.19 mmol) and 2-cyclopropylpropan-2-amine afforded the title compound (10.4 mg, 19%) as an off-white solid. $^1$H NMR (500 MHz, CDCl$_3$): δ 8.71 (s, 1H), 7.49 (d, J=3.0 Hz, 1H), 6.90 (d, J=3.5 Hz, 1H), 3.15 (t, J=7.5 Hz, 2H), 3.01 (t, J=7.5 Hz, 2H), 2.53 (s, 3H), 2.33 (m, J=7.5 Hz, 2H), 1.49 (s, 6H), 1.41-1.38 (m, 1H), 0.55-0.50 (m, 4H). LC-MS m/z: 298.1 [M+H]$^+$. HPLC Purity (254 nm): 99%; $t_R$=9.23 min.

N-(2-Cyclopropylpropan-2-yl)-9-methyl-2,3-dihydro-1H-cyclopenta[d]pyrrolo[1,2-a]pyrimidine-5-carboxamide

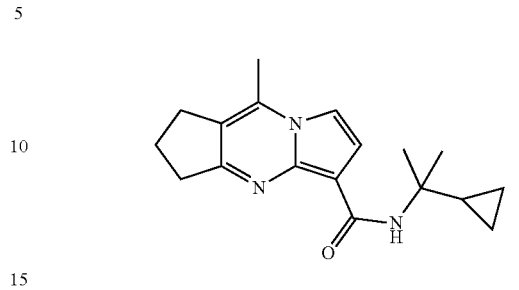

Following general procedure A, 9-methyl-2,3-dihydro-1H-cyclopenta[d]pyrrolo[1,2-a]pyrimidine-5-carboxylic acid (40 mg, 0.19 mmol) and 2-cyclopropylpropan-2-amine afforded the title compound (25.9 mg, 48%) as an off-white solid. $^1$H NMR (500 MHz, CDCl$_3$): δ 8.39 (s, 1H), 7.31 (d, J=3.5 Hz, 1H), 7.16 (d, J=3.0 Hz, 1H), 2.97-2.93 (m, 4H), 2.56 (s, 3H), 2.12 (m, J=7.5 Hz, 2H), 1.35 (s, 6H), 1.34-1.30 (m, 1H), 0.44-0.41 (m, 4H). LC-MS m/z: 298.2 [M+H]$^+$. HPLC Purity (254 nm): 99%; $t_R$=9.15 min.

(S)—N-(1-Cyclopropylethyl)-3-(4-fluorophenyl)pyrrolo[1,2-a]pyrimidine-8-carboxamide

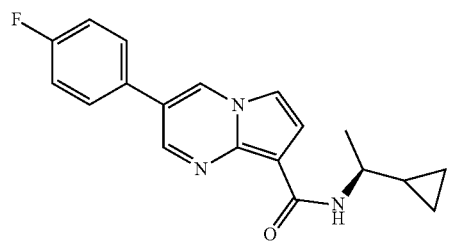 [SMILES: C[C@H](NC(=O)c1ccn2cc(-c3ccc(F)cc3)cnc12)C1CC1]

To anhydrous DMF (11 mL) at 5-10° C. was added dropwise POCl$_3$ (2.75 mL, 30 mmol) and the mixture was stirred for 2 h at RT followed by the addition of 2-(4-fluorophenyl)acetic acid (1.54 g, 10.0 mmol). The mixture was stirred for 4 h at 90-95° C. and then stirred overnight at RT. The resulting black mixture was poured on crushed ice and a saturated solution of NaClO$_4$.H$_2$O (4 g) was added with stirring. The resulting nearly white crystalline deposit of perchlorate salt was filtered and washed with 4 mL portions of water. The solid was added to a warm solution of 1.0 g NaOH in 6 mL of water. The mixture was heated with stirring for 15 min at 90° C. until complete dissolution of the organic salt followed by the addition of 10% HCl (to pH=5) resulting in the precipitation of 2-(4-fluorophenyl)malonaldehyde (750 mg, 45%) as a gray white solid. LC-MS m/z: 167.7 [M+H]$^+$.

To a solution of ethyl 2-amino-1H-pyrrole-3-carboxylate (500 mg, 3.24 mmol) in AcOH (15 mL) was added 2-(4-fluorophenyl)malonaldehyde (664 mg, 4.0 mmol) at 90° C. Then the reaction mixture was stirred for 2 h at 90° C., cooled, and concentrated in vacuo. The residue was purified by silica gel column (PE/EA=3/1) to afford ethyl 3-(4-fluorophenyl)pyrrolo[1,2-a]pyrimidine-8-carboxylate (252 mg, 26%) as a yellow solid. LC-MS m/z: 239.0 [M+H]$^+$.

Following general procedure B, ethyl 3-(4-fluorophenyl)pyrrolo[1,2-a]pyrimidine-8-carboxylate (100 mg, 0.35 mmol) afforded 3-(4-fluorophenyl)pyrrolo[1,2-a]pyrimidine-8-carboxylic acid (60 mg, 67%) as a white solid. LC-MS m/z: 257.9 [M+H]+.

Following general procedure A, 3-(4-fluorophenyl)pyrrolo[1,2-a]pyrimidine-8-carboxylic acid (35 mg, 0.14 mmol) and (S)-1-cyclopropylethanamine afforded the title compound (28 mg, 62%). $^1$H NMR (500 MHz, DMSO-$d_6$): δ 9.22 (d, J=2.0 Hz, 1H), 8.79 (d, J=2.5 Hz, 1H), 8.15 (d, J=8.5 Hz, 1H), 7.84 (m, J=3.5 Hz, 2H), 7.54 (d, J=3.0 Hz, 1H), 7.38 (td, J=7.0 Hz, 2.5 Hz, 2H), 7.33 (d, J=3.0 Hz, 1H), 3.62-3.60 (m, 1H), 1.25 (d, J=6.5 Hz, 3H), 1.01-0.99 (m, 1H), 0.49-0.42 (m, 2H), 0.34-0.32 (m, 1H), 0.27-0.25 (m, 1H). LC-MS m/z: 324.2 [M+H]+. HPLC Purity (214 nm): >99%; $t_R$=8.75 min.

(S)—N-(1-Cyclopropylethyl)-2-(4-fluorophenyl)-3-methylpyrrolo[1,2-a]pyrimidine-8-carboxamide

To a solution of 1-ethoxyprop-1-ene (10.2 mL, 92 mmol) and pyridine (8 mL, 99.5 mmol) in DCM (30 mL) was added 2,2,2-trichloroacetyl chloride (10.2 mL, 91.3 mmol) at −10° C. under a N$_2$ atmosphere. The reaction mixture was then slowly warmed to 23° C. and stirred for 20 h. The reaction mixture was diluted with DCM (50 mL), washed with 0.01N HCl (3×50 mL) and brine (50 mL), dried over anhydrous sodium sulfate, filtered and concentrated in vacuo. To the crude residue was added sodium ethoxide (7.45 g, 109.6 mmol) slowly via syringe. After 30 min the reaction mixture was partitioned between DCM (500 mL) and water (500 mL). The organic phase was separated and the aqueous layer was extracted with DCM (200 mL×3). The combined organic extracts were dried over Na$_2$SO$_4$, and filtered. The filtrate was concentrated in vacuo to afford ethyl 3-ethoxy-2-methylacrylate (15 g, 82%) as an orange oil. LC-MS m/z: 159.1 [M+1]+. LCMS: Purity 73% (214 nm) $t_R$=1.79 min.

A solution of ethyl 3-ethoxy-2-methylacrylate (1.896 g, 12 mmol), ethyl 2-amino-1H-pyrrole-3-carboxylate (1.54 g, 10 mol) and Cs$_2$CO$_3$ (3.9 g, 12 mmol) in DMF (20 mL) was heated at 150° C. for 3 h. The solvent was removed by concentration in vacuo and the residue was purified by silica gel column (PE/EA: 2/1) to afford ethyl 3-methyl-2-oxo-1,2-dihydropyrrolo[1,2-a]pyrimidine-8-carboxylate (1.2 g, 54%) as a yellow solid. $^1$H NMR (400 MHz, CDCl$_3$) 9.72 (s, 1H), 7.64 (d, J=1.2 Hz, 1H), 7.27 (s, 1H), 6.69 (d, J=3.6 Hz, 1H), 6.58 (d, J=3.2 Hz, 1H), 4.33 (q, J=7.2 Hz, 2H), 2.09 (s, 3H), 1.37 (t, J=7.2 Hz, 3H). LC-MS m/z: 221.0 [M+H]+. LCMS: Purity (214 nm): 97%; $t_R$=1.49 min.

To a solution of ethyl 3-methyl-2-oxo-1,2-dihydropyrrolo[1,2-a]pyrimidine-8-carboxylate (600 mg, 2.72 mmol) in DCM (30 mL) was added POCl$_3$ (1.25 g, 8.18 mmol) at 0° C. under nitrogen atmosphere. The reaction mixture was stirred at 70° C. for 3 hours, diluted with DCM (60 mL) and poured into ice. The organic phase was separated, washed with saturated NaHCO$_3$ (30 mL) and brine (20 mL), dried over Na$_2$SO$_4$, and filtered. The filtrate was concentrated in vacuo and the residue was purified by silica gel column (PE/EA: 2/1) to afford ethyl 2-chloro-3-methylpyrrolo[1,2-a]pyrimidine-8-carboxylate (100 mg, 15%) as a yellow solid. LC-MS m/z: 238.9 [M+H]+. LCMS: Purity (214 nm): 97%; $t_R$=1.79 min.

Following general procedure D, ethyl 2-chloro-3-methylpyrrolo[1,2-a]pyrimidine-8-carboxylate (100 mg, 0.42 mmol) and 4-fluorophenylboronic acid afforded ethyl 2-(4-fluorophenyl)-3-methylpyrrolo[1,2-a]pyrimidine-8-carboxylate (120 mg, 96%) as a yellow solid. LC-MS m/z: 298.9 [M+H]+. HPLC: Purity (254 nm): >99%; $t_R$=1.96 min.

Following general procedure B, ethyl 2-(4-fluorophenyl)-3-methylpyrrolo[1,2-a]pyrimidine-8-carboxylate (120 mg, 0.4 mmol) afforded 2-(4-fluorophenyl)-3-methylpyrrolo[1,2-a]pyrimidine-8-carboxylic acid (80 mg, 74%) as a yellow solid. $^1$H NMR (500 MHz, DMSO-$d_6$) δ 8.98 (s, 1H), 7.75 (s, 1H), 6.68 (s, 1H), 2.45 (s, 3H), 2.43 (s, 3H). LC-MS m/z: 270.9 [M+H]+. LCMS: Purity (214 nm): 95%; $t_R$=1.74 min.

Following general procedure A, 2-(4-fluorophenyl)-3-methylpyrrolo[1,2-a]pyrimidine-8-carboxylic acid (27 mg, 0.1 mmol) and (S)-1-cyclopropylethanamine afforded the title compound (27 mg, 74%) as a pale yellow solid. $^1$H NMR (500 MHz, DMSO-$d_6$) 8.81 (d, J=1.0 Hz, 1H), 8.32 (d, J=7.5 Hz, 1H), 7.81-7.83 (m, 2H), 7.47 (d, J=1.5 Hz, 1H), 7.41-7.38 (m, 2H), 7.26 (d, J=3.0 Hz, 1H), 3.62-3.60 (m, 1H), 2.33 (s, 3H), 1.18 (d, J=6.5 Hz, 3H), 0.92-0.90 (m, 1H), 0.42-0.36 (m, 2H), 0.29-0.26 (m, 2H). LC-MS m/z: 338.2 [M+H]+. HPLC: Purity (214 nm): >99%; $t_R$=10.62 min.

(S)—N-(1-Cyclopropylethyl)-3-(4-fluorophenyl)-4-methylpyrrolo[1,2-a]pyrimidine-8-carboxamide

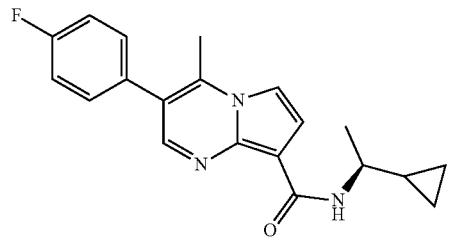 [SMILES: Cc1c(-c2ccc(F)cc2)cnc2c(C(=O)N[C@@H](C)C3CC3)ccn12]

A mixture of 1-(4-fluorophenyl)propan-2-one (4.56 g, 30 mmol) and ((dimethylamino)(methoxy)methoxy)methylium (18.0 g, 150 mmol) was stirred at 100° C. overnight. Then the solvent was concentrated in vacuo to afford 4-(dimethylamino)-3-(4-fluorophenyl)but-3-en-2-one (6.2 g, 100%) as a yellow solid, which was used directly in the next step. LC-MS m/z: 208.1 [M+H]+. Purity (254 nm): >94%; $t_R$=1.57 min.

A mixture of 4-(dimethylamino)-3-(4-fluorophenyl)but-3-en-2-one (210 mg, 1.0 mmol) and ethyl 2-amino-1H-pyrrole-3-carboxylate (177 mg, 1.15 mmol) was stirred in toluene (10 mL) under reflux overnight, and concentrated in vacuo. The resulting residue was purified by silica gel chromatography (PE/EA; 1/1) to afford ethyl 3-(4-fluorophenyl)-4-methylpyrrolo[1,2-a]pyrimidine-8-carboxylate (75 mg, 25%) as a purple solid. LC-MS m/z: 298.9 [M+H]+. Purity (254 nm): >99%; $t_R$=1.90 min.

Following general procedure B, ethyl 3-(4-fluorophenyl)-4-methylpyrrolo[1,2-a]pyrimidine-8-carboxylate (75 mg, 025 mmol) afforded 3-(4-fluorophenyl)-4-methylpyrrolo[1,2-a]pyrimidine-8-carboxylic acid (70 mg, 100%) as a white solid. LC-MS m/z: 253.0 [M+H]+. Purity (254 nm): >88%; $t_R$=1.41 min.

Following general procedure A, 3-(4-fluorophenyl)-4-methylpyrrolo[1,2-c]pyrimidine-8-carboxylic acid (50 mg, 0.18 mmol) and (S)-1-cyclopropylethanamine afforded the title compound (25 mg, 40%) as a yellow solid. $^1$H NMR (500 MHz, DMSO-$d_6$): δ 8.95 (d, J=7.5 Hz, 1H), 8.37 (s, 1H), 8.28 (d, J=8.0 Hz, 1H), 7.58 (d, J=3.0 Hz 1H), 7.56 (t, J=6.5 Hz, 2H), 7.40 (d, J=3.0 Hz, 1H), 7.37 (t, J=9.0 Hz, 2H), 3.62 (q, J=7.5 Hz, 1H), 2.60 (s, 3H), 1.26 (d, J=6.5 Hz, 3H), 1.00 (m, 1H), 0.43 (m, 2H), 0.27 (m, 2H); LC-MS m/z: 338.2 [M+H]$^+$. HPLC Purity (214 nm): >99%; $t_R$=9.08 min.

N-(4-Ethynylphenyl)-4-methyl-2-(pyridin-3-0)pyr-rolo[1,2-a]pyrimidine-8-carboxamide

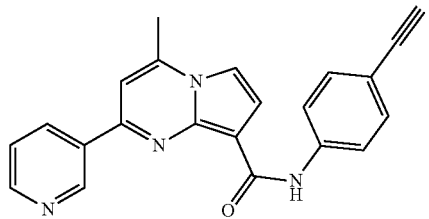 [SMILES: C#Cc1ccc(NC(=O)c2ccn3c(C)cc(-c4cccnc4)nc23)cc1]

Following general procedure D, ethyl 2-chloro-4-methylpyrrolo[1,2-a]pyrimidine-8-carboxylate (400 mg, 1.3 mmol) and pyridin-3-ylboronic acid afforded ethyl 4-methyl-2-(pyridin-3-yl)pyrrolo[1,2-a]pyrimidine-8-carboxylate (300 mg, 63.5%) as a yellow solid. LC-MS m/z: 282.1 [M+H]$^+$.

Following general procedure B, ethyl 4-methyl-2-(pyridin-3-yl)pyrrolo[1,2-a]pyrimidine-8-carboxylate (250 mg, 0.89 mmol) afforded 4-methyl-2-(pyridin-3-yl)pyrrolo[1,2-a]pyrimidine-8-carboxylic acid (200 mg, 89%) as a yellow solid. LC-MS m/z: 254.1 [M+H]$^+$.

Following general procedure A, 4-methyl-2-(pyridin-3-yl)pyrrolo[1,2-a]pyrimidine-8-carboxylic acid (40 mg, 0.16 mmol) and 4-ethynylaniline afforded the title compound (20 mg, 36%). $^1$H NMR (500 MHz, CDCl$_3$): δ 10.72 (s, 1H), 9.34 (d, J=2.0 Hz, 1H), 8.78 (dd, J=4.5 Hz, 1.0 Hz, 1H), 8.37 (d, J=8.0 Hz, 1H), 7.77 (d, J=9.0 Hz, 2H), 7.71 (d, J=3.0 Hz, 1H), 7.54-7.52 (m, 1H), 7.51 (d, J=9.0 Hz, 2H), 7.23 (d, J=3.0 Hz, 1H), 7.13 (s, 1H), 3.05 (s, 1H), 2.75 (s, 3H). LC-MS m/z: 353.1 [M+H]$^+$. HPLC Purity (214 nm): 95%; $t_R$=7.91 min.

2-(Methoxymethyl)-4-methyl-N-((1R,4R)-4-(neo-pentyloxy)cyclohexyl)pyrrolo[1,2-a]pyrimidine-8-carboxamide

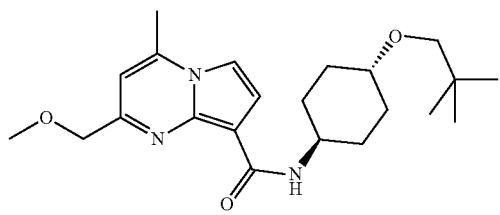 [SMILES: COCc1cc(C)n2ccc(C(=O)N[C@H]3CC[C@H](OCC(C)(C)C)CC3)c2n1]

Following general procedure A, 2-(methoxymethyl)-4-methylpyrrolo[1,2-a]pyrimidine-8-carboxylic acid (60 mg, 0.27 mmol) and (1R,4R)-4-(neopentyloxy)cyclohexan-1-amine afforded the title compound (48 mg, 62%) as a yellow solid. $^1$H NMR (400 MHz, DMSO-$d_6$): δ 8.44 (d, J=7.6 Hz, 1H), 7.44 (d, J=3.2 Hz, 1H), 7.30 (d, J=3.2 Hz, 1H), 6.90 (s, 1H), 4.54 (s, 2H), 3.88-3.78 (m, 1H), 3.40 (s, 3H), 3.33-3.26 (m, 1H), 3.07 (s, 2H), 2.65 (s, 3H), 1.98-1.94 (m, 4H), 1.40-1.30 (m, 4H), 0.87 (s, 9H). LC-MS m/z: 388.3 [M+H]$^+$. HPLC Purity (254 nm): >99%; $t_R$=9.52 min.

4-(Methoxymethyl)-2-methyl-N-(1R,4R)-4-(neopen-tyloxy)cyclohexyl)pyrrolo[1,2-a]pyrimidine-8-car-boxamide

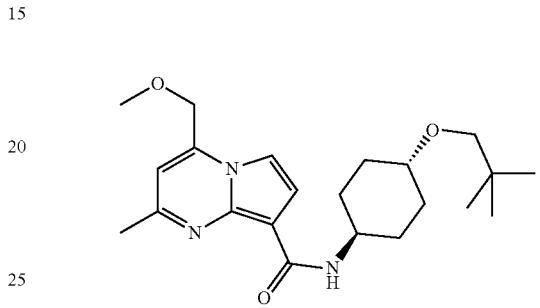

Following general procedure A, 4-(methoxymethyl)-2-methylpyrrolo[1,2-a]pyrimidine-8-carboxylic acid (60 mg, 0.27 mmol) and (1R,4R)-4-(neopentyloxy)cyclohexan-1-amine afforded the title compound (22 mg, 23%) as a yellow solid. $^1$H NMR (400 MHz, DMSO-$d_6$): δ 8.45 (d, J=7.6 Hz, 1H), 7.32 (d, J=3.2 Hz, 1H), 7.23 (d, J=3.2 Hz, 1H), 6.89 (s, 1H), 4.76 (s, 2H), 3.86-3.78 (m, 1H), 3.40 (s, 3H), 3.33-3.26 (m, 1H), 3.07 (s, 2H), 2.55 (s, 3H), 1.98-1.94 (m, 4H), 1.40-1.30 (m, 4H), 0.86 (s, 9H). LC-MS m/z: 388.3 [M+H]$^+$. HPLC Purity (254 nm): >99%; $t_R$=9.84 min.

N-((1R,4R)-4-iso-butoxycyclohexyl)-4-(methoxym-ethyl)-2-methylpyrrolo[1,2-a]pyrimidine-8-carbox-amide

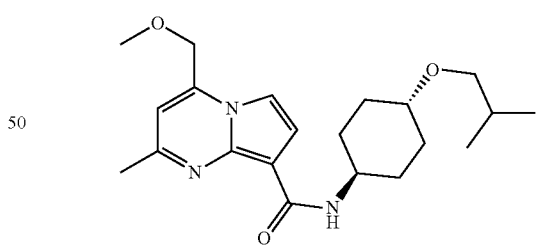

Following general procedure A, 4-(methoxymethyl)-2-methylpyrrolo[1,2-a]pyrimidine-8-carboxylic acid (110 mg, 0.50 mmol) and (1R,4R)-4-iso-butoxycyclohexan-1-amine afforded the title compound (51 mg, 26%) as a yellow solid. $^1$H NMR (500 MHz, CDCl$_3$): δ 8.54 (d, J=7.5 Hz, 1H), 7.53 (d, J=3.0 Hz, 1H), 7.10 (d, J=3.0 Hz, 1H), 6.68 (s, 1H), 4.66 (s, 2H), 4.10-4.04 (m, 1H), 3.52 (s, 3H), 3.33-3.26 (m, 1H), 3.24 (d, J=7.0 Hz, 2H), 2.61 (s, 3H), 2.22-2.18 (m, 2H), 2.10-2.04 (m, 2H), 1.88-1.80 (m, 1H), 1.58-1.48 (m, 2H), 1.47-1.38 (m, 2H), 0.93 (d, J=6.5 Hz, 6H). LC-MS m/z: 374.2 [M+H]$^+$. HPLC Purity (214 nm): 94%; $t_R$=9.16 min.

N-((1R,4R)-4-iso-butoxycyclohexyl)-2-(methoxymethyl)-4-methylpyrrolo[1,2-a]pyrimidine-8-carboxamide

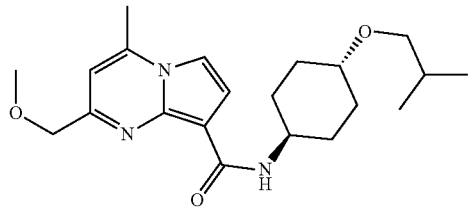 [SMILES: COCc1cc(C)n2ccc(C(=O)N[C@H]3CC[C@H](OCC(C)C)CC3)c2n1]

Following general procedure A, 2-(methoxymethyl)-4-methylpyrrolo[1,2-a]pyrimidine-8-carboxylic acid (110 mg, 0.50 mmol) and (1R,4R)-4-isobutoxycyclohexan-1-amine afforded the title compound (41.5 mg, 20%) as a yellow solid. $^1$H NMR (500 MHz, CDCl$_3$): δ 8.44 (d, J=7.5 Hz, 1H), 7.60 (d, J=3.5 Hz, 1H), 7.12 (d, J=3.5 Hz, 1H), 6.79 (s, 1H), 4.58 (s, 2H), 4.12-4.02 (m, 1H), 3.52 (s, 3H), 3.36-3.26 (m, 1H), 3.24 (d, J=7.0 Hz, 2H), 2.64 (s, 3H), 2.22-2.18 (m, 2H), 2.10-2.04 (m, 2H), 1.88-1.80 (m, 1H), 1.58-1.42 (m, 2H), 1.41-1.36 (m, 2H), 0.93 (d, J=7.0 Hz, 6H). LC-MS m/z: 374.3 [M+H]$^+$. HPLC Purity (214 nm): 98%; $t_R$=8.77 min.

N-((1R,4R)-4-tert-butoxycyclohexyl)-4-ethyl-2-methylpyrrolo[1,2-a]pyrimidine-8-carboxamide

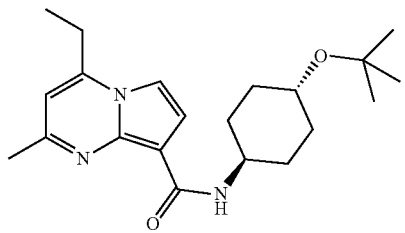 [SMILES: CCc1cc(C)nc2c(C(=O)N[C@H]3CC[C@H](OC(C)(C)C)CC3)ccn12]

To a solution of ethyl 2-amino-1H-pyrrole-3-carboxylate (500 mg, 3.25 mmol) in AcOH (10 mL) was added hexane-2,4-dione (370 mg, 3.25 mmol) at 110° C. The mixture was stirred at 110° C. for 0.5 hour, and concentrated in vacuo. The residue was purified by prep-HPLC (NH$_4$HCO$_3$/CH$_3$CN) to afford ethyl 4-ethyl-2-methylpyrrolo[1,2-a]pyrimidine-8-carboxylate (A) (300 mg, 40%) as a brown solid and ethyl 2-ethyl-4-methylpyrrolo[1,2-a]pyrimidine-8-carboxylate (B) (100 mg, 13%) as a dark red solid. A: $^1$H NMR (400 MHz, MeOD-d$_4$): δ 7.34 (d, J=3.6 Hz, 1H), 7.31 (d, J=2.4 Hz, 1H), 6.80 (s, 1H), 4.37 (q, J=7.2 Hz, 2H), 2.97 (q, J=7.2 Hz, 2H), 2.65 (s, 3H), 1.42 (t, J=7.2 Hz, 3H), 1.40 (t, J=7.2 Hz, 3H). LC-MS m/z: 233.1 [M+H]$^+$. LCMS: $t_R$=1.32 min B: $^1$H NMR (400 MHz, MeOD-d$_4$): 7.24 (d, J=2.4 Hz, 1H), 7.14 (d, J=3.6 Hz, 1H), 6.71 (s, 1H), 4.33 (q, J=7.2 Hz, 2H), 2.83 (q, J=7.2 Hz, 2H), 2.57 (s, 3H), 1.38 (t, J=7.2 Hz, 3H), 1.31 (t, J=7.2 Hz, 3H). LC-MS m/z: 233.1 [M+H]$^+$. LCMS: $t_R$=1.74 min.

Following general procedure B*, ethyl 4-ethyl-2-methylpyrrolo[1,2-a]pyrimidine-8-carboxylate (260 mg, 1.12 mmol) afforded 4-ethyl-2-methylpyrrolo[1,2-a]pyrimidine-8-carboxylic acid (230 mg, 100%) as a brown solid. LC-MS m/z: 205.2 [M+H]$^+$. LCMS: $t_R$=1.56 min.

Following general procedure A, 4-ethyl-2-methylpyrrolo[1,2-a]pyrimidine-8-carboxylic acid (30 mg, 0.15 mmol) and (1R,4R)-4-tert-butoxycyclohexanamine afforded the title compound (17 mg, 32%) as a light yellow solid. $^1$H NMR (500 MHz, MeOD-d$_4$) δ 8.95 (d, J=8.0 Hz, 1H), 7.37 (d, J=3.5 Hz, 1H), 7.34 (d, J=3.0 Hz, 1H), 6.74 (s, 1H), 3.92-3.88 (m, 1H), 3.64-3.60 (m, 1H), 3.00 (q, J=7.5 Hz, 2H), 2.61 (s, 3H), 2.17-2.12 (m, 2H), 1.95-1.90 (m, 2H), 1.52-1.47 (m, 4H), 1.45 (t, J=7.5 Hz, 2H), 1.25 (s, 9H). LC-MS m/z: 358.3 [M+H]$^+$. HPLC: Purity (254 nm): >99%; $t_R$=8.99 min.

N-((1R,4R)-4-tert-butoxycyclohexyl)-2-ethyl-4-methylpyrrolo[1,2-a]pyrimidine-8-carboxamide

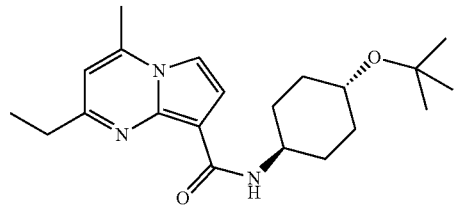 [SMILES: CCc1cc(C)n2ccc(C(=O)N[C@H]3CC[C@H](OC(C)(C)C)CC3)c2n1]

Following general procedure B*, ethyl 2-ethyl-4-methylpyrrolo[1,2-a]pyrimidine-8-carboxylate (100 mg, 0.43 mmol) afforded 2-ethyl-4-methylpyrrolo[1,2-a]pyrimidine-8-carboxylic acid (88 mg, 100%) as a brown solid. LC-MS m/z: 205.2 [M+H]$^+$. LCMS: $t_R$=1.58 min.

Following general procedure A, 2-ethyl-4-methylpyrrolo[1,2-a]pyrimidine-8-carboxylic acid (30 mg, 0.15 mmol) and (1R,4R)-4-tert-butoxycyclohexanamine afforded the title compound (25 mg, 48%) as a light yellow solid. $^1$H NMR (500 MHz, MeOD-d$_4$) δ 7.37 (d, J=4.0 Hz, 1H), 7.28 (d, J=4.5 Hz, 1H), 6.72 (s, 1H), 3.92-3.82 (m, 1H), 3.64-3.55 (m, 1H), 2.90 (q, J=9.5 Hz, 2H), 2.64 (s, 3H), 2.17-2.10 (m, 2H), 1.95-1.90 (m, 2H), 1.52-1.42 (m, 4H), 1.39 (t, J=9.5 Hz, 2H), 1.24 (s, 9H). LC-MS m/z: 358.3 [M+H]$^+$. HPLC: Purity (254 nm): >99%; $t_R$=8.95 min.

2-(3-Carbamoylphenyl)-N-(1-cyclopropyl-2,2,2-trifluoroethyl)-4-methylpyrrolo[1,2-a]pyrimidine-8-carboxamide

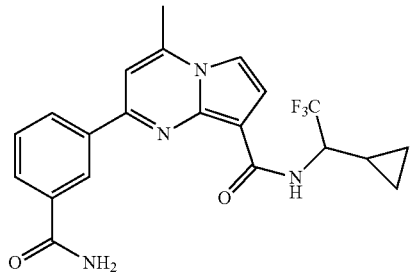 [SMILES: Cc1cc(-c2cccc(C(N)=O)c2)nc2c(C(=O)NC(C3CC3)C(F)(F)F)ccn12]

Following general procedure D, ethyl 2-chloro-4-methylpyrrolo[1,2-a]pyrimidine-8-carboxylate (300 mg, 1.3 mmol) and 3-cyanophenylboronic acid afforded ethyl 2-(3-cyanophenyl)-4-methylpyrrolo[1,2-a]pyrimidine-8-carboxylate (200 mg, 51%) as a white solid. LC-MS m/z: 306.2 [M+H]$^+$.

Following general procedure B*, ethyl 2-(3-cyanophenyl)-4-methylpyrrolo[1,2-a]pyrimidine-8-carboxylate (150 mg, 0.49 mmol) afforded 2-(3-carbamoylphenyl)-4-methylpyrrolo[1,2-a]pyrimidine-8-carboxylic acid.

Following general procedure A, 2-(3-carbamoylphenyl)-4-methylpyrrolo[1,2-a]pyrimidine-8-carboxylic acid and 1-cyclopropyl-2,2,2-trifluoroethanamine hydrochloride afforded 2-(3-carbamoylphenyl)-N-(1-cyclopropyl-2,2,2-trifluoroethyl)-4-methylpyrrolo[1,2-a]pyrimidine-8-carboxamide (3 mg, 10% yield) as a yellow solid. $^1$H NMR (500 MHz, DMSO-d$_6$): δ 9.10 (d, J=9.5 Hz, 1H), 8.70 (s, 1H), 8.29 (d, J=7.5 Hz, 1H), 8.12 (s, 1H), 8.02 (d, J=7.5 Hz, 1H), 7.72 (s, 1H), 7.67 (t, J=8.0 Hz, 1H), 7.60 (d, J=3.0 Hz, 1H), 7.54 (s, 1H), 7.42 (d, J=3.0 Hz, 1H), 4.41-4.37 (m, 1H), 2.78 (s, 3H), 1.43-1.40 (m, 1H), 0.70-0.66 (m, 1H), 0.61-0.57 (m, 2H), 0.38-0.36 (m, 1H). LC-MS m/z: 417.1 [M+H]$^+$. HPLC Purity (214 nm): >99%; t$_R$=7.17 min.

N-((1R,4R)-4-tert-butoxycyclohexyl)-4-(difluoromethyl)-2-methylpyrrolo[1,2-a]pyrimidine-8-carboxamide

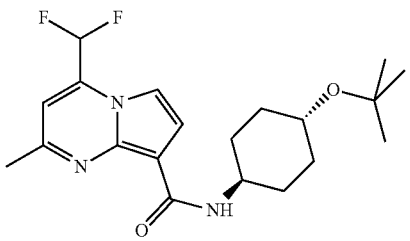 [SMILES: Cc1cc(C(F)F)n2ccc(C(=O)N[C@H]3CC[C@H](OC(C)(C)C)CC3)c2n1]

Following general procedure A, 4-(difluoromethyl)-2-methylpyrrolo[1,2-a]pyrimidine-8-carboxylic acid (50 mg, 0.22 mmol) and (1R,4R)-4-tert-butoxycyclohexan-1-amine afforded the title compound (42.5 mg, 51%) as a yellow solid. $^1$H NMR (500 MHz, DMSO-d$_6$) δ 8.29 (d, J=7.5 Hz, 1H), 7.52 (d, J=3.0 Hz, 1H), 7.51 (t, J=53.0 Hz, 1H), 7.34 (d, J=3.0 Hz, 1H), 7.20 (s, 1H), 3.80-3.72 (m, 1H), 3.55-3.49 (m, 1H), 2.62 (s, 3H), 1.96-1.95 (m, 2H), 1.78-1.76 (m, 2H), 1.45-1.30 (m, 4H), 1.15 (s, 9H). LC-MS m/z: 380.2 [M+H]$^+$. HPLC Purity (214 nm): >99%; t$_R$=8.91 min.

4-(Difluoromethyl)-N-((1R,4R)-4-isobutoxycyclohexyl)-2-methylpyrrolo[1,2-a]pyrimidine-8-carboxamide

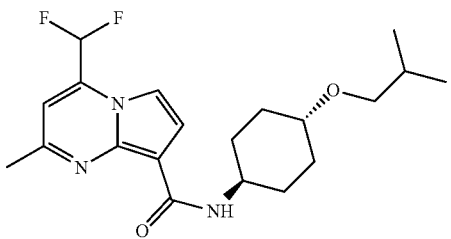 [SMILES: Cc1cc(C(F)F)n2ccc(C(=O)N[C@H]3CC[C@H](OCC(C)C)CC3)c2n1]

Following general procedure A, 4-(difluoromethyl)-2-methylpyrrolo[1,2-a]pyrimidine-8-carboxylic acid (50 mg, 0.22 mmol) and (1R,4R)-4-isobutoxycyclohexan-1-amine afforded the title compound (40 mg, 50%) as a yellow solid. $^1$H NMR (500 MHz, DMSO-d$_6$) δ 8.34 (d, J=8.0 Hz, 1H), 7.52 (d, J=3.0 Hz, 1H), 7.51 (t, J=52.5 Hz, 1H), 7.34 (d, J=3.5 Hz, 1H), 7.21 (s, 1H), 3.88-3.80 (m, 1H), 3.32-3.26 (m, 1H), 3.18 (d, J=6.5 Hz, 2H), 2.62 (s, 3H), 2.01-1.94 (m, 4H), 1.79-1.71 (m, 1H), 1.40-1.32 (m, 4H), 0.87 (d, J=6.5 Hz, 6H). LC-MS m/z: 380.2 [M+H]$^+$. HPLC: Purity (214 nm): >99%; t$_R$=9.42 min.

4-(Difluoromethyl)-2-methyl-N-((1R,4R)-4-(neopentyloxy)cyclohexyl)pyrrolo[1,2-a]pyrimidine-8-carboxamide

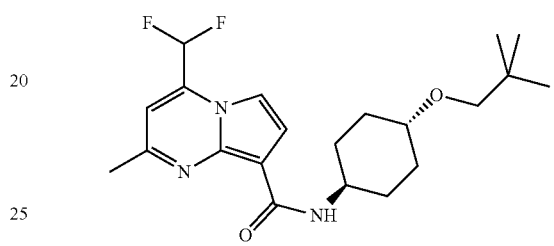

Following general procedure A, 4-(difluoromethyl)-2-methylpyrrolo[1,2-a]pyrimidine-8-carboxylic acid (50 mg, 0.22 mmol) and (1R,4R)-4-(neopentyloxy)cyclohexan-1-amine afforded the title compound (48 mg, 55%) as a yellow solid. $^1$H NMR (500 MHz, DMSO-d$_6$) δ 8.36 (d, J=7.5 Hz, 1H), 7.52 (d, J=3.0 Hz, 1H), 7.51 (t, J=52.0 Hz, 1H), 7.34 (d, J=3.0 Hz, 1H), 7.21 (s, 1H), 3.88-3.82 (m, 1H), 3.31-3.25 (m, 1H), 3.09 (s, 2H), 2.62 (s, 3H), 1.99-1.95 (m, 4H), 1.45-1.33 (m, 4H), 0.88 (s, 9H). LC-MS m/z: 394.2 [M+H]$^+$. HPLC: Purity (214 nm): >99%; t$_R$=10.09 min.

4-(Difluoromethyl)-2-methyl-N-((1R,4R)-4-propoxycyclohexyl)pyrrolo[1,2-a]pyrimidine-8-carboxamide

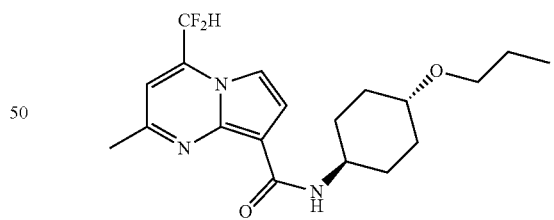

Following general procedure A, 4-(difluoromethyl)-2-methylpyrrolo[1,2-a]pyrimidine-8-carboxylic acid (30 mg, 0.13 mmol) and (1R,4R)-4-propoxycyclohexan-1-amine (25 mg, 0.16 mmol) afforded the title compound (39 mg, 82%) as a yellow solid. $^1$H NMR (500 MHz, DMSO-d$_6$): δ 8.33 (d, J=7.5 Hz, 1H), 7.52 (d, J=3.0 Hz, 1H), 7.51 (t, J=52.0 Hz, 1H), 7.33 (d, J=3.5 Hz, 1H), 7.20 (s, 1H), 3.84-3.81 (m, 1H), 3.36 (t, J=6.5 Hz, 2H), 3.42-3.36 (m, 1H), 2.61 (s, 3H), 1.98-1.94 (m, 4H), 1.53-1.46 (m, 2H), 1.37-1.31 (m, 4H), 0.87 (t, J=6.0 Hz, 3H). LCMS m/z: 366.1 [M+H]$^+$. LCMS Purity (214 nm): >99%; t$_R$=1.88 min.

2-(Difluoromethyl)-4-methyl-N-((1R,4R)-4-propoxycyclohexyl)pyrrolo[1,2-a]pyrimidine-8-carboxamide

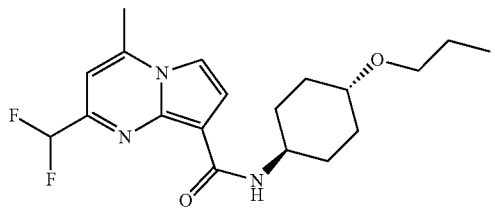 [SMILES: CCCO[C@H]1CC[C@H](NC(=O)c2ccn3c(C)cc(C(F)F)nc23)CC1]

Following general procedure A, 2-(difluoromethyl)-4-methylpyrrolo[1,2-a]pyrimidine-8-carboxylic acid (30 mg, 0.13 mmol) and (1R,4R)-4-propoxycyclohexan-1-amine afforded the title compound (23 mg, 48%) as a yellow solid. $^1$H NMR (500 MHz, DMSO-d$_6$): δ 8.19 (d, J=8.0 Hz, 1H), 7.65 (d, J=3.0 Hz, 1H), 7.48 (d, J=3.0 Hz, 1H), 7.18 (s, 1H), 7.04 (t, J=54.0 Hz, 1H), 3.88-3.81 (m, 1H), 3.37 (t, J=6.5 Hz, 2H), 3.29 (s, 1H), 2.74 (s, 3H), 2.00-1.94 (m, 4H), 1.52-1.46 (m, 2H), 1.37-1.31 (m, 4H), 0.87 (t, J=7.5 Hz, 3H). HPLC m/z: 356.1 [M+H]$^+$. HPLC Purity (214 nm): >99%; t$_R$=8.64 min.

2-(Difluoromethyl)-N-((1R,4R)-4-isobutoxycyclohexyl)-4-methylpyrrolo[1,2-a]pyrimidine-8-carboxamide

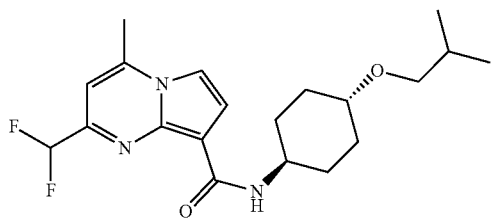 [SMILES: Cc1cc(C(F)F)nc2c(C(=O)N[C@H]3CC[C@H](OCC(C)C)CC3)ccn12]

Following general procedure A, 2-(difluoromethyl)-4-methylpyrrolo[1,2-a]pyrimidine-8-carboxylic acid (30 mg, 0.13 mmol) and (1R,4R)-4-isobutoxycyclohexan-1-amine afforded the title compound (17 mg, 34%) as a yellow solid. $^1$H NMR (500 MHz, DMSO-d$_6$): δ 8.19 (d, J=7.5 Hz, 1H), 7.65 (d, J=3.5 Hz, 1H), 7.48 (d, J=3.0 Hz, 1H), 7.18 (s, 1H), 7.04 (t, J=50.0 Hz, 1H), 3.86-3.82 (m, 1H), 3.30-3.26 (m, 1H), 3.18 (d, J=6.5 Hz, 2H), 2.74 (s, 3H), 1.98-1.96 (m, 4H), 1.77-1.72 (m, 1H), 1.40-1.31 (m, 4H), 0.86 (d, J=6.5 Hz, 6H). HPLC m/z: 380.2 [M+H]$^+$. HPLC Purity (214 nm): >99%; t$_R$=9.24 min.

(S)-4-Methyl-2-(oxazol-4-yl)-N-(1,2,3,4-tetrahydronaphthalen-1-yl)pyrrolo[1,2-a]pyrimidine-8-carboxamide

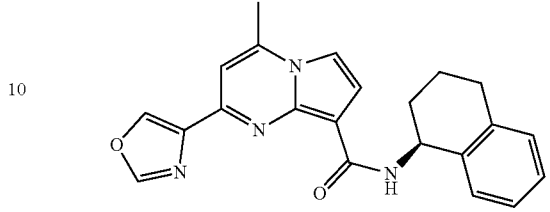

A mixture of 1-(oxazol-4-yl)butane-1,3-dione (550 mg, 3.59 mmol) and ethyl 2-amino-1H-pyrrole-3-carboxylate (553 mg, 3.59 mmol) in AcOH (10 mL) was stirred at 100° C. for 2 h until the reaction was complete. The reaction mixture was concentrated in vacuo, and the residue was purified by silica gel column (PE/EA: 1/1) to afford ethyl 4-methyl-2-(oxazol-4-yl)pyrrolo[1,2-a]pyrimidine-8-carboxylate (100 mg, 10%). $^1$H NMR (500 MHz, CDCl$_3$) 8.34 (s, 1H), 8.13 (s, 1H), 7.71 (d, J=3.5 Hz, 1H), 7.44 (d, J=3.5 Hz, 1H), 7.07 (s, 1H), 4.42 (q, J=7.0 Hz, 1H), 2.69 (s, 1H), 1.43 (t, J=7.0 Hz, 1H). LC-MS m/z: 272.0 [M+H]$^+$. LC-MS Purity (254 nm): 95%; t$_R$=1.58 min.

Following general procedure B, ethyl 4-methyl-2-(oxazol-4-yl)pyrrolo[1,2-a]pyrimidine-8-carboxylate (50 mg, 0.18 mmol) afforded 4-methyl-2-(oxazol-4-yl)pyrrolo[1,2-a]pyrimidine-8-carboxylic acid (20 mg, 45%) as a yellow solid. LC-MS m/z: 244.1 [M+H]$^+$. LCMS: Purity (254 nm): 76%; t$_R$=1.23 min.

Following general procedure A, 4-methyl-2-(oxazol-4-yl)pyrrolo[1,2-a]pyrimidine-8-carboxylic acid (20 mg, 0.08 mmol) and (S)-1,2,3,4-tetrahydronaphthalen-1-amine afforded the title compound (3 mg, 10%) as a pale yellow solid. $^1$H NMR (500 MHz, CDCl$_3$) δ 8.97 (d, J=8.5 Hz, 1H), 8.35 (s, 1H), 8.12 (s, 1H), 7.67 (d, J=8.5 Hz, 1H), 7.65 (d, J=3.0 Hz, 1H), 7.51-7.53 (m, 1H), 7.12-7.17 (m, 3H), 7.04 (s, 1H), 5.57-5.50 (m, 1H), 2.91-2.86 (m, 2H), 2.50 (s, 3H), 2.30-2.23 (m, 1H), 2.02-1.93 (m, 3H). LC-MS m/z: 373.1 [M+H]$^+$. HPLC: Purity (214 nm): >99%; t$_R$=9.30 min.

2-(Difluoromethyl)-4-methyl-N-((1R,4R)-4-(neopentyloxy)cyclohexyl)pyrrolo[1,2-a]pyrimidine-8-carboxamide

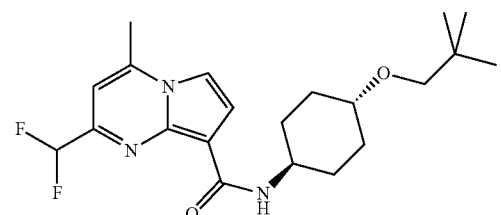

Following general procedure A, 2-(difluoromethyl)-4-methylpyrrolo[1,2-a]pyrimidine-8-carboxylic acid (30 mg, 0.13 mmol) and (1R,4R)-4-(neopentyloxy)cyclohexan-1-amine afforded the title compound (37 mg, 72%) as yellow solid. $^1$H NMR (500 MHz, DMSO-d$_6$): δ 8.21 (d, J=8.0 Hz, 1H), 7.65 (d, J=3.5 Hz, 1H), 7.48 (d, J=3.0 Hz, 1H), 7.18 (s, 1H), 7.04 (t, J=54.5 Hz, 1H), 3.88-3.82 (m, 1H), 3.28-3.24

(m, 1H), 3.08 (s, 2H), 2.74 (s, 3H), 1.99-1.94 (m, 4H), 1.41-1.33 (m, 4H), 0.87 (s, 9H). HPLC m/z: 394.2 [M+H]⁺. HPLC Purity (214 nm): >99%; $t_R$=9.91 min.

N-((1R,4R)-4-tert-butoxycyclohexyl)-2-(difluoromethyl)-4-methylpyrrolo[1,2-a]pyrimidine-8-carboxamide

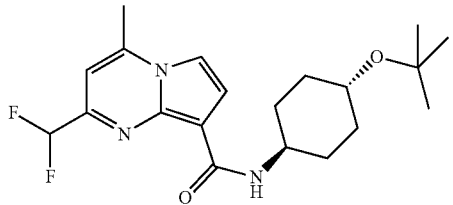 [SMILES: Cc1cc(C(F)F)nc2c(C(=O)N[C@H]3CC[C@H](OC(C)(C)C)CC3)ccn12]

Following general procedure A, 2-(difluoromethyl)-4-methylpyrrolo[1,2-a]pyrimidine-8-carboxylic acid (30 mg, 0.13 mmol) and (1R,4R)-4-tert-butoxycyclohexan-1-amine afforded the title compound (21.5 mg, 55%) as a yellow solid. ¹H NMR (500 MHz, DMSO-d₆): δ 8.14 (d, J=8.0 Hz, 1H), 7.64 (d, J=3.5 Hz, 1H), 7.48 (d, J=3.0 Hz, 1H), 7.18 (s, 1H), 7.04 (t, J=54.5 Hz, 1H), 3.79-3.76 (m, 1H), 3.51-3.34 (m, 1H), 2.74 (s, 3H), 1.97-1.93 (m, 2H), 1.79-1.75 (m, 2H), 1.45-1.32 (m, 4H), 1.14 (s, 9H). HPLC m/z: 380.2 [M+H]⁺. HPLC Purity (214 nm): >99%; $t_R$=8.75 min.

Example 2 Preparation of N-(2-Cyclopropylpropan-2-yl)-2-fluoro-4-methylpyrrolo[1,2-a]pyrimidine-8-carboxamide

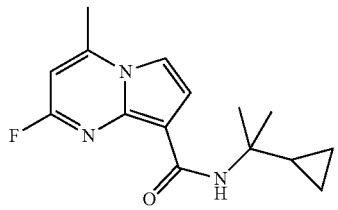 [SMILES: Cc1cc(F)nc2c(C(=O)NC(C)(C)C3CC3)ccn12]

To a solution of 2-chloro-N-(2-cyclopropylpropan-2-yl)-4-methylpyrrolo[1,2-a]pyrimidine-8-carboxamide (40 mg, 0.13 mmol) in anhydrous DMF (1.0 mL) was added KF (80 mg, 1.3 mmol). The reaction mixture was stirred for 2 h at 160° C. under microwave conditions, then cooled to RT, and further purified by pre-HPLC (MeCN/10 mM NH₄HCO₃) to afford the title compound (6.0 mg, 16%) as a yellow solid. ¹H NMR (500 MHz, CDCl₃): δ 7.81 (s, 1H), 7.52 (d, J=3.0 Hz, 1H), 7.07 (d, J=3.0 Hz, 1H), 6.32 (s, 1H), 2.63 (s, 3H), 1.42 (s, 6H), 1.40-1.37 (m, 1H), 0.49-0.46 (m, 4H). LC-MS m/z: 276.2 [M+H]⁺. HPLC Purity (214 nm): 93%; $t_R$=10.17 min.

Example 3 Preparation of N-(Cyclopropanecarbonyl)-2,4-dimethylpyrrolo[1,2-a]pyrimidine-8-carboxamide

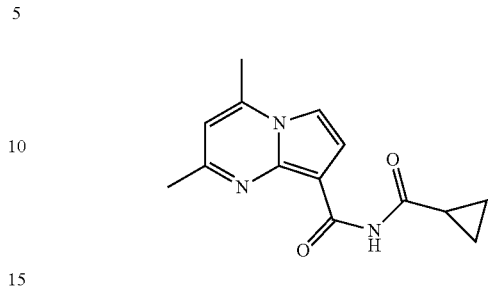

To a solution of cyclopropanecarboxamide (320 mg, 4 mmol) in THF (10 mL) was added n-BuLi (1.6 M, 2.5 mL, 4 mmol) dropwise at −78° C. The reaction mixture was stirred for 30 min at −70° C., followed by the slow addition of the solution of ethyl 2,4-dimethylpyrrolo[1,2-a]pyrimidine-8-carboxylate (436 mg, 2 mmol) in 5 mL of THF. The reaction mixture was warmed to RT, stirred for 2 h, and quenched with saturated NH₄Cl aqueous solution (50 mL). The aqueous phase was extracted with EtOAc twice (25 mL×2), and the organic phases were washed with brine (50 mL), dried over Na₂SO₄, and filtered. The filtrate was concentrated in vacuo, and the residue was purified by prep-HPLC (MeCN/10 mM NH₄HCO₃) to afford the title compound (90 mg, 22%) as a light brown solid. ¹H NMR (500 MHz, CD3OD-d₄) δ 7.45 (d, J=3.5 Hz, 1H), 7.41 (d, J=3.5 Hz, 1H), 6.86 (s, 1H), 2.69 (s, 3H), 2.65 (s, 3H), 2.58 (s, 1H), 1.15-1.12 (m, 2H), 1.07-1.03 (m, 2H). LC-MS m/z: 258.2 [M+H]⁺. HPLC Purity (214 nm): 99.5%; $t_R$=8.85 min.

Example 4 Biological Activity Evaluation

The ability of exemplary compounds to activate glucocerebrosidase (Gcase) was measured. Experimental procedures and results are provided below.

Part I: Assay Procedure

A 484 µL aliquot of a 1.0 mg/mL solution of phosphatidylserine (PS) (Sigma P7769) in chloroform was evaporated under a stream of nitrogen for 1 hour. The lipid film was dissolved over 4 minutes of vigorous vortexing in 40 mL of 176 mM K₂HPO₄/50 mM citric acid (pH 4.7) containing 7.5 µL of triton X-100, resulting in a mixed micellar preparation with a composition of 0.32 mM triton and 0.37 mol % PS. 4-Methylumbelliferyl-beta-D-glucopyranoside (ACROS-337025000) was dissolved in the micellar solution to a final concentration of 2 mM for use as the reaction substrate.

Test compounds were diluted to the desired concentrations with dimethylsulfoxide (DMSO) from 10 mM stocks, and 0.41 µL of the DMSO compound mixture was added to 100 µL of micellar solution containing 10 nM GCase and 100 nM saposin C (Enzo ALX-201-262-C050). Pre-incubation was allowed to occur for 30 minutes at room temperature, after which the reaction was initiated by combining 25 µL of substrate solution with 25 µL of compound/GCase/saposin mixture. The reaction proceeded for 15 minutes at room temperature and was stopped by adding 150 µL of 1M glycine, pH 12.5. The endpoint of the reaction was monitored by measuring fluorescence intensity (excitation: 365 nm; emission: 440 nm) on a SpectraMax i3 instrument (Molecular Devices). Test compounds were screened at 1.0 and 0.1 µM final concentration, and subsequent 8-point dose response curves were obtained using 3-fold dilutions from a maximum final concentration of 5 μM.

Part II: Results

Gcase activation values for tested compounds are provided in Tables 3 and 4 below, along with cLogP, PSA, and compound solubility in water. For experiments in which the test compound was used at a concentration of 1.0 μM, the symbol "+" indicates less than 30% Gcase activation; the symbol "++" indicates Gcase activation in the range of 30% up to 60%; and the symbol "+++" indicates Gcase activation greater than 60%. For experiments in which the test compound was used at a concentration of 0.1 μM, the symbol "*" indicates less than 10% Gcase activation; the symbol "" indicates Gcase activation in the range of 10% up to 20%; and the symbol "*" indicates greater than 20% Gcase activation.

TABLE 3

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| III-3 | [structure] | 2.3 | 53.9 | 3.8 | +++ | *** |
| III-4 | [structure] | 2.3 | 53.9 | 17.0 | +++ | *** |
| III-5 | [structure] | 3.5 | 44.7 | 3.0 | +++ | ** |
| III-6 | [structure] | 2.3 | 44.7 | 33.5 | +++ | ** |
| III-7 | [structure] | 2.6 | 44.7 | 9.5 | +++ | *** |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-8 | 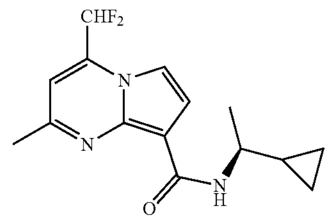 [SMILES: Cc1cc(C(F)F)n2ccc(C(=O)N[C@@H](C)C3CC3)c2n1] | 2.6 | 44.7 | 20.1 | +++ | *** |
| III-9 | 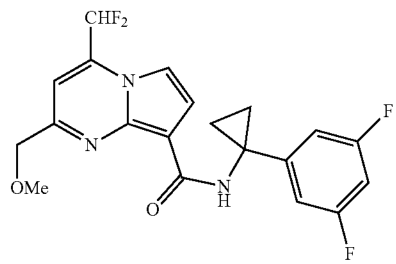 [SMILES: COCc1cc(C(F)F)n2ccc(C(=O)NC3(c4cc(F)cc(F)c4)CC3)c2n1] | 3.2 | 53.9 | N/A | + | * |
| III-10 | 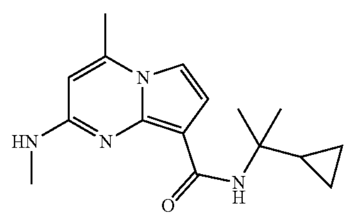 [SMILES: CNc1cc(C)n2ccc(C(=O)NC(C)(C)C3CC3)c2n1] | 3.3 | 56.7 | 11.0 | +++ | *** |
| III-11 | 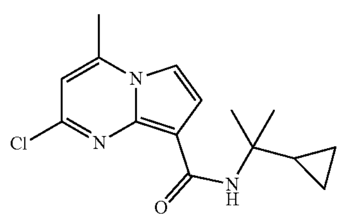 [SMILES: Cc1cc(Cl)nc2c(C(=O)NC(C)(C)C3CC3)ccn12] | 3.5 | 44.7 | 1.1 | +++ | *** |
| III-12 | 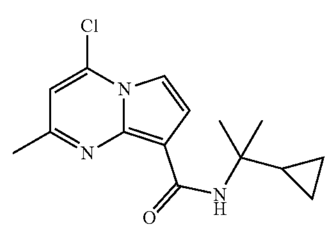 [SMILES: Cc1cc(Cl)n2ccc(C(=O)NC(C)(C)C3CC3)c2n1] | 3.5 | 44.7 | 5.8 | +++ | ** |
| III-13 | 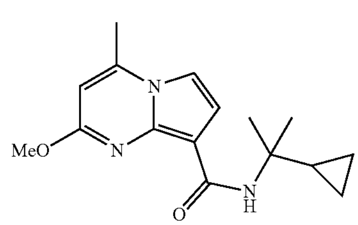 [SMILES: COc1cc(C)n2ccc(C(=O)NC(C)(C)C3CC3)c2n1] | 3.6 | 53.9 | 11.5 | +++ | ** |

TABLE 3-continued

| Compound No. | Compound Structure | cLogP | PSA | Compound Solubility in Water (μg/mL) | Percent Gcase Activation 1 μM Test Compound | 0.1 μM Test Compound |
|---|---|---|---|---|---|---|
| III-14 | 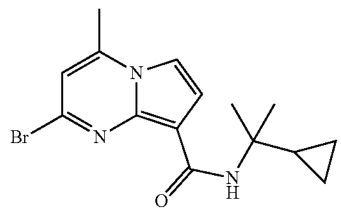 | 3.7 | 44.7 | 2.9 | +++ | ** |
| III-15 | 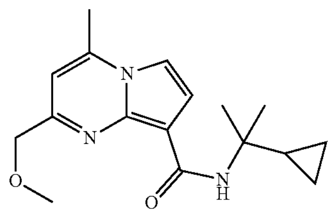 [SMILES: COCc1cc(C)n2ccc(C(=O)NC(C)(C)C3CC3)c2n1] | 2.6 | 53.9 | 21.9 | +++ | ** |
| III 16 | 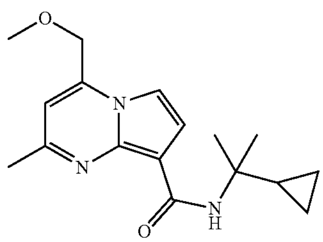 [SMILES: COCc1cc(C)nc2c(C(=O)NC(C)(C)C3CC3)ccn12] | 2.6 | 53.9 | 19.8 | +++ | *** |
| III-17 | 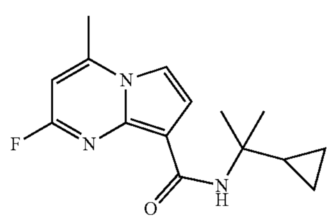 [SMILES: Cc1cc(F)nc2c(C(=O)NC(C)(C)C3CC3)ccn12] | 3.0 | 44.7 | 6.3 | +++ | ** |
| III-18 | 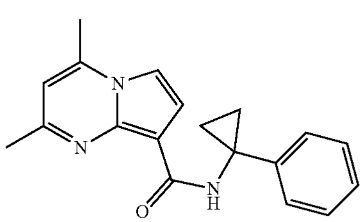 [SMILES: Cc1cc(C)n2ccc(C(=O)NC3(c4ccccc4)CC3)c2n1] | 3.9 | 44.7 | 7.7 | +++ | ** |
| III-19 | 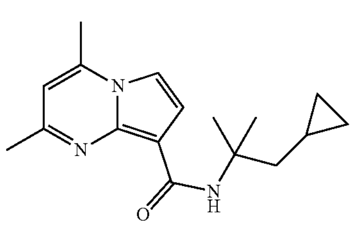 [SMILES: Cc1cc(C)n2ccc(C(=O)NC(C)(C)CC3CC3)c2n1] | 3.8 | 44.7 | 14.7 | +++ | *** |

TABLE 3-continued

| Compound No. | Compound Structure | cLogP | PSA | Compound Solubility in Water (µg/mL) | Percent Gcase Activation 1 µM Test Compound | Percent Gcase Activation 0.1 µM Test Compound |
|---|---|---|---|---|---|---|
| III-20 | 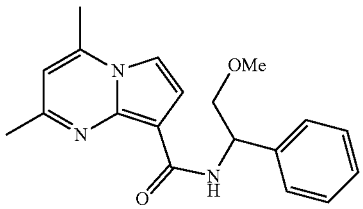 [SMILES: COCC(NC(=O)c1ccn2c(C)cc(C)nc12)c1ccccc1] | 3.5 | 53.9 | 13.7 | +++ | * |
| III-21 | 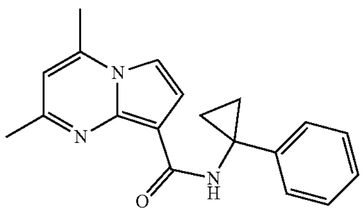 [SMILES: Cc1cc(C)n2ccc(C(=O)NC3(c4ccccc4)CC3)c2n1] | 3.9 | 44.7 | 7.7 | +++ | ** |
| III-22 | 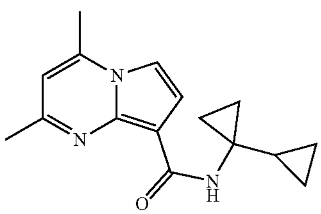 [SMILES: Cc1cc(C)n2ccc(C(=O)NC3(C4CC4)CC3)c2n1] | 2.9 | 44.7 | 21.4 | +++ | ** |
| III-23 | 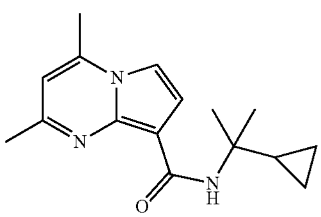 [SMILES: Cc1cc(C)n2ccc(C(=O)NC(C)(C)C3CC3)c2n1] | 3.3 | 44.7 | 18.7 | +++ | *** |
| III-24 | 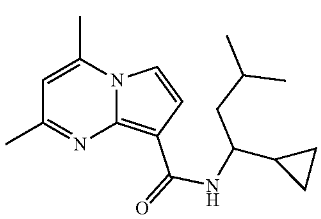 [SMILES: Cc1cc(C)n2ccc(C(=O)NC(CC(C)C)C3CC3)c2n1] | 4.4 | 44.7 | 10.9 | +++ | *** |
| III-25 | 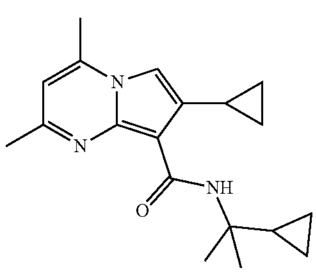 [SMILES: Cc1cc(C)n2cc(C3CC3)c(C(=O)NC(C)(C)C3CC3)c2n1] | 3.6 | 44.7 | 0.3 | ++ | * |

TABLE 3-continued
| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| III-26 | 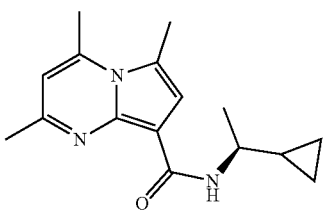 [SMILES: Cc1cc(C)n2c(C)cc(C(=O)N[C@@H](C)C3CC3)c2n1] | 3.4 | 44.7 | 8.6 | +++ | ** |
| III-27 | 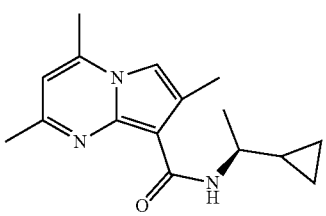 [SMILES: Cc1cc(C)n2cc(C)c(C(=O)N[C@@H](C)C3CC3)c2n1] | 3.1 | 44.7 | 8.6 | +++ | ** |
| III-28 | 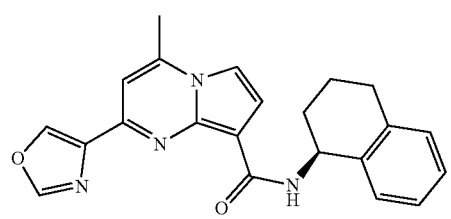 [SMILES: Cc1cc(-c2cocn2)nc2c(C(=O)N[C@H]3CCCc4ccccc43)ccn12] | 4.1 | 66.3 | 1.4 | ++ | * |
| III-29 | 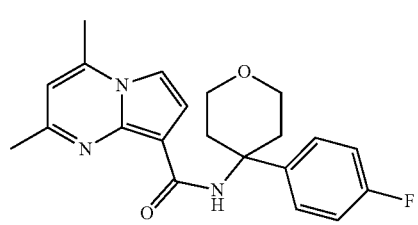 [SMILES: Cc1cc(C)n2ccc(C(=O)NC3(c4ccc(F)cc4)CCOCC3)c2n1] | 3.4 | 53.9 | 2.4 | ++ | * |
| III-30 | 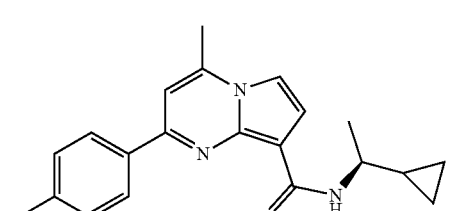 | 4.7 | 44.7 | 0.1 | +++ | *** |
| III-31 | 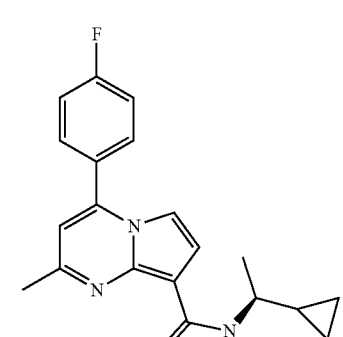 | 4.7 | 44.7 | 0.7 | ++ | * |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-32 | 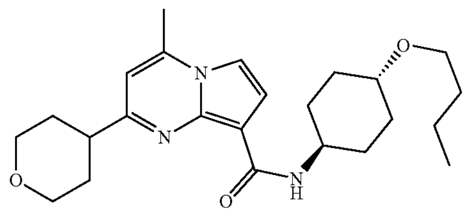 [SMILES: CCCCO[C@H]1CC[C@H](NC(=O)c2ccn3c(C)cc(C4CCOCC4)nc23)CC1] | 3.5 | 63.3 | N/A | ++ | * |
| III-33 | 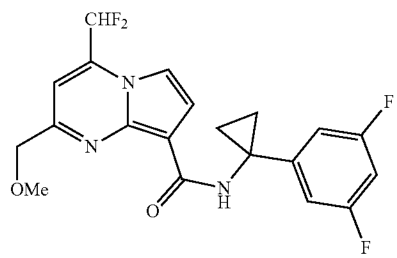 [SMILES: COCc1cc(C(F)F)n2ccc(C(=O)NC3(c4cc(F)cc(F)c4)CC3)c2n1] | 3.2 | 53.9 | N/A | + | * |
| III-34 | 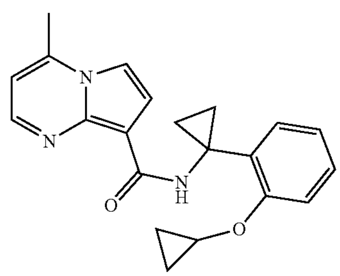 [SMILES: Cc1ccnc2c(C(=O)NC3(c4ccccc4OC4CC4)CC3)ccn12] | 3.9 | 53.9 | 6.3 | ++ | * |
| III-35 | 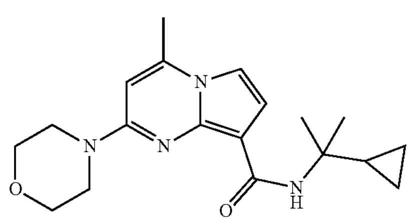 [SMILES: Cc1cc(N2CCOCC2)nc2c(C(=O)NC(C)(C)C3CC3)ccn12] | 2.8 | 57.2 | 14.0 | +++ | ** |
| III-36 | 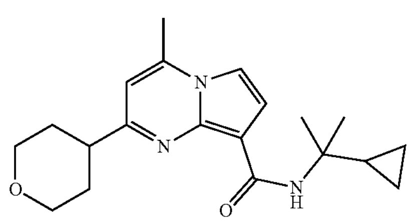 [SMILES: Cc1cc(C2CCOCC2)nc2c(C(=O)NC(C)(C)C3CC3)ccn12] | 3.0 | 53.9 | 21.3 | ++ | * |
| III-37 | | 4.0 | 66.0 | 10.2 | ++ | * |

TABLE 3-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| III-38 | 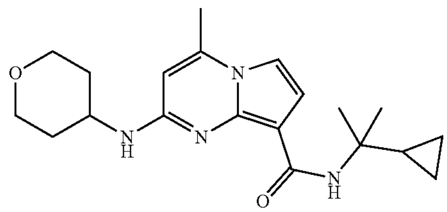 [SMILES: Cc1cc(NC2CCOCC2)nc2c(C(=O)NC(C)(C)C3CC3)ccn12] | 3.0 | 66.0 | 10.1 | +++ | ** |
| III-39 | 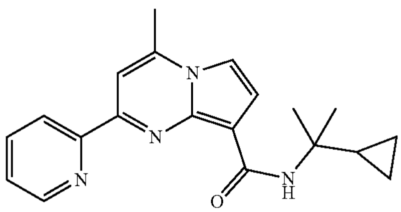 [SMILES: Cc1cc(-c2ccccn2)nc2c(C(=O)NC(C)(C)C3CC3)ccn12] | 3.7 | 57.1 | 0.7 | +++ | *** |
| III-40 | 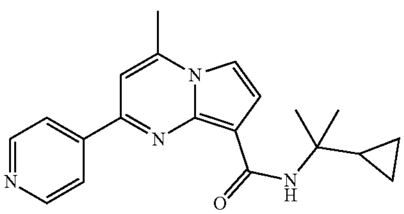 [SMILES: Cc1cc(-c2ccncc2)nc2c(C(=O)NC(C)(C)C3CC3)ccn12] | 3.5 | 57.1 | 3.5 | +++ | ** |
| III-41 | 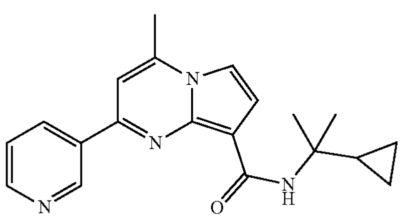 [SMILES: Cc1cc(-c2cccnc2)nc2c(C(=O)NC(C)(C)C3CC3)ccn12] | 3.5 | 57.1 | 2.5 | +++ | *** |
| III-42 | 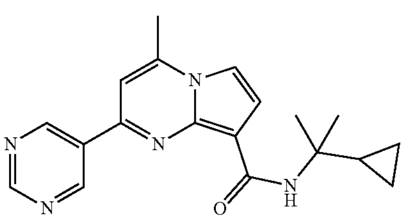 [SMILES: Cc1cc(-c2cncnc2)nc2c(C(=O)NC(C)(C)C3CC3)ccn12] | 2.5 | 69.4 | 3.4 | +++ | ** |
| III-43 | 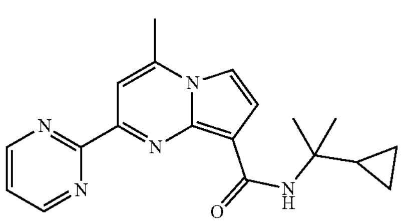 [SMILES: Cc1cc(-c2ncccn2)nc2c(C(=O)NC(C)(C)C3CC3)ccn12] | 2.7 | 69.4 | N/A | +++ | ** |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-44 | 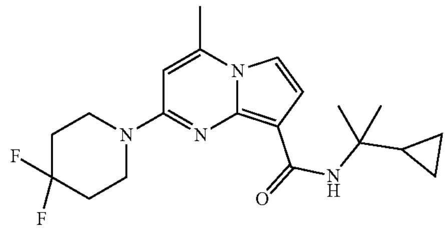 [SMILES: Cc1cc(N2CCC(F)(F)CC2)nc2c(C(=O)NC(C)(C)C3CC3)ccn12] | 3.6 | 47.9 | 1.4 | +++ | ** |
| III-45 | 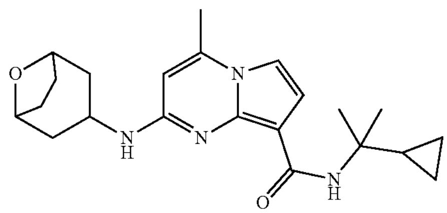 [SMILES: Cc1cc(NC2CC3CCC(C2)O3)nc2c(C(=O)NC(C)(C)C3CC3)ccn12] | 3.4 | 66.0 | 12.3 | ++ | * |
| III-46 | 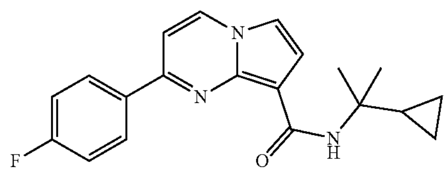 [SMILES: CC(C)(NC(=O)c1ccn2ccc(-c3ccc(F)cc3)nc12)C1CC1] | 4.6 | 44.7 | 0.3 | ++ | * |
| III-47 | 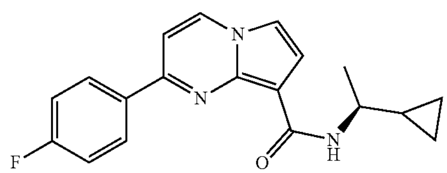 [SMILES: C[C@H](NC(=O)c1ccn2ccc(-c3ccc(F)cc3)nc12)C1CC1] | 4.2 | 44.7 | 0.1 | ++ | * |
| III-48 | 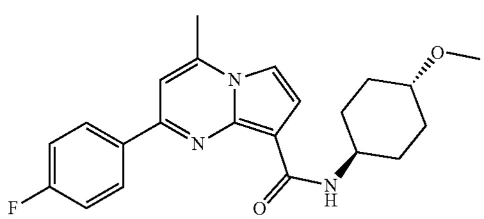 [SMILES: CO[C@H]1CC[C@H](NC(=O)c2ccn3c(C)cc(-c4ccc(F)cc4)nc23)CC1] | 4.0 | 53.9 | 0.9 | +++ | ** |
| III-49 | 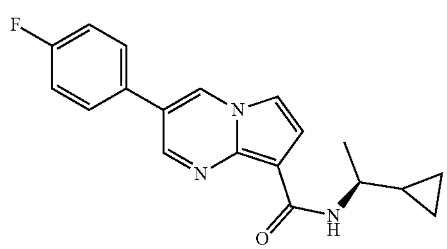 [SMILES: C[C@H](NC(=O)c1ccn2cc(-c3ccc(F)cc3)cnc12)C1CC1] | 3.9 | 44.7 | 0.3 | + | * |
| III-50 | 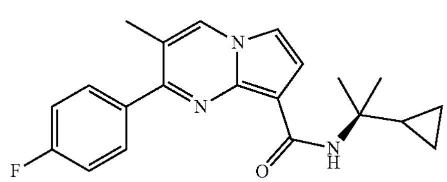 | 4.4 | 44.7 | NA | +++ | * |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-51 | 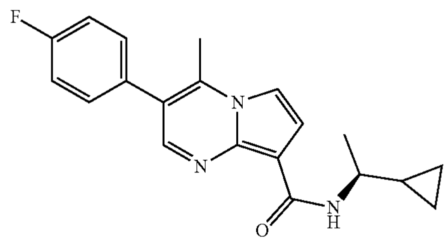 [SMILES: Cc1c(-c2ccc(F)cc2)cnc2c(C(=O)N[C@@H](C)C3CC3)ccn12] | 4.1 | 44.7 | 0.1 | + | * |
| III-52 | 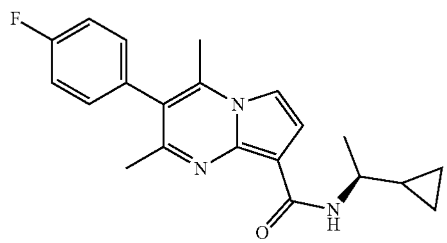 [SMILES: Cc1nc2c(C(=O)N[C@@H](C)C3CC3)ccn2c(C)c1-c1ccc(F)cc1] | 4.3 | 44.7 | 1.7 | + | * |
| III-55 | 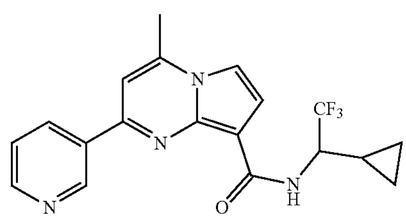 [SMILES: Cc1cc(-c2cccnc2)nc2c(C(=O)NC(C3CC3)C(F)(F)F)ccn12] | 3.3 | 57.1 | 2.9 | +++ | *** |
| III-56 | 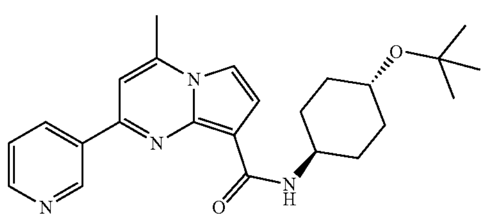 [SMILES: Cc1cc(-c2cccnc2)nc2c(C(=O)N[C@H]3CC[C@H](OC(C)(C)C)CC3)ccn12] | 3.5 | 66.3 | 11.6 | +++ | ** |
| III-57 | 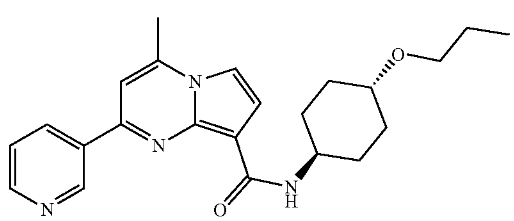 [SMILES: CCCO[C@H]1CC[C@H](NC(=O)c2ccn3c(C)cc(-c4cccnc4)nc23)CC1] | 3.4 | 66.3 | 14.9 | +++ | ** |
| III-58 | 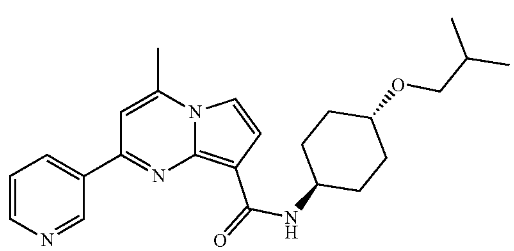 [SMILES: Cc1cc(-c2cccnc2)nc2c(C(=O)N[C@H]3CC[C@H](OCC(C)C)CC3)ccn12] | 3.8 | 66.3 | 1.9 | +++ | *** |

TABLE 3-continued

| Compound No. | Compound Structure | cLogP | PSA | Compound Solubility in Water (µg/mL) | Percent Gcase Activation 1 µM Test Compound | Percent Gcase Activation 0.1 µM Test Compound |
|---|---|---|---|---|---|---|
| III-59 | 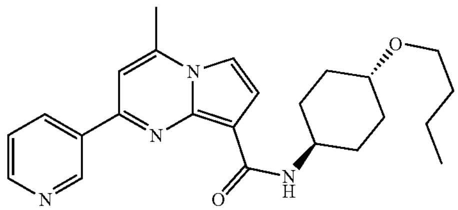 [SMILES: CCCCO[C@H]1CC[C@H](NC(=O)c2ccn3c(C)cc(-c4cccnc4)nc23)CC1] | 3.9 | 66.3 | 1.9 | +++ | *** |
| III-60 | 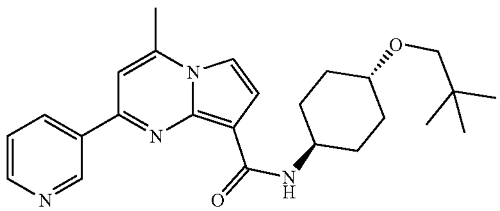 [SMILES: Cc1cc(-c2cccnc2)nc2c(C(=O)N[C@H]3CC[C@H](OCC(C)(C)C)CC3)ccn12] | 4.2 | 66.3 | 1.3 | +++ | *** |
| III-61 | 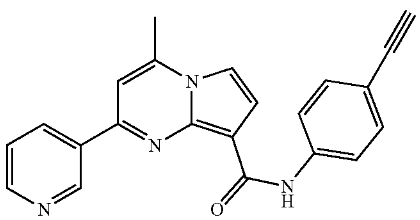 [SMILES: C#Cc1ccc(NC(=O)c2ccn3c(C)cc(-c4cccnc4)nc23)cc1] | 3.8 | 57.1 | 1.2 | +++ | *** |
| III-62 | 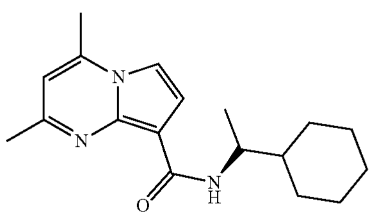 | 4.6 | 44.7 | 5.1 | +++ | *** |
| III-63 | 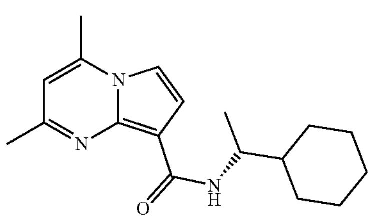 | 4.6 | 44.7 | 4.2 | +++ | *** |
| III-64 | 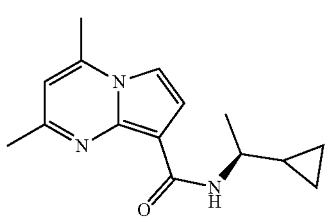 [SMILES: Cc1cc(C)n2ccc(C(=O)N[C@@H](C)C3CC3)c2n1] | 2.9 | 44.7 | 21.7 | +++ | *** |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-65 | 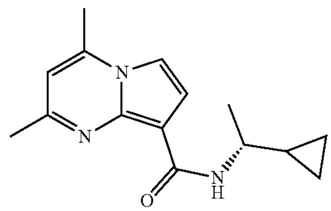 [SMILES: Cc1cc(C)n2ccc(C(=O)N[C@H](C)C3CC3)c2n1] | 2.9 | 44.7 | 20.7 | ++ | * |
| III-66 | 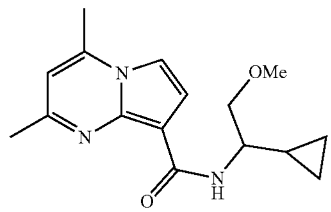 [SMILES: COCC(NC(=O)c1ccn2c(C)cc(C)nc12)C1CC1] | 2.6 | 53.9 | N/A | + | * |
| III-67 | 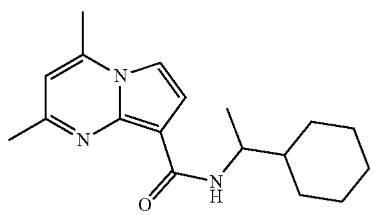 [SMILES: Cc1cc(C)n2ccc(C(=O)NC(C)C3CCCCC3)c2n1] | 4.6 | 44.7 | N/A | +++ | *** |
| III-68 | 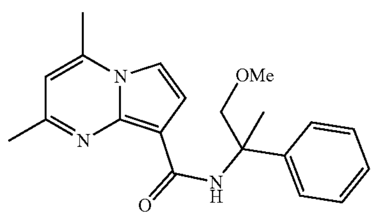 [SMILES: COCC(C)(NC(=O)c1ccn2c(C)cc(C)nc12)c1ccccc1] | 3.9 | 53.9 | N/A | +++ | * |
| III-69 | 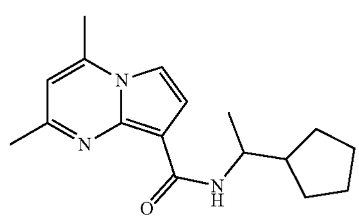 [SMILES: Cc1cc(C)n2ccc(C(=O)NC(C)C3CCCC3)c2n1] | 4.0 | 44.7 | N/A | +++ | ** |
| III-70 | 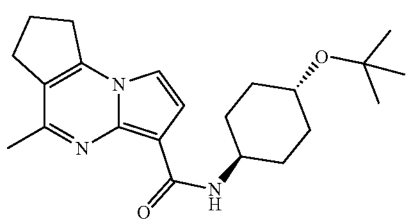 [SMILES: Cc1nc2c(C(=O)N[C@H]3CC[C@H](OC(C)(C)C)CC3)ccn2c2c1CCC2] | 3.9 | 53.9 | 1.5 | + | * |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-71 | 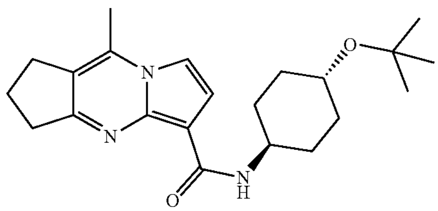 [SMILES: Cc1c2c(nc3c(C(=O)N[C@H]4CC[C@H](OC(C)(C)C)CC4)ccn13)CCC2] | 3.9 | 53.9 | 8.0 | ++ | * |
| III-72 | 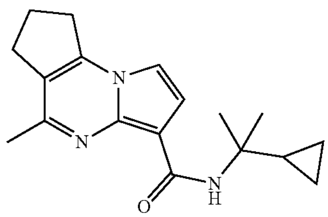 [SMILES: Cc1nc2c(C(=O)NC(C)(C)C3CC3)ccn2c2c1CCC2] | 3.8 | 44.7 | 1.5 | +++ | * |
| III-73 | 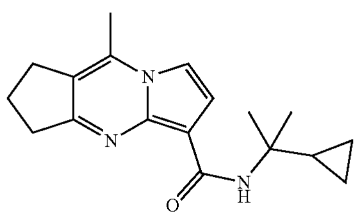 [SMILES: Cc1c2c(nc3c(C(=O)NC(C)(C)C4CC4)ccn13)CCC2] | 3.8 | 44.7 | 0.9 | +++ | ** |
| III-74 | 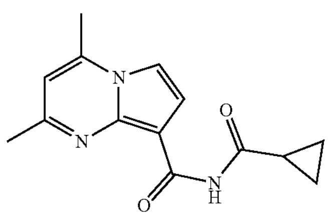 [SMILES: Cc1cc(C)n2ccc(C(=O)NC(=O)C3CC3)c2n1] | 2.0 | 61.8 | 24.8 | + | * |

TABLE 4

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-1 | 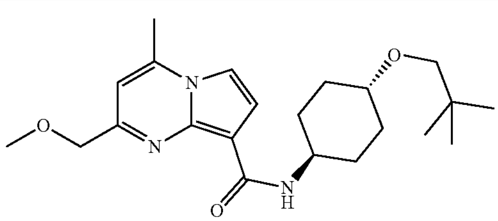 [SMILES: COCc1cc(C)n2ccc(C(=O)N[C@H]3CC[C@H](OCC(C)(C)C)CC3)c2n1] | 3.3 | 63.2 | 2.5 | +++ | *** |

TABLE 4-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-2 | 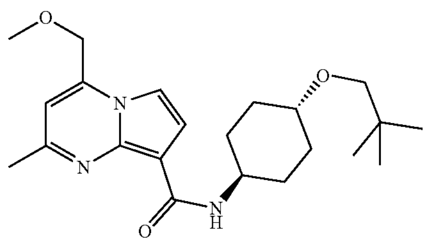 [SMILES: COCc1cc(C)nc2c(C(=O)N[C@H]3CC[C@H](OCC(C)(C)C)CC3)ccn12] | 3.3 | 63.2 | 4.2 | +++ | *** |
| IV-3 | 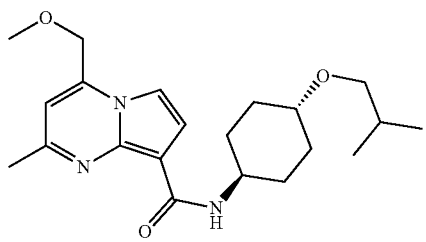 [SMILES: COCc1cc(C)nc2c(C(=O)N[C@H]3CC[C@H](OCC(C)C)CC3)ccn12] | 2.9 | 63.2 | 15.9 | +++ | *** |
| IV-4 | 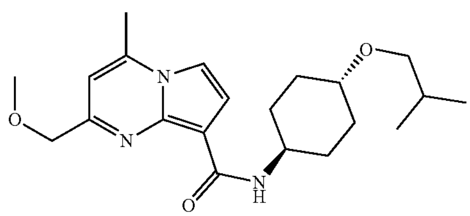 [SMILES: COCc1cc(C)n2ccc(C(=O)N[C@H]3CC[C@H](OCC(C)C)CC3)c2n1] | 2.9 | 63.2 | 16.9 | +++ | ** |
| IV-5 | 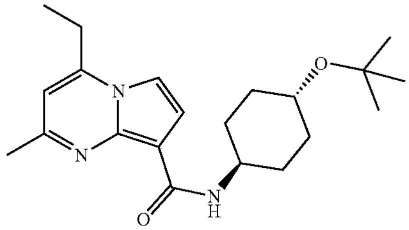 [SMILES: CCc1cc(C)nc2c(C(=O)N[C@H]3CC[C@H](OC(C)(C)C)CC3)ccn12] | 3.9 | 53.9 | 8.1 | +++ | ** |
| IV-6 | 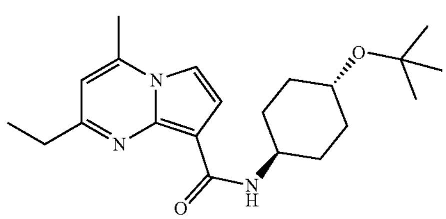 [SMILES: CCc1cc(C)n2ccc(C(=O)N[C@H]3CC[C@H](OC(C)(C)C)CC3)c2n1] | 3.9 | 53.9 | 7.9 | +++ | ** |
| IV-7 | 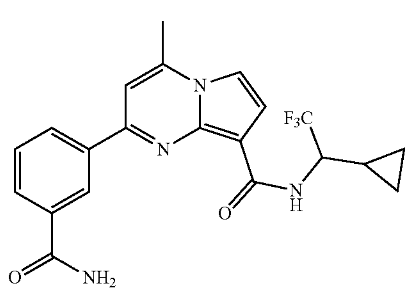 [SMILES: Cc1cc(-c2cccc(C(N)=O)c2)nc2c(C(=O)NC(C3CC3)C(F)(F)F)ccn12] | 3.4 | 87.8 | 0.4 | +++ | *** |

TABLE 4-continued

| Compound No. | Compound Structure | cLogP | PSA | Compound Solubility in Water (μg/mL) | Percent Gcase Activation 1 μM Test Compound | 0.1 μM Test Compound |
|---|---|---|---|---|---|---|
| IV-8 | 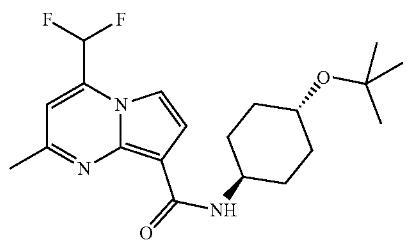 [SMILES: Cc1cc(C(F)F)n2ccc(C(=O)N[C@H]3CC[C@H](OC(C)(C)C)CC3)c2n1] | 3.1 | 53.9 | 0.9 | +++ | ** |
| IV-9 | 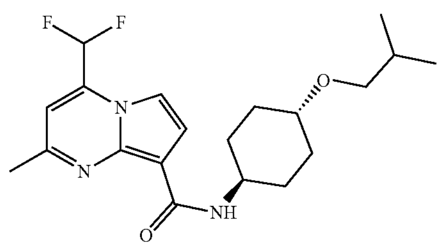 [SMILES: Cc1cc(C(F)F)n2ccc(C(=O)N[C@H]3CC[C@H](OCC(C)C)CC3)c2n1] | 3.3 | 53.9 | 1.5 | +++ | *** |
| IV-10 | 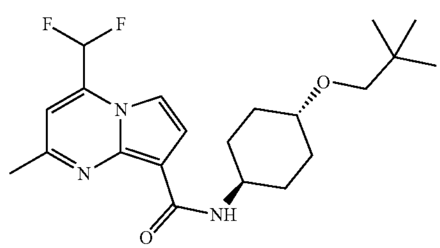 [SMILES: Cc1cc(C(F)F)n2ccc(C(=O)N[C@H]3CC[C@H](OCC(C)(C)C)CC3)c2n1] | 3.7 | 53.9 | 0.3 | +++ | *** |
| IV-11 | 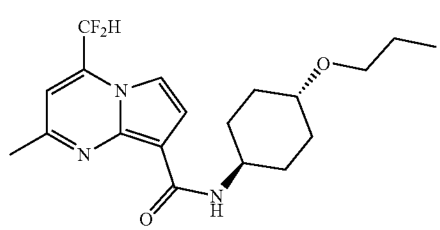 [SMILES: CCCO[C@H]1CC[C@H](NC(=O)c2ccn3c(C(F)F)cc(C)nc23)CC1] | 2.9 | 53.9 | 9.0 | +++ | *** |
| IV-12 | 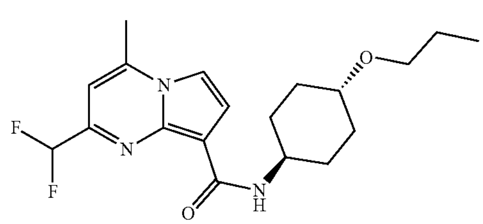 [SMILES: CCCO[C@H]1CC[C@H](NC(=O)c2ccn3c(C)cc(C(F)F)nc23)CC1] | 2.9 | 53.9 | 18.5 | +++ | ** |
| IV-13 | 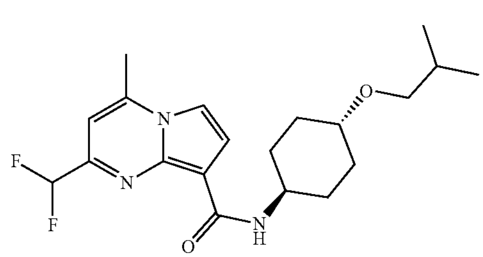 [SMILES: Cc1cc(C(F)F)nc2c(C(=O)N[C@H]3CC[C@H](OCC(C)C)CC3)ccn12] | 3.3 | 53.9 | 5.0 | +++ | *** |

TABLE 4-continued

| Compound No. | Compound Structure | cLogP | PSA | Compound Solubility in Water (μg/mL) | Percent Gcase Activation 1 μM Test Compound | Percent Gcase Activation 0.1 μM Test Compound |
|---|---|---|---|---|---|---|
| IV-14 | 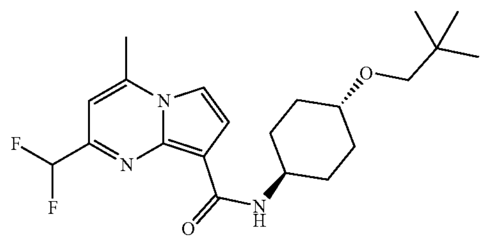 [SMILES: Cc1cc(C(F)F)nc2c(C(=O)N[C@H]3CC[C@H](OCC(C)(C)C)CC3)ccn12] | 3.7 | 53.9 | 0.8 | +++ | *** |
| IV-15 | 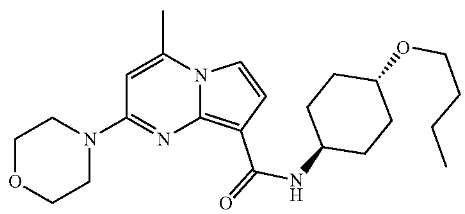 [SMILES: CCCCO[C@H]1CC[C@H](NC(=O)c2ccn3c(C)cc(N4CCOCC4)nc23)CC1] | 3.2 | 66.4 | 8.4 | +++ | ** |
| IV-16 | 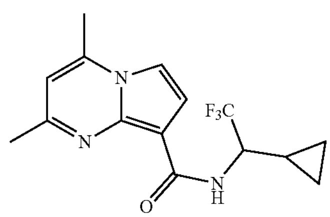 [SMILES: Cc1cc(C)n2ccc(C(=O)NC(C3CC3)C(F)(F)F)c2n1] | 3.2 | 44.7 | 3.1 | +++ | *** |
| IV-17 | 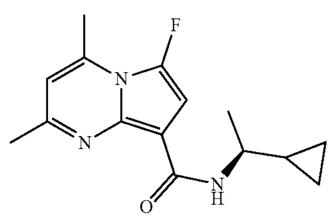 [SMILES: Cc1cc(C)n2c(F)cc(C(=O)N[C@@H](C)C3CC3)c2n1] | 3.1 | 44.7 | 21.6 | +++ | ** |
| IV-18 | 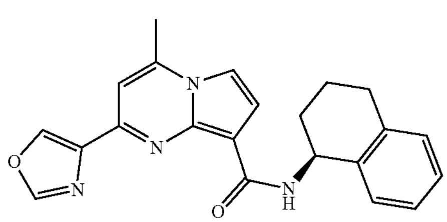 [SMILES: Cc1cc(-c2cocn2)nc2c(C(=O)N[C@H]3CCCc4ccccc43)ccn12] | 4.1 | 66.3 | 1.4 | ++ | * |
| IV-19 | 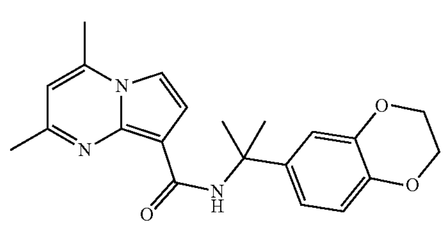 [SMILES: Cc1cc(C)n2ccc(C(=O)NC(C)(C)c3ccc4c(c3)OCCO4)c2n1] | 4.0 | 44.7 | 2.1 | +++ | *** |

TABLE 4-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| IV-20 | 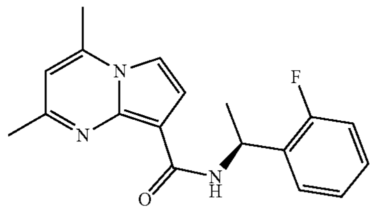 [SMILES: Cc1cc(C)n2ccc(C(=O)N[C@@H](C)c3ccccc3F)c2n1] | 4.0 | 44.7 | 2.5 | +++ | *** |
| IV-21 | 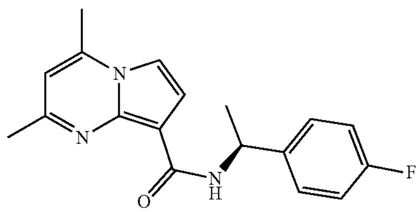 [SMILES: Cc1cc(C)n2ccc(C(=O)N[C@@H](C)c3ccc(F)cc3)c2n1] | 5.0 | 44.7 | 3.3 | +++ | *** |
| IV-22 | 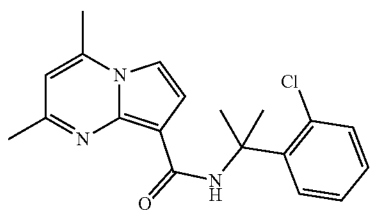 [SMILES: Cc1cc(C)n2ccc(C(=O)NC(C)(C)c3ccccc3Cl)c2n1] | 5.1 | 44.7 | 1.3 | +++ | ** |
| IV-23 | 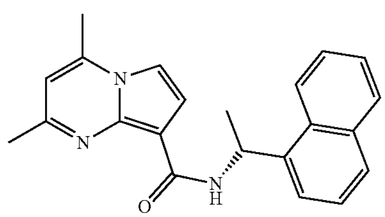 | 5.1 | 44.7 | 0.2 | +++ | ** |
| IV-24 | 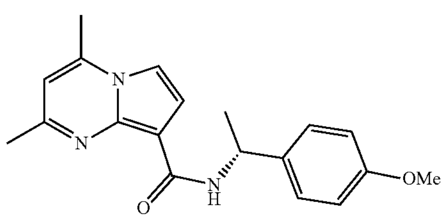 [SMILES: COc1ccc([C@@H](C)NC(=O)c2ccn3c(C)cc(C)nc23)cc1] | 3.8 | 53.9 | 5.3 | +++ | * |
| IV-25 | 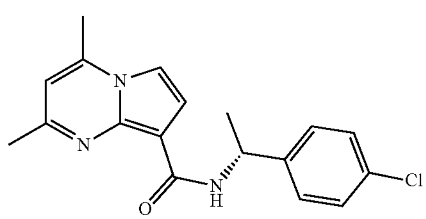 [SMILES: Cc1cc(C)n2ccc(C(=O)N[C@H](C)c3ccc(Cl)cc3)c2n1] | 4.6 | 44.7 | 0.6 | +++ | *** |
| IV-26 | 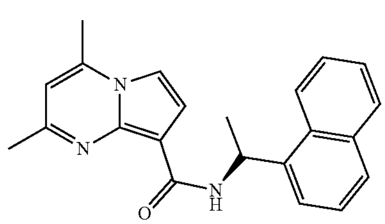 | 5.1 | 44.7 | 0.2 | +++ | ** |

TABLE 4-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-27 | 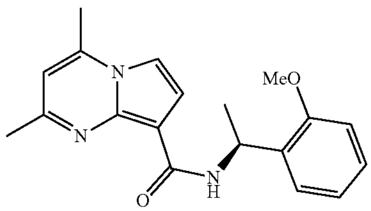 [SMILES: COc1ccccc1[C@H](C)NC(=O)c1ccn2c(C)cc(C)nc12] | 3.8 | 53.9 | 3.0 | +++ | *** |
| IV-28 | 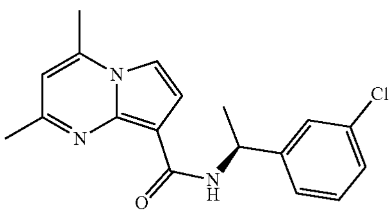 [SMILES: Cc1cc(C)n2ccc(C(=O)N[C@@H](C)c3cccc(Cl)c3)c2n1] | 4.6 | 44.7 | 0.7 | +++ | ** |
| IV-29 | 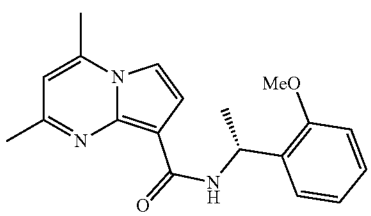 [SMILES: COc1ccccc1[C@@H](C)NC(=O)c1ccn2c(C)cc(C)nc12] | 3.8 | 53.9 | 2.3 | +++ | ** |
| IV-30 | 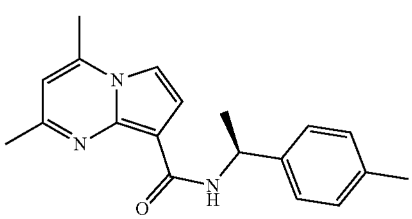 | 4.4 | 44.7 | 2.6 | +++ | ** |
| IV-31 | 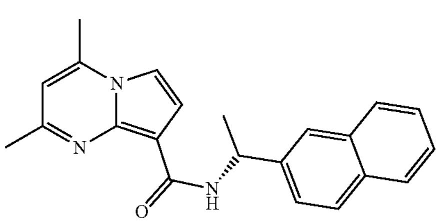 | 5.1 | 44.7 | 0.2 | +++ | *** |
| IV-32 | 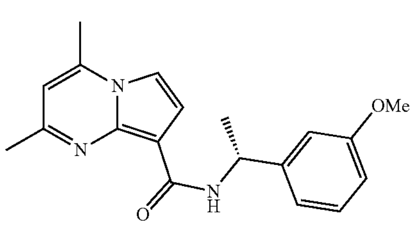 [SMILES: COc1cccc([C@@H](C)NC(=O)c2ccn3c(C)cc(C)nc23)c1] | 3.8 | 53.9 | 7.8 | +++ | ** |

TABLE 4-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-33 | 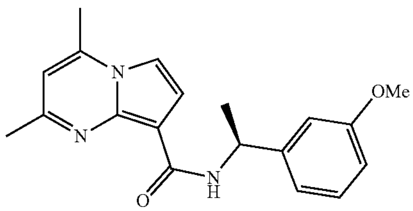 [SMILES: COc1cccc([C@H](C)NC(=O)c2ccn3c(C)cc(C)nc23)c1] | 3.8 | 53.9 | 9.4 | +++ | ** |
| IV-34 | 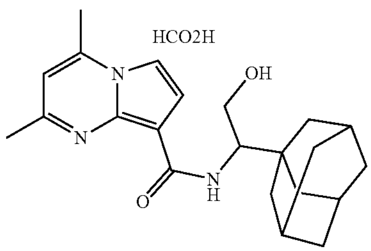 [SMILES: Cc1cc(C)n2ccc(C(=O)NC(CO)C34CC5CC(CC(C5)C3)C4)c2n1 ; "HCO2H"] | 5.2 | 64.9 | N/A | ++ | * |
| IV-35 | 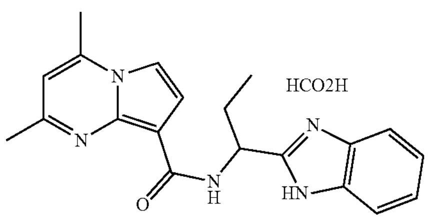 [SMILES: CCC(NC(=O)c1ccn2c(C)cc(C)nc12)c1nc2ccccc2[nH]1 ; "HCO2H"] | 3.9 | 69.1 | N/A | + | * |
| IV-36 | 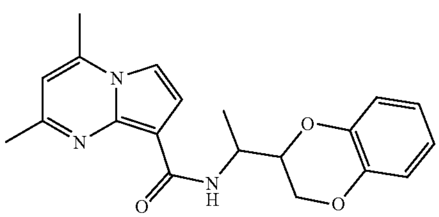 [SMILES: Cc1cc(C)n2ccc(C(=O)NC(C)C3COc4ccccc4O3)c2n1] | 3.9 | 63.2 | N/A | + | * |
| IV-37 | 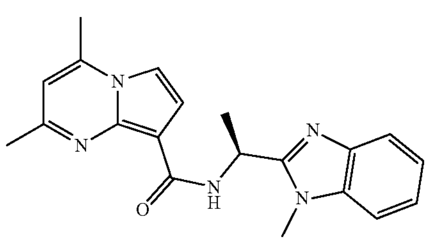 [SMILES: Cc1cc(C)n2ccc(C(=O)N[C@@H](C)c3nc4ccccc4n3C)c2n1] | 3.3 | 60.3 | N/A | + | * |
| IV-38 | 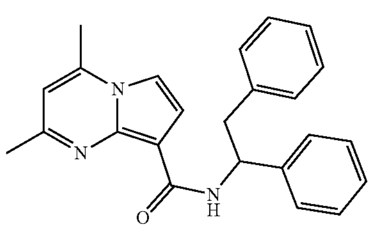 [SMILES: Cc1cc(C)n2ccc(C(=O)NC(Cc3ccccc3)c3ccccc3)c2n1] | 5.5 | 44.7 | 0.2 | +++ | *** |

TABLE 4-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| IV-39 | 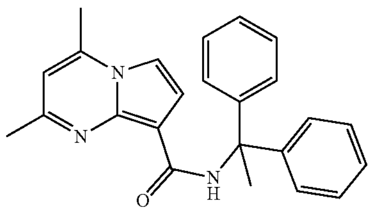 [SMILES: Cc1cc(C)n2ccc(C(=O)NC(C)(c3ccccc3)c3ccccc3)c2n1] | 5.3 | 44.7 | 0.8 | +++ | ** |
| IV-40 | 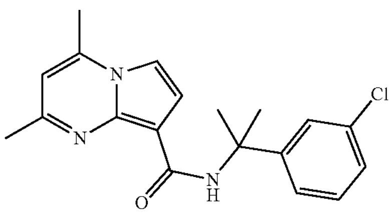 [SMILES: Cc1cc(C)n2ccc(C(=O)NC(C)(C)c3cccc(Cl)c3)c2n1] | 5.0 | 44.7 | 1.5 | +++ | ** |
| IV-41 | 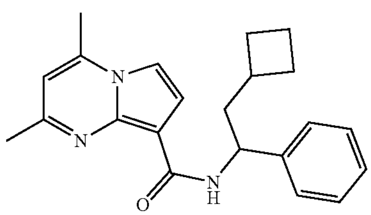 [SMILES: Cc1cc(C)n2ccc(C(=O)NC(CC3CCC3)c3ccccc3)c2n1] | 5.4 | 44.7 | 0.5 | +++ | *** |
| IV-42 | 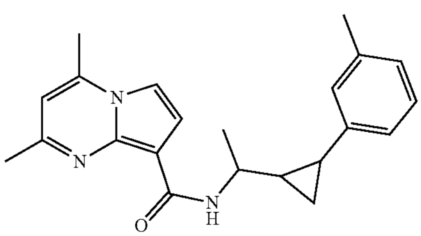 [SMILES: Cc1cccc(C2CC2C(C)NC(=O)c2ccn3c(C)cc(C)nc23)c1] | 4.8 | 44.7 | 1.1 | +++ | *** |
| IV-43 | 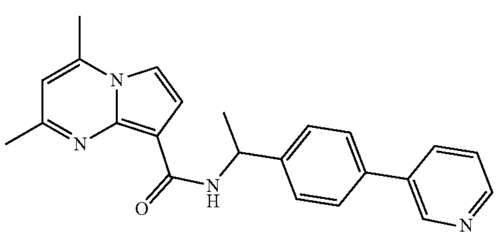 [SMILES: Cc1cc(C)n2ccc(C(=O)NC(C)c3ccc(-c4cccnc4)cc3)c2n1] | 4.3 | 57.1 | N/A | ++ | * |
| IV-44 | 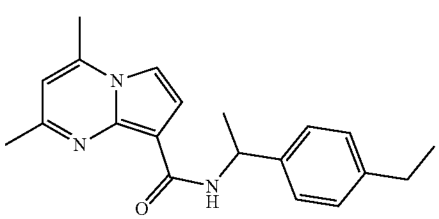 [SMILES: CCc1ccc(C(C)NC(=O)c2ccn3c(C)cc(C)nc23)cc1] | 4.9 | 44.7 | 2.0 | +++ | *** |

TABLE 4-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-45 | 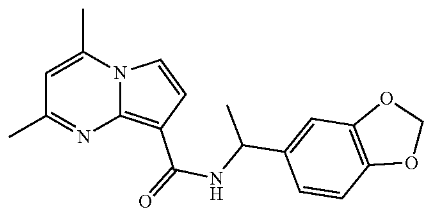 [SMILES: Cc1cc(C)n2ccc(C(=O)NC(C)c3ccc4c(c3)OCO4)c2n1] | 3.9 | 63.2 | 5.7 | ++ | * |
| IV-46 | 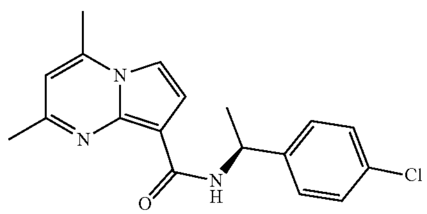 [SMILES: Cc1cc(C)n2ccc(C(=O)N[C@@H](C)c3ccc(Cl)cc3)c2n1] | 4.6 | 44.7 | 0.4 | +++ | *** |
| IV-47 | 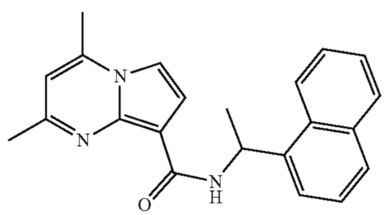 [SMILES: Cc1cc(C)n2ccc(C(=O)NC(C)c3cccc4ccccc34)c2n1] | 5.1 | 44.7 | 0.7 | +++ | *** |
| IV-48 | 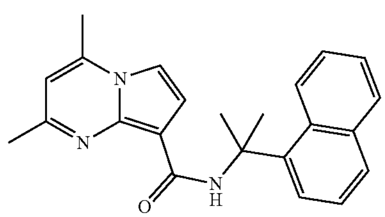 [SMILES: Cc1cc(C)n2ccc(C(=O)NC(C)(C)c3cccc4ccccc34)c2n1] | 5.5 | 44.7 | 0.6 | +++ | *** |
| IV-49 | 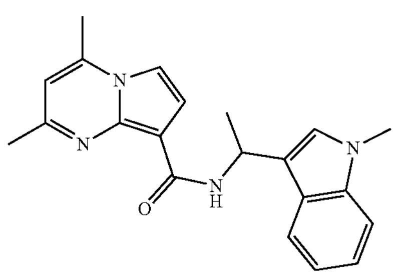 | 4.4 | 47.9 | 2.1 | +++ | ** |
| IV-50 | 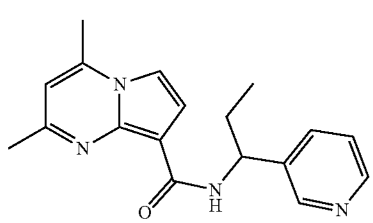 [SMILES: CCC(NC(=O)c1ccn2c(C)cc(C)nc12)c1cccnc1] | 2.9 | 57.1 | 24.7 | ++ | * |

TABLE 4-continued

| Compound No. | Compound Structure | cLogP | PSA | Compound Solubility in Water (µg/mL) | Percent Gcase Activation 1 µM Test Compound | Percent Gcase Activation 0.1 µM Test Compound |
|---|---|---|---|---|---|---|
| IV-51 | 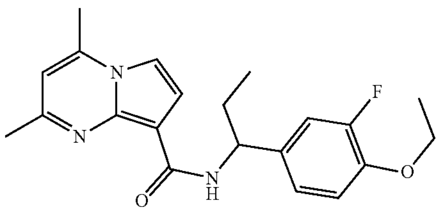 [SMILES: CCOc1ccc(C(CC)NC(=O)c2ccn3c(C)cc(C)nc23)cc1F] | 4.4 | 53.9 | 0.3 | +++ | *** |
| IV-52 | 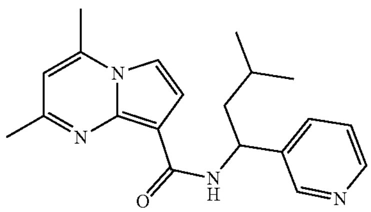 [SMILES: Cc1cc(C)n2ccc(C(=O)NC(CC(C)C)c3cccnc3)c2n1] | 3.9 | 57.1 | 17.3 | ++ | * |
| IV-53 | 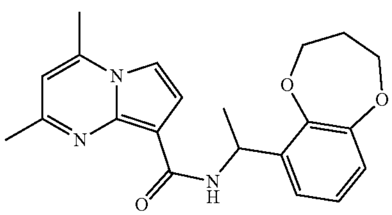 [SMILES: Cc1cc(C)n2ccc(C(=O)NC(C)c3cccc4c3OCCCO4)c2n1] | 4.0 | 63.2 | 5.1 | +++ | ** |
| IV-54 | 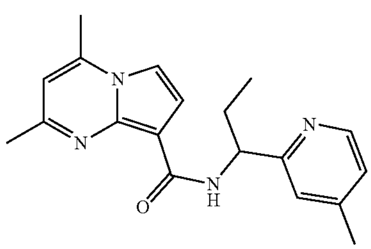 [SMILES: CCC(NC(=O)c1ccn2c(C)cc(C)nc12)c1cc(C)ccn1] | 3.4 | 57.1 | 23.2 | + | * |
| IV-55 | 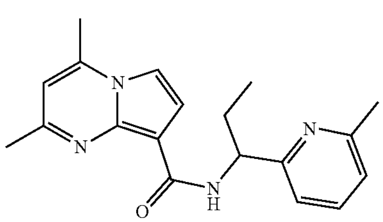 | 3.4 | 57.1 | 17.6 | + | * |
| IV-56 | 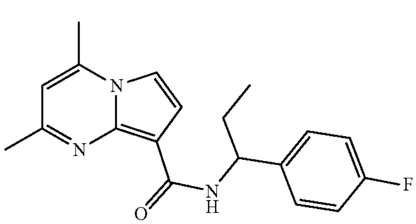 [SMILES: CCC(NC(=O)c1ccn2c(C)cc(C)nc12)c1ccc(F)cc1] | 4.6 | 44.7 | 2.0 | +++ | *** |

TABLE 4-continued

| Compound No. | Compound Structure | cLogP | PSA | Compound Solubility in Water (μg/mL) | Percent Gcase Activation 1 μM Test Compound | Percent Gcase Activation 0.1 μM Test Compound |
|---|---|---|---|---|---|---|
| IV-57 | 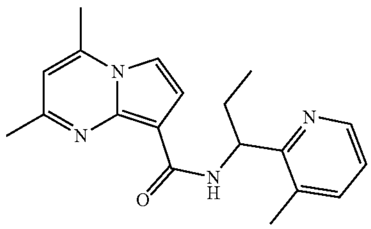 [SMILES: CCC(NC(=O)c1ccn2c(C)cc(C)nc12)c1ncccc1C] | 3.4 | 57.1 | N/A | + | * |
| IV-58 | 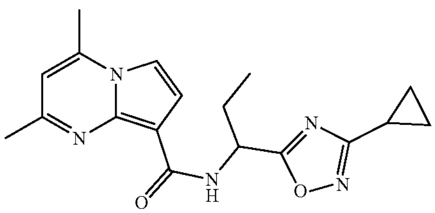 [SMILES: CCC(NC(=O)c1ccn2c(C)cc(C)nc12)c1nc(C2CC2)no1] | 2.5 | 78.7 | 18.5 | ++ | * |
| IV-59 | 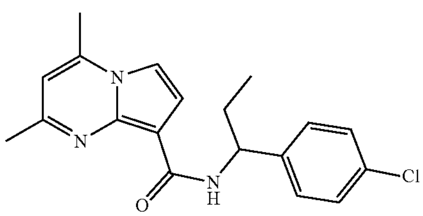 [SMILES: CCC(NC(=O)c1ccn2c(C)cc(C)nc12)c1ccc(Cl)cc1] | 5.1 | 44.7 | 0.8 | +++ | *** |
| IV-60 | 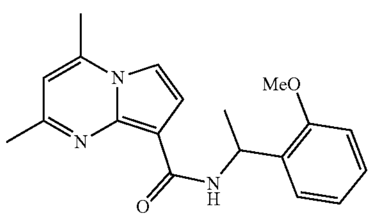 [SMILES: COc1ccccc1C(C)NC(=O)c1ccn2c(C)cc(C)nc12] | 3.8 | 53.9 | N/A | +++ | *** |
| IV-61 | 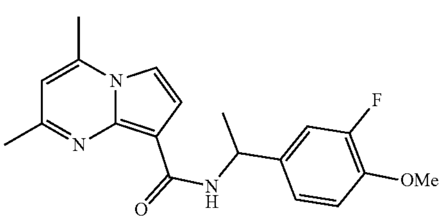 [SMILES: COc1ccc(C(C)NC(=O)c2ccn3c(C)cc(C)nc23)cc1F] | 3.9 | 53.9 | 1.9 | +++ | *** |
| IV-62 | 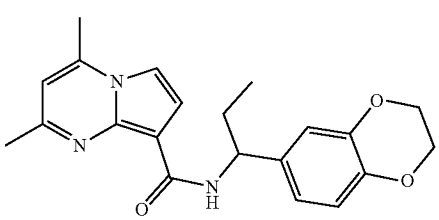 [SMILES: CCC(NC(=O)c1ccn2c(C)cc(C)nc12)c1ccc2c(c1)OCCO2] | 4.3 | 63.2 | 1.1 | +++ | ** |

TABLE 4-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-63 | 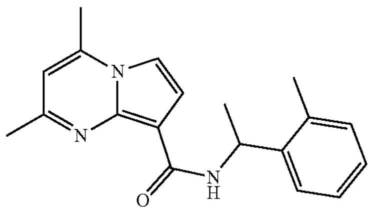 [SMILES: Cc1cc(C)n2ccc(C(=O)NC(C)c3ccccc3C)c2n1] | 4.4 | 44.7 | N/A | +++ | *** |
| IV-64 | 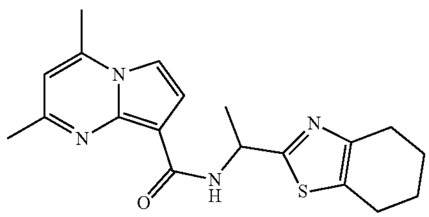 [SMILES: Cc1cc(C)n2ccc(C(=O)NC(C)c3nc4c(s3)CCCC4)c2n1] | 3.8 | 57.1 | 4.9 | +++ | ** |
| IV-65 | 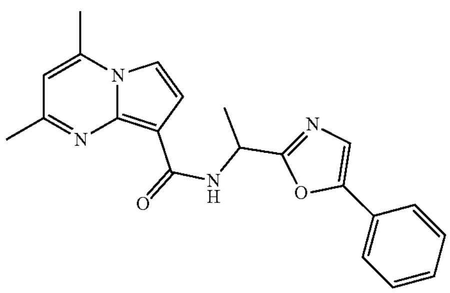 [SMILES: Cc1cc(C)n2ccc(C(=O)NC(C)c3ncc(-c4ccccc4)o3)c2n1] | 3.7 | 66.3 | N/A | +++ | ** |
| IV-66 | 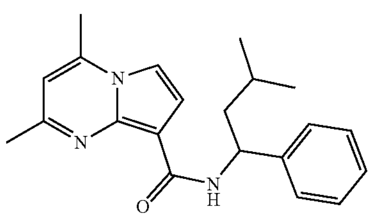 [SMILES: Cc1cc(C)n2ccc(C(=O)NC(CC(C)C)c3ccccc3)c2n1] | 5.4 | 44.7 | 1.0 | +++ | *** |
| IV-67 | 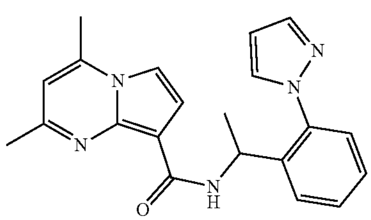 [SMILES: Cc1cc(C)n2ccc(C(=O)NC(C)c3ccccc3-n3cccn3)c2n1] | 4.0 | 60.3 | N/A | ++ | * |
| IV-68 | 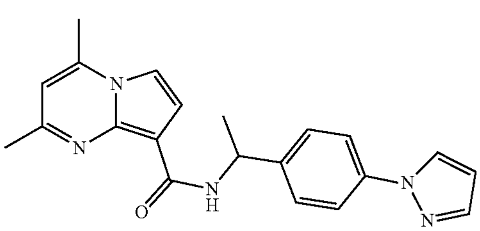 [SMILES: Cc1cc(C)n2ccc(C(=O)NC(C)c3ccc(-n4cccn4)cc3)c2n1] | 4.0 | 60.3 | N/A | +++ | ** |

TABLE 4-continued

| Compound No. | Compound Structure | cLogP | PSA | Compound Solubility in Water (μg/mL) | Percent Gcase Activation 1 μM Test Compound | 0.1 μM Test Compound |
|---|---|---|---|---|---|---|
| IV-69 | 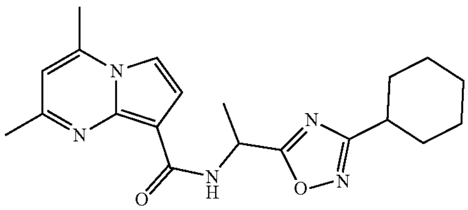 [SMILES: Cc1cc(C)n2ccc(C(=O)NC(C)c3nc(C4CCCCC4)no3)c2n1] | 3.6 | 78.7 | N/A | +++ | ** |
| IV-70 | 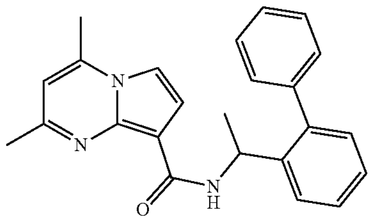 [SMILES: Cc1cc(C)n2ccc(C(=O)NC(C)c3ccccc3-c3ccccc3)c2n1] | 5.5 | 44.7 | N/A | +++ | * |
| IV-71 | 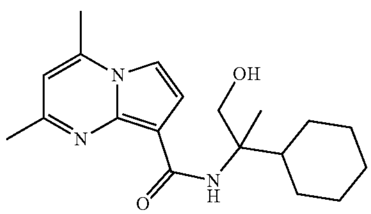 [SMILES: Cc1cc(C)n2ccc(C(=O)NC(C)(CO)C3CCCCC3)c2n1] | 3.9 | 64.9 | N/A | N/A | N/A |
| IV-72 | 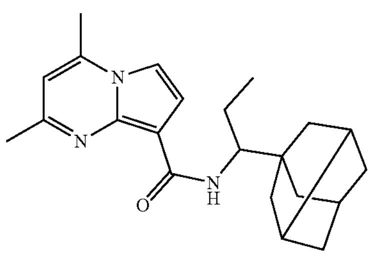 [SMILES: CCC(NC(=O)c1ccn2c(C)cc(C)nc12)C12CC3CC(C1)C(C3)C2] | 6.8 | 44.7 | N/A | +++ | *** |
| IV-73 | 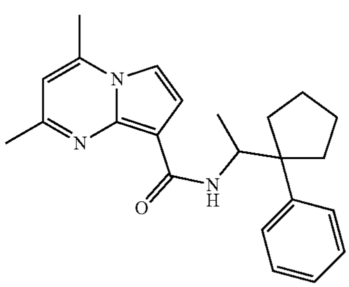 [SMILES: Cc1cc(C)n2ccc(C(=O)NC(C)C3(c4ccccc4)CCCC3)c2n1] | 5.6 | 44.7 | 1.5 | +++ | *** |
| IV-74 | 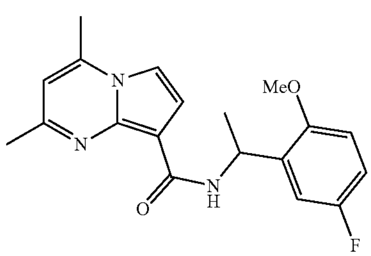 [SMILES: COc1ccc(F)cc1C(C)NC(=O)c1ccn2c(C)cc(C)nc12] | 4.1 | 53.9 | N/A | +++ | *** |

TABLE 4-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| IV-75 | 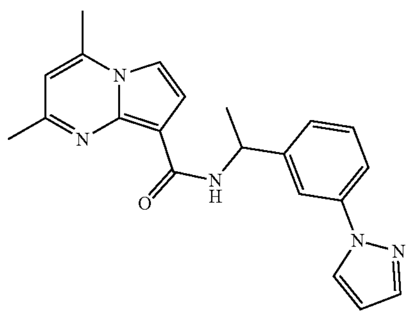 [SMILES: Cc1cc(C)n2ccc(C(=O)NC(C)c3cccc(-n4cccn4)c3)c2n1] | 4.0 | 60.3 | N/A | +++ | ** |
| IV-76 | 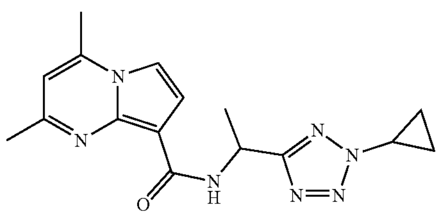 [SMILES: Cc1cc(C)n2ccc(C(=O)NC(C)c3nnn(C4CC4)n3)c2n1] | 1.9 | 85.0 | N/A | + | * |
| IV-77 | 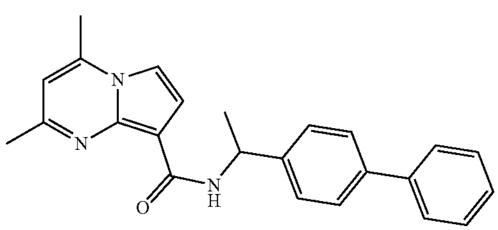 [SMILES: Cc1cc(C)n2ccc(C(=O)NC(C)c3ccc(-c4ccccc4)cc3)c2n1] | 5.8 | 44.7 | N/A | +++ | *** |
| IV-78 | 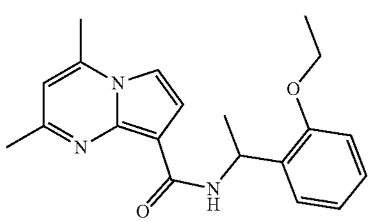 [SMILES: CCOc1ccccc1C(C)NC(=O)c1ccn2c(C)cc(C)nc12] | 4.4 | 53.9 | 2.1 | +++ | *** |
| IV-79 | 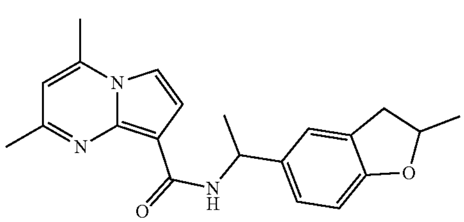 | 4.5 | 53.9 | 2.6 | +++ | *** |
| IV-80 | 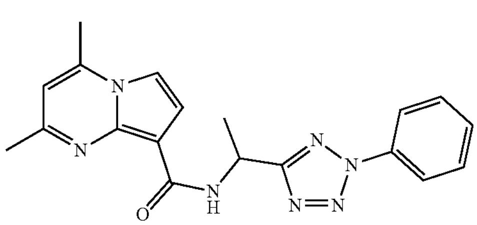 [SMILES: Cc1cc(C)n2ccc(C(=O)NC(C)c3nnn(-c4ccccc4)n3)c2n1] | 3.2 | 85.0 | N/A | + | * |

TABLE 4-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| IV-81 | 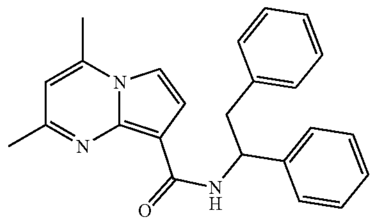 [SMILES: Cc1cc(C)n2ccc(C(=O)NC(Cc3ccccc3)c3ccccc3)c2n1] | 5.5 | 44.7 | N/A | +++ | *** |
| IV-82 | 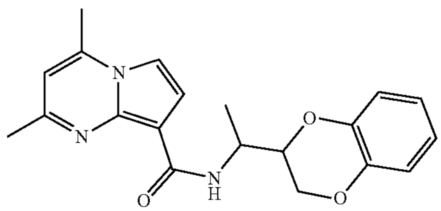 [SMILES: Cc1cc(C)n2ccc(C(=O)NC(C)C3COc4ccccc4O3)c2n1] | 3.9 | 63.2 | N/A | +++ | * |
| IV-83 | 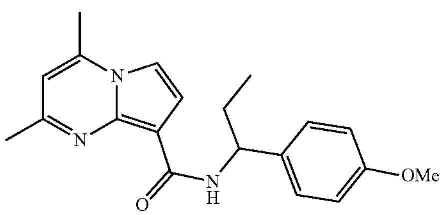 [SMILES: CCC(NC(=O)c1ccn2c(C)cc(C)nc12)c1ccc(OC)cc1] | 4.4 | 53.9 | N/A | +++ | *** |
| IV-84 | 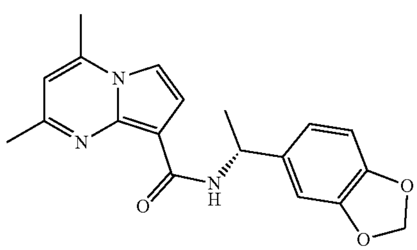 [SMILES: Cc1cc(C)n2ccc(C(=O)N[C@H](C)c3ccc4c(c3)OCO4)c2n1] | 3.9 | 63.2 | N/A | +++ | ** |
| IV-85 | 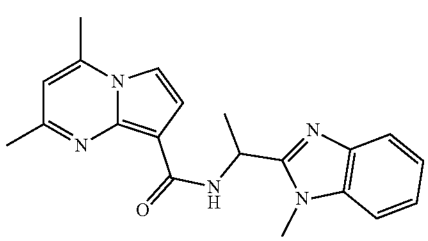 [SMILES: Cc1cc(C)n2ccc(C(=O)NC(C)c3nc4ccccc4n3C)c2n1] | 3.3 | 60.3 | N/A | + | * |
| IV-86 | 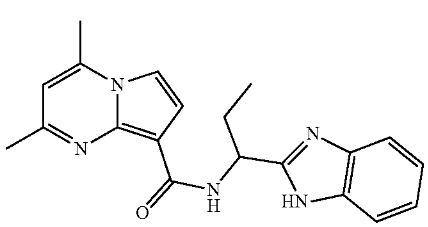 [SMILES: CCC(NC(=O)c1ccn2c(C)cc(C)nc12)c1nc2ccccc2[nH]1] | 3.9 | 69.1 | N/A | + | * |

TABLE 4-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| IV-87 | 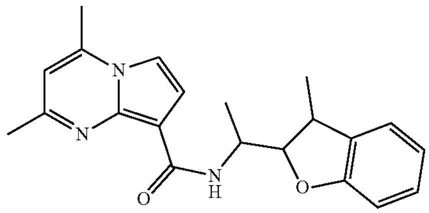 [SMILES: Cc1cc(C)n2ccc(C(=O)NC(C)C3Oc4ccccc4C3C)c2n1] | 4.5 | 53.9 | N/A | +++ | ** |
| IV-88 | 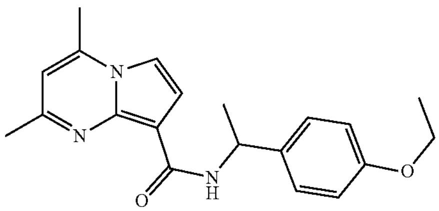 [SMILES: CCOc1ccc(C(C)NC(=O)c2ccn3c(C)cc(C)nc23)cc1] | 4.4 | 53.9 | N/A | +++ | *** |
| IV-89 | 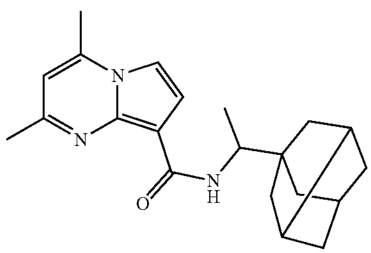 [SMILES: Cc1cc(C)n2ccc(C(=O)NC(C)C34CC5CC(C3)C(C5)C4)c2n1] | 6.3 | 44.7 | N/A | +++ | *** |
| IV-90 | 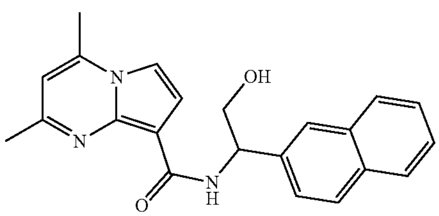 [SMILES: Cc1cc(C)n2ccc(C(=O)NC(CO)c3ccc4ccccc4c3)c2n1] | 3.9 | 64.9 | N/A | + | * |
| IV-91 | 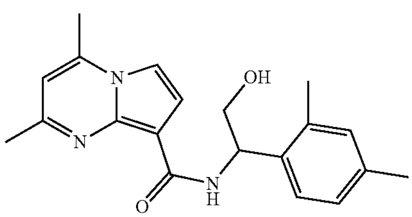 | 3.7 | 64.9 | N/A | + | * |
| IV-92 | 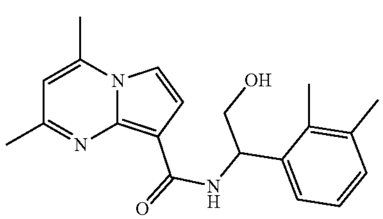 | 3.7 | 64.9 | N/A | + | * |

TABLE 4-continued

| Compound No. | Compound Structure | cLogP | PSA | Compound Solubility in Water (μg/mL) | Percent Gcase Activation 1 μM Test Compound | 0.1 μM Test Compound |
|---|---|---|---|---|---|---|
| IV-93 | 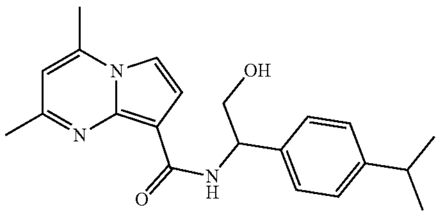 [SMILES: Cc1cc(C)n2ccc(C(=O)NC(CO)c3ccc(C(C)C)cc3)c2n1] | 4.1 | 64.9 | N/A | + | * |
| IV-94 | 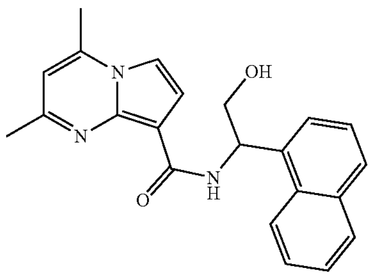 [SMILES: Cc1cc(C)n2ccc(C(=O)NC(CO)c3cccc4ccccc34)c2n1] | 3.9 | 64.9 | N/A | ++ | * |
| IV-95 | 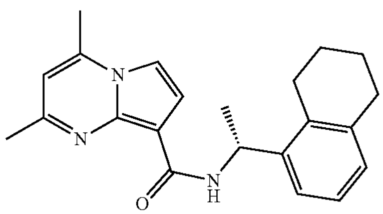 [SMILES: Cc1cc(C)n2ccc(C(=O)N[C@H](C)c3cccc4c3CCCC4)c2n1] | 5.5 | 44.7 | N/A | +++ | ** |
| IV-96 | 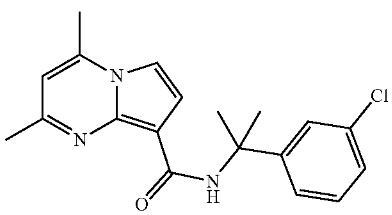 [SMILES: Cc1cc(C)n2ccc(C(=O)NC(C)(C)c3cccc(Cl)c3)c2n1] | 5.0 | 44.7 | N/A | +++ | *** |
| IV-97 | 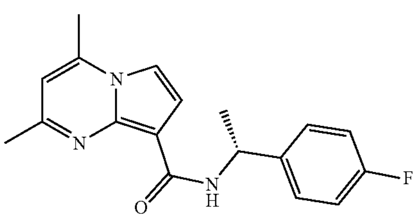 [SMILES: Cc1cc(C)n2ccc(C(=O)N[C@H](C)c3ccc(F)cc3)c2n1] | 4.0 | 44.7 | N/A | +++ | ** |
| IV-98 | 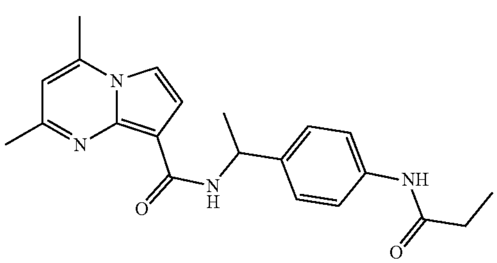 [SMILES: CCC(=O)Nc1ccc(C(C)NC(=O)c2ccn3c(C)cc(C)nc23)cc1] | 3.5 | 73.8 | N/A | +++ | *** |

TABLE 4-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-99 | 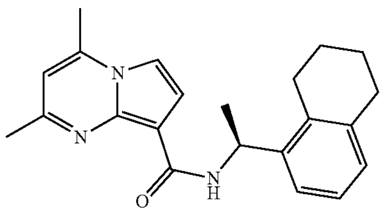 [SMILES: Cc1cc(C)n2ccc(C(=O)N[C@@H](C)c3cccc4c3CCCC4)c2n1] | 5.5 | 44.7 | N/A | +++ | *** |
| IV-100 | 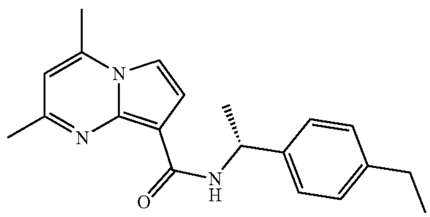 [SMILES: CCc1ccc([C@@H](C)NC(=O)c2ccn3c(C)cc(C)nc23)cc1] | 4.9 | 44.7 | N/A | +++ | ** |
| IV-101 | 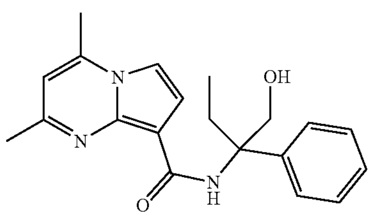 [SMILES: CCC(CO)(NC(=O)c1ccn2c(C)cc(C)nc12)c1ccccc1] | 3.6 | 64.9 | N/A | ++ | * |
| IV-102 | 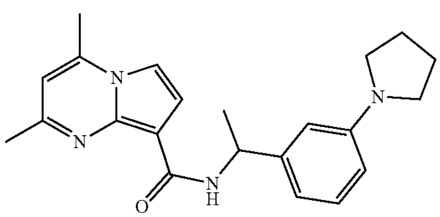 [SMILES: Cc1cc(C)n2ccc(C(=O)NC(C)c3cccc(N4CCCC4)c3)c2n1] | 4.2 | 49.9 | N/A | +++ | * |
| IV-103 | 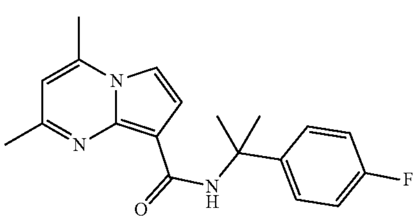 [SMILES: Cc1cc(C)n2ccc(C(=O)NC(C)(C)c3ccc(F)cc3)c2n1] | 4.4 | 44.7 | N/A | +++ | *** |
| IV-104 | 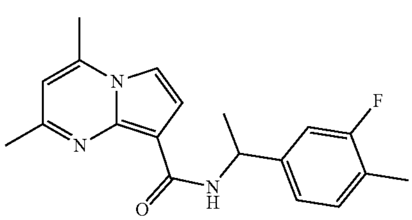 | 4.5 | 44.7 | N/A | +++ | *** |

TABLE 4-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-105 | 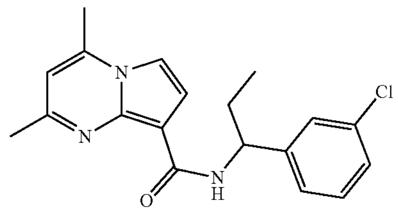 [SMILES: CCC(NC(=O)c1ccn2c(C)cc(C)nc12)c1cccc(Cl)c1] | 5.1 | 44.7 | N/A | +++ | *** |
| IV-106 | 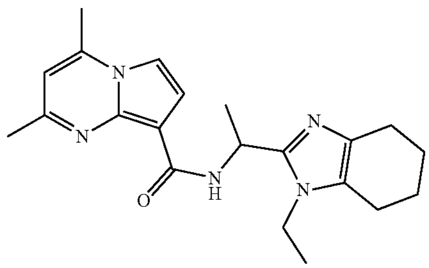 [SMILES: CCn1c(C(C)NC(=O)c2ccn3c(C)cc(C)nc23)nc2c1CCCC2] | 3.9 | 60.3 | N/A | + | * |
| IV-107 | 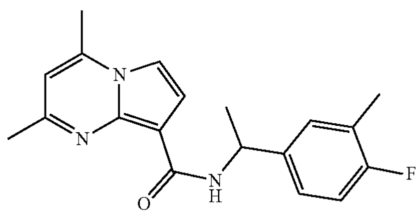 [SMILES: Cc1cc(C)n2ccc(C(=O)NC(C)c3ccc(F)c(C)c3)c2n1] | 4.5 | 44.7 | N/A | +++ | ** |
| IV-108 | 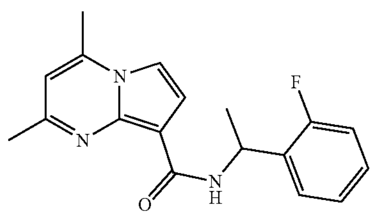 [SMILES: Cc1cc(C)n2ccc(C(=O)NC(C)c3ccccc3F)c2n1] | 4.0 | 44.7 | N/A | +++ | ** |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound represented by Formula I-A:

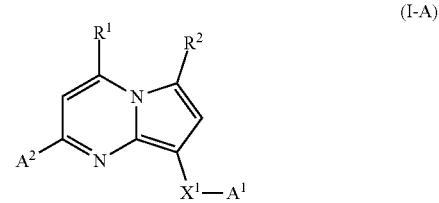

or a pharmaceutically acceptable salt thereof, wherein:
$R^1$ represents independently for each occurrence $C_{1-4}$ alkyl, $C_{1-4}$haloalkyl, $C_{1-4}$ alkoxyl, —($C_{1-4}$ alkylene)-($C_{1-4}$ alkoxyl), cyclopropyl, chloro, or fluoro;
$R^2$ is hydrogen;
$R^3$ and $R^4$ each represent independently for each occurrence hydrogen or $C_{1-4}$ alkyl;
$X^1$ is a carbonyl-containing linker selected from —C(O)N(H)-ψ, —C(O)N(H)($C_{1-6}$ alkylene optionally substituted $C_{3-6}$ cycloalkyl)-ψ, or —C(O)N(H)($C_{1-6}$ haloalkylene)-ψ; where ψ is a bond to $A^1$;

$A^1$ is a cyclic group selected from:

$C_{3-10}$ cycloalkyl substituted by 0 or 1 occurrence of $Y^1$ and 0, 1, or 2 occurrences of $Y^2$; and phenyl substituted by 0 or 1 occurrence of $Y^1$ and 0, 1, or 2 occurrences of $Y^2$;

$A^2$ is a 5-12 membered heterocyclyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, and hydroxyl;

$Y^1$ represents, independently for each occurrence, one of the following:

2-8 membered alkoxyl or —O—($C_{2-6}$ alkynyl); or $C_{2-6}$ alkynyl or —C≡C—($C_{1-6}$ alkylene)-$OR^4$; and $Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, or —N($R^3$)$_2$.

2. The compound of claim 1, wherein $R^1$ represents independently for each occurrence methyl, halomethyl, —(CH$_2$)$_{1-2}$—O—($C_{1-3}$ alkyl), cyclopropyl, chloro, or fluoro.

3. The compound of claim 1, wherein $A^1$ is $C_{3-7}$ cycloalkyl substituted once by $Y^1$ and 0-1 occurrences of $Y^2$.

4. The compound of claim 1, wherein $A^1$ is cyclohexyl substituted once by $Y^1$.

5. The compound of claim 1, wherein $A^1$ is $C_{3-7}$ cycloalkyl.

6. The compound of claim 1, wherein $A^1$ is cyclopropyl.

7. The compound of claim 1, wherein any occurrence of $Y^2$ is independently $C_{1-3}$ alkyl, halogen, or $C_{1-3}$ haloalkyl.

8. The compound of claim 1, wherein $Y^1$ is a 2-8 membered alkoxyl.

9. The compound of claim 1, wherein $Y^1$ is —O—($C_{1-7}$ alkyl).

10. The compound of claim 1, wherein $Y^1$ is —O-butyl, —O-pentyl, or —O-hexyl.

11. The compound of claim 1, wherein $A^2$ is a 5-6 membered heteroaryl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N($R^4$)$_2$.

12. The compound of claim 1, wherein $A^2$ is a 5-6 membered heteroaryl selected from the group consisting of pyridinyl, pyrimidinyl, pyrazinyl, furanyl, pyrrolyl, thiophenyl, oxazolyl, isoxazolyl, and thiazolyl, each of which is optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N($R^4$)$_2$.

13. The compound of claim 1, wherein $A^2$ is pyridinyl optionally substituted by 1, 2, or 3 substituents independently selected from the group consisting of $C_{1-4}$ alkyl, $C_{1-4}$ haloalkyl, $C_{1-4}$ alkoxyl, $C_{3-5}$ cycloalkyl, cyano, halogen, hydroxyl, and —N($R^4$)$_2$.

14. The compound of claim 1, wherein $A^2$ is 3-pyridinyl optionally substituted by 1 or 2 3 substituents independently selected from the group consisting of $C_{1-4}$ alkyl, $C_{1-4}$ haloalkyl, $C_{1-4}$ alkoxyl, $C_{3-5}$ cycloalkyl, cyano, and halogen.

15. The compound of claim 1, wherein the compound is selected from the group consisting of:

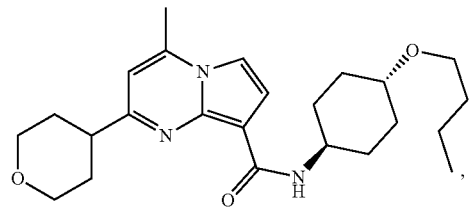

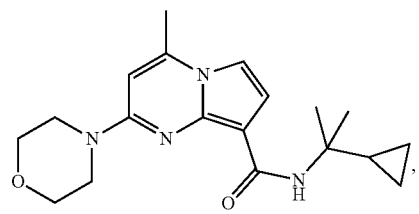

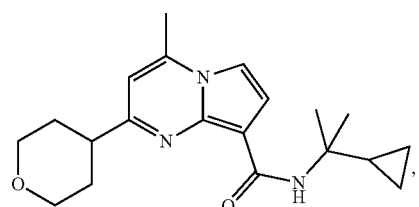

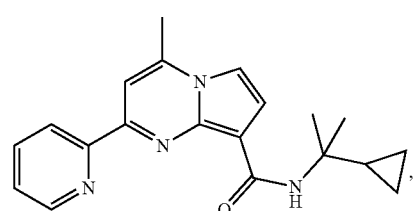

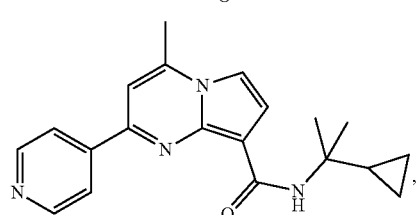

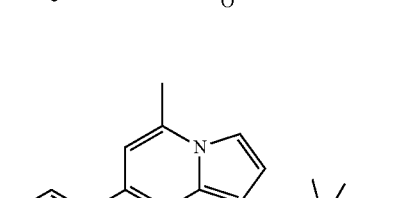

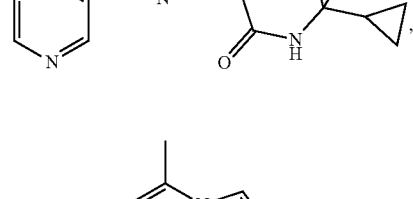

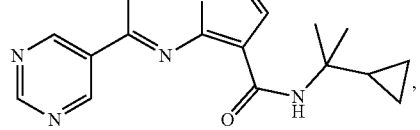

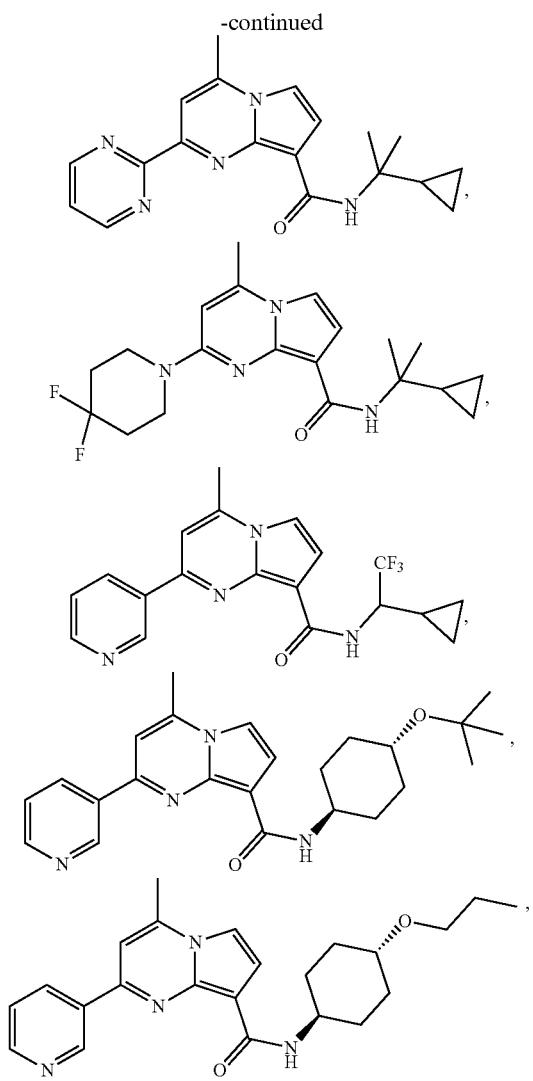
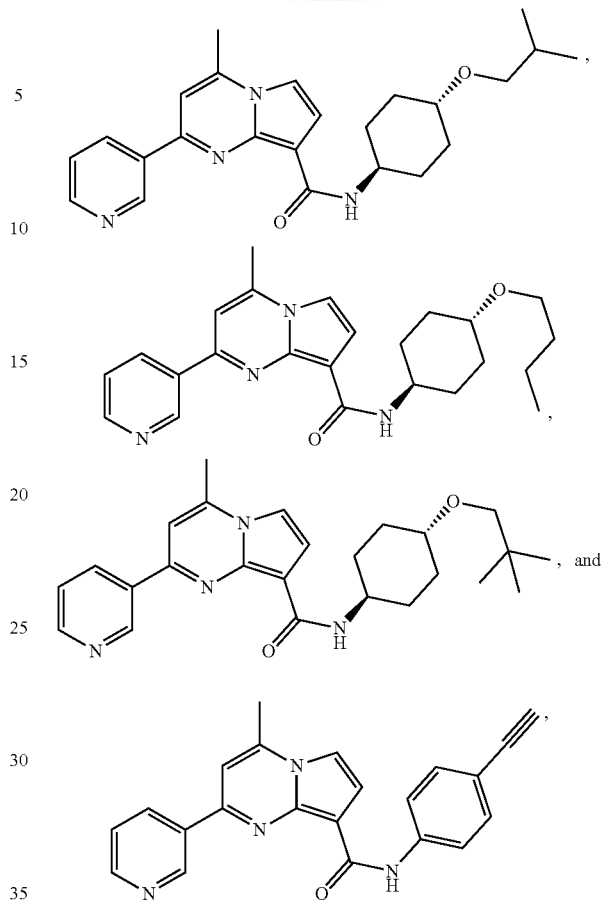
or a pharmaceutically acceptable salt thereof.
16. A pharmaceutical composition comprising a compound of claim 1 and a pharmaceutically acceptable carrier.
* * * * *